United States Patent
Yu et al.

(10) Patent No.: US 9,540,657 B2
(45) Date of Patent: Jan. 10, 2017

(54) EXPRESSION OF SECRETED AND CELL-SURFACE POLYPEPTIDES

(71) Applicant: California Institute of Technology, Pasadena, CA (US)

(72) Inventors: Kenneth Yu, Pasadena, CA (US); David Baltimore, Pasadena, CA (US); Lili Yang, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 59 days.

(21) Appl. No.: 13/901,940

(22) Filed: May 24, 2013

(65) Prior Publication Data

US 2013/0316366 A1    Nov. 28, 2013

Related U.S. Application Data

(60) Provisional application No. 61/652,006, filed on May 25, 2012.

(51) Int. Cl.

| | |
|---|---|
| *C12N 15/85* | (2006.01) |
| *C12N 15/86* | (2006.01) |
| *C12N 15/90* | (2006.01) |
| *G01N 33/58* | (2006.01) |
| *G01N 33/68* | (2006.01) |

(52) U.S. Cl.
CPC .............. *C12N 15/85* (2013.01); *C12N 15/86* (2013.01); *G01N 33/582* (2013.01); *G01N 33/68* (2013.01); *C07K 2319/00* (2013.01); *C12N 15/907* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 4,736,866 A | 4/1988 | Leder et al. | |
| 5,489,743 A | 2/1996 | Robinson et al. | |
| 5,602,307 A | 2/1997 | Beaudet et al. | |
| 8,945,876 B2 | 2/2015 | Su et al. | |
| 2005/0042721 A1 | 2/2005 | Fang et al. | |
| 2006/0252096 A1 | 11/2006 | Zha et al. | |

FOREIGN PATENT DOCUMENTS

| | | |
|---|---|---|
| EP | 1 132 479 A1 | 9/2001 |
| EP | 1 873 251 A1 | 1/2008 |
| EP | 1972640 A1 * | 9/2008 |
| WO | WO 2004078995 A2 * | 9/2004 |
| WO | WO 2006012393 A2 * | 2/2006 |
| WO | WO 2013/148284 | 10/2013 |

OTHER PUBLICATIONS

Provost E et al. Viral 2A Peptides Allow Expression of Multiple Proteins from a Single ORF in Transgenic Zebrafish Embryos. 2007. Genesis. 45:625-629.*

Tang W et al. Faithful Expression of Multiple Proteins via 2A-Peptide Self-Processing: A Versatile and Reliable Method for Manipulating Brain Circuits. 2009. The Journal of Neuroscience. 29(27):8621-8629.*

GenBank P0887.1. 2010. p. 1-11.*

Alberts et al., "Molecular Biology of the Cell, 4th Edition", New York, Garland Science (2002).

Alexopoulou et al., "The CMV early enhancer/chicken B actin (CAG) promoter can be used to drive transgene expression during the differentiation of murine embryonic stem cells into vascular progenitors", BMC Cell Biology vol. 9, No. 2, (2008).

Amoah et al., "Biotechnological advances in goat reproduction", J. Animal Science, vol. 75, No. 2, pp. 578-585, (1997).

Brenin et al., Transgenic technology: an overview of approaches useful in surgical research, Surgical Oncology, vol. 6, No. 2, pp. 99-110, (1997).

Brisson et al., "Expression of a bacterial gene in plants by using a viral vector", Nature vol. 310, pp. 511-514, Aug. 9, 1984.

Donnelly et al., "The 'cleavage' activities of foot-and-mouth disease virus 2A site-directed mutants and naturally occurring 2A-like sequences", J Gen Virol, vol. 82, pp. 1027-1041, (2001).

Galli et al., "Poly(A) site choice rather than splice site choice governs the regulated production of IgM heavy-chain RNAs", Proc Natl Acad Sci USA, vol. 85, pp. 2439-2443, Apr. 1988.

Gurley et al., "Upstream sequences required for efficient expression of a soybean heat shock gene", Mol. Cell. Biol., vol. 6, No. 2, pp. 559-565, (1986).

Houdebine, LM, "The production of pharmaceutical proteins from the milk of transgenic animals", Reprod. Nutr. Dev., vol. 35, pp. 609-617, (1995).

International Search and Written Opinion in Application No. PCT/US2013/042688 dated Sep. 11, 2013.

Kim et al., "Development of a Positive Method for Male Stem Cell-Mediated Gene Transfer in Mouse and Pig", Mol. Reprod. Dev., vol. 46, pp. 515-526, (1997).

Klein et al., "Examination of the contributions of size and avidity to the neutralization mechanisms of the anti-HIV antibodies b12 and 4E10", Proc Natl Acad Sci USA, vol. 106, No. 18, pp. 7385-7390, May 5, 2009.

Lois et al., Germline Transmission and Tissue-Specific Expression of Transgenes Delivered by Lentiviral Vectors, Science, vol. 295, pp. 868-872, (2002).

Luo et al., "Engineering human hematopoietic stem/progenitor cells to produce a broadly neutralizing anti-HIV antibody after in vitro maturation to human B lymphocytes", Blood, Dec. 4, 2008, vol. 113, No. 7, pp. 1422-1431.

(Continued)

*Primary Examiner* — Paul Holland
(74) *Attorney, Agent, or Firm* — Knobbe, Martens Olson & Bear, LLP

(57) ABSTRACT

Some embodiments herein provide compositions and methods for expressing secreted and cell-surface-bound polypeptides in a single cell. In some embodiments, secreted and cell-surface polypeptide are produced from a single polynucleotide. The polynucleotide can comprise a sequence (or sequence encoding a polypeptide) that mediates separation of a membrane anchor from the polypeptide. In some embodiments, a desired ratio of secreted to surface-bound polypeptide is obtained by selecting a sequence that mediates a desired level of separation of the membrane anchor from the polypeptide.

32 Claims, 16 Drawing Sheets

(56) References Cited

OTHER PUBLICATIONS

Mostoslavsky et al., "Efficiency of transduction of highly purified murine hematopoietic stem cells by lentiviral and oncoretroviral vectors under conditions of minimal in vitro manipulation", Mol Ther, vol. 11, No. 6, pp. 932-940, Jun. 2005.
Mullins et al., "Transgenesis in nonmurine species", Hypertension, vol. 22, pp. 630-633, (1993).
O'Connell et al., "Lentiviral Vector Delivery of Human Interleukin-7 (hIL-7) to Human Immune System (HIS) Mice Expands T Lymphocyte Populations", PLoS One, vol. 5, No. 8, e12009, 11 pages, Aug. 2010.
Petters, R.M., "Transgenic Livestock as Genetic Models of Human Disease", Reprod. Fertil. Dev., vol. 6, pp. 643-645, (1994).
Ponomarev et al., Imaging TCR-Dependent NFAT-Mediated T-Cell Activation with Positron Emission Tomography in Vivo, Neoplasia, vol. 3, No. 6, pp. 480-488, (2001).
Schnieke et al., "Human Factor IX Transgenic Sheep Produced by Transfer of Nuclei from Transfected Fetal Fibroblasts", Science, vol. 278, pp. 2130-2133, (1997).
Tuan, R.S., "Recombinant Gene Expression Protocols", Methods in Molecular Biology, vol. 62, Humana Press, (1997).
Tweeddale et al., "The presence of clonogenic cells in high-grade malignant lymphoma: a prognostic factor", Blood, vol. 69, No. 5, pp. 1307-1314, May 1987.
Walhout et al., "Gateway recombinational cloning: application to the cloning of large numbers of open reading frames or ORFeomes", Methods Enzymol, vol. 328, pp. 575-592, (2000).
Yu et al., "Use of mutated self-cleaving 2A peptides as a molecular rheostat to direct simultaneous formation of membrane and secreted anti-HIV immunoglobulins", PLoS One, Nov. 28, 2012, vol. 7, No. 11, pp. 1-12 (e50438).
Zhang et al, "Molecular mechanism of serial VH gene replacement", Ann N Y Acad Sci, vol. 987, pp. 270-273, (2003).
Zhang Z, "VH replacement in mice and humans", Trends Immunol, vol. 28, No. 3, pp. 132-137, (2007).
Alberts, et al. Molecular Biology of the Cell, 4th Ed., "The Endoplasmic Reticulum", New York: Garland Science 2002, accessible on the world wide web at www.ncbi.nlm.nih/books/NBK26841,in 17 pages.
Lodish, et al., Molecular Cell Biology, "17.4 Translocation of secretory proteins across the ER membrane" and "17.5 Insertion of membrane proteins into the ER membrane", New York: W.H. Freeman 2000, accessible on the world wide web at www.ncbi.nlm.nih/books/NBK21532,in 10 pages.

* cited by examiner

SEQUENCE LISTING

<160> NUMBER OF SEQ ID NOS: 552

<210> SEQ ID NO 1
<211> LENGTH: 20
<212> TYPE: PRT
<213> ORGANISM: Homo sapiens

<400> SEQUENCE: 1

Gln Leu Leu Asn Phe Asp Leu Leu Lys Leu Ala Gly Asp Val Glu Ser
1               5                   10                  15

Asn Pro Gly Pro
            20

<210> SEQ ID NO 2
<211> LENGTH: 19
<212> TYPE: PRT
<213> ORGANISM: Homo sapiens

<400> SEQUENCE: 2

Leu Leu Asn Phe Asp Leu Leu Lys Leu Ala Gly Asp Val Glu Ser Asn
1               5                   10                  15

Pro Gly Pro

<210> SEQ ID NO 3
<211> LENGTH: 18
<212> TYPE: PRT
<213> ORGANISM: Homo sapiens

<400> SEQUENCE: 3

Leu Asn Phe Asp Leu Leu Lys Leu Ala Gly Asp Val Glu Ser Asn Pro
1               5                   10                  15

Gly Pro

<210> SEQ ID NO 4
<211> LENGTH: 17
<212> TYPE: PRT
<213> ORGANISM: Homo sapiens

<400> SEQUENCE: 4

Asn Phe Asp Leu Leu Lys Leu Ala Gly Asp Val Glu Ser Asn Pro Gly
1               5                   10                  15

Pro

<210> SEQ ID NO 5
<211> LENGTH: 16
<212> TYPE: PRT
<213> ORGANISM: Homo sapiens

<400> SEQUENCE: 5

Phe Asp Leu Leu Lys Leu Ala Gly Asp Val Glu Ser Asn Pro Gly Pro
1               5                   10                  15

<210> SEQ ID NO 6
<211> LENGTH: 15
<212> TYPE: PRT
<213> ORGANISM: Homo sapiens

<400> SEQUENCE: 6

Asp Leu Leu Lys Leu Ala Gly Asp Val Glu Ser Asn Pro Gly Pro
1               5                   10                  15

<210> SEQ ID NO 7
<211> LENGTH: 14
<212> TYPE: PRT
<213> ORGANISM: Homo sapiens

<400> SEQUENCE: 7

Leu Leu Lys Leu Ala Gly Asp Val Glu Ser Asn Pro Gly Pro

```
                1               5                   10

<210> SEQ ID NO 8
<211> LENGTH: 13
<212> TYPE: PRT
<213> ORGANISM: Homo sapiens

<400> SEQUENCE: 8

Leu Lys Leu Ala Gly Asp Val Glu Ser Asn Pro Gly Pro
1               5                   10

<210> SEQ ID NO 9
<211> LENGTH: 20
<212> TYPE: PRT
<213> ORGANISM: Homo sapiens

<400> SEQUENCE: 9

Gln Leu Leu Asn Phe Asp Leu Leu Lys Leu Ala Gly Asp Val Gln Ser
1               5                   10                  15

Asn Pro Gly Pro
            20

<210> SEQ ID NO 10
<211> LENGTH: 20
<212> TYPE: PRT
<213> ORGANISM: Homo sapiens

<400> SEQUENCE: 10

Gln Leu Leu Asn Phe Asp Leu Leu Lys Leu Ala Gly Asp Val Glu Ile
1               5                   10                  15

Asn Pro Gly Pro
            20

<210> SEQ ID NO 11
<211> LENGTH: 20
<212> TYPE: PRT
<213> ORGANISM: Homo sapiens

<400> SEQUENCE: 11

Gln Leu Leu Asn Phe Asp Leu Leu Lys Leu Ala Gly Asp Val Glu Ser
1               5                   10                  15

Glu Pro Gly Pro
            20

<210> SEQ ID NO 12
<211> LENGTH: 20
<212> TYPE: PRT
<213> ORGANISM: Homo sapiens

<400> SEQUENCE: 12

Gln Leu Leu Asn Phe Asp Leu Leu Lys Leu Ala Gly Asp Val Glu Ser
1               5                   10                  15

Asn Pro Ala Pro
            20

<210> SEQ ID NO 13
<211> LENGTH: 20
<212> TYPE: PRT
<213> ORGANISM: Homo sapiens

<400> SEQUENCE: 13

Thr Arg Ala Glu Ile Glu Asp Glu Leu Ile Arg Arg Gly Ile Glu Ser
1               5                   10                  15
```

Asn Pro Gly Pro
        20

<210> SEQ ID NO 14
<211> LENGTH: 20
<212> TYPE: PRT
<213> ORGANISM: Homo sapiens

<400> SEQUENCE: 14

Thr Arg Ala Glu Ile Glu Asp Glu Leu Ile Arg Ala Gly Ile Glu Ser
1               5                   10                  15

Asn Pro Gly Pro
        20

<210> SEQ ID NO 15
<211> LENGTH: 20
<212> TYPE: PRT
<213> ORGANISM: Homo sapiens

<400> SEQUENCE: 15

Thr Arg Ala Glu Ile Glu Asp Glu Leu Ile Arg Arg Gly Ile Glu Ser
1               5                   10                  15

Asn Pro Gly Pro
        20

<210> SEQ ID NO 16
<211> LENGTH: 20
<212> TYPE: PRT
<213> ORGANISM: Homo sapiens

<400> SEQUENCE: 16

Thr Arg Ala Glu Ile Glu Asp Glu Leu Ile Arg Arg Gly Ile Glu Ser
1               5                   10                  15

Asn Pro Ala Pro
        20

<210> SEQ ID NO 17
<211> LENGTH: 60
<212> TYPE: DNA
<213> ORGANISM: Homo sapiens

<400> SEQUENCE: 17
cagctgttga attttgacct tcttaagctt gcgggagacg tcgagtccaa ccccgggccc       60

<210> SEQ ID NO 18
<211> LENGTH: 57
<212> TYPE: DNA
<213> ORGANISM: Homo sapiens

<400> SEQUENCE: 18
ctgttgaatt ttgaccttct taagcttgcg ggagacgtcg agtccaaccc cgggccc          57

<210> SEQ ID NO 19
<211> LENGTH: 54
<212> TYPE: DNA
<213> ORGANISM: Homo sapiens

<400> SEQUENCE: 19
ttgaattttg accttcttaa gcttgcggga gacgtcgagt ccaaccccgg gccc              54

<210> SEQ ID NO 20
<211> LENGTH: 51

<212> TYPE: DNA
<213> ORGANISM: Homo sapiens

<400> SEQUENCE: 20
aattttgacc ttcttaagct tgcgggagac gtcgagtcca accccgggcc c         51

<210> SEQ ID NO 21
<211> LENGTH: 48
<212> TYPE: DNA
<213> ORGANISM: Homo sapiens

<400> SEQUENCE: 21
tttgaccttc ttaagcttgc gggagacgtc gagtccaacc ccgggccc               48

<210> SEQ ID NO 22
<211> LENGTH: 45
<212> TYPE: DNA
<213> ORGANISM: Homo sapiens

<400> SEQUENCE: 22
gaccttctta agcttgcggg agacgtcgag tccaacccccg ggccc                 45

<210> SEQ ID NO 23
<211> LENGTH: 42
<212> TYPE: DNA
<213> ORGANISM: Homo sapiens

<400> SEQUENCE: 23
cttcttaagc ttgcgggaga cgtcgagtcc aaccccgggc cc                     42

<210> SEQ ID NO 24
<211> LENGTH: 39
<212> TYPE: DNA
<213> ORGANISM: Homo sapiens

<400> SEQUENCE: 24
cttaagcttg cgggagacgt cgagtccaac cccgggccc                         39

<210> SEQ ID NO 25
<211> LENGTH: 60
<212> TYPE: DNA
<213> ORGANISM: Homo sapiens

<400> SEQUENCE: 25
cagctgttga attttgacct tcttaagctt gcgggagacg tccagtccaa ccccgggccc  60

<210> SEQ ID NO 26
<211> LENGTH: 60
<212> TYPE: DNA
<213> ORGANISM: Homo sapiens

<400> SEQUENCE: 26
cagctgttga attttgacct tcttaagctt gcgggagacg tcgagattaa ccccgggccc  60

<210> SEQ ID NO 27
<211> LENGTH: 60
<212> TYPE: DNA
<213> ORGANISM: Homo sapiens

<400> SEQUENCE: 27
cagctgttga attttgacct tcttaagctt gcgggagacg tcgagtccga gcccgggccc  60

<210> SEQ ID NO 28

```
<211> LENGTH: 60
<212> TYPE: DNA
<213> ORGANISM: Homo sapiens

<400> SEQUENCE: 28
cagctgttga attttgacct tcttaagctt gcgggagacg tcgagtccaa ccccgcgccc    60

<210> SEQ ID NO 29
<211> LENGTH: 60
<212> TYPE: DNA
<213> ORGANISM: Homo sapiens

<400> SEQUENCE: 29
acgagggcgg agattgagga tgaattgatt cgtcgaggaa ttgaatcaaa tcctgggccc    60

<210> SEQ ID NO 30
<211> LENGTH: 60
<212> TYPE: DNA
<213> ORGANISM: Homo sapiens

<400> SEQUENCE: 30
acgagggcgg agattgagga tgaattgatt cgtgcaggaa ttgaatcaaa tcctggaccc    60

<210> SEQ ID NO 31
<211> LENGTH: 60
<212> TYPE: DNA
<213> ORGANISM: Homo sapiens

<400> SEQUENCE: 31
acgagggcgg agattgagga tgaattgatt cgtcgaggaa ttgaatcaaa tcctggaccc    60

<210> SEQ ID NO 32
<211> LENGTH: 60
<212> TYPE: DNA
<213> ORGANISM: Homo sapiens

<400> SEQUENCE: 32
acgagggcgg agattgagga tgaattgatt cgtcgaggaa ttgaatcaaa tcctgcgccc    60

<210> SEQ ID NO 33
<211> LENGTH: 14
<212> TYPE: PRT
<213> ORGANISM: Homo sapiens

<400> SEQUENCE: 33

Met Leu Val Leu Gly Leu Leu Val Ala Gly Ala Ala Asp Gly
  1               5                  10

<210> SEQ ID NO 34
<211> LENGTH: 14
<212> TYPE: PRT
<213> ORGANISM: Homo sapiens

<400> SEQUENCE: 34

Met Leu Leu Pro Leu Leu Leu Leu Leu Pro Met Cys Trp Ala
  1               5                  10

<210> SEQ ID NO 35
<211> LENGTH: 15
<212> TYPE: PRT
<213> ORGANISM: Homo sapiens

<400> SEQUENCE: 35

Met Lys Phe Phe Leu Leu Leu Phe Thr Ile Gly Phe Cys Trp Ala
```

-continued

```
                1               5                  10                 15

<210> SEQ ID NO 36
<211> LENGTH: 15
<212> TYPE: PRT
<213> ORGANISM: Homo sapiens

<400> SEQUENCE: 36

Met Arg Pro Leu Leu Val Leu Leu Leu Gly Leu Ala Ala Gly
  1               5                  10                 15

<210> SEQ ID NO 37
<211> LENGTH: 15
<212> TYPE: PRT
<213> ORGANISM: Homo sapiens

<400> SEQUENCE: 37

Met Lys Trp Leu Leu Leu Leu Gly Leu Val Ala Leu Ser Glu Cys
  1               5                  10                 15

<210> SEQ ID NO 38
<211> LENGTH: 15
<212> TYPE: PRT
<213> ORGANISM: Homo sapiens

<400> SEQUENCE: 38

Met Arg Leu Leu Ile Leu Thr Cys Leu Val Ala Val Ala Leu Ala
  1               5                  10                 15

<210> SEQ ID NO 39
<211> LENGTH: 15
<212> TYPE: PRT
<213> ORGANISM: Homo sapiens

<400> SEQUENCE: 39

Met Leu Ala Leu Leu Val Leu Val Thr Val Ala Leu Ala Ser Ala
  1               5                  10                 15

<210> SEQ ID NO 40
<211> LENGTH: 15
<212> TYPE: PRT
<213> ORGANISM: Homo sapiens

<400> SEQUENCE: 40

Met Leu Arg Val Leu Val Gly Ala Val Leu Pro Ala Met Leu Leu
  1               5                  10                 15

<210> SEQ ID NO 41
<211> LENGTH: 15
<212> TYPE: PRT
<213> ORGANISM: Homo sapiens

<400> SEQUENCE: 41

Met Trp Cys Ile Val Leu Phe Ser Leu Leu Ala Trp Val Tyr Ala
  1               5                  10                 15

<210> SEQ ID NO 42
<211> LENGTH: 15
<212> TYPE: PRT
<213> ORGANISM: Homo sapiens

<400> SEQUENCE: 42

Met Asn Pro Leu Leu Ile Leu Thr Phe Val Ala Ala Ala Leu Ala
  1               5                  10                 15
```

<210> SEQ ID NO 43
<211> LENGTH: 15
<212> TYPE: PRT
<213> ORGANISM: Homo sapiens

<400> SEQUENCE: 43

Met Arg Leu Ile Leu Pro Val Gly Leu Ile Ala Thr Thr Leu Ala
1               5                   10                  15

<210> SEQ ID NO 44
<211> LENGTH: 15
<212> TYPE: PRT
<213> ORGANISM: Homo sapiens

<400> SEQUENCE: 44

Met Lys Val Leu Ile Leu Ala Cys Leu Val Ala Leu Ala Leu Ala
1               5                   10                  15

<210> SEQ ID NO 45
<211> LENGTH: 15
<212> TYPE: PRT
<213> ORGANISM: Homo sapiens

<400> SEQUENCE: 45

Met Asn Leu Leu Leu Ile Leu Thr Phe Val Ala Ala Ala Val Ala
1               5                   10                  15

<210> SEQ ID NO 46
<211> LENGTH: 15
<212> TYPE: PRT
<213> ORGANISM: Homo sapiens

<400> SEQUENCE: 46

Met Lys Leu Leu Val Leu Ala Val Leu Leu Thr Val Ala Ala Ala
1               5                   10                  15

<210> SEQ ID NO 47
<211> LENGTH: 15
<212> TYPE: PRT
<213> ORGANISM: Homo sapiens

<400> SEQUENCE: 47

Met Trp Phe Leu Thr Thr Leu Leu Leu Trp Val Pro Val Asp Gly
1               5                   10                  15

<210> SEQ ID NO 48
<211> LENGTH: 15
<212> TYPE: PRT
<213> ORGANISM: Homo sapiens

<400> SEQUENCE: 48

Met Lys Phe Phe Leu Leu Leu Phe Thr Ile Gly Phe Cys Trp Ala
1               5                   10                  15

<210> SEQ ID NO 49
<211> LENGTH: 16
<212> TYPE: PRT
<213> ORGANISM: Homo sapiens

<400> SEQUENCE: 49

Met Leu Leu Ile Leu Leu Ser Val Ala Leu Leu Ala Leu Ser Ser Ala
1               5                   10                  15

<210> SEQ ID NO 50

<211> LENGTH: 16
<212> TYPE: PRT
<213> ORGANISM: Homo sapiens

<400> SEQUENCE: 50

Met Gly Thr Trp Ile Leu Phe Ala Cys Leu Leu Gly Ala Ala Phe Ala
1               5                   10                  15

<210> SEQ ID NO 51
<211> LENGTH: 16
<212> TYPE: PRT
<213> ORGANISM: Homo sapiens

<400> SEQUENCE: 51

Met Lys Val Ser Ala Val Leu Leu Cys Leu Leu Met Thr Ala Ala
1               5                   10                  15

<210> SEQ ID NO 52
<211> LENGTH: 16
<212> TYPE: PRT
<213> ORGANISM: Homo sapiens

<400> SEQUENCE: 52

Met Val Trp Lys Trp Met Pro Leu Leu Leu Leu Val Cys Val Ala
1               5                   10                  15

<210> SEQ ID NO 53
<211> LENGTH: 16
<212> TYPE: PRT
<213> ORGANISM: Homo sapiens

<400> SEQUENCE: 53

Met Trp Ser Gly Trp Trp Leu Trp Pro Leu Val Ala Val Cys Thr Ala
1               5                   10                  15

<210> SEQ ID NO 54
<211> LENGTH: 16
<212> TYPE: PRT
<213> ORGANISM: Homo sapiens

<400> SEQUENCE: 54

Met Pro Leu Leu Leu Leu Leu Leu Leu Pro Ser Pro Leu His Pro
1               5                   10                  15

<210> SEQ ID NO 55
<211> LENGTH: 16
<212> TYPE: PRT
<213> ORGANISM: Homo sapiens

<400> SEQUENCE: 55

Met Ile Arg Thr Leu Leu Leu Ser Thr Leu Val Ala Gly Ala Leu Ser
1               5                   10                  15

<210> SEQ ID NO 56
<211> LENGTH: 16
<212> TYPE: PRT
<213> ORGANISM: Homo sapiens

<400> SEQUENCE: 56

Met Lys Arg Val Leu Val Leu Leu Leu Ala Val Ala Phe Gly His Ala
1               5                   10                  15

<210> SEQ ID NO 57
<211> LENGTH: 16
<212> TYPE: PRT

<213> ORGANISM: Homo sapiens

<400> SEQUENCE: 57

Met Phe Thr Ile Lys Leu Leu Leu Phe Ile Val Pro Leu Val Ile Ser
1               5                   10                  15

<210> SEQ ID NO 58
<211> LENGTH: 16
<212> TYPE: PRT
<213> ORGANISM: Homo sapiens

<400> SEQUENCE: 58

Met Ile Arg Thr Leu Leu Leu Ser Thr Leu Val Ala Gly Ala Leu Ser
1               5                   10                  15

<210> SEQ ID NO 59
<211> LENGTH: 16
<212> TYPE: PRT
<213> ORGANISM: Homo sapiens

<400> SEQUENCE: 59

Met Ala Leu Arg Val Leu Leu Leu Thr Ala Leu Thr Leu Cys His Gly
1               5                   10                  15

<210> SEQ ID NO 60
<211> LENGTH: 16
<212> TYPE: PRT
<213> ORGANISM: Homo sapiens

<400> SEQUENCE: 60

Met Leu Leu Ile Leu Leu Ser Val Ala Leu Leu Ala Phe Ser Ser Ala
1               5                   10                  15

<210> SEQ ID NO 61
<211> LENGTH: 16
<212> TYPE: PRT
<213> ORGANISM: Homo sapiens

<400> SEQUENCE: 61

Met Lys Thr Ala Leu Ile Leu Leu Ser Ile Leu Gly Met Ala Cys Ala
1               5                   10                  15

<210> SEQ ID NO 62
<211> LENGTH: 16
<212> TYPE: PRT
<213> ORGANISM: Homo sapiens

<400> SEQUENCE: 62

Met Pro Ala Trp Gly Ala Leu Phe Leu Leu Trp Ala Thr Ala Glu Ala
1               5                   10                  15

<210> SEQ ID NO 63
<211> LENGTH: 16
<212> TYPE: PRT
<213> ORGANISM: Homo sapiens

<400> SEQUENCE: 63

Met Lys Leu Pro Leu Leu Leu Ala Leu Leu Phe Gly Ala Val Ser Ala
1               5                   10                  15

<210> SEQ ID NO 64
<211> LENGTH: 16
<212> TYPE: PRT
<213> ORGANISM: Homo sapiens

```
<400> SEQUENCE: 64

Met Arg Gly Leu Leu Val Leu Ser Val Leu Leu Gly Ala Val Phe Gly
 1               5                  10                  15

<210> SEQ ID NO 65
<211> LENGTH: 16
<212> TYPE: PRT
<213> ORGANISM: Homo sapiens

<400> SEQUENCE: 65

Met Phe Arg Leu Trp Leu Leu Leu Ala Gly Leu Cys Gly Leu Leu Ala
 1               5                  10                  15

<210> SEQ ID NO 66
<211> LENGTH: 16
<212> TYPE: PRT
<213> ORGANISM: Homo sapiens

<400> SEQUENCE: 66

Met Leu Phe Leu Leu Leu Pro Leu Leu Ala Val Leu Pro Gly Asp Gly
 1               5                  10                  15

<210> SEQ ID NO 67
<211> LENGTH: 16
<212> TYPE: PRT
<213> ORGANISM: Homo sapiens

<400> SEQUENCE: 67

Met Leu Leu Ile Leu Leu Ser Val Ala Leu Leu Ala Leu Ser Ser Ala
 1               5                  10                  15

<210> SEQ ID NO 68
<211> LENGTH: 16
<212> TYPE: PRT
<213> ORGANISM: Homo sapiens

<400> SEQUENCE: 68

Met Tyr Ala Leu Phe Leu Leu Ala Ser Leu Leu Gly Ala Ala Leu Ala
 1               5                  10                  15

<210> SEQ ID NO 69
<211> LENGTH: 16
<212> TYPE: PRT
<213> ORGANISM: Homo sapiens

<400> SEQUENCE: 69

Met Leu Thr Val Ala Leu Leu Ala Leu Leu Cys Ala Ser Ala Ser Gly
 1               5                  10                  15

<210> SEQ ID NO 70
<211> LENGTH: 16
<212> TYPE: PRT
<213> ORGANISM: Homo sapiens

<400> SEQUENCE: 70

Met Thr Ala Glu Phe Leu Ser Leu Leu Cys Leu Gly Leu Cys Leu Gly
 1               5                  10                  15

<210> SEQ ID NO 71
<211> LENGTH: 16
<212> TYPE: PRT
<213> ORGANISM: Homo sapiens

<400> SEQUENCE: 71
```

-continued

Met Arg Ser Thr Ile Leu Leu Phe Cys Leu Leu Gly Ser Thr Arg Ser
1               5                   10                  15

<210> SEQ ID NO 72
<211> LENGTH: 16
<212> TYPE: PRT
<213> ORGANISM: Homo sapiens

<400> SEQUENCE: 72

Met Lys Trp Met Val Val Val Leu Val Cys Leu Gln Leu Leu Glu Ala
1               5                   10                  15

<210> SEQ ID NO 73
<211> LENGTH: 16
<212> TYPE: PRT
<213> ORGANISM: Homo sapiens

<400> SEQUENCE: 73

Met Leu Pro Leu Trp Thr Leu Ser Leu Leu Leu Gly Ala Val Ala Gly
1               5                   10                  15

<210> SEQ ID NO 74
<211> LENGTH: 16
<212> TYPE: PRT
<213> ORGANISM: Homo sapiens

<400> SEQUENCE: 74

Met Thr Thr Leu Leu Trp Val Phe Val Thr Leu Arg Val Ile Thr Ala
1               5                   10                  15

<210> SEQ ID NO 75
<211> LENGTH: 17
<212> TYPE: PRT
<213> ORGANISM: Homo sapiens

<400> SEQUENCE: 75

Met Ala Leu Asp Tyr Leu Leu Leu Leu Leu Ala Ser Ala Val Ala
1               5                   10                  15

Ala

<210> SEQ ID NO 76
<211> LENGTH: 17
<212> TYPE: PRT
<213> ORGANISM: Homo sapiens

<400> SEQUENCE: 76

Met Ile Ser Pro Phe Leu Val Leu Ala Ile Gly Thr Cys Leu Thr Asn
1               5                   10                  15

Ser

<210> SEQ ID NO 77
<211> LENGTH: 17
<212> TYPE: PRT
<213> ORGANISM: Homo sapiens

<400> SEQUENCE: 77

Met Leu Gln Asn Ser Ala Val Leu Leu Val Leu Val Ile Ser Ala Ser
1               5                   10                  15

Ala

<210> SEQ ID NO 78
<211> LENGTH: 17
<212> TYPE: PRT

<213> ORGANISM: Homo sapiens

<400> SEQUENCE: 78

Met Ile Ile Leu Ile Tyr Leu Phe Leu Leu Trp Glu Asp Thr Gln
1               5                   10                  15

Gly

<210> SEQ ID NO 79
<211> LENGTH: 17
<212> TYPE: PRT
<213> ORGANISM: Homo sapiens

<400> SEQUENCE: 79

Met Glu Lys Ile Leu Ile Leu Leu Leu Val Ala Leu Ser Val Ala Tyr
1               5                   10                  15

Ala

<210> SEQ ID NO 80
<211> LENGTH: 17
<212> TYPE: PRT
<213> ORGANISM: Homo sapiens

<400> SEQUENCE: 80

Met Leu Leu Lys Thr Val Leu Leu Gly His Val Ala Gln Val Leu
1               5                   10                  15

Met

<210> SEQ ID NO 81
<211> LENGTH: 17
<212> TYPE: PRT
<213> ORGANISM: Homo sapiens

<400> SEQUENCE: 81

Met Val Trp Lys Val Ala Val Phe Leu Ser Val Ala Leu Gly Ile Gly
1               5                   10                  15

Ala

<210> SEQ ID NO 82
<211> LENGTH: 17
<212> TYPE: PRT
<213> ORGANISM: Homo sapiens

<400> SEQUENCE: 82

Met Trp Leu Leu Tyr Leu Leu Val Pro Ala Leu Phe Cys Arg Ala Gly
1               5                   10                  15

Gly

<210> SEQ ID NO 83
<211> LENGTH: 17
<212> TYPE: PRT
<213> ORGANISM: Homo sapiens

<400> SEQUENCE: 83

Met Lys Leu Val Asn Ile Trp Leu Leu Leu Val Val Leu Leu Cys
1               5                   10                  15

Gly

<210> SEQ ID NO 84
<211> LENGTH: 17
<212> TYPE: PRT
<213> ORGANISM: Homo sapiens

```
<400> SEQUENCE: 84

Met Val Pro Val Leu Leu Ser Leu Leu Leu Leu Gly Pro Ala Val
1               5                   10                  15

Pro

<210> SEQ ID NO 85
<211> LENGTH: 17
<212> TYPE: PRT
<213> ORGANISM: Homo sapiens

<400> SEQUENCE: 85

Met His Leu Leu Leu Phe Gln Leu Leu Val Leu Leu Pro Leu Gly Lys
1               5                   10                  15

Thr

<210> SEQ ID NO 86
<211> LENGTH: 17
<212> TYPE: PRT
<213> ORGANISM: Homo sapiens

<400> SEQUENCE: 86

Met Phe Phe Trp Cys Ala Cys Cys Leu Met Val Ala Trp Arg Val Ser
1               5                   10                  15

Ala

<210> SEQ ID NO 87
<211> LENGTH: 17
<212> TYPE: PRT
<213> ORGANISM: Homo sapiens

<400> SEQUENCE: 87

Met Asp Tyr Leu Leu Met Ile Phe Ser Leu Leu Phe Val Ala Cys Gln
1               5                   10                  15

Gly

<210> SEQ ID NO 88
<211> LENGTH: 17
<212> TYPE: PRT
<213> ORGANISM: Homo sapiens

<400> SEQUENCE: 88

Met Trp Val Pro Val Val Phe Leu Thr Leu Ser Val Thr Trp Ile Gly
1               5                   10                  15

Ala

<210> SEQ ID NO 89
<211> LENGTH: 17
<212> TYPE: PRT
<213> ORGANISM: Homo sapiens

<400> SEQUENCE: 89

Met Arg Leu Thr Val Leu Cys Ala Val Cys Leu Leu Pro Gly Ser Leu
1               5                   10                  15

Ala

<210> SEQ ID NO 90
<211> LENGTH: 17
<212> TYPE: PRT
<213> ORGANISM: Homo sapiens
```

```
<400> SEQUENCE: 90

Met Ser Leu Val Leu Leu Ser Leu Ala Ala Leu Cys Arg Ser Ala Val
1               5                   10                  15

Pro

<210> SEQ ID NO 91
<211> LENGTH: 17
<212> TYPE: PRT
<213> ORGANISM: Homo sapiens

<400> SEQUENCE: 91

Met Ala Leu Phe Gly Ala Leu Phe Leu Ala Leu Leu Ala Gly Ala His
1               5                   10                  15

Ala

<210> SEQ ID NO 92
<211> LENGTH: 17
<212> TYPE: PRT
<213> ORGANISM: Homo sapiens

<400> SEQUENCE: 92

Met Met Arg Glu Trp Val Leu Leu Met Ser Val Leu Leu Cys Gly Leu
1               5                   10                  15

Ala

<210> SEQ ID NO 93
<211> LENGTH: 17
<212> TYPE: PRT
<213> ORGANISM: Homo sapiens

<400> SEQUENCE: 93

Met Leu Leu Ser Val Pro Leu Leu Leu Gly Leu Leu Gly Leu Ala Val
1               5                   10                  15

Ala

<210> SEQ ID NO 94
<211> LENGTH: 17
<212> TYPE: PRT
<213> ORGANISM: Homo sapiens

<400> SEQUENCE: 94

Met Trp Leu Gln Ser Leu Leu Leu Leu Gly Thr Val Ala Cys Ser Ile
1               5                   10                  15

Ser

<210> SEQ ID NO 95
<211> LENGTH: 17
<212> TYPE: PRT
<213> ORGANISM: Homo sapiens

<400> SEQUENCE: 95

Met Leu Ala Ala Thr Val Leu Thr Leu Ala Leu Leu Gly Asn Ala His
1               5                   10                  15

Ala

<210> SEQ ID NO 96
<211> LENGTH: 17
<212> TYPE: PRT
<213> ORGANISM: Homo sapiens

<400> SEQUENCE: 96
```

Met Lys Val Leu Leu Arg Leu Ile Cys Phe Ile Ala Leu Leu Ile Ser
1               5                   10                  15

Ser

<210> SEQ ID NO 97
<211> LENGTH: 17
<212> TYPE: PRT
<213> ORGANISM: Homo sapiens

<400> SEQUENCE: 97

Met Leu Arg Arg Ala Leu Leu Cys Leu Ala Val Ala Ala Leu Val Arg
1               5                   10                  15

Ala

<210> SEQ ID NO 98
<211> LENGTH: 17
<212> TYPE: PRT
<213> ORGANISM: Homo sapiens

<400> SEQUENCE: 98

Met Ala Val Phe Leu Gln Leu Leu Pro Leu Leu Leu Ser Arg Ala Gln
1               5                   10                  15

Gly

<210> SEQ ID NO 99
<211> LENGTH: 17
<212> TYPE: PRT
<213> ORGANISM: Homo sapiens

<400> SEQUENCE: 99

Met Ala Leu Leu Phe Leu Leu Pro Leu Val Met Gln Gly Val Ser Arg
1               5                   10                  15

Ala

<210> SEQ ID NO 100
<211> LENGTH: 17
<212> TYPE: PRT
<213> ORGANISM: Homo sapiens

<400> SEQUENCE: 100

Met Asp Phe Pro Cys Leu Trp Leu Gly Leu Leu Leu Pro Leu Val Ala
1               5                   10                  15

Ala

<210> SEQ ID NO 101
<211> LENGTH: 17
<212> TYPE: PRT
<213> ORGANISM: Homo sapiens

<400> SEQUENCE: 101

Met Ala Leu Met Leu Ser Leu Val Leu Ser Leu Leu Lys Leu Gly Ser
1               5                   10                  15

Gly

<210> SEQ ID NO 102
<211> LENGTH: 17
<212> TYPE: PRT
<213> ORGANISM: Homo sapiens

<400> SEQUENCE: 102

Met Leu Pro Gly Leu Ala Leu Leu Leu Ala Ala Trp Thr Ala Arg
1               5                   10                  15

Ala

<210> SEQ ID NO 103
<211> LENGTH: 17
<212> TYPE: PRT
<213> ORGANISM: Homo sapiens

<400> SEQUENCE: 103

Met Ile Trp Tyr Ile Leu Ile Gly Ile Leu Leu Pro Gln Ser Leu
1               5                   10                  15

Ala

<210> SEQ ID NO 104
<211> LENGTH: 17
<212> TYPE: PRT
<213> ORGANISM: Homo sapiens

<400> SEQUENCE: 104

Met Arg Ala Trp Ile Phe Phe Leu Leu Cys Leu Ala Gly Arg Ala Leu
1               5                   10                  15

Ala

<210> SEQ ID NO 105
<211> LENGTH: 17
<212> TYPE: PRT
<213> ORGANISM: Homo sapiens

<400> SEQUENCE: 105

Met Ala Arg Ile Leu Leu Leu Phe Leu Pro Gly Leu Val Ala Val Cys
1               5                   10                  15

Ala

<210> SEQ ID NO 106
<211> LENGTH: 18
<212> TYPE: PRT
<213> ORGANISM: Homo sapiens

<400> SEQUENCE: 106

Met Arg Ser Ala Ala Val Leu Ala Leu Leu Leu Cys Ala Gly Gln Val
1               5                   10                  15

Thr Ala

<210> SEQ ID NO 107
<211> LENGTH: 18
<212> TYPE: PRT
<213> ORGANISM: Homo sapiens

<400> SEQUENCE: 107

Met Arg Val Leu Leu Ala Ala Leu Gly Leu Leu Phe Leu Gly Ala Leu
1               5                   10                  15

Arg Ala

<210> SEQ ID NO 108
<211> LENGTH: 18
<212> TYPE: PRT
<213> ORGANISM: Homo sapiens

<400> SEQUENCE: 108

Met Lys Leu Leu Thr Gly Leu Val Phe Cys Ser Leu Val Leu Gly Val

```
                1               5                  10                 15

Ser Ser

<210> SEQ ID NO 109
<211> LENGTH: 18
<212> TYPE: PRT
<213> ORGANISM: Homo sapiens

<400> SEQUENCE: 109

Met Arg Leu Leu Val Leu Leu Trp Gly Cys Leu Leu Leu Pro Gly Tyr
1               5                   10                  15

Glu Ala

<210> SEQ ID NO 110
<211> LENGTH: 18
<212> TYPE: PRT
<213> ORGANISM: Homo sapiens

<400> SEQUENCE: 110

Met Gln Pro Leu Leu Leu Leu Ala Phe Leu Leu Pro Thr Gly Ala
1               5                   10                  15

Glu Ala

<210> SEQ ID NO 111
<211> LENGTH: 18
<212> TYPE: PRT
<213> ORGANISM: Homo sapiens

<400> SEQUENCE: 111

Met Trp Leu Phe His Thr Leu Leu Cys Ile Ala Ser Leu Ala Leu Leu
1               5                   10                  15

Ala Ala

<210> SEQ ID NO 112
<211> LENGTH: 18
<212> TYPE: PRT
<213> ORGANISM: Homo sapiens

<400> SEQUENCE: 112

Met Lys Leu Leu His Val Phe Leu Leu Phe Leu Cys Phe His Leu Arg
1               5                   10                  15

Phe Cys

<210> SEQ ID NO 113
<211> LENGTH: 18
<212> TYPE: PRT
<213> ORGANISM: Homo sapiens

<400> SEQUENCE: 113

Met Ser Leu Ser Ala Phe Thr Leu Phe Leu Ala Leu Ile Gly Gly Thr
1               5                   10                  15

Ser Gly

<210> SEQ ID NO 114
<211> LENGTH: 18
<212> TYPE: PRT
<213> ORGANISM: Homo sapiens

<400> SEQUENCE: 114

Met Lys Leu Ser Leu Val Ala Ala Met Leu Leu Leu Leu Ser Ala Ala
1               5                   10                  15
```

Arg Ala

<210> SEQ ID NO 115
<211> LENGTH: 18
<212> TYPE: PRT
<213> ORGANISM: Homo sapiens

<400> SEQUENCE: 115

Met Lys Leu Leu Met Val Leu Met Leu Ala Ala Leu Leu Leu His Cys
1               5                   10                  15

Tyr Ala

<210> SEQ ID NO 116
<211> LENGTH: 18
<212> TYPE: PRT
<213> ORGANISM: Homo sapiens

<400> SEQUENCE: 116

Met Leu Leu Ala Met Val Leu Thr Ser Ala Leu Leu Leu Cys Ser Val
1               5                   10                  15

Ala Gly

<210> SEQ ID NO 117
<211> LENGTH: 18
<212> TYPE: PRT
<213> ORGANISM: Homo sapiens

<400> SEQUENCE: 117

Met Trp Leu Leu Val Ser Val Ile Leu Ile Ser Arg Ile Ser Ser Val
1               5                   10                  15

Gly Gly

<210> SEQ ID NO 118
<211> LENGTH: 18
<212> TYPE: PRT
<213> ORGANISM: Homo sapiens

<400> SEQUENCE: 118

Met Gln Pro Ser Ser Leu Leu Pro Leu Ala Leu Cys Leu Leu Ala Ala
1               5                   10                  15

Pro Ala

<210> SEQ ID NO 119
<211> LENGTH: 18
<212> TYPE: PRT
<213> ORGANISM: Homo sapiens

<400> SEQUENCE: 119

Met Lys Trp Val Glu Ser Ile Phe Leu Ile Phe Leu Leu Asn Phe Thr
1               5                   10                  15

Glu Ser

<210> SEQ ID NO 120
<211> LENGTH: 18
<212> TYPE: PRT
<213> ORGANISM: Homo sapiens

<400> SEQUENCE: 120

Met Lys Pro Leu Leu Leu Ala Val Ser Leu Gly Leu Ile Ala Ala Leu
1               5                   10                  15

Gln Ala

<210> SEQ ID NO 121
<211> LENGTH: 18
<212> TYPE: PRT
<213> ORGANISM: Homo sapiens

<400> SEQUENCE: 121

Met Gly Ala Pro Arg Ser Leu Leu Ala Leu Ala Ala Gly Leu Ala
1               5                   10                  15

Val Ala

<210> SEQ ID NO 122
<211> LENGTH: 18
<212> TYPE: PRT
<213> ORGANISM: Homo sapiens

<400> SEQUENCE: 122

Met Val Leu His Leu Leu Leu Phe Leu Leu Thr Pro Gln Gly Gly
1               5                   10                  15

His Ser

<210> SEQ ID NO 123
<211> LENGTH: 18
<212> TYPE: PRT
<213> ORGANISM: Homo sapiens

<400> SEQUENCE: 123

Met Leu Gly Val Leu Val Leu Gly Ala Leu Ala Leu Ala Gly Leu Gly
1               5                   10                  15

Phe Pro

<210> SEQ ID NO 124
<211> LENGTH: 18
<212> TYPE: PRT
<213> ORGANISM: Homo sapiens

<400> SEQUENCE: 124

Met Leu Cys Leu Leu Leu Thr Leu Gly Val Ala Leu Val Cys Gly Val
1               5                   10                  15

Pro Ala

<210> SEQ ID NO 125
<211> LENGTH: 18
<212> TYPE: PRT
<213> ORGANISM: Homo sapiens

<400> SEQUENCE: 125

Met Asp Tyr Pro Thr Leu Leu Leu Ala Leu Leu His Val Tyr Arg Ala
1               5                   10                  15

Leu Cys

<210> SEQ ID NO 126
<211> LENGTH: 18
<212> TYPE: PRT
<213> ORGANISM: Homo sapiens

<400> SEQUENCE: 126

Met Glu Phe Leu Trp Ala Pro Leu Leu Gly Leu Cys Cys Ser Leu Ala
1               5                   10                  15

Ala Ala

<210> SEQ ID NO 127
<211> LENGTH: 18
<212> TYPE: PRT
<213> ORGANISM: Homo sapiens

<400> SEQUENCE: 127

Met Ser Ala Leu Gly Ala Val Ile Ala Leu Leu Leu Trp Gly Gln Leu
 1               5                  10                  15

Phe Ala

<210> SEQ ID NO 128
<211> LENGTH: 18
<212> TYPE: PRT
<213> ORGANISM: Homo sapiens

<400> SEQUENCE: 128

Met Lys Leu Ile Thr Ile Leu Phe Leu Cys Ser Arg Leu Leu Leu Ser
 1               5                  10                  15

Leu Thr

<210> SEQ ID NO 129
<211> LENGTH: 18
<212> TYPE: PRT
<213> ORGANISM: Homo sapiens

<400> SEQUENCE: 129

Met Lys Thr Leu Gln Phe Phe Phe Leu Phe Cys Cys Trp Lys Ala Ile
 1               5                  10                  15

Cys Cys

<210> SEQ ID NO 130
<211> LENGTH: 18
<212> TYPE: PRT
<213> ORGANISM: Homo sapiens

<400> SEQUENCE: 130

Met Lys Ala Ala Val Leu Thr Leu Ala Val Leu Phe Leu Thr Gly Ser
 1               5                  10                  15

Gln Ala

<210> SEQ ID NO 131
<211> LENGTH: 18
<212> TYPE: PRT
<213> ORGANISM: Homo sapiens

<400> SEQUENCE: 131

Met Ile Phe Leu Tyr Gln Val Val His Phe Ile Leu Phe Thr Ser Val
 1               5                  10                  15

Ser Gly

<210> SEQ ID NO 132
<211> LENGTH: 18
<212> TYPE: PRT
<213> ORGANISM: Homo sapiens

<400> SEQUENCE: 132

Met Leu Leu Phe Val Leu Thr Cys Leu Leu Ala Val Phe Pro Ala Ile
 1               5                  10                  15

Ser Thr

<210> SEQ ID NO 133
<211> LENGTH: 18
<212> TYPE: PRT
<213> ORGANISM: Homo sapiens

<400> SEQUENCE: 133

Met Arg Leu Leu Pro Arg Leu Leu Leu Leu Leu Leu Val Phe Pro
1               5                   10                  15

Ala Thr

<210> SEQ ID NO 134
<211> LENGTH: 18
<212> TYPE: PRT
<213> ORGANISM: Homo sapiens

<400> SEQUENCE: 134

Met Val Ala Ala Val Leu Leu Gly Leu Ser Trp Leu Cys Ser Pro Leu
1               5                   10                  15

Gly Ala

<210> SEQ ID NO 135
<211> LENGTH: 18
<212> TYPE: PRT
<213> ORGANISM: Homo sapiens

<400> SEQUENCE: 135

Met Arg Leu Leu Ala Lys Ile Ile Cys Leu Met Leu Trp Ala Ile Cys
1               5                   10                  15

Val Ala

<210> SEQ ID NO 136
<211> LENGTH: 18
<212> TYPE: PRT
<213> ORGANISM: Homo sapiens

<400> SEQUENCE: 136

Met Lys Trp Val Thr Phe Ile Ser Leu Leu Phe Leu Phe Ser Ser Ala
1               5                   10                  15

Tyr Ser

<210> SEQ ID NO 137
<211> LENGTH: 18
<212> TYPE: PRT
<213> ORGANISM: Homo sapiens

<400> SEQUENCE: 137

Met Gly Thr Gln Glu Gly Trp Cys Leu Leu Leu Cys Leu Ala Leu Ser
1               5                   10                  15

Gly Ala

<210> SEQ ID NO 138
<211> LENGTH: 18
<212> TYPE: PRT
<213> ORGANISM: Homo sapiens

<400> SEQUENCE: 138

Met Ala Leu Ser Trp Val Leu Thr Val Leu Ser Leu Leu Pro Leu Leu
1               5                   10                  15

Glu Ala

```
<210> SEQ ID NO 139
<211> LENGTH: 18
<212> TYPE: PRT
<213> ORGANISM: Homo sapiens

<400> SEQUENCE: 139

Met Gly Leu Ala Trp Gly Leu Gly Val Leu Phe Leu Met His Val Cys
 1               5                  10                  15

Gly Thr

<210> SEQ ID NO 140
<211> LENGTH: 18
<212> TYPE: PRT
<213> ORGANISM: Homo sapiens

<400> SEQUENCE: 140

Met Pro Val Met Arg Leu Phe Pro Cys Phe Leu Gln Leu Leu Ala Gly
 1               5                  10                  15

Leu Ala

<210> SEQ ID NO 141
<211> LENGTH: 18
<212> TYPE: PRT
<213> ORGANISM: Homo sapiens

<400> SEQUENCE: 141

Met Arg Leu Phe Thr Gly Ile Val Phe Cys Ser Leu Val Met Gly Val
 1               5                  10                  15

Thr Ser

<210> SEQ ID NO 142
<211> LENGTH: 18
<212> TYPE: PRT
<213> ORGANISM: Homo sapiens

<400> SEQUENCE: 142

Met Gln Pro Ile Leu Leu Leu Ala Phe Leu Leu Leu Pro Arg Ala
 1               5                  10                  15

Asp Ala

<210> SEQ ID NO 143
<211> LENGTH: 18
<212> TYPE: PRT
<213> ORGANISM: Homo sapiens

<400> SEQUENCE: 143

Met His Ser Ser Ala Leu Leu Cys Cys Leu Val Leu Leu Thr Gly Val
 1               5                  10                  15

Arg Ala

<210> SEQ ID NO 144
<211> LENGTH: 18
<212> TYPE: PRT
<213> ORGANISM: Homo sapiens

<400> SEQUENCE: 144

Met Gly Phe Trp Ile Leu Ala Ile Leu Thr Ile Leu Met Tyr Ser Thr
 1               5                  10                  15

Ala Ala

<210> SEQ ID NO 145
```

```
<211> LENGTH: 18
<212> TYPE: PRT
<213> ORGANISM: Homo sapiens

<400> SEQUENCE: 145

Met Leu Arg Leu Leu Leu Ala Leu Asn Leu Phe Pro Ser Ile Gln Val
1               5                   10                  15

Thr Gly

<210> SEQ ID NO 146
<211> LENGTH: 18
<212> TYPE: PRT
<213> ORGANISM: Homo sapiens

<400> SEQUENCE: 146

Met Arg Ala Cys Ile Ser Leu Val Leu Ala Val Leu Cys Gly Leu Ala
1               5                   10                  15

Trp Ala

<210> SEQ ID NO 147
<211> LENGTH: 18
<212> TYPE: PRT
<213> ORGANISM: Homo sapiens

<400> SEQUENCE: 147

Met Trp Leu Arg Ala Phe Ile Leu Ala Thr Leu Ser Ala Ser Ala Ala
1               5                   10                  15

Trp Gly

<210> SEQ ID NO 148
<211> LENGTH: 18
<212> TYPE: PRT
<213> ORGANISM: Homo sapiens

<400> SEQUENCE: 148

Met Thr Pro Pro Arg Leu Phe Trp Val Trp Leu Leu Val Ala Gly Thr
1               5                   10                  15

Gln Gly

<210> SEQ ID NO 149
<211> LENGTH: 18
<212> TYPE: PRT
<213> ORGANISM: Homo sapiens

<400> SEQUENCE: 149

Met Asn Gln Leu Ser Phe Leu Leu Phe Leu Ile Ala Thr Thr Arg Gly
1               5                   10                  15

Trp Ser

<210> SEQ ID NO 150
<211> LENGTH: 18
<212> TYPE: PRT
<213> ORGANISM: Homo sapiens

<400> SEQUENCE: 150

Met Lys Leu Leu Ala Ala Thr Val Leu Leu Leu Thr Ile Cys Ser Leu
1               5                   10                  15

Glu Gly

<210> SEQ ID NO 151
<211> LENGTH: 18
```

```
<212> TYPE: PRT
<213> ORGANISM: Homo sapiens

<400> SEQUENCE: 151

Met Leu Leu Leu Gly Ala Val Leu Leu Leu Ala Leu Pro Gly His
1               5                   10                  15

Asp Gln

<210> SEQ ID NO 152
<211> LENGTH: 18
<212> TYPE: PRT
<213> ORGANISM: Homo sapiens

<400> SEQUENCE: 152

Met Lys Ala Leu Ile Ala Ala Leu Leu Leu Ile Thr Leu Gln Tyr Ser
1               5                   10                  15

Cys Ala

<210> SEQ ID NO 153
<211> LENGTH: 18
<212> TYPE: PRT
<213> ORGANISM: Homo sapiens

<400> SEQUENCE: 153

Met Ala Leu Ser Trp Val Leu Thr Val Leu Ser Leu Leu Pro Leu Leu
1               5                   10                  15

Glu Ala

<210> SEQ ID NO 154
<211> LENGTH: 18
<212> TYPE: PRT
<213> ORGANISM: Homo sapiens

<400> SEQUENCE: 154

Met Gln Pro Phe Leu Leu Leu Leu Ala Phe Leu Leu Thr Pro Gly Ala
1               5                   10                  15

Gly Thr

<210> SEQ ID NO 155
<211> LENGTH: 18
<212> TYPE: PRT
<213> ORGANISM: Homo sapiens

<400> SEQUENCE: 155

Met Lys Trp Val Trp Ala Leu Leu Leu Leu Ala Ala Leu Gly Ser Gly
1               5                   10                  15

Arg Ala

<210> SEQ ID NO 156
<211> LENGTH: 18
<212> TYPE: PRT
<213> ORGANISM: Homo sapiens

<400> SEQUENCE: 156

Met Lys Ser Leu Val Leu Leu Leu Cys Leu Ala Gln Leu Trp Gly Cys
1               5                   10                  15

His Ser

<210> SEQ ID NO 157
<211> LENGTH: 18
<212> TYPE: PRT
```

<213> ORGANISM: Homo sapiens

<400> SEQUENCE: 157

Met Phe Ala Leu Gly Leu Pro Phe Leu Val Leu Leu Val Ala Ser Val
1               5                   10                  15

Glu Ser

<210> SEQ ID NO 158
<211> LENGTH: 18
<212> TYPE: PRT
<213> ORGANISM: Homo sapiens

<400> SEQUENCE: 158

Met Lys Val Leu Trp Ala Ala Leu Leu Val Thr Phe Leu Ala Gly Cys
1               5                   10                  15

Gln Ala

<210> SEQ ID NO 159
<211> LENGTH: 18
<212> TYPE: PRT
<213> ORGANISM: Homo sapiens

<400> SEQUENCE: 159

Met Ala Phe Leu Trp Leu Leu Ser Cys Trp Ala Leu Leu Gly Thr Thr
1               5                   10                  15

Phe Gly

<210> SEQ ID NO 160
<211> LENGTH: 18
<212> TYPE: PRT
<213> ORGANISM: Homo sapiens

<400> SEQUENCE: 160

Met Asn Cys Arg Glu Leu Pro Leu Thr Leu Trp Val Leu Ile Ser Val
1               5                   10                  15

Ser Thr

<210> SEQ ID NO 161
<211> LENGTH: 18
<212> TYPE: PRT
<213> ORGANISM: Homo sapiens

<400> SEQUENCE: 161

Met Lys Ala Leu Ile Val Leu Gly Leu Val Leu Leu Ser Val Thr Val
1               5                   10                  15

Gln Gly

<210> SEQ ID NO 162
<211> LENGTH: 18
<212> TYPE: PRT
<213> ORGANISM: Homo sapiens

<400> SEQUENCE: 162

Met Arg Pro Leu Leu Leu Leu Ala Leu Leu Gly Trp Leu Leu Leu Ala
1               5                   10                  15

Glu Ala

<210> SEQ ID NO 163
<211> LENGTH: 18
<212> TYPE: PRT
<213> ORGANISM: Homo sapiens

<400> SEQUENCE: 163

Met Glu Lys Leu Leu Cys Phe Leu Val Leu Thr Ser Leu Ser His Ala
1               5                   10                  15

Phe Gly

<210> SEQ ID NO 164
<211> LENGTH: 18
<212> TYPE: PRT
<213> ORGANISM: Homo sapiens

<400> SEQUENCE: 164

Met Leu Ala Leu Leu Cys Ser Cys Leu Leu Leu Ala Ala Gly Ala Ser
1               5                   10                  15

Asp Ala

<210> SEQ ID NO 165
<211> LENGTH: 18
<212> TYPE: PRT
<213> ORGANISM: Homo sapiens

<400> SEQUENCE: 165

Met Arg His Leu Gly Ala Phe Leu Phe Leu Leu Gly Val Leu Gly Ala
1               5                   10                  15

Leu Thr

<210> SEQ ID NO 166
<211> LENGTH: 18
<212> TYPE: PRT
<213> ORGANISM: Homo sapiens

<400> SEQUENCE: 166

Met Arg Met Leu Leu Ala Leu Leu Ala Leu Ser Ala Ala Arg Pro Ser
1               5                   10                  15

Ala Ser

<210> SEQ ID NO 167
<211> LENGTH: 19
<212> TYPE: PRT
<213> ORGANISM: Homo sapiens

<400> SEQUENCE: 167

Met Pro Leu Leu Thr Leu Tyr Leu Leu Leu Phe Trp Leu Ser Gly Tyr
1               5                   10                  15

Ser Ile Ala

<210> SEQ ID NO 168
<211> LENGTH: 19
<212> TYPE: PRT
<213> ORGANISM: Homo sapiens

<400> SEQUENCE: 168

Met Pro Ala Leu Gly Trp Ala Val Ala Ala Ile Leu Met Leu Gln Thr
1               5                   10                  15

Ala Met Ala

<210> SEQ ID NO 169
<211> LENGTH: 19
<212> TYPE: PRT
<213> ORGANISM: Homo sapiens

```
<400> SEQUENCE: 169

Met Ala Leu Val Leu Glu Ile Phe Thr Leu Leu Ala Ser Ile Cys Trp
1               5                   10                  15

Val Ser Ala

<210> SEQ ID NO 170
<211> LENGTH: 19
<212> TYPE: PRT
<213> ORGANISM: Homo sapiens

<400> SEQUENCE: 170

Met Ser Arg Leu Pro Val Leu Leu Leu Gln Leu Leu Val Arg Pro
1               5                   10                  15

Gly Leu Gln

<210> SEQ ID NO 171
<211> LENGTH: 19
<212> TYPE: PRT
<213> ORGANISM: Homo sapiens

<400> SEQUENCE: 171

Met Asp Ile Leu Cys Ser Thr Leu Leu Leu Thr Val Pro Ser Gly
1               5                   10                  15

Val Leu Ser

<210> SEQ ID NO 172
<211> LENGTH: 19
<212> TYPE: PRT
<213> ORGANISM: Homo sapiens

<400> SEQUENCE: 172

Met Lys Thr Leu Leu Leu Leu Leu Val Leu Leu Glu Leu Gly Glu
1               5                   10                  15

Ala Gln Gly

<210> SEQ ID NO 173
<211> LENGTH: 19
<212> TYPE: PRT
<213> ORGANISM: Homo sapiens

<400> SEQUENCE: 173

Met Ala Pro Leu Arg Pro Leu Leu Ile Leu Ala Leu Leu Ala Trp Val
1               5                   10                  15

Ala Leu Ala

<210> SEQ ID NO 174
<211> LENGTH: 19
<212> TYPE: PRT
<213> ORGANISM: Homo sapiens

<400> SEQUENCE: 174

Met Asn Trp His Leu Pro Leu Phe Leu Leu Ala Ser Val Thr Leu Pro
1               5                   10                  15

Ser Ile Cys

<210> SEQ ID NO 175
<211> LENGTH: 19
<212> TYPE: PRT
<213> ORGANISM: Homo sapiens

<400> SEQUENCE: 175
```

```
Met Lys Phe Phe Val Phe Ala Leu Val Leu Ala Leu Met Ile Ser Met
1               5                   10                  15

Ile Ser Ala

<210> SEQ ID NO 176
<211> LENGTH: 19
<212> TYPE: PRT
<213> ORGANISM: Homo sapiens

<400> SEQUENCE: 176

Met Tyr Gly Lys Ile Ile Phe Val Leu Leu Leu Ser Glu Ile Val Ser
1               5                   10                  15

Ile Ser Ala

<210> SEQ ID NO 177
<211> LENGTH: 19
<212> TYPE: PRT
<213> ORGANISM: Homo sapiens

<400> SEQUENCE: 177

Met Ile Leu Phe Lys Gln Ala Thr Tyr Phe Ile Ser Leu Phe Ala Thr
1               5                   10                  15

Val Ser Cys

<210> SEQ ID NO 178
<211> LENGTH: 19
<212> TYPE: PRT
<213> ORGANISM: Homo sapiens

<400> SEQUENCE: 178

Met Asp Trp Thr Trp Arg Ile Leu Phe Leu Val Ala Ala Ala Thr Gly
1               5                   10                  15

Ala His Ser

<210> SEQ ID NO 179
<211> LENGTH: 19
<212> TYPE: PRT
<213> ORGANISM: Homo sapiens

<400> SEQUENCE: 179

Met Gln Gly Pro Trp Val Leu Leu Leu Leu Gly Leu Arg Leu Gln Leu
1               5                   10                  15

Ser Leu Gly

<210> SEQ ID NO 180
<211> LENGTH: 19
<212> TYPE: PRT
<213> ORGANISM: Homo sapiens

<400> SEQUENCE: 180

Met Ser Arg Gly Leu Gln Leu Leu Leu Leu Ser Cys Ala Tyr Ser Leu
1               5                   10                  15

Ala Pro Ala

<210> SEQ ID NO 181
<211> LENGTH: 19
<212> TYPE: PRT
<213> ORGANISM: Homo sapiens

<400> SEQUENCE: 181
```

-continued

```
Met Arg Leu Leu Trp Gly Leu Ile Trp Ala Ser Ser Phe Phe Thr Leu
1               5                   10                  15

Ser Leu Gln

<210> SEQ ID NO 182
<211> LENGTH: 19
<212> TYPE: PRT
<213> ORGANISM: Homo sapiens

<400> SEQUENCE: 182

Met Pro Asp Thr Met Leu Pro Ala Cys Phe Leu Gly Leu Leu Ala Phe
1               5                   10                  15

Ser Ser Ala

<210> SEQ ID NO 183
<211> LENGTH: 19
<212> TYPE: PRT
<213> ORGANISM: Homo sapiens

<400> SEQUENCE: 183

Met Arg Thr Leu Ala Ile Leu Ala Ala Ile Leu Leu Val Ala Leu Gln
1               5                   10                  15

Ala Gln Ala

<210> SEQ ID NO 184
<211> LENGTH: 19
<212> TYPE: PRT
<213> ORGANISM: Homo sapiens

<400> SEQUENCE: 184

Met Arg Met Leu Leu His Leu Ser Leu Leu Ala Leu Gly Ala Ala Tyr
1               5                   10                  15

Val Tyr Ala

<210> SEQ ID NO 185
<211> LENGTH: 19
<212> TYPE: PRT
<213> ORGANISM: Homo sapiens

<400> SEQUENCE: 185

Met Ala Trp Ala Pro Leu Leu Leu Thr Leu Leu Ala His Cys Thr Asp
1               5                   10                  15

Cys Trp Ala

<210> SEQ ID NO 186
<211> LENGTH: 19
<212> TYPE: PRT
<213> ORGANISM: Homo sapiens

<400> SEQUENCE: 186

Met Lys Ser Val Leu Leu Leu Thr Thr Leu Leu Val Pro Ala His Leu
1               5                   10                  15

Val Ala Ala

<210> SEQ ID NO 187
<211> LENGTH: 19
<212> TYPE: PRT
<213> ORGANISM: Homo sapiens

<400> SEQUENCE: 187

Met Ile Phe Leu Leu Leu Met Leu Ser Leu Glu Leu Gln Leu His Gln
```

-continued

```
                1               5              10              15
Ile Ala Ala

<210> SEQ ID NO 188
<211> LENGTH: 19
<212> TYPE: PRT
<213> ORGANISM: Homo sapiens

<400> SEQUENCE: 188

Met Trp Arg Ser Leu Gly Leu Ala Leu Ala Leu Cys Leu Leu Pro Ser
1               5                   10                  15

Gly Gly Thr

<210> SEQ ID NO 189
<211> LENGTH: 19
<212> TYPE: PRT
<213> ORGANISM: Homo sapiens

<400> SEQUENCE: 189

Met Gly Ile Leu Leu Gly Leu Leu Leu Gly His Leu Thr Val Asp
1               5                   10                  15

Thr Tyr Gly

<210> SEQ ID NO 190
<211> LENGTH: 19
<212> TYPE: PRT
<213> ORGANISM: Homo sapiens

<400> SEQUENCE: 190

Met Trp Leu Leu Leu Thr Met Ala Ser Leu Ile Ser Val Leu Gly Thr
1               5                   10                  15

Thr His Gly

<210> SEQ ID NO 191
<211> LENGTH: 19
<212> TYPE: PRT
<213> ORGANISM: Homo sapiens

<400> SEQUENCE: 191

Met Arg Ala Ala Arg Ala Leu Leu Pro Leu Leu Leu Gln Ala Cys Trp
1               5                   10                  15

Thr Ala Ala

<210> SEQ ID NO 192
<211> LENGTH: 19
<212> TYPE: PRT
<213> ORGANISM: Homo sapiens

<400> SEQUENCE: 192

Met Gln Ile Glu Leu Ser Thr Cys Phe Phe Leu Cys Leu Leu Arg Phe
1               5                   10                  15

Cys Phe Ser

<210> SEQ ID NO 193
<211> LENGTH: 19
<212> TYPE: PRT
<213> ORGANISM: Homo sapiens

<400> SEQUENCE: 193

Met Ser Leu Trp Gln Pro Leu Val Leu Val Leu Leu Val Leu Gly Cys
1               5                   10                  15
```

-continued

Cys Phe Ala

<210> SEQ ID NO 194
<211> LENGTH: 19
<212> TYPE: PRT
<213> ORGANISM: Homo sapiens

<400> SEQUENCE: 194

Met Ala Leu Leu Phe Ser Leu Ile Leu Ala Ile Cys Thr Arg Pro Gly
1               5                   10                  15

Phe Leu Ala

<210> SEQ ID NO 195
<211> LENGTH: 19
<212> TYPE: PRT
<213> ORGANISM: Homo sapiens

<400> SEQUENCE: 195

Met Leu Leu Leu Phe Leu Leu Phe Glu Gly Leu Cys Cys Pro Gly Glu
1               5                   10                  15

Asn Thr Ala

<210> SEQ ID NO 196
<211> LENGTH: 19
<212> TYPE: PRT
<213> ORGANISM: Homo sapiens

<400> SEQUENCE: 196

Met Leu Ala Val Gly Cys Ala Leu Leu Ala Ala Leu Leu Ala Ala Pro
1               5                   10                  15

Gly Ala Ala

<210> SEQ ID NO 197
<211> LENGTH: 18
<212> TYPE: PRT
<213> ORGANISM: Homo sapiens

<400> SEQUENCE: 197

Met Asp Trp Thr Trp Ile Leu Phe Leu Val Ala Ala Ala Thr Arg Val
1               5                   10                  15

His Ser

<210> SEQ ID NO 198
<211> LENGTH: 19
<212> TYPE: PRT
<213> ORGANISM: Homo sapiens

<400> SEQUENCE: 198

Met Phe Cys Pro Leu Lys Leu Ile Leu Leu Pro Val Leu Leu Asp Tyr
1               5                   10                  15

Ser Leu Gly

<210> SEQ ID NO 199
<211> LENGTH: 19
<212> TYPE: PRT
<213> ORGANISM: Homo sapiens

<400> SEQUENCE: 199

Met Arg Arg Leu Leu Glu Pro Cys Trp Trp Ile Leu Phe Leu Lys Ile
1               5                   10                  15

Thr Ser Ser

<210> SEQ ID NO 200
<211> LENGTH: 19
<212> TYPE: PRT
<213> ORGANISM: Homo sapiens

<400> SEQUENCE: 200

Met Lys Ile Leu Ile Leu Gly Ile Phe Leu Phe Leu Cys Ser Thr Pro
1               5                   10                  15

Ala Trp Ala

<210> SEQ ID NO 201
<211> LENGTH: 19
<212> TYPE: PRT
<213> ORGANISM: Homo sapiens

<400> SEQUENCE: 201

Met Arg Ala Leu Leu Leu Gly Phe Leu Leu Val Ser Leu Glu Ser
1               5                   10                  15

Thr Leu Ser

<210> SEQ ID NO 202
<211> LENGTH: 19
<212> TYPE: PRT
<213> ORGANISM: Homo sapiens

<400> SEQUENCE: 202

Met Lys Ser Leu Ile Leu Leu Ala Ile Leu Ala Ala Leu Ala Val Val
1               5                   10                  15

Thr Leu Cys

<210> SEQ ID NO 203
<211> LENGTH: 19
<212> TYPE: PRT
<213> ORGANISM: Homo sapiens

<400> SEQUENCE: 203

Met Tyr Gly Lys Ile Ile Phe Val Leu Leu Leu Ser Ala Ile Val Ser
1               5                   10                  15

Ile Ser Ala

<210> SEQ ID NO 204
<211> LENGTH: 19
<212> TYPE: PRT
<213> ORGANISM: Homo sapiens

<400> SEQUENCE: 204

Met Gln Ala Leu Val Leu Leu Leu Cys Ile Gly Ala Leu Leu Gly His
1               5                   10                  15

Ser Ser Cys

<210> SEQ ID NO 205
<211> LENGTH: 19
<212> TYPE: PRT
<213> ORGANISM: Homo sapiens

<400> SEQUENCE: 205

Met Pro Arg Gly Trp Ala Ala Pro Leu Leu Leu Leu Leu Gln Gly
1               5                   10                  15

Gly Trp Gly

<210> SEQ ID NO 206
<211> LENGTH: 19
<212> TYPE: PRT
<213> ORGANISM: Homo sapiens

<400> SEQUENCE: 206

Met Arg Phe Phe Val Pro Leu Phe Leu Val Gly Ile Leu Phe Pro Ala
 1               5                  10                  15

Ile Leu Ala

<210> SEQ ID NO 207
<211> LENGTH: 19
<212> TYPE: PRT
<213> ORGANISM: Homo sapiens

<400> SEQUENCE: 207

Met Arg Leu Ala Val Gly Ala Leu Leu Val Cys Ala Val Leu Gly Leu
 1               5                  10                  15

Cys Leu Ala

<210> SEQ ID NO 208
<211> LENGTH: 19
<212> TYPE: PRT
<213> ORGANISM: Homo sapiens

<400> SEQUENCE: 208

Met Phe Ser Met Arg Ile Val Cys Leu Val Leu Ser Val Val Gly Thr
 1               5                  10                  15

Ala Trp Thr

<210> SEQ ID NO 209
<211> LENGTH: 19
<212> TYPE: PRT
<213> ORGANISM: Homo sapiens

<400> SEQUENCE: 209

Met Val Ala Leu Pro Met Val Leu Val Leu Leu Leu Val Leu Ser Arg
 1               5                  10                  15

Gly Glu Ser

<210> SEQ ID NO 210
<211> LENGTH: 19
<212> TYPE: PRT
<213> ORGANISM: Homo sapiens

<400> SEQUENCE: 210

Met Thr Arg Thr Arg Ala Ala Leu Leu Leu Phe Thr Ala Leu Ala Thr
 1               5                  10                  15

Ser Leu Gly

<210> SEQ ID NO 211
<211> LENGTH: 19
<212> TYPE: PRT
<213> ORGANISM: Homo sapiens

<400> SEQUENCE: 211

Met Ala Thr Leu Leu Leu Leu Leu Gly Val Leu Val Val Ser Pro Asp
 1               5                  10                  15

Ala Leu Gly

-continued

<210> SEQ ID NO 212
<211> LENGTH: 19
<212> TYPE: PRT
<213> ORGANISM: Homo sapiens

<400> SEQUENCE: 212

Met Lys Leu Ala Ser Gly Phe Leu Val Leu Trp Leu Ser Leu Gly Gly
 1               5                  10                  15

Gly Leu Ala

<210> SEQ ID NO 213
<211> LENGTH: 19
<212> TYPE: PRT
<213> ORGANISM: Homo sapiens

<400> SEQUENCE: 213

Met Ile Ser Pro Val Leu Ile Leu Phe Ser Ser Phe Leu Cys His Val
 1               5                  10                  15

Ala Ile Ala

<210> SEQ ID NO 214
<211> LENGTH: 19
<212> TYPE: PRT
<213> ORGANISM: Homo sapiens

<400> SEQUENCE: 214

Met Lys Phe Leu Val Phe Ala Phe Ile Leu Ala Leu Met Val Ser Met
 1               5                  10                  15

Ile Gly Ala

<210> SEQ ID NO 215
<211> LENGTH: 19
<212> TYPE: PRT
<213> ORGANISM: Homo sapiens

<400> SEQUENCE: 215

Met Arg Leu Leu Trp Gly Leu Ile Trp Ala Ser Ser Phe Phe Thr Leu
 1               5                  10                  15

Ser Leu Gln

<210> SEQ ID NO 216
<211> LENGTH: 19
<212> TYPE: PRT
<213> ORGANISM: Homo sapiens

<400> SEQUENCE: 216

Met Lys Ile Ser Val Ala Ala Ile Pro Phe Phe Leu Leu Ile Thr Ile
 1               5                  10                  15

Ala Leu Gly

<210> SEQ ID NO 217
<211> LENGTH: 19
<212> TYPE: PRT
<213> ORGANISM: Homo sapiens

<400> SEQUENCE: 217

Met Gly Ser Gly Leu Pro Leu Val Leu Leu Thr Leu Leu Gly Ser
 1               5                  10                  15

Ser His Gly

```
<210> SEQ ID NO 218
<211> LENGTH: 19
<212> TYPE: PRT
<213> ORGANISM: Homo sapiens

<400> SEQUENCE: 218

Met Arg Phe Met Thr Leu Leu Phe Leu Thr Ala Leu Ala Gly Ala Leu
1               5                   10                  15

Val Cys Ala

<210> SEQ ID NO 219
<211> LENGTH: 19
<212> TYPE: PRT
<213> ORGANISM: Homo sapiens

<400> SEQUENCE: 219

Met Tyr Gly Lys Ile Ile Phe Val Leu Leu Leu Ser Gly Ile Val Ser
1               5                   10                  15

Ile Ser Ala

<210> SEQ ID NO 220
<211> LENGTH: 19
<212> TYPE: PRT
<213> ORGANISM: Homo sapiens

<400> SEQUENCE: 220

Met Arg Gly Ala Thr Arg Val Ser Ile Met Leu Leu Leu Val Thr Val
1               5                   10                  15

Ser Asp Cys

<210> SEQ ID NO 221
<211> LENGTH: 19
<212> TYPE: PRT
<213> ORGANISM: Homo sapiens

<400> SEQUENCE: 221

Met Lys Leu Val Phe Leu Val Leu Leu Phe Leu Gly Ala Leu Gly Leu
1               5                   10                  15

Cys Leu Ala

<210> SEQ ID NO 222
<211> LENGTH: 19
<212> TYPE: PRT
<213> ORGANISM: Homo sapiens

<400> SEQUENCE: 222

Met Asn Leu Ala Ile Ser Ile Ala Leu Leu Leu Thr Val Leu Gln Val
1               5                   10                  15

Ser Arg Gly

<210> SEQ ID NO 223
<211> LENGTH: 19
<212> TYPE: PRT
<213> ORGANISM: Homo sapiens

<400> SEQUENCE: 223

Met Arg Leu Phe Leu Trp Asn Ala Val Leu Thr Leu Phe Val Thr Ser
1               5                   10                  15

Leu Ile Gly

<210> SEQ ID NO 224
```

```
<211> LENGTH: 19
<212> TYPE: PRT
<213> ORGANISM: Homo sapiens

<400> SEQUENCE: 224

Met Asp Trp Thr Trp Arg Val Phe Cys Leu Leu Ala Val Ala Pro Gly
1               5                   10                  15

Ala His Ser

<210> SEQ ID NO 225
<211> LENGTH: 19
<212> TYPE: PRT
<213> ORGANISM: Homo sapiens

<400> SEQUENCE: 225

Met Ile Phe Leu Thr Ala Leu Pro Leu Phe Trp Ile Met Ile Ser Ala
1               5                   10                  15

Ser Arg Gly

<210> SEQ ID NO 226
<211> LENGTH: 19
<212> TYPE: PRT
<213> ORGANISM: Homo sapiens

<400> SEQUENCE: 226

Met Lys His Ser Leu Asn Ala Leu Leu Ile Phe Leu Ile Ile Thr Ser
1               5                   10                  15

Ala Trp Gly

<210> SEQ ID NO 227
<211> LENGTH: 19
<212> TYPE: PRT
<213> ORGANISM: Homo sapiens

<400> SEQUENCE: 227

Met Lys His Leu Trp Phe Leu Leu Leu Trp Cys Gln Leu Pro Asp Val
1               5                   10                  15

Gly Val Leu

<210> SEQ ID NO 228
<211> LENGTH: 19
<212> TYPE: PRT
<213> ORGANISM: Homo sapiens

<400> SEQUENCE: 228

Met Asp Leu Arg Gln Phe Leu Met Cys Leu Ser Leu Cys Thr Ala Phe
1               5                   10                  15

Ala Leu Ser

<210> SEQ ID NO 229
<211> LENGTH: 19
<212> TYPE: PRT
<213> ORGANISM: Homo sapiens

<400> SEQUENCE: 229

Met His Ser Phe Pro Pro Leu Leu Leu Leu Phe Trp Gly Val Val
1               5                   10                  15

Ser His Ser

<210> SEQ ID NO 230
<211> LENGTH: 19
```

```
<212> TYPE: PRT
<213> ORGANISM: Homo sapiens

<400> SEQUENCE: 230

Met Ala Arg Pro His Pro Trp Trp Leu Cys Val Leu Gly Thr Leu Val
1               5                   10                  15

Gly Leu Ser

<210> SEQ ID NO 231
<211> LENGTH: 19
<212> TYPE: PRT
<213> ORGANISM: Homo sapiens

<400> SEQUENCE: 231

Met Arg Gly Pro Ser Gly Ala Leu Trp Leu Leu Leu Ala Leu Arg Thr
1               5                   10                  15

Val Leu Gly

<210> SEQ ID NO 232
<211> LENGTH: 19
<212> TYPE: PRT
<213> ORGANISM: Homo sapiens

<400> SEQUENCE: 232

Met Arg Ser Leu Gly Ala Leu Leu Leu Leu Ser Ala Cys Leu Ala
1               5                   10                  15

Val Ser Ala

<210> SEQ ID NO 233
<211> LENGTH: 19
<212> TYPE: PRT
<213> ORGANISM: Homo sapiens

<400> SEQUENCE: 233

Met Gln Leu Phe Leu Leu Leu Cys Leu Val Leu Leu Ser Pro Gln Gly
1               5                   10                  15

Ala Ser Leu

<210> SEQ ID NO 234
<211> LENGTH: 19
<212> TYPE: PRT
<213> ORGANISM: Homo sapiens

<400> SEQUENCE: 234

Met Leu Leu Trp Ser Leu Leu Val Ile Phe Asp Ala Val Thr Glu Gln
1               5                   10                  15

Ala Asp Ser

<210> SEQ ID NO 235
<211> LENGTH: 19
<212> TYPE: PRT
<213> ORGANISM: Homo sapiens

<400> SEQUENCE: 235

Met Asn Lys Pro Leu Leu Trp Ile Ser Val Leu Thr Ser Leu Leu Glu
1               5                   10                  15

Ala Phe Ala

<210> SEQ ID NO 236
<211> LENGTH: 19
<212> TYPE: PRT
```

<213> ORGANISM: Homo sapiens

<400> SEQUENCE: 236

Met Ala Trp Ser Leu Gly Ser Trp Leu Gly Gly Cys Leu Leu Val Ser
1               5                   10                  15
Ala Leu Gly

<210> SEQ ID NO 237
<211> LENGTH: 19
<212> TYPE: PRT
<213> ORGANISM: Homo sapiens

<400> SEQUENCE: 237

Met Leu Leu Leu Pro Leu Pro Leu Leu Phe Leu Leu Cys Ser Arg
1               5                   10                  15
Ala Glu Ala

<210> SEQ ID NO 238
<211> LENGTH: 19
<212> TYPE: PRT
<213> ORGANISM: Homo sapiens

<400> SEQUENCE: 238

Met Glu Leu Ser Trp His Val Val Phe Ile Ala Leu Leu Ser Phe Ser
1               5                   10                  15
Cys Trp Gly

<210> SEQ ID NO 239
<211> LENGTH: 19
<212> TYPE: PRT
<213> ORGANISM: Homo sapiens

<400> SEQUENCE: 239

Met Glu Arg Ala Ser Cys Leu Leu Leu Leu Leu Pro Leu Val His
1               5                   10                  15
Val Ser Ala

<210> SEQ ID NO 240
<211> LENGTH: 19
<212> TYPE: PRT
<213> ORGANISM: Homo sapiens

<400> SEQUENCE: 240

Met Glu His Lys Glu Val Val Leu Leu Leu Leu Phe Leu Lys Ser
1               5                   10                  15
Ala Ala Pro

<210> SEQ ID NO 241
<211> LENGTH: 19
<212> TYPE: PRT
<213> ORGANISM: Homo sapiens

<400> SEQUENCE: 241

Met Lys Phe Phe Val Phe Ala Leu Ile Leu Ala Leu Met Leu Ser Met
1               5                   10                  15
Thr Gly Ala

<210> SEQ ID NO 242
<211> LENGTH: 19
<212> TYPE: PRT
<213> ORGANISM: Homo sapiens -continued

<400> SEQUENCE: 242

Met Thr Cys Ser Pro Leu Leu Leu Thr Leu Leu Ile His Cys Thr Gly
1               5                   10                  15

Ser Trp Ala

<210> SEQ ID NO 243
<211> LENGTH: 19
<212> TYPE: PRT
<213> ORGANISM: Homo sapiens

<400> SEQUENCE: 243

Met Val Glu Met Leu Pro Thr Ala Ile Leu Leu Val Leu Ala Val Ser
1               5                   10                  15

Val Val Ala

<210> SEQ ID NO 244
<211> LENGTH: 19
<212> TYPE: PRT
<213> ORGANISM: Homo sapiens

<400> SEQUENCE: 244

Met Ala Gly Pro Ser Leu Ala Cys Cys Leu Leu Gly Leu Leu Ala Leu
1               5                   10                  15

Thr Ser Ala

<210> SEQ ID NO 245
<211> LENGTH: 19
<212> TYPE: PRT
<213> ORGANISM: Homo sapiens

<400> SEQUENCE: 245

Met Glu Phe Gly Leu Ser Trp Leu Phe Leu Val Ala Ile Leu Lys Gly
1               5                   10                  15

Val Gln Cys

<210> SEQ ID NO 246
<211> LENGTH: 19
<212> TYPE: PRT
<213> ORGANISM: Homo sapiens

<400> SEQUENCE: 246

Met Met Trp Thr Trp Ala Leu Trp Met Leu Pro Ser Leu Cys Lys Phe
1               5                   10                  15

Ser Leu Ala

<210> SEQ ID NO 247
<211> LENGTH: 19
<212> TYPE: PRT
<213> ORGANISM: Homo sapiens

<400> SEQUENCE: 247

Met Val Val Ala Leu Arg Tyr Val Trp Pro Leu Leu Leu Cys Ser Pro
1               5                   10                  15

Cys Leu Leu

<210> SEQ ID NO 248
<211> LENGTH: 19
<212> TYPE: PRT
<213> ORGANISM: Homo sapiens

```
<400> SEQUENCE: 248

Met Gly Leu Gln Ala Cys Leu Leu Gly Leu Phe Ala Leu Ile Leu Ser
 1               5                  10                  15

Gly Lys Cys

<210> SEQ ID NO 249
<211> LENGTH: 19
<212> TYPE: PRT
<213> ORGANISM: Homo sapiens

<400> SEQUENCE: 249

Met Arg Thr Leu Ala Ile Leu Ala Ala Ile Leu Leu Val Ala Leu Gln
 1               5                  10                  15

Ala Gln Ala

<210> SEQ ID NO 250
<211> LENGTH: 19
<212> TYPE: PRT
<213> ORGANISM: Homo sapiens

<400> SEQUENCE: 250

Met Glu His Lys Glu Val Val Leu Leu Leu Leu Leu Phe Leu Lys Ser
 1               5                  10                  15

Gly Gln Gly

<210> SEQ ID NO 251
<211> LENGTH: 20
<212> TYPE: PRT
<213> ORGANISM: Homo sapiens

<400> SEQUENCE: 251

Met Trp Leu Cys Pro Leu Ala Leu Asn Leu Ile Leu Met Ala Ala Ser
 1               5                  10                  15

Gly Ala Val Cys
            20

<210> SEQ ID NO 252
<211> LENGTH: 20
<212> TYPE: PRT
<213> ORGANISM: Homo sapiens

<400> SEQUENCE: 252

Met Ala Trp Gln Gly Leu Val Leu Ala Ala Cys Leu Leu Met Phe Pro
 1               5                  10                  15

Ser Thr Thr Ala
            20

<210> SEQ ID NO 253
<211> LENGTH: 20
<212> TYPE: PRT
<213> ORGANISM: Homo sapiens

<400> SEQUENCE: 253

Met Val Leu Gln Thr Gln Val Phe Ile Ser Leu Leu Leu Trp Ile Ser
 1               5                  10                  15

Gly Ala Tyr Gly
            20

<210> SEQ ID NO 254
<211> LENGTH: 20
<212> TYPE: PRT
```

<213> ORGANISM: Homo sapiens

<400> SEQUENCE: 254

Met Glu Ala Pro Ala Gln Leu Leu Phe Leu Leu Leu Trp Leu Pro
1               5                   10                  15

Asp Thr Thr Arg
            20

<210> SEQ ID NO 255
<211> LENGTH: 20
<212> TYPE: PRT
<213> ORGANISM: Homo sapiens

<400> SEQUENCE: 255

Met Lys Gly Phe Thr Ala Thr Leu Phe Leu Trp Thr Leu Ile Phe Pro
1               5                   10                  15

Ser Cys Ser Gly
            20

<210> SEQ ID NO 256
<211> LENGTH: 20
<212> TYPE: PRT
<213> ORGANISM: Homo sapiens

<400> SEQUENCE: 256

Met Lys Gly Leu Ala Ala Ala Leu Leu Val Leu Val Cys Thr Met Ala
1               5                   10                  15

Leu Cys Ser Cys
            20

<210> SEQ ID NO 257
<211> LENGTH: 20
<212> TYPE: PRT
<213> ORGANISM: Homo sapiens

<400> SEQUENCE: 257

Met Glu Pro Trp Pro Leu Leu Leu Phe Ser Leu Cys Ser Ala Gly
1               5                   10                  15

Leu Val Leu Gly
            20

<210> SEQ ID NO 258
<211> LENGTH: 20
<212> TYPE: PRT
<213> ORGANISM: Homo sapiens

<400> SEQUENCE: 258

Met Glu Thr Pro Ala Gln Leu Leu Phe Leu Leu Leu Leu Trp Leu Pro
1               5                   10                  15

Asp Thr Thr Gly
            20

<210> SEQ ID NO 259
<211> LENGTH: 20
<212> TYPE: PRT
<213> ORGANISM: Homo sapiens

<400> SEQUENCE: 259

Met Met Trp Pro Met His Thr Pro Leu Leu Leu Leu Thr Ala Leu Met
1               5                   10                  15

Val Ala Val Ala
            20

<210> SEQ ID NO 260
<211> LENGTH: 20
<212> TYPE: PRT
<213> ORGANISM: Homo sapiens

<400> SEQUENCE: 260

Met Thr Ala Leu Phe Leu Met Ser Met Leu Phe Gly Leu Ala Cys Gly
 1               5                  10                  15

Gln Ala Met Ser
            20

<210> SEQ ID NO 261
<211> LENGTH: 20
<212> TYPE: PRT
<213> ORGANISM: Homo sapiens

<400> SEQUENCE: 261

Met Ser Asp Leu Leu Ser Val Phe Leu His Leu Leu Leu Phe Lys
 1               5                  10                  15

Leu Val Ala Pro
            20

<210> SEQ ID NO 262
<211> LENGTH: 20
<212> TYPE: PRT
<213> ORGANISM: Homo sapiens

<400> SEQUENCE: 262

Met Gly Arg Leu Gln Leu Val Val Leu Gly Leu Thr Cys Cys Trp Ala
 1               5                  10                  15

Val Ala Ser Ala
            20

<210> SEQ ID NO 263
<211> LENGTH: 20
<212> TYPE: PRT
<213> ORGANISM: Homo sapiens

<400> SEQUENCE: 263

Met Lys Ala Val Leu Leu Ala Leu Leu Met Ala Gly Leu Ala Leu Gln
 1               5                  10                  15

Pro Gly Thr Ala
            20

<210> SEQ ID NO 264
<211> LENGTH: 20
<212> TYPE: PRT
<213> ORGANISM: Homo sapiens

<400> SEQUENCE: 264

Met Ala Trp Ala Ser Arg Leu Gly Leu Leu Ala Leu Leu Leu Pro
 1               5                  10                  15

Val Val Gly Ala
            20

<210> SEQ ID NO 265
<211> LENGTH: 20
<212> TYPE: PRT
<213> ORGANISM: Homo sapiens

<400> SEQUENCE: 265

```
Met Phe Ser Leu Lys Thr Leu Pro Phe Leu Leu Leu His Val Gln
1               5                   10                  15

Ile Ser Lys Ala
            20

<210> SEQ ID NO 266
<211> LENGTH: 20
<212> TYPE: PRT
<213> ORGANISM: Homo sapiens

<400> SEQUENCE: 266

Met Pro Val Pro Trp Phe Leu Leu Ser Leu Ala Leu Gly Arg Ser Pro
1               5                   10                  15

Val Val Leu Ser
            20

<210> SEQ ID NO 267
<211> LENGTH: 20
<212> TYPE: PRT
<213> ORGANISM: Homo sapiens

<400> SEQUENCE: 267

Met Lys Ser Leu Ser Leu Leu Leu Ala Val Ala Leu Gly Leu Ala Thr
1               5                   10                  15

Ala Val Ser Ala
            20

<210> SEQ ID NO 268
<211> LENGTH: 20
<212> TYPE: PRT
<213> ORGANISM: Homo sapiens

<400> SEQUENCE: 268

Met Gly Ala Ala Gly Leu Leu Gly Val Phe Leu Ala Leu Val Ala Pro
1               5                   10                  15

Gly Val Leu Gly
            20

<210> SEQ ID NO 269
<211> LENGTH: 20
<212> TYPE: PRT
<213> ORGANISM: Homo sapiens

<400> SEQUENCE: 269

Met Lys Ser Ile Tyr Phe Val Ala Gly Leu Phe Val Met Leu Val Gln
1               5                   10                  15

Gly Ser Trp Gln
            20

<210> SEQ ID NO 270
<211> LENGTH: 20
<212> TYPE: PRT
<213> ORGANISM: Homo sapiens

<400> SEQUENCE: 270

Met Ala Thr Pro Arg Gly Leu Gly Ala Leu Leu Leu Leu Leu Leu Leu
1               5                   10                  15

Pro Thr Ser Gly
            20

<210> SEQ ID NO 271
<211> LENGTH: 20
```

-continued

```
<212> TYPE: PRT
<213> ORGANISM: Homo sapiens

<400> SEQUENCE: 271

Met Asn Arg Cys Trp Ala Leu Phe Leu Ser Leu Cys Cys Tyr Leu Arg
1               5                   10                  15

Leu Val Ser Ala
            20

<210> SEQ ID NO 272
<211> LENGTH: 20
<212> TYPE: PRT
<213> ORGANISM: Homo sapiens

<400> SEQUENCE: 272

Met Gly Leu Phe Met Ile Ile Ala Ile Leu Leu Phe Gln Lys Pro Thr
1               5                   10                  15

Val Thr Glu Gln
            20

<210> SEQ ID NO 273
<211> LENGTH: 20
<212> TYPE: PRT
<213> ORGANISM: Homo sapiens

<400> SEQUENCE: 273

Met Trp Leu Cys Pro Leu Ala Leu Asn Leu Ile Leu Met Ala Ala Ser
1               5                   10                  15

Gly Ala Ala Cys
            20

<210> SEQ ID NO 274
<211> LENGTH: 20
<212> TYPE: PRT
<213> ORGANISM: Homo sapiens

<400> SEQUENCE: 274

Met Lys Leu Met Val Leu Val Phe Thr Ile Gly Leu Thr Leu Leu Leu
1               5                   10                  15

Gly Val Gln Ala
            20

<210> SEQ ID NO 275
<211> LENGTH: 20
<212> TYPE: PRT
<213> ORGANISM: Homo sapiens

<400> SEQUENCE: 275

Met Arg Pro Ala Asp Leu Leu Gln Leu Val Leu Leu Leu Asp Leu Pro
1               5                   10                  15

Arg Asp Leu Gly
            20

<210> SEQ ID NO 276
<211> LENGTH: 20
<212> TYPE: PRT
<213> ORGANISM: Homo sapiens

<400> SEQUENCE: 276

Met Tyr Arg Met Gln Leu Leu Ser Cys Ile Ala Leu Ser Leu Ala Leu
1               5                   10                  15

Val Thr Asn Ser
```

20

<210> SEQ ID NO 277
<211> LENGTH: 20
<212> TYPE: PRT
<213> ORGANISM: Homo sapiens

<400> SEQUENCE: 277

Met Gln Pro Thr Leu Leu Leu Ser Leu Leu Gly Ala Val Gly Leu Ala
1               5                   10                  15

Ala Val Asn Ser
            20

<210> SEQ ID NO 278
<211> LENGTH: 20
<212> TYPE: PRT
<213> ORGANISM: Homo sapiens

<400> SEQUENCE: 278

Met Ala Leu Pro Phe Ala Leu Leu Met Ala Leu Val Val Leu Ser Cys
1               5                   10                  15

Lys Ser Ser Cys
            20

<210> SEQ ID NO 279
<211> LENGTH: 20
<212> TYPE: PRT
<213> ORGANISM: Homo sapiens

<400> SEQUENCE: 279

Met Thr Ser Lys Leu Ala Val Ala Leu Leu Ala Ala Phe Leu Ile Ser
1               5                   10                  15

Ala Ala Leu Cys
            20

<210> SEQ ID NO 280
<211> LENGTH: 20
<212> TYPE: PRT
<213> ORGANISM: Homo sapiens

<400> SEQUENCE: 280

Met Lys Thr Leu Gln Ser Thr Leu Leu Leu Leu Leu Val Pro Leu
1               5                   10                  15

Ile Lys Pro Ala
            20

<210> SEQ ID NO 281
<211> LENGTH: 20
<212> TYPE: PRT
<213> ORGANISM: Homo sapiens

<400> SEQUENCE: 281

Met Asp Pro Arg Leu Pro Ala Trp Ala Leu Val Leu Leu Gly Pro Ala
1               5                   10                  15

Leu Val Phe Ala
            20

<210> SEQ ID NO 282
<211> LENGTH: 20
<212> TYPE: PRT
<213> ORGANISM: Homo sapiens

<400> SEQUENCE: 282

-continued

Met Ser Arg Ser Val Ala Leu Ala Val Leu Ala Leu Leu Ser Leu Ser
1               5                   10                  15

Gly Leu Glu Ala
            20

<210> SEQ ID NO 283
<211> LENGTH: 20
<212> TYPE: PRT
<213> ORGANISM: Homo sapiens

<400> SEQUENCE: 283

Met Ala Trp Pro Leu Cys Thr Leu Leu Leu Leu Ala Thr Gln Ala
1               5                   10                  15

Val Ala Leu Ala
            20

<210> SEQ ID NO 284
<211> LENGTH: 20
<212> TYPE: PRT
<213> ORGANISM: Homo sapiens

<400> SEQUENCE: 284

Met Glu Ala Pro Ala Gln Leu Leu Phe Leu Leu Leu Leu Trp Leu Pro
1               5                   10                  15

Asp Thr Thr Gly
            20

<210> SEQ ID NO 285
<211> LENGTH: 20
<212> TYPE: PRT
<213> ORGANISM: Homo sapiens

<400> SEQUENCE: 285

Met Arg Trp Ala Leu Leu Val Leu Leu Ala Phe Leu Ser Pro Ala Ser
1               5                   10                  15

Gln Lys Ser Ser
            20

<210> SEQ ID NO 286
<211> LENGTH: 20
<212> TYPE: PRT
<213> ORGANISM: Homo sapiens

<400> SEQUENCE: 286

Met Ile Ile Val Ala His Val Leu Leu Ile Leu Leu Gly Ala Thr Glu
1               5                   10                  15

Ile Leu Gln Ala
            20

<210> SEQ ID NO 287
<211> LENGTH: 20
<212> TYPE: PRT
<213> ORGANISM: Homo sapiens

<400> SEQUENCE: 287

Met Lys Ser Phe Leu Leu Val Val Asn Ala Leu Ala Leu Thr Leu Pro
1               5                   10                  15

Phe Leu Ala Val
            20

<210> SEQ ID NO 288

```
<211> LENGTH: 20
<212> TYPE: PRT
<213> ORGANISM: Homo sapiens

<400> SEQUENCE: 288

Met Arg Ala Leu Leu Ala Arg Leu Leu Leu Cys Val Leu Val Val Ser
1               5                   10                  15

Asp Ser Lys Gly
            20

<210> SEQ ID NO 289
<211> LENGTH: 20
<212> TYPE: PRT
<213> ORGANISM: Homo sapiens

<400> SEQUENCE: 289

Met Phe Leu Lys Ala Val Val Leu Thr Leu Ala Leu Val Ala Val Ala
1               5                   10                  15

Gly Ala Arg Ala
            20

<210> SEQ ID NO 290
<211> LENGTH: 20
<212> TYPE: PRT
<213> ORGANISM: Homo sapiens

<400> SEQUENCE: 290

Met Glu Ala Pro Ala Gln Leu Leu Phe Leu Leu Leu Leu Trp Leu Pro
1               5                   10                  15

Asp Thr Thr Gly
            20

<210> SEQ ID NO 291
<211> LENGTH: 20
<212> TYPE: PRT
<213> ORGANISM: Homo sapiens

<400> SEQUENCE: 291

Ile Phe Ala Ser Leu Leu Arg Ala Val Ile Ala Ser Ile Cys Val Val
1               5                   10                  15

Ser Ser Met Ala
            20

<210> SEQ ID NO 292
<211> LENGTH: 20
<212> TYPE: PRT
<213> ORGANISM: Homo sapiens

<400> SEQUENCE: 292

Met Leu Pro Pro Gly Thr Ala Thr Leu Leu Thr Leu Leu Leu Ala Ala
1               5                   10                  15

Gly Ser Leu Gly
            20

<210> SEQ ID NO 293
<211> LENGTH: 20
<212> TYPE: PRT
<213> ORGANISM: Homo sapiens

<400> SEQUENCE: 293

Met Phe Ile Asn Ile Lys Ser Ile Leu Trp Met Cys Ser Thr Leu Ile
1               5                   10                  15
```

```
Val Thr His Ala
        20

<210> SEQ ID NO 294
<211> LENGTH: 20
<212> TYPE: PRT
<213> ORGANISM: Homo sapiens

<400> SEQUENCE: 294

Met Asp Arg His Ser Ser Tyr Ile Phe Ile Trp Leu Gln Leu Glu Leu
1               5                   10                  15

Cys Ala Met Ala
        20

<210> SEQ ID NO 295
<211> LENGTH: 20
<212> TYPE: PRT
<213> ORGANISM: Homo sapiens

<400> SEQUENCE: 295

Met Asn Ser Gly Val Cys Leu Cys Val Leu Met Ala Val Leu Ala Ala
1               5                   10                  15

Gly Ala Leu Thr
        20

<210> SEQ ID NO 296
<211> LENGTH: 20
<212> TYPE: PRT
<213> ORGANISM: Homo sapiens

<400> SEQUENCE: 296

Met Ser Leu Phe Pro Ser Leu Pro Leu Leu Leu Ser Met Val Ala
1               5                   10                  15

Ala Ser Tyr Ser
        20

<210> SEQ ID NO 297
<211> LENGTH: 20
<212> TYPE: PRT
<213> ORGANISM: Homo sapiens

<400> SEQUENCE: 297

Met Gly Ser Gln Val His Leu Leu Ser Phe Leu Leu Leu Trp Ile Ser
1               5                   10                  15

Asp Thr Arg Ala
        20

<210> SEQ ID NO 298
<211> LENGTH: 20
<212> TYPE: PRT
<213> ORGANISM: Homo sapiens

<400> SEQUENCE: 298

Met Val Tyr Lys Thr Leu Phe Ala Leu Cys Ile Leu Thr Ala Gly Trp
1               5                   10                  15

Arg Val Gln Ser
        20

<210> SEQ ID NO 299
<211> LENGTH: 20
<212> TYPE: PRT
<213> ORGANISM: Homo sapiens
```

```
<400> SEQUENCE: 299

Met Asp Cys Gln Leu Ser Ile Leu Leu Leu Ser Cys Ser Val Leu
1               5                   10                  15

Asp Ser Phe Gly
            20

<210> SEQ ID NO 300
<211> LENGTH: 20
<212> TYPE: PRT
<213> ORGANISM: Homo sapiens

<400> SEQUENCE: 300

Met Trp Lys Arg Trp Leu Ala Leu Ala Leu Val Ala Val Ala
1               5                   10                  15

Trp Val Arg Ala
            20

<210> SEQ ID NO 301
<211> LENGTH: 20
<212> TYPE: PRT
<213> ORGANISM: Homo sapiens

<400> SEQUENCE: 301

Met Glu Lys Ile Pro Val Ser Ala Phe Leu Leu Leu Val Ala Leu Ser
1               5                   10                  15

Tyr Thr Leu Ala
            20

<210> SEQ ID NO 302
<211> LENGTH: 20
<212> TYPE: PRT
<213> ORGANISM: Homo sapiens

<400> SEQUENCE: 302

Met Gln Pro Arg Val Leu Leu Val Val Ala Leu Leu Ala Leu Leu Ala
1               5                   10                  15

Ser Ala Arg Ala
            20

<210> SEQ ID NO 303
<211> LENGTH: 20
<212> TYPE: PRT
<213> ORGANISM: Homo sapiens

<400> SEQUENCE: 303

Met Arg Leu Pro Ala Gln Leu Leu Gly Leu Leu Met Leu Trp Val Pro
1               5                   10                  15

Gly Ser Ser Gly
            20

<210> SEQ ID NO 304
<211> LENGTH: 20
<212> TYPE: PRT
<213> ORGANISM: Homo sapiens

<400> SEQUENCE: 304

Met Lys Phe Leu Ala Val Leu Val Leu Leu Gly Val Ser Ile Phe Leu
1               5                   10                  15

Val Ser Ala Gln
            20
```

```
<210> SEQ ID NO 305
<211> LENGTH: 20
<212> TYPE: PRT
<213> ORGANISM: Homo sapiens

<400> SEQUENCE: 305

Met Val Lys Tyr Leu Leu Leu Ser Ile Leu Gly Leu Ala Phe Leu Ser
1               5                   10                  15

Glu Ala Ala Ala
            20

<210> SEQ ID NO 306
<211> LENGTH: 20
<212> TYPE: PRT
<213> ORGANISM: Homo sapiens

<400> SEQUENCE: 306

Met Ala Gln His Leu Ser Thr Leu Leu Leu Leu Ala Thr Leu Ala
1               5                   10                  15

Val Ala Leu Ala
            20

<210> SEQ ID NO 307
<211> LENGTH: 20
<212> TYPE: PRT
<213> ORGANISM: Homo sapiens

<400> SEQUENCE: 307

Met Lys Leu Ala Ala Leu Leu Gly Leu Cys Val Ala Leu Ser Cys Ser
1               5                   10                  15

Ser Ala Ala Ala
            20

<210> SEQ ID NO 308
<211> LENGTH: 20
<212> TYPE: PRT
<213> ORGANISM: Homo sapiens

<400> SEQUENCE: 308

Met Leu Leu Leu Leu Val Pro Val Leu Glu Val Ile Phe Thr Leu Gly
1               5                   10                  15

Gly Thr Arg Ala
            20

<210> SEQ ID NO 309
<211> LENGTH: 20
<212> TYPE: PRT
<213> ORGANISM: Homo sapiens

<400> SEQUENCE: 309

Met Glu Thr Pro Ala Gln Leu Leu Phe Leu Leu Leu Leu Trp Leu Pro
1               5                   10                  15

Asp Thr Thr Gly
            20

<210> SEQ ID NO 310
<211> LENGTH: 20
<212> TYPE: PRT
<213> ORGANISM: Homo sapiens

<400> SEQUENCE: 310

Met Ala Trp Thr Pro Leu Phe Leu Phe Leu Leu Thr Cys Cys Pro Gly
1               5                   10                  15
```

Gly Ser Asn Ser
            20

<210> SEQ ID NO 311
<211> LENGTH: 20
<212> TYPE: PRT
<213> ORGANISM: Homo sapiens

<400> SEQUENCE: 311

Met Pro Leu Gly Leu Leu Trp Leu Gly Leu Ala Leu Leu Gly Ala Leu
 1               5                  10                  15

His Ala Gln Ala
            20

<210> SEQ ID NO 312
<211> LENGTH: 20
<212> TYPE: PRT
<213> ORGANISM: Homo sapiens

<400> SEQUENCE: 312

Met Ser Pro Phe Leu Tyr Leu Val Leu Leu Val Leu Gly Leu His Ala
 1               5                  10                  15

Thr Ile His Cys
            20

<210> SEQ ID NO 313
<211> LENGTH: 20
<212> TYPE: PRT
<213> ORGANISM: Homo sapiens

<400> SEQUENCE: 313

Met Gly Pro Leu Met Val Leu Phe Cys Leu Leu Phe Leu Tyr Pro Gly
 1               5                  10                  15

Leu Ala Asp Ser
            20

<210> SEQ ID NO 314
<211> LENGTH: 20
<212> TYPE: PRT
<213> ORGANISM: Homo sapiens

<400> SEQUENCE: 314

Met Arg Leu Lys Asn Leu Thr Phe Ile Ile Leu Ile Ile Ser Gly
 1               5                  10                  15

Glu Leu Tyr Ala
            20

<210> SEQ ID NO 315
<211> LENGTH: 20
<212> TYPE: PRT
<213> ORGANISM: Homo sapiens

<400> SEQUENCE: 315

Met Ser Cys Pro Val Pro Ala Cys Cys Ala Leu Leu Leu Val Leu Gly
 1               5                  10                  15

Leu Cys Arg Ala
            20

<210> SEQ ID NO 316
<211> LENGTH: 20
<212> TYPE: PRT
<213> ORGANISM: Homo sapiens

<400> SEQUENCE: 316

Met Val Arg Leu Pro Leu Gln Cys Val Leu Trp Gly Cys Leu Leu Thr
1               5                   10                  15

Ala Val His Pro
            20

<210> SEQ ID NO 317
<211> LENGTH: 20
<212> TYPE: PRT
<213> ORGANISM: Homo sapiens

<400> SEQUENCE: 317

Met Val Leu Gln Thr Gln Val Phe Ile Ser Leu Leu Leu Trp Ile Ser
1               5                   10                  15

Gly Ala Tyr Gly
            20

<210> SEQ ID NO 318
<211> LENGTH: 20
<212> TYPE: PRT
<213> ORGANISM: Homo sapiens

<400> SEQUENCE: 318

Met Lys Met Trp Leu Leu Val Ser His Leu Val Ile Ile Ser Ile Thr
1               5                   10                  15

Thr Cys Leu Ala
            20

<210> SEQ ID NO 319
<211> LENGTH: 20
<212> TYPE: PRT
<213> ORGANISM: Homo sapiens

<400> SEQUENCE: 319

Met Tyr Lys Leu Ala Ser Cys Cys Leu Leu Phe Ile Gly Phe Leu Asn
1               5                   10                  15

Pro Leu Leu Ser
            20

<210> SEQ ID NO 320
<211> LENGTH: 20
<212> TYPE: PRT
<213> ORGANISM: Homo sapiens

<400> SEQUENCE: 320

Met Gln His Arg Gly Phe Leu Leu Thr Leu Leu Ala Leu Leu Ala
1               5                   10                  15

Leu Thr Ser Ala
            20

<210> SEQ ID NO 321
<211> LENGTH: 20
<212> TYPE: PRT
<213> ORGANISM: Homo sapiens

<400> SEQUENCE: 321

Met Asn Val Leu Leu Gly Ser Val Val Ile Phe Ala Thr Phe Val Thr
1               5                   10                  15

Leu Cys Asn Ala
            20

```
<210> SEQ ID NO 322
<211> LENGTH: 20
<212> TYPE: PRT
<213> ORGANISM: Homo sapiens

<400> SEQUENCE: 322

Met Glu Met Phe Gln Gly Leu Leu Leu Leu Leu Leu Ser Met Gly
1               5                   10                  15

Gly Thr Trp Ala
            20

<210> SEQ ID NO 323
<211> LENGTH: 20
<212> TYPE: PRT
<213> ORGANISM: Homo sapiens

<400> SEQUENCE: 323

Met Gly Asp His Leu Asp Leu Leu Gly Val Val Leu Met Ala Gly
1               5                   10                  15

Pro Val Phe Gly
            20

<210> SEQ ID NO 324
<211> LENGTH: 20
<212> TYPE: PRT
<213> ORGANISM: Homo sapiens

<400> SEQUENCE: 324

Met Ala Ser His Arg Leu Leu Leu Cys Leu Ala Gly Leu Val Phe
1               5                   10                  15

Val Ser Glu Ala
            20

<210> SEQ ID NO 325
<211> LENGTH: 20
<212> TYPE: PRT
<213> ORGANISM: Homo sapiens

<400> SEQUENCE: 325

Met Glu Thr Pro Ala Gln Leu Leu Phe Leu Leu Leu Trp Leu Pro
1               5                   10                  15

Asp Thr Thr Gly
            20

<210> SEQ ID NO 326
<211> LENGTH: 20
<212> TYPE: PRT
<213> ORGANISM: Homo sapiens

<400> SEQUENCE: 326

Met Ala Arg Pro Leu Cys Thr Leu Leu Leu Met Ala Thr Leu Ala
1               5                   10                  15

Gly Ala Leu Ala
            20

<210> SEQ ID NO 327
<211> LENGTH: 20
<212> TYPE: PRT
<213> ORGANISM: Homo sapiens

<400> SEQUENCE: 327

Met Gly Leu Pro Gly Leu Phe Cys Leu Ala Val Leu Ala Ala Ser Ser
```

```
                1               5                  10                 15

Phe Ser Lys Ala
                20

<210> SEQ ID NO 328
<211> LENGTH: 20
<212> TYPE: PRT
<213> ORGANISM: Homo sapiens

<400> SEQUENCE: 328

Met Asn Leu Gln Pro Ile Phe Trp Ile Gly Leu Ile Ser Ser Val Cys
1               5                   10                  15

Cys Val Phe Ala
                20

<210> SEQ ID NO 329
<211> LENGTH: 20
<212> TYPE: PRT
<213> ORGANISM: Homo sapiens

<400> SEQUENCE: 329

Met Thr Ile Leu Gly Thr Thr Phe Gly Met Val Phe Ser Leu Leu Gln
1               5                   10                  15

Val Val Ser Gly
                20

<210> SEQ ID NO 330
<211> LENGTH: 20
<212> TYPE: PRT
<213> ORGANISM: Homo sapiens

<400> SEQUENCE: 330

Met Leu Arg Met Arg Val Pro Ala Leu Leu Val Leu Leu Phe Cys Phe
1               5                   10                  15

Arg Gly Arg Ala
                20

<210> SEQ ID NO 331
<211> LENGTH: 20
<212> TYPE: PRT
<213> ORGANISM: Homo sapiens

<400> SEQUENCE: 331

Met Val Leu Gln Thr Gln Val Phe Ile Ser Leu Leu Leu Trp Ile Ser
1               5                   10                  15

Gly Ala Tyr Gly
                20

<210> SEQ ID NO 332
<211> LENGTH: 20
<212> TYPE: PRT
<213> ORGANISM: Homo sapiens

<400> SEQUENCE: 332

Met Glu Met Leu Gln Gly Leu Leu Leu Leu Leu Leu Ser Met Gly
1               5                   10                  15

Gly Ala Trp Ala
                20

<210> SEQ ID NO 333
<211> LENGTH: 20
<212> TYPE: PRT
```

```
<213> ORGANISM: Homo sapiens

<400> SEQUENCE: 333

Met Lys Thr Leu Leu Leu Ala Val Ile Met Ile Phe Gly Leu Leu
1               5                   10                  15
Gln Ala His Gly
            20

<210> SEQ ID NO 334
<211> LENGTH: 20
<212> TYPE: PRT
<213> ORGANISM: Homo sapiens

<400> SEQUENCE: 334

Met Arg Thr Leu Ala Cys Leu Leu Leu Gly Cys Gly Tyr Leu Ala
1               5                   10                  15
His Val Leu Ala
            20

<210> SEQ ID NO 335
<211> LENGTH: 20
<212> TYPE: PRT
<213> ORGANISM: Homo sapiens

<400> SEQUENCE: 335

Met Val Met Leu Leu Leu Leu Ser Ala Leu Ala Gly Leu Phe Gly
1               5                   10                  15
Ala Ala Glu Gly
            20

<210> SEQ ID NO 336
<211> LENGTH: 20
<212> TYPE: PRT
<213> ORGANISM: Homo sapiens

<400> SEQUENCE: 336

Met Ala Arg Ala Pro Leu Gly Val Leu Leu Leu Gly Leu Leu Gly
1               5                   10                  15
Arg Gly Val Gly
            20

<210> SEQ ID NO 337
<211> LENGTH: 20
<212> TYPE: PRT
<213> ORGANISM: Homo sapiens

<400> SEQUENCE: 337

Met Ala Leu Leu Leu Thr Thr Val Ile Ala Leu Thr Cys Leu Gly Gly
1               5                   10                  15
Phe Ala Ser Pro
            20

<210> SEQ ID NO 338
<211> LENGTH: 20
<212> TYPE: PRT
<213> ORGANISM: Homo sapiens

<400> SEQUENCE: 338

Met Arg Thr Ala Leu Leu Leu Ala Ala Leu Ala Val Ala Thr Gly
1               5                   10                  15
Pro Ala Leu Thr
            20
```

-continued

```
<210> SEQ ID NO 339
<211> LENGTH: 21
<212> TYPE: PRT
<213> ORGANISM: Homo sapiens

<400> SEQUENCE: 339

Met Ala Ala Ala Leu Phe Val Leu Leu Gly Phe Ala Leu Leu Gly Thr
1               5                   10                  15

His Gly Ala Ser Gly
            20

<210> SEQ ID NO 340
<211> LENGTH: 21
<212> TYPE: PRT
<213> ORGANISM: Homo sapiens

<400> SEQUENCE: 340

Met Arg Leu Leu Ile Leu Ala Leu Leu Gly Ile Cys Ser Leu Thr Ala
1               5                   10                  15

Tyr Ile Val Glu Gly
            20

<210> SEQ ID NO 341
<211> LENGTH: 21
<212> TYPE: PRT
<213> ORGANISM: Homo sapiens

<400> SEQUENCE: 341

Met Lys Leu Val Ser Val Ala Leu Met Tyr Leu Gly Ser Leu Ala Phe
1               5                   10                  15

Leu Gly Ala Asp Thr
            20

<210> SEQ ID NO 342
<211> LENGTH: 21
<212> TYPE: PRT
<213> ORGANISM: Homo sapiens

<400> SEQUENCE: 342

Met Lys Phe Gln Gly Pro Leu Ala Cys Leu Leu Leu Ala Leu Cys Leu
1               5                   10                  15

Gly Ser Gly Glu Ala
            20

<210> SEQ ID NO 343
<211> LENGTH: 21
<212> TYPE: PRT
<213> ORGANISM: Homo sapiens

<400> SEQUENCE: 343

Met Glu Leu Thr Glu Leu Leu Leu Val Val Met Leu Leu Leu Thr Ala
1               5                   10                  15

Arg Leu Thr Leu Ser
            20

<210> SEQ ID NO 344
<211> LENGTH: 21
<212> TYPE: PRT
<213> ORGANISM: Homo sapiens

<400> SEQUENCE: 344
```

```
Met Trp Ala Thr Gln Gly Leu Ala Val Ala Leu Ala Leu Ser Val Leu
1               5                   10                  15

Pro Gly Ser Arg Ala
            20
```

<210> SEQ ID NO 345
<211> LENGTH: 21
<212> TYPE: PRT
<213> ORGANISM: Homo sapiens

<400> SEQUENCE: 345

```
Met Arg Ala Leu Trp Val Leu Gly Leu Cys Cys Val Leu Leu Thr Phe
1               5                   10                  15

Gly Ser Val Arg Ala
            20
```

<210> SEQ ID NO 346
<211> LENGTH: 21
<212> TYPE: PRT
<213> ORGANISM: Homo sapiens

<400> SEQUENCE: 346

```
Met Ala Pro Arg Ser Leu Leu Leu Leu Ser Gly Ala Leu Ala Leu
1               5                   10                  15

Thr Asp Thr Trp Ala
            20
```

<210> SEQ ID NO 347
<211> LENGTH: 21
<212> TYPE: PRT
<213> ORGANISM: Homo sapiens

<400> SEQUENCE: 347

```
Met Ala Ala Arg Ala Leu Cys Met Leu Gly Leu Val Leu Ala Leu Leu
1               5                   10                  15

Ser Ser Ser Ser Ala
            20
```

<210> SEQ ID NO 348
<211> LENGTH: 21
<212> TYPE: PRT
<213> ORGANISM: Homo sapiens

<400> SEQUENCE: 348

```
Met Ala Ala Arg Leu Leu Leu Leu Gly Ile Leu Leu Leu Leu Pro
1               5                   10                  15

Leu Pro Val Pro Ala
            20
```

<210> SEQ ID NO 349
<211> LENGTH: 21
<212> TYPE: PRT
<213> ORGANISM: Homo sapiens

<400> SEQUENCE: 349

```
Met Ala Leu Leu Phe Pro Leu Leu Ala Ala Leu Val Met Thr Ser Tyr
1               5                   10                  15

Ser Pro Val Gly Ser
            20
```

<210> SEQ ID NO 350
<211> LENGTH: 21

```
<212> TYPE: PRT
<213> ORGANISM: Homo sapiens

<400> SEQUENCE: 350

Met Leu Pro Leu Cys Leu Val Ala Ala Leu Leu Ala Ala Gly Pro
1               5                   10                  15

Gly Pro Ser Leu Gly
            20

<210> SEQ ID NO 351
<211> LENGTH: 21
<212> TYPE: PRT
<213> ORGANISM: Homo sapiens

<400> SEQUENCE: 351

Met Asn Gln Thr Ala Ile Leu Ile Cys Cys Leu Ile Phe Leu Thr Leu
1               5                   10                  15

Ser Gly Ile Gln Gly
            20

<210> SEQ ID NO 352
<211> LENGTH: 21
<212> TYPE: PRT
<213> ORGANISM: Homo sapiens

<400> SEQUENCE: 352

Met Lys Val Val Pro Ser Leu Leu Leu Ser Val Leu Leu Ala Gln Val
1               5                   10                  15

Trp Leu Val Pro Gly
            20

<210> SEQ ID NO 353
<211> LENGTH: 21
<212> TYPE: PRT
<213> ORGANISM: Homo sapiens

<400> SEQUENCE: 353

Met Glu Ser Arg Val Leu Leu Arg Thr Phe Cys Leu Ile Phe Gly Leu
1               5                   10                  15

Gly Ala Val Trp Gly
            20

<210> SEQ ID NO 354
<211> LENGTH: 21
<212> TYPE: PRT
<213> ORGANISM: Homo sapiens

<400> SEQUENCE: 354

Met Trp Arg Cys Pro Leu Gly Leu Leu Leu Leu Pro Leu Ala Gly
1               5                   10                  15

His Leu Ala Leu Gly
            20

<210> SEQ ID NO 355
<211> LENGTH: 21
<212> TYPE: PRT
<213> ORGANISM: Homo sapiens

<400> SEQUENCE: 355

Met Met Leu His Ser Ala Leu Gly Leu Cys Leu Leu Leu Val Thr Val
1               5                   10                  15

Ser Ser Asn Leu Ala
```

-continued

```
                20

<210> SEQ ID NO 356
<211> LENGTH: 21
<212> TYPE: PRT
<213> ORGANISM: Homo sapiens

<400> SEQUENCE: 356

Met Ser Gly Ala Arg Ser Lys Leu Ala Leu Phe Leu Cys Gly Cys Tyr
1               5                   10                  15

Val Val Ala Leu Gly
            20

<210> SEQ ID NO 357
<211> LENGTH: 21
<212> TYPE: PRT
<213> ORGANISM: Homo sapiens

<400> SEQUENCE: 357

Met Glu Ile Lys His Leu Leu Phe Leu Val Ala Ala Ala Cys Leu Leu
1               5                   10                  15

Pro Met Leu Ser Met
            20

<210> SEQ ID NO 358
<211> LENGTH: 21
<212> TYPE: PRT
<213> ORGANISM: Homo sapiens

<400> SEQUENCE: 358

Met Trp Val Ser Trp Ala Pro Gly Leu Trp Leu Leu Gly Leu Trp Ala
1               5                   10                  15

Thr Phe Gly His Gly
            20

<210> SEQ ID NO 359
<211> LENGTH: 21
<212> TYPE: PRT
<213> ORGANISM: Homo sapiens

<400> SEQUENCE: 359

Met Leu Pro Cys Leu Val Val Leu Leu Ala Ala Leu Leu Ser Leu Arg
1               5                   10                  15

Leu Gly Ser Asp Ala
            20

<210> SEQ ID NO 360
<211> LENGTH: 21
<212> TYPE: PRT
<213> ORGANISM: Homo sapiens

<400> SEQUENCE: 360

Met Ala Thr Ser Met Gly Leu Leu Leu Leu Leu Leu Leu Leu Leu Thr
1               5                   10                  15

Gln Pro Gly Ala Gly
            20

<210> SEQ ID NO 361
<211> LENGTH: 21
<212> TYPE: PRT
<213> ORGANISM: Homo sapiens

<400> SEQUENCE: 361
```

```
Met Ile Ala Ser Gln Phe Leu Ser Ala Leu Thr Leu Val Leu Leu Ile
1               5                   10                  15

Lys Glu Ser Gly Ala
            20

<210> SEQ ID NO 362
<211> LENGTH: 21
<212> TYPE: PRT
<213> ORGANISM: Homo sapiens

<400> SEQUENCE: 362

Met Asn Ala Phe Leu Leu Phe Ala Leu Cys Leu Leu Gly Ala Trp Ala
1               5                   10                  15

Ala Leu Ala Gly Gly
            20

<210> SEQ ID NO 363
<211> LENGTH: 21
<212> TYPE: PRT
<213> ORGANISM: Homo sapiens

<400> SEQUENCE: 363

Met Ala Leu Pro Val Thr Ala Leu Leu Leu Pro Leu Ala Leu Leu Leu
1               5                   10                  15

His Ala Ala Arg Pro
            20

<210> SEQ ID NO 364
<211> LENGTH: 21
<212> TYPE: PRT
<213> ORGANISM: Homo sapiens

<400> SEQUENCE: 364

Met Gly Leu Ser Thr Val Pro Asp Leu Leu Leu Pro Leu Val Leu Leu
1               5                   10                  15

Glu Leu Leu Val Gly
            20

<210> SEQ ID NO 365
<211> LENGTH: 21
<212> TYPE: PRT
<213> ORGANISM: Homo sapiens

<400> SEQUENCE: 365

Met Lys Ala Leu Leu Ala Leu Pro Leu Leu Leu Leu Ser Thr Pro
1               5                   10                  15

Pro Cys Ala Pro Gln
            20

<210> SEQ ID NO 366
<211> LENGTH: 21
<212> TYPE: PRT
<213> ORGANISM: Homo sapiens

<400> SEQUENCE: 366

Met Ala Leu Leu Leu Ala Leu Ser Leu Leu Val Leu Trp Thr Ser Pro
1               5                   10                  15

Ala Pro Thr Leu Ser
            20

<210> SEQ ID NO 367
```

```
<211> LENGTH: 21
<212> TYPE: PRT
<213> ORGANISM: Homo sapiens

<400> SEQUENCE: 367

Met Gly Thr Ser Leu Leu Cys Trp Met Ala Leu Cys Leu Leu Gly Ala
1               5                   10                  15

Asp His Ala Asp Thr
            20

<210> SEQ ID NO 368
<211> LENGTH: 21
<212> TYPE: PRT
<213> ORGANISM: Homo sapiens

<400> SEQUENCE: 368

Met Gly Val Lys Ala Ser Gln Thr Gly Phe Val Val Leu Val Leu Leu
1               5                   10                  15

Gln Cys Cys Ser Ala
            20

<210> SEQ ID NO 369
<211> LENGTH: 21
<212> TYPE: PRT
<213> ORGANISM: Homo sapiens

<400> SEQUENCE: 369

Met Glu His Ser Thr Phe Leu Ser Gly Leu Val Leu Ala Thr Leu Leu
1               5                   10                  15

Ser Gln Val Ser Pro
            20

<210> SEQ ID NO 370
<211> LENGTH: 21
<212> TYPE: PRT
<213> ORGANISM: Homo sapiens

<400> SEQUENCE: 370

Met Ala Ala Ala Leu Ala Leu Val Ala Gly Val Leu Ser Gly Ala Val
1               5                   10                  15

Leu Pro Leu Trp Ser
            20

<210> SEQ ID NO 371
<211> LENGTH: 21
<212> TYPE: PRT
<213> ORGANISM: Homo sapiens

<400> SEQUENCE: 371

Met Arg Pro Arg Leu Trp Leu Leu Leu Ala Ala Gln Leu Thr Val Leu
1               5                   10                  15

His Gly Asn Ser Val
            20

<210> SEQ ID NO 372
<211> LENGTH: 21
<212> TYPE: PRT
<213> ORGANISM: Homo sapiens

<400> SEQUENCE: 372

Met Val Gly Lys Met Trp Pro Val Leu Trp Thr Leu Cys Ala Val Arg
1               5                   10                  15
```

Val Thr Val Asp Ala
            20

<210> SEQ ID NO 373
<211> LENGTH: 21
<212> TYPE: PRT
<213> ORGANISM: Homo sapiens

<400> SEQUENCE: 373

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 374
<211> LENGTH: 21
<212> TYPE: PRT
<213> ORGANISM: Homo sapiens

<400> SEQUENCE: 374

Met Glu Arg Gly Leu Pro Leu Leu Cys Ala Val Leu Ala Leu Val Leu
1               5                   10                  15

Ala Pro Ala Gly Ala
            20

<210> SEQ ID NO 375
<211> LENGTH: 21
<212> TYPE: PRT
<213> ORGANISM: Homo sapiens

<400> SEQUENCE: 375

Met Ser Val Lys Gly Met Ala Ile Ala Leu Ala Val Ile Leu Cys Ala
1               5                   10                  15

Thr Val Val Gln Gly
            20

<210> SEQ ID NO 376
<211> LENGTH: 21
<212> TYPE: PRT
<213> ORGANISM: Homo sapiens

<400> SEQUENCE: 376

Met Ile Cys Gln Lys Phe Cys Val Val Leu Leu His Trp Glu Phe Ile
1               5                   10                  15

Tyr Val Ile Thr Ala
            20

<210> SEQ ID NO 377
<211> LENGTH: 21
<212> TYPE: PRT
<213> ORGANISM: Homo sapiens

<400> SEQUENCE: 377

Met Lys Val Leu Ile Ser Ser Leu Leu Leu Leu Pro Leu Met Leu
1               5                   10                  15

Met Ser Met Val Ser
            20

<210> SEQ ID NO 378
<211> LENGTH: 21
<212> TYPE: PRT
<213> ORGANISM: Homo sapiens -continued

```
<400> SEQUENCE: 378

Met Gln Arg Leu Gly Ala Thr Leu Leu Cys Leu Leu Leu Ala Ala Ala
1               5                   10                  15

Val Pro Thr Ala Pro
            20

<210> SEQ ID NO 379
<211> LENGTH: 21
<212> TYPE: PRT
<213> ORGANISM: Homo sapiens

<400> SEQUENCE: 379

Met Ala Leu Pro Phe Val Leu Leu Met Ala Leu Val Val Leu Asn Cys
1               5                   10                  15

Lys Ser Ile Cys Ser
            20

<210> SEQ ID NO 380
<211> LENGTH: 21
<212> TYPE: PRT
<213> ORGANISM: Homo sapiens

<400> SEQUENCE: 380

Met Asp Ser Tyr Leu Leu Met Trp Gly Leu Leu Thr Phe Ile Met Val
1               5                   10                  15

Pro Gly Cys Gln Ala
            20

<210> SEQ ID NO 381
<211> LENGTH: 21
<212> TYPE: PRT
<213> ORGANISM: Homo sapiens

<400> SEQUENCE: 381

Met Ala Gln Gly Val Leu Trp Ile Leu Leu Gly Leu Leu Trp Ser
1               5                   10                  15

Asp Pro Gly Thr Ala
            20

<210> SEQ ID NO 382
<211> LENGTH: 21
<212> TYPE: PRT
<213> ORGANISM: Homo sapiens

<400> SEQUENCE: 382

Met Lys Pro Val Trp Val Ala Thr Leu Leu Trp Met Leu Leu Leu Val
1               5                   10                  15

Pro Arg Leu Gly Ala
            20

<210> SEQ ID NO 383
<211> LENGTH: 21
<212> TYPE: PRT
<213> ORGANISM: Homo sapiens

<400> SEQUENCE: 383

Met Ala Gln His His Leu Trp Ile Leu Leu Leu Cys Leu Gln Thr Trp
1               5                   10                  15

Pro Glu Ala Ala Gly
            20
```

-continued

<210> SEQ ID NO 384
<211> LENGTH: 21
<212> TYPE: PRT
<213> ORGANISM: Homo sapiens

<400> SEQUENCE: 384

Met Ser Met Leu Val Val Phe Leu Leu Leu Trp Gly Val Thr Trp Gly
1               5                   10                  15

Pro Val Thr Glu Ala
            20

<210> SEQ ID NO 385
<211> LENGTH: 21
<212> TYPE: PRT
<213> ORGANISM: Homo sapiens

<400> SEQUENCE: 385

Met Arg Leu Ser Val Cys Leu Leu Leu Thr Leu Ala Leu Cys Cys
1               5                   10                  15

Tyr Arg Ala Asn Ala
            20

<210> SEQ ID NO 386
<211> LENGTH: 21
<212> TYPE: PRT
<213> ORGANISM: Homo sapiens

<400> SEQUENCE: 386

Met Val Asp Gly Thr Leu Leu Leu Leu Ser Glu Ala Leu Ala Leu
1               5                   10                  15

Thr Gln Thr Trp Ala
            20

<210> SEQ ID NO 387
<211> LENGTH: 21
<212> TYPE: PRT
<213> ORGANISM: Homo sapiens

<400> SEQUENCE: 387

Met Ala Ser Arg Trp Ala Val Gln Leu Leu Val Ala Ala Trp Ser
1               5                   10                  15

Met Gly Cys Gly Glu
            20

<210> SEQ ID NO 388
<211> LENGTH: 21
<212> TYPE: PRT
<213> ORGANISM: Homo sapiens

<400> SEQUENCE: 388

Met Lys Leu Ala Val Thr Leu Thr Leu Val Thr Leu Ala Leu Cys Cys
1               5                   10                  15

Ser Ser Ala Ser Ala
            20

<210> SEQ ID NO 389
<211> LENGTH: 21
<212> TYPE: PRT
<213> ORGANISM: Homo sapiens

<400> SEQUENCE: 389

Met Leu Leu Ala Trp Val Gln Ala Phe Leu Val Ser Asn Met Leu Leu
1               5                   10                  15

Ala Glu Ala Tyr Gly
            20

<210> SEQ ID NO 390
<211> LENGTH: 21
<212> TYPE: PRT
<213> ORGANISM: Homo sapiens

<400> SEQUENCE: 390

Met Arg Pro Ala Phe Ala Leu Cys Leu Leu Trp Gln Ala Leu Trp Pro
 1               5                  10                  15

Gly Pro Gly Gly Gly
            20

<210> SEQ ID NO 391
<211> LENGTH: 21
<212> TYPE: PRT
<213> ORGANISM: Homo sapiens

<400> SEQUENCE: 391

Met Arg Leu Leu Leu Ala Leu Leu Gly Val Leu Leu Ser Val Pro Gly
 1               5                  10                  15

Pro Pro Val Leu Ser
            20

<210> SEQ ID NO 392
<211> LENGTH: 21
<212> TYPE: PRT
<213> ORGANISM: Homo sapiens

<400> SEQUENCE: 392

Met Ala Arg Arg Ser Val Leu Tyr Phe Ile Leu Leu Asn Ala Leu Ile
 1               5                  10                  15

Asn Lys Gly Gln Ala
            20

<210> SEQ ID NO 393
<211> LENGTH: 21
<212> TYPE: PRT
<213> ORGANISM: Homo sapiens

<400> SEQUENCE: 393

Met Arg Leu Ser Val Cys Leu Leu Met Val Ser Leu Ala Leu Cys Cys
 1               5                  10                  15

Tyr Gln Ala His Ala
            20

<210> SEQ ID NO 394
<211> LENGTH: 21
<212> TYPE: PRT
<213> ORGANISM: Homo sapiens

<400> SEQUENCE: 394

Met Ser Ala Val Leu Leu Leu Ala Leu Leu Gly Phe Ile Leu Pro Leu
 1               5                  10                  15

Pro Gly Val Gln Ala
            20

<210> SEQ ID NO 395
<211> LENGTH: 21
<212> TYPE: PRT
<213> ORGANISM: Homo sapiens

<400> SEQUENCE: 395

Met Arg Gly Leu Ala Val Leu Leu Thr Val Ala Leu Ala Thr Leu Leu
1               5                   10                  15

Ala Pro Gly Ala Gly
            20

<210> SEQ ID NO 396
<211> LENGTH: 21
<212> TYPE: PRT
<213> ORGANISM: Homo sapiens

<400> SEQUENCE: 396

Met Ser Leu Leu Val Val Ser Met Ala Cys Val Gly Phe Phe Leu Leu
1               5                   10                  15

Gln Gly Ala Trp Pro
            20

<210> SEQ ID NO 397
<211> LENGTH: 21
<212> TYPE: PRT
<213> ORGANISM: Homo sapiens

<400> SEQUENCE: 397

Met Lys Trp Lys Ala Leu Phe Thr Ala Ala Ile Leu Gln Ala Gln Leu
1               5                   10                  15

Pro Ile Thr Glu Ala
            20

<210> SEQ ID NO 398
<211> LENGTH: 21
<212> TYPE: PRT
<213> ORGANISM: Homo sapiens

<400> SEQUENCE: 398

Met Gln Gly Pro Pro Leu Leu Thr Ala Ala His Leu Leu Cys Val Cys
1               5                   10                  15

Thr Ala Ala Leu Ala
            20

<210> SEQ ID NO 399
<211> LENGTH: 21
<212> TYPE: PRT
<213> ORGANISM: Homo sapiens

<400> SEQUENCE: 399

Met Ala Ala Ala Met Pro Leu Ala Leu Leu Val Leu Leu Leu Leu Gly
1               5                   10                  15

Pro Gly Gly Trp Cys
            20

<210> SEQ ID NO 400
<211> LENGTH: 21
<212> TYPE: PRT
<213> ORGANISM: Homo sapiens

<400> SEQUENCE: 400

Met Pro Leu Arg Lys Met Lys Ile Pro Phe Leu Leu Leu Phe Phe Leu
1               5                   10                  15

Trp Glu Ala Glu Ser
            20

<210> SEQ ID NO 401
<211> LENGTH: 21
<212> TYPE: PRT
<213> ORGANISM: Homo sapiens

<400> SEQUENCE: 401

Met Leu Trp Leu Phe Gln Ser Leu Leu Phe Val Phe Cys Phe Gly Pro
1               5                   10                  15

Gly Asn Val Val Ser
            20

<210> SEQ ID NO 402
<211> LENGTH: 21
<212> TYPE: PRT
<213> ORGANISM: Homo sapiens

<400> SEQUENCE: 402

Met Glu Leu Trp Gly Ala Tyr Leu Leu Cys Leu Phe Ser Leu Leu
1               5                   10                  15

Thr Gln Val Thr Thr
            20

<210> SEQ ID NO 403
<211> LENGTH: 21
<212> TYPE: PRT
<213> ORGANISM: Homo sapiens

<400> SEQUENCE: 403

Met Lys Val Ser Val Ala Ala Leu Ser Cys Leu Met Leu Val Ala Val
1               5                   10                  15

Leu Gly Ser Gln Ala
            20

<210> SEQ ID NO 404
<211> LENGTH: 21
<212> TYPE: PRT
<213> ORGANISM: Homo sapiens

<400> SEQUENCE: 404

Met Arg Leu Ser Trp Phe Arg Val Leu Thr Val Leu Ser Ile Cys Leu
1               5                   10                  15

Ser Ala Val Ala Thr
            20

<210> SEQ ID NO 405
<211> LENGTH: 21
<212> TYPE: PRT
<213> ORGANISM: Homo sapiens

<400> SEQUENCE: 405

Met Met Pro Lys His Cys Phe Leu Gly Phe Leu Ile Ser Phe Phe Leu
1               5                   10                  15

Thr Gly Val Ala Gly
            20

<210> SEQ ID NO 406
<211> LENGTH: 21
<212> TYPE: PRT
<213> ORGANISM: Homo sapiens

<400> SEQUENCE: 406

Met Val Trp Arg Val Pro Pro Phe Leu Leu Pro Ile Leu Phe Leu Ala

```
                1               5                   10                  15

Ser His Val Gly Ala
                20

<210> SEQ ID NO 407
<211> LENGTH: 21
<212> TYPE: PRT
<213> ORGANISM: Homo sapiens

<400> SEQUENCE: 407

Met Ala Leu Thr Ala His Pro Ser Cys Leu Leu Ala Leu Leu Val Ala
1               5                   10                  15

Gly Leu Ala Gln Gly
                20

<210> SEQ ID NO 408
<211> LENGTH: 21
<212> TYPE: PRT
<213> ORGANISM: Homo sapiens

<400> SEQUENCE: 408

Met Val Pro Pro Lys Leu His Val Leu Phe Cys Leu Cys Gly Cys Leu
1               5                   10                  15

Ala Val Val Tyr Pro
                20

<210> SEQ ID NO 409
<211> LENGTH: 21
<212> TYPE: PRT
<213> ORGANISM: Homo sapiens

<400> SEQUENCE: 409

Met Asp Met Trp Thr Ala Leu Leu Ile Leu Gln Ala Leu Leu Leu Pro
1               5                   10                  15

Ser Leu Ala Asp Gly
                20

<210> SEQ ID NO 410
<211> LENGTH: 21
<212> TYPE: PRT
<213> ORGANISM: Homo sapiens

<400> SEQUENCE: 410

Met Gly Leu Leu Gln Leu Leu Ala Phe Ser Phe Leu Ala Leu Cys Arg
1               5                   10                  15

Ala Arg Val Arg Ala
                20

<210> SEQ ID NO 411
<211> LENGTH: 21
<212> TYPE: PRT
<213> ORGANISM: Homo sapiens

<400> SEQUENCE: 411

Met Asn Lys Leu Leu Cys Cys Ala Leu Val Phe Leu Asp Ile Ser Ile
1               5                   10                  15

Lys Trp Thr Thr Gln
                20

<210> SEQ ID NO 412
<211> LENGTH: 21
<212> TYPE: PRT
```

-continued

<213> ORGANISM: Homo sapiens

<400> SEQUENCE: 412

Met Lys Val Ser Val Ala Ala Leu Ser Cys Leu Met Leu Val Thr Ala
1               5                   10                  15
Leu Gly Ser Gln Ala
            20

<210> SEQ ID NO 413
<211> LENGTH: 21
<212> TYPE: PRT
<213> ORGANISM: Homo sapiens

<400> SEQUENCE: 413

Met Gln Ala Ala Trp Leu Leu Gly Ala Leu Val Val Pro Gln Leu Leu
1               5                   10                  15
Gly Phe Gly His Gly
            20

<210> SEQ ID NO 414
<211> LENGTH: 21
<212> TYPE: PRT
<213> ORGANISM: Homo sapiens

<400> SEQUENCE: 414

Met Gln Arg Leu Cys Val Tyr Val Leu Ile Phe Ala Leu Ala Leu Ala
1               5                   10                  15
Ala Phe Ser Glu Ala
            20

<210> SEQ ID NO 415
<211> LENGTH: 21
<212> TYPE: PRT
<213> ORGANISM: Homo sapiens

<400> SEQUENCE: 415

Met Gly Pro Trp Gly Trp Lys Leu Arg Trp Thr Val Ala Leu Leu Leu
1               5                   10                  15
Ala Ala Ala Gly Thr
            20

<210> SEQ ID NO 416
<211> LENGTH: 21
<212> TYPE: PRT
<213> ORGANISM: Homo sapiens

<400> SEQUENCE: 416

Met Ala Pro Leu Ala Leu His Leu Leu Val Leu Val Pro Ile Leu Leu
1               5                   10                  15
Ser Leu Val Ala Ser
            20

<210> SEQ ID NO 417
<211> LENGTH: 21
<212> TYPE: PRT
<213> ORGANISM: Homo sapiens

<400> SEQUENCE: 417

Met Ser Ala Cys Arg Ser Phe Ala Val Ala Ile Cys Ile Leu Glu Ile
1               5                   10                  15
Ser Ile Leu Thr Ala
            20

<210> SEQ ID NO 418
<211> LENGTH: 21
<212> TYPE: PRT
<213> ORGANISM: Homo sapiens

<400> SEQUENCE: 418

Met Leu Gly Gln Val Val Thr Leu Ile Leu Leu Leu Leu Lys Val
1               5                   10                  15

Tyr Gln Gly Lys Gly
            20

<210> SEQ ID NO 419
<211> LENGTH: 21
<212> TYPE: PRT
<213> ORGANISM: Homo sapiens

<400> SEQUENCE: 419

Met Val Arg Ser Val Ala Trp Ala Gly Phe Met Val Leu Leu Met Ile
1               5                   10                  15

Pro Trp Gly Ser Ala
            20

<210> SEQ ID NO 420
<211> LENGTH: 22
<212> TYPE: PRT
<213> ORGANISM: Homo sapiens

<400> SEQUENCE: 420

Met Gly His Pro Pro Leu Leu Pro Leu Leu Leu Leu His Thr Cys
1               5                   10                  15

Val Pro Ala Ser Trp Gly
            20

<210> SEQ ID NO 421
<211> LENGTH: 22
<212> TYPE: PRT
<213> ORGANISM: Homo sapiens

<400> SEQUENCE: 421

Met Ala Lys Val Phe Ser Phe Ile Leu Val Thr Thr Ala Leu Thr Met
1               5                   10                  15

Gly Arg Glu Ile Ser Ala
            20

<210> SEQ ID NO 422
<211> LENGTH: 22
<212> TYPE: PRT
<213> ORGANISM: Homo sapiens

<400> SEQUENCE: 422

Met Gln Ser Gly Thr His Trp Arg Val Leu Gly Leu Cys Leu Leu Ser
1               5                   10                  15

Val Gly Val Trp Gly Gln
            20

<210> SEQ ID NO 423
<211> LENGTH: 22
<212> TYPE: PRT
<213> ORGANISM: Homo sapiens

<400> SEQUENCE: 423

Met Arg Thr Pro Gly Pro Leu Pro Val Leu Leu Leu Leu Ala Gly
1               5                   10                  15

Ala Pro Ala Ala Arg Pro
            20

<210> SEQ ID NO 424
<211> LENGTH: 22
<212> TYPE: PRT
<213> ORGANISM: Homo sapiens

<400> SEQUENCE: 424

Met Glu Gln Gly Lys Gly Leu Ala Val Leu Ile Leu Ala Ile Ile Leu
1               5                   10                  15

Leu Gln Gly Thr Leu Ala
            20

<210> SEQ ID NO 425
<211> LENGTH: 22
<212> TYPE: PRT
<213> ORGANISM: Homo sapiens

<400> SEQUENCE: 425

Met Lys Val Ile Ser Leu Phe Ile Leu Val Gly Phe Ile Gly Glu Phe
1               5                   10                  15

Gln Ser Phe Ser Ser Ala
            20

<210> SEQ ID NO 426
<211> LENGTH: 22
<212> TYPE: PRT
<213> ORGANISM: Homo sapiens

<400> SEQUENCE: 426

Met Pro Leu Leu Leu Tyr Thr Cys Leu Leu Trp Leu Pro Thr Ser Gly
1               5                   10                  15

Leu Trp Thr Val Gln Ala
            20

<210> SEQ ID NO 427
<211> LENGTH: 22
<212> TYPE: PRT
<213> ORGANISM: Homo sapiens

<400> SEQUENCE: 427

Met Arg Ile His Tyr Leu Leu Phe Ala Leu Leu Phe Leu Phe Leu Val
1               5                   10                  15

Pro Val Pro Gly His Gly
            20

<210> SEQ ID NO 428
<211> LENGTH: 22
<212> TYPE: PRT
<213> ORGANISM: Homo sapiens

<400> SEQUENCE: 428

Met Ala Ser Arg Leu Thr Leu Leu Thr Leu Leu Leu Leu Leu Leu Ala
1               5                   10                  15

Gly Asp Arg Ala Ser Ser
            20

<210> SEQ ID NO 429
<211> LENGTH: 22

<212> TYPE: PRT
<213> ORGANISM: Homo sapiens

<400> SEQUENCE: 429

Met Cys Pro Ala Arg Ser Leu Leu Leu Val Ala Thr Leu Val Leu Leu
1               5                   10                  15

Asp His Leu Ser Leu Ala
            20

<210> SEQ ID NO 430
<211> LENGTH: 22
<212> TYPE: PRT
<213> ORGANISM: Homo sapiens

<400> SEQUENCE: 430

Met Gln Leu Thr Arg Cys Cys Phe Val Phe Leu Val Gln Gly Ser Leu
1               5                   10                  15

Tyr Leu Val Ile Cys Gly
            20

<210> SEQ ID NO 431
<211> LENGTH: 22
<212> TYPE: PRT
<213> ORGANISM: Homo sapiens

<400> SEQUENCE: 431

Met Ala Ser Ser Ile Arg Arg Gly Arg Gly Ala Trp Thr Arg Leu Leu
1               5                   10                  15

Ser Leu Leu Leu Leu Ala
            20

<210> SEQ ID NO 432
<211> LENGTH: 22
<212> TYPE: PRT
<213> ORGANISM: Homo sapiens

<400> SEQUENCE: 432

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 433
<211> LENGTH: 22
<212> TYPE: PRT
<213> ORGANISM: Homo sapiens

<400> SEQUENCE: 433

Met Asp Pro Ala Arg Pro Leu Gly Leu Ser Ile Leu Leu Leu Phe Leu
1               5                   10                  15

Thr Glu Ala Ala Leu Gly
            20

<210> SEQ ID NO 434
<211> LENGTH: 22
<212> TYPE: PRT
<213> ORGANISM: Homo sapiens

<400> SEQUENCE: 434

Met Ala Pro Pro Gly Ser Ser Thr Val Phe Leu Leu Ala Leu Thr Ile
1               5                   10                  15

Ile Ala Ser Thr Trp Ala

```
<210> SEQ ID NO 435
<211> LENGTH: 22
<212> TYPE: PRT
<213> ORGANISM: Homo sapiens

<400> SEQUENCE: 435

Met Asp Met Arg Val Pro Ala Gln Leu Leu Gly Leu Leu Leu Leu Trp
 1               5                  10                  15

Leu Arg Gly Ala Arg Cys
            20

<210> SEQ ID NO 436
<211> LENGTH: 22
<212> TYPE: PRT
<213> ORGANISM: Homo sapiens

<400> SEQUENCE: 436

Met Ala Thr His His Thr Leu Trp Met Gly Leu Ala Leu Leu Gly Val
 1               5                  10                  15

Leu Gly Asp Leu Gln Ala
            20

<210> SEQ ID NO 437
<211> LENGTH: 22
<212> TYPE: PRT
<213> ORGANISM: Homo sapiens

<400> SEQUENCE: 437

Met Ala Met Thr Trp Ile Val Phe Ser Leu Trp Pro Leu Thr Val Phe
 1               5                  10                  15

Met Gly His Ile Gly Gly
            20

<210> SEQ ID NO 438
<211> LENGTH: 22
<212> TYPE: PRT
<213> ORGANISM: Homo sapiens

<400> SEQUENCE: 438

Met Gly Pro Arg Ala Arg Pro Ala Leu Leu Leu Met Leu Leu Gln
 1               5                  10                  15

Thr Ala Val Leu Gln Gly
            20

<210> SEQ ID NO 439
<211> LENGTH: 22
<212> TYPE: PRT
<213> ORGANISM: Homo sapiens

<400> SEQUENCE: 439

Met Ala Pro Val Ala Val Trp Ala Ala Leu Ala Val Gly Leu Glu Leu
 1               5                  10                  15

Trp Ala Ala Ala His Ala
            20

<210> SEQ ID NO 440
<211> LENGTH: 22
<212> TYPE: PRT
<213> ORGANISM: Homo sapiens

<400> SEQUENCE: 440
```

```
Met Ala Arg Ala Pro Pro Leu Leu Ala Ala Leu Thr Ala Leu Leu Ala
1               5                   10                  15

Ala Ala Ala Ala Gly Gly
            20

<210> SEQ ID NO 441
<211> LENGTH: 22
<212> TYPE: PRT
<213> ORGANISM: Homo sapiens

<400> SEQUENCE: 441

Met Gly Ser Pro Gly Met Val Leu Gly Leu Leu Val Gln Ile Trp Ala
1               5                   10                  15

Leu Gln Glu Ala Ser Ser
            20

<210> SEQ ID NO 442
<211> LENGTH: 22
<212> TYPE: PRT
<213> ORGANISM: Homo sapiens

<400> SEQUENCE: 442

Met Ala Leu Gly Val Pro Ile Ser Val Tyr Leu Leu Phe Asn Ala Met
1               5                   10                  15

Thr Ala Leu Thr Glu Glu
            20

<210> SEQ ID NO 443
<211> LENGTH: 22
<212> TYPE: PRT
<213> ORGANISM: Homo sapiens

<400> SEQUENCE: 443

Met Ala Leu Lys Asn Lys Phe Ser Cys Leu Trp Ile Leu Gly Leu Cys
1               5                   10                  15

Leu Val Ala Thr Thr Ser
            20

<210> SEQ ID NO 444
<211> LENGTH: 22
<212> TYPE: PRT
<213> ORGANISM: Homo sapiens

<400> SEQUENCE: 444

Met Phe His Gln Ile Trp Ala Ala Leu Leu Tyr Phe Tyr Gly Ile Ile
1               5                   10                  15

Leu Asn Ser Ile Tyr Gln
            20

<210> SEQ ID NO 445
<211> LENGTH: 22
<212> TYPE: PRT
<213> ORGANISM: Homo sapiens

<400> SEQUENCE: 445

Met Leu Lys Pro Ser Leu Pro Phe Thr Ser Leu Leu Phe Leu Gln Leu
1               5                   10                  15

Pro Leu Leu Gly Val Gly
            20

<210> SEQ ID NO 446
```

```
<211> LENGTH: 22
<212> TYPE: PRT
<213> ORGANISM: Homo sapiens

<400> SEQUENCE: 446

Met Asp Ala Met Lys Arg Gly Leu Cys Cys Val Leu Leu Cys Gly
1               5                   10                  15

Ala Val Phe Val Ser Pro
            20

<210> SEQ ID NO 447
<211> LENGTH: 22
<212> TYPE: PRT
<213> ORGANISM: Homo sapiens

<400> SEQUENCE: 447

Met Glu Gly Pro Arg Gly Trp Leu Val Leu Cys Val Leu Ala Ile Ser
1               5                   10                  15

Leu Ala Ser Met Val Thr
            20

<210> SEQ ID NO 448
<211> LENGTH: 22
<212> TYPE: PRT
<213> ORGANISM: Homo sapiens

<400> SEQUENCE: 448

Met Gly Ala Met Thr Gln Leu Leu Ala Gly Val Phe Leu Ala Phe Leu
1               5                   10                  15

Ala Leu Ala Thr Glu Gly
            20

<210> SEQ ID NO 449
<211> LENGTH: 22
<212> TYPE: PRT
<213> ORGANISM: Homo sapiens

<400> SEQUENCE: 449

Met Leu Thr Leu Gln Thr Trp Leu Val Gln Ala Leu Phe Ile Phe Leu
1               5                   10                  15

Thr Thr Glu Ser Thr Gly
            20

<210> SEQ ID NO 450
<211> LENGTH: 22
<212> TYPE: PRT
<213> ORGANISM: Homo sapiens

<400> SEQUENCE: 450

Met Lys Val Leu Ala Ala Gly Val Val Pro Leu Leu Leu Val Leu His
1               5                   10                  15

Trp Lys His Gly Ala Gly
            20

<210> SEQ ID NO 451
<211> LENGTH: 22
<212> TYPE: PRT
<213> ORGANISM: Homo sapiens

<400> SEQUENCE: 451

Met Leu Gly Pro Cys Met Leu Leu Leu Leu Leu Leu Leu Gly Leu Arg
1               5                   10                  15
```

-continued

Leu Gln Leu Ser Leu Gly
            20

<210> SEQ ID NO 452
<211> LENGTH: 22
<212> TYPE: PRT
<213> ORGANISM: Homo sapiens

<400> SEQUENCE: 452

Met Lys Ser Leu Thr Trp Ile Leu Gly Leu Trp Ala Leu Ala Ala Cys
1               5                   10                  15

Phe Thr Pro Gly Glu Ser
            20

<210> SEQ ID NO 453
<211> LENGTH: 22
<212> TYPE: PRT
<213> ORGANISM: Homo sapiens

<400> SEQUENCE: 453

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 454
<211> LENGTH: 22
<212> TYPE: PRT
<213> ORGANISM: Homo sapiens

<400> SEQUENCE: 454

Met Ala Gln Thr Ser Ser Tyr Phe Met Leu Ile Ser Cys Leu Met Phe
1               5                   10                  15

Leu Ser Gln Ser Gln Gly
            20

<210> SEQ ID NO 455
<211> LENGTH: 22
<212> TYPE: PRT
<213> ORGANISM: Homo sapiens

<400> SEQUENCE: 455

Met Ala Asn Leu Gly Cys Trp Met Leu Val Leu Phe Val Ala Thr Trp
1               5                   10                  15

Ser Asp Leu Gly Leu Cys
            20

<210> SEQ ID NO 456
<211> LENGTH: 22
<212> TYPE: PRT
<213> ORGANISM: Homo sapiens

<400> SEQUENCE: 456

Met Cys His Gln Gln Leu Val Ile Ser Trp Phe Ser Leu Val Phe Leu
1               5                   10                  15

Ala Ser Pro Leu Val Ala
            20

<210> SEQ ID NO 457
<211> LENGTH: 22
<212> TYPE: PRT
<213> ORGANISM: Homo sapiens -continued

```
<400> SEQUENCE: 457

Met Trp Ala Thr Leu Pro Leu Leu Cys Ala Gly Ala Trp Leu Leu Gly
1               5                   10                  15

Val Pro Val Cys Gly Ala
            20

<210> SEQ ID NO 458
<211> LENGTH: 22
<212> TYPE: PRT
<213> ORGANISM: Homo sapiens

<400> SEQUENCE: 458

Met Ile Pro Ala Arg Phe Ala Gly Val Leu Leu Ala Leu Ala Leu Ile
1               5                   10                  15

Leu Pro Gly Thr Leu Cys
            20

<210> SEQ ID NO 459
<211> LENGTH: 22
<212> TYPE: PRT
<213> ORGANISM: Homo sapiens

<400> SEQUENCE: 459

Met Gly Glu Leu Met Ala Phe Leu Leu Pro Leu Ile Ile Val Leu Met
1               5                   10                  15

Val Lys His Ser Asp Ser
            20

<210> SEQ ID NO 460
<211> LENGTH: 22
<212> TYPE: PRT
<213> ORGANISM: Homo sapiens

<400> SEQUENCE: 460

Met Gly Thr Arg Leu Leu Pro Ala Leu Phe Leu Val Leu Leu Val Leu
1               5                   10                  15

Gly Phe Glu Val Gln Gly
            20

<210> SEQ ID NO 461
<211> LENGTH: 22
<212> TYPE: PRT
<213> ORGANISM: Homo sapiens

<400> SEQUENCE: 461

Met Thr Ser Ser Arg Leu Trp Phe Ser Leu Leu Leu Ala Ala Ala Phe
1               5                   10                  15

Ala Gly Arg Ala Thr Ala
            20

<210> SEQ ID NO 462
<211> LENGTH: 22
<212> TYPE: PRT
<213> ORGANISM: Homo sapiens

<400> SEQUENCE: 462

Met Asp Met Arg Val Leu Ala Gln Leu Leu Gly Leu Leu Leu Leu Cys
1               5                   10                  15

Phe Pro Gly Ala Arg Cys
            20
```

```
<210> SEQ ID NO 463
<211> LENGTH: 22
<212> TYPE: PRT
<213> ORGANISM: Homo sapiens

<400> SEQUENCE: 463

Met Ala Arg Ser Leu Leu Leu Pro Leu Gln Ile Leu Leu Leu Ser Leu
1               5                   10                  15

Ala Leu Glu Thr Ala Gly
            20

<210> SEQ ID NO 464
<211> LENGTH: 22
<212> TYPE: PRT
<213> ORGANISM: Homo sapiens

<400> SEQUENCE: 464

Met Glu Lys Lys Cys Thr Leu Tyr Phe Leu Val Leu Pro Phe Phe
1               5                   10                  15

Met Ile Leu Val Thr Ala
            20

<210> SEQ ID NO 465
<211> LENGTH: 22
<212> TYPE: PRT
<213> ORGANISM: Homo sapiens

<400> SEQUENCE: 465

Met Arg Val Leu Ser Gly Thr Ser Leu Met Leu Cys Ser Leu Leu Leu
1               5                   10                  15

Leu Leu Gln Ala Leu Cys
            20

<210> SEQ ID NO 466
<211> LENGTH: 22
<212> TYPE: PRT
<213> ORGANISM: Homo sapiens

<400> SEQUENCE: 466

Met Ala Gly Ser Pro Thr Cys Leu Thr Leu Ile Tyr Ile Leu Trp Gln
1               5                   10                  15

Leu Thr Gly Ser Ala Ala
            20

<210> SEQ ID NO 467
<211> LENGTH: 22
<212> TYPE: PRT
<213> ORGANISM: Homo sapiens

<400> SEQUENCE: 467

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 468
<211> LENGTH: 22
<212> TYPE: PRT
<213> ORGANISM: Homo sapiens

<400> SEQUENCE: 468

Met Asp Thr Ser Pro Leu Cys Phe Ser Ile Leu Leu Val Leu Cys Ile
1               5                   10                  15
```

-continued

Phe Ile Gln Ser Ser Ala
            20

<210> SEQ ID NO 469
<211> LENGTH: 22
<212> TYPE: PRT
<213> ORGANISM: Homo sapiens

<400> SEQUENCE: 469

Met Gly Pro Thr Ser Gly Pro Ser Leu Leu Leu Leu Leu Leu Thr His
1               5                   10                  15

Leu Pro Leu Ala Leu Gly
            20

<210> SEQ ID NO 470
<211> LENGTH: 22
<212> TYPE: PRT
<213> ORGANISM: Homo sapiens

<400> SEQUENCE: 470

Met Leu Gly Leu Arg Pro Pro Leu Leu Ala Leu Val Gly Leu Leu Ser
1               5                   10                  15

Leu Gly Cys Val Leu Ser
            20

<210> SEQ ID NO 471
<211> LENGTH: 22
<212> TYPE: PRT
<213> ORGANISM: Homo sapiens

<400> SEQUENCE: 471

Met Arg Gly Met Lys Leu Leu Gly Ala Leu Leu Ala Leu Ala Ala Leu
1               5                   10                  15

Leu Gln Gly Ala Val Ser
            20

<210> SEQ ID NO 472
<211> LENGTH: 22
<212> TYPE: PRT
<213> ORGANISM: Homo sapiens

<400> SEQUENCE: 472

Met Ala Ala Gly Thr Ala Val Gly Ala Trp Val Leu Val Leu Ser Leu
1               5                   10                  15

Trp Gly Ala Val Val Gly
            20

<210> SEQ ID NO 473
<211> LENGTH: 22
<212> TYPE: PRT
<213> ORGANISM: Homo sapiens

<400> SEQUENCE: 473

Met Val Met Arg Pro Leu Trp Ser Leu Leu Leu Trp Glu Ala Leu Leu
1               5                   10                  15

Pro Ile Thr Val Thr Gly
            20

<210> SEQ ID NO 474
<211> LENGTH: 22
<212> TYPE: PRT
<213> ORGANISM: Homo sapiens

```
<400> SEQUENCE: 474

Met Lys Lys Ser Gly Val Leu Phe Leu Leu Gly Ile Ile Leu Leu Val
1               5                   10                  15
Leu Ile Gly Val Gln Gly
            20

<210> SEQ ID NO 475
<211> LENGTH: 22
<212> TYPE: PRT
<213> ORGANISM: Homo sapiens

<400> SEQUENCE: 475

Met Gly Ala Pro Ala Cys Ala Leu Ala Leu Cys Val Ala Val Ala Ile
1               5                   10                  15
Val Ala Gly Ala Ser Ser
            20

<210> SEQ ID NO 476
<211> LENGTH: 22
<212> TYPE: PRT
<213> ORGANISM: Homo sapiens

<400> SEQUENCE: 476

Met Phe Ser Phe Val Asp Leu Arg Leu Leu Leu Leu Leu Ala Ala Thr
1               5                   10                  15
Ala Leu Leu Thr His Gly
            20

<210> SEQ ID NO 477
<211> LENGTH: 22
<212> TYPE: PRT
<213> ORGANISM: Homo sapiens

<400> SEQUENCE: 477

Met Ala Arg Gly Ser Ala Val Ala Trp Ala Ala Leu Gly Pro Leu Leu
1               5                   10                  15
Trp Gly Cys Ala Leu Gly
            20

<210> SEQ ID NO 478
<211> LENGTH: 22
<212> TYPE: PRT
<213> ORGANISM: Homo sapiens

<400> SEQUENCE: 478

Met Asp Ser Leu Ala Ser Leu Val Leu Cys Gly Val Ser Leu Leu Leu
1               5                   10                  15
Ser Gly Thr Val Glu Gly
            20

<210> SEQ ID NO 479
<211> LENGTH: 22
<212> TYPE: PRT
<213> ORGANISM: Homo sapiens

<400> SEQUENCE: 479

Met Arg Ala Ser Ser Phe Leu Ile Val Val Phe Leu Ile Ala Gly
1               5                   10                  15
Thr Leu Val Leu Glu Ala
            20
```

<210> SEQ ID NO 480
<211> LENGTH: 22
<212> TYPE: PRT
<213> ORGANISM: Homo sapiens

<400> SEQUENCE: 480

Met Glu Pro Gly Pro Ala Leu Ala Trp Leu Leu Leu Ser Leu Leu
1               5                   10                  15

Ala Asp Cys Leu Lys Ala
            20

<210> SEQ ID NO 481
<211> LENGTH: 22
<212> TYPE: PRT
<213> ORGANISM: Homo sapiens

<400> SEQUENCE: 481

Met Gly Trp Thr Met Arg Leu Val Thr Ala Ala Leu Leu Gly Leu
1               5                   10                  15

Met Met Val Val Thr Gly
            20

<210> SEQ ID NO 482
<211> LENGTH: 22
<212> TYPE: PRT
<213> ORGANISM: Homo sapiens

<400> SEQUENCE: 482

Met Arg Ala Pro Gly Cys Gly Arg Leu Val Pro Leu Leu Leu Leu
1               5                   10                  15

Ala Ala Ala Ala Leu Ala
            20

<210> SEQ ID NO 483
<211> LENGTH: 22
<212> TYPE: PRT
<213> ORGANISM: Homo sapiens

<400> SEQUENCE: 483

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 484
<211> LENGTH: 22
<212> TYPE: PRT
<213> ORGANISM: Homo sapiens

<400> SEQUENCE: 484

Met Ala Arg Gly Ala Ala Leu Ala Leu Leu Leu Phe Gly Leu Leu Gly
1               5                   10                  15

Val Leu Val Ala Ala Pro
            20

<210> SEQ ID NO 485
<211> LENGTH: 22
<212> TYPE: PRT
<213> ORGANISM: Homo sapiens

<400> SEQUENCE: 485

Met Asp Met Arg Val Pro Ala Gln Leu Leu Gly Leu Leu Leu Leu Trp

-continued

```
                1               5                  10                 15

Leu Arg Arg Val Arg Cys
            20

<210> SEQ ID NO 486
<211> LENGTH: 22
<212> TYPE: PRT
<213> ORGANISM: Homo sapiens

<400> SEQUENCE: 486

Met Lys Gly Ser Ile Phe Thr Leu Phe Leu Phe Ser Val Leu Phe Ala
1               5                   10                  15

Ile Ser Glu Val Arg Ser
            20

<210> SEQ ID NO 487
<211> LENGTH: 22
<212> TYPE: PRT
<213> ORGANISM: Homo sapiens

<400> SEQUENCE: 487

Met Ala Leu Glu Arg Leu Cys Ser Val Leu Lys Val Leu Leu Ile Thr
1               5                   10                  15

Val Leu Val Val Glu Gly
            20

<210> SEQ ID NO 488
<211> LENGTH: 22
<212> TYPE: PRT
<213> ORGANISM: Homo sapiens

<400> SEQUENCE: 488

Met Ala Ser Arg Ser Met Arg Leu Leu Leu Leu Ser Cys Leu Ala
1               5                   10                  15

Lys Thr Gly Val Leu Gly
            20

<210> SEQ ID NO 489
<211> LENGTH: 23
<212> TYPE: PRT
<213> ORGANISM: Homo sapiens

<400> SEQUENCE: 489

Met Ala Ser Pro Phe Ala Leu Leu Met Val Leu Val Val Leu Ser Cys
1               5                   10                  15

Lys Ser Ser Cys Ser Leu Gly
            20

<210> SEQ ID NO 490
<211> LENGTH: 23
<212> TYPE: PRT
<213> ORGANISM: Homo sapiens

<400> SEQUENCE: 490

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 491
<211> LENGTH: 23
<212> TYPE: PRT
```

<213> ORGANISM: Homo sapiens

<400> SEQUENCE: 491

Met Gln Ile Ile Thr Thr Ala Leu Val Cys Leu Leu Leu Ala Gly Met
1               5                   10                  15

Trp Pro Glu Asp Val Asp Ser
            20

<210> SEQ ID NO 492
<211> LENGTH: 23
<212> TYPE: PRT
<213> ORGANISM: Homo sapiens

<400> SEQUENCE: 492

Met Gly Leu Gly Pro Val Phe Leu Leu Leu Ala Gly Ile Phe Pro Phe
1               5                   10                  15

Ala Pro Pro Gly Ala Ala Ala
            20

<210> SEQ ID NO 493
<211> LENGTH: 23
<212> TYPE: PRT
<213> ORGANISM: Homo sapiens

<400> SEQUENCE: 493

Met Lys Leu Cys Val Thr Val Leu Ser Leu Leu Met Leu Val Ala Ala
1               5                   10                  15

Phe Cys Ser Pro Ala Leu Ser
            20

<210> SEQ ID NO 494
<211> LENGTH: 23
<212> TYPE: PRT
<213> ORGANISM: Homo sapiens

<400> SEQUENCE: 494

Met Gly Leu Pro Arg Leu Val Cys Ala Phe Leu Leu Ala Ala Cys Cys
1               5                   10                  15

Cys Cys Pro Arg Val Ala Gly
            20

<210> SEQ ID NO 495
<211> LENGTH: 23
<212> TYPE: PRT
<213> ORGANISM: Homo sapiens

<400> SEQUENCE: 495

Met Arg Gln Thr Leu Pro Cys Ile Tyr Phe Trp Gly Gly Leu Leu Pro
1               5                   10                  15

Phe Gly Met Leu Cys Ala Ser
            20

<210> SEQ ID NO 496
<211> LENGTH: 23
<212> TYPE: PRT
<213> ORGANISM: Homo sapiens

<400> SEQUENCE: 496

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 497
<211> LENGTH: 23
<212> TYPE: PRT
<213> ORGANISM: Homo sapiens

<400> SEQUENCE: 497

Met Ala Arg Val Leu Gly Ala Pro Val Ala Leu Gly Leu Trp Ser Leu
1               5                   10                  15

Cys Trp Ser Leu Ala Ile Ala
            20

<210> SEQ ID NO 498
<211> LENGTH: 23
<212> TYPE: PRT
<213> ORGANISM: Homo sapiens

<400> SEQUENCE: 498

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 499
<211> LENGTH: 23
<212> TYPE: PRT
<213> ORGANISM: Homo sapiens

<400> SEQUENCE: 499

Met Ala Pro Leu Lys Met Leu Ala Leu Val Thr Leu Leu Leu Gly Ala
1               5                   10                  15

Ser Leu Gln His Ile His Ala
            20

<210> SEQ ID NO 500
<211> LENGTH: 23
<212> TYPE: PRT
<213> ORGANISM: Homo sapiens

<400> SEQUENCE: 500

Met Gly Gly His Pro Gln Leu Arg Leu Val Lys Ala Leu Leu Leu Leu
1               5                   10                  15

Gly Leu Asn Pro Val Ser Ala
            20

<210> SEQ ID NO 501
<211> LENGTH: 23
<212> TYPE: PRT
<213> ORGANISM: Homo sapiens

<400> SEQUENCE: 501

Met Asp Leu Leu Trp Ile Leu Pro Ser Leu Trp Leu Leu Leu Leu Gly
1               5                   10                  15

Gly Pro Ala Cys Leu Lys Thr
            20

<210> SEQ ID NO 502
<211> LENGTH: 23
<212> TYPE: PRT
<213> ORGANISM: Homo sapiens

<400> SEQUENCE: 502

```
Met Lys Val Ser Glu Ala Ala Leu Ser Leu Leu Val Leu Ile Leu Ile
1               5                   10                  15

Ile Thr Ser Ala Ser Arg Ser
            20
```

<210> SEQ ID NO 503
<211> LENGTH: 23
<212> TYPE: PRT
<213> ORGANISM: Homo sapiens

<400> SEQUENCE: 503

```
Met Gly Thr Ser His Pro Ala Phe Leu Val Leu Gly Cys Leu Leu Thr
1               5                   10                  15

Gly Leu Ser Leu Ile Leu Cys
            20
```

<210> SEQ ID NO 504
<211> LENGTH: 23
<212> TYPE: PRT
<213> ORGANISM: Homo sapiens

<400> SEQUENCE: 504

```
Met Ile Leu Asn Lys Ala Leu Met Leu Gly Ser Leu Ala Leu Thr Thr
1               5                   10                  15

Val Met Ser Pro Cys Gly Gly
            20
```

<210> SEQ ID NO 505
<211> LENGTH: 23
<212> TYPE: PRT
<213> ORGANISM: Homo sapiens

<400> SEQUENCE: 505

```
Met Lys Pro Asn Ile Ile Phe Val Leu Ser Leu Leu Ile Leu Glu
1               5                   10                  15

Lys Gln Ala Ala Val Met Gly
            20
```

<210> SEQ ID NO 506
<211> LENGTH: 23
<212> TYPE: PRT
<213> ORGANISM: Homo sapiens

<400> SEQUENCE: 506

```
Met Ile Leu Asn Lys Ala Leu Leu Leu Gly Ala Leu Ala Leu Thr Thr
1               5                   10                  15

Val Met Ser Pro Cys Gly Gly
            20
```

<210> SEQ ID NO 507
<211> LENGTH: 23
<212> TYPE: PRT
<213> ORGANISM: Homo sapiens

<400> SEQUENCE: 507

```
Met Asp Ser Leu Arg Lys Met Leu Ile Ser Val Ala Met Leu Gly Ala
1               5                   10                  15

Gly Ala Gly Val Gly Tyr Ala
            20
```

<210> SEQ ID NO 508
<211> LENGTH: 23

-continued

```
<212> TYPE: PRT
<213> ORGANISM: Homo sapiens

<400> SEQUENCE: 508

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 509
<211> LENGTH: 23
<212> TYPE: PRT
<213> ORGANISM: Homo sapiens

<400> SEQUENCE: 509

Met Ser Ala Phe Arg Leu Trp Pro Gly Leu Leu Ile Met Leu Gly Ser
1               5                   10                  15

Leu Cys His Arg Gly Ser Pro
            20

<210> SEQ ID NO 510
<211> LENGTH: 23
<212> TYPE: PRT
<213> ORGANISM: Homo sapiens

<400> SEQUENCE: 510

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 511
<211> LENGTH: 23
<212> TYPE: PRT
<213> ORGANISM: Homo sapiens

<400> SEQUENCE: 511

Met Phe Ala Arg Met Ser Asp Leu His Val Leu Leu Leu Met Ala Leu
1               5                   10                  15

Val Gly Lys Thr Ala Cys Gly
            20

<210> SEQ ID NO 512
<211> LENGTH: 23
<212> TYPE: PRT
<213> ORGANISM: Homo sapiens

<400> SEQUENCE: 512

Met Ala Gln Ser Leu Ala Leu Ser Leu Leu Ile Leu Val Leu Ala Phe
1               5                   10                  15

Gly Ile Pro Arg Thr Gln Gly
            20

<210> SEQ ID NO 513
<211> LENGTH: 23
<212> TYPE: PRT
<213> ORGANISM: Homo sapiens

<400> SEQUENCE: 513

Met Thr Pro Gly Lys Thr Ser Leu Val Ser Leu Leu Leu Leu Leu Ser
1               5                   10                  15

Leu Glu Ala Ile Val Lys Ala
```

<210> SEQ ID NO 514
<211> LENGTH: 23
<212> TYPE: PRT
<213> ORGANISM: Homo sapiens

<400> SEQUENCE: 514

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 515
<211> LENGTH: 23
<212> TYPE: PRT
<213> ORGANISM: Homo sapiens

<400> SEQUENCE: 515

Met Lys Val Ser Ala Ala Leu Leu Trp Leu Leu Leu Ile Ala Ala Ala
1               5                   10                  15

Phe Ser Pro Gln Gly Leu Ala
            20

<210> SEQ ID NO 516
<211> LENGTH: 23
<212> TYPE: PRT
<213> ORGANISM: Homo sapiens

<400> SEQUENCE: 516

Met Gln Val Ser Thr Ala Ala Leu Ala Val Leu Leu Cys Thr Met Ala
1               5                   10                  15

Leu Cys Asn Gln Phe Ser Ala
            20

<210> SEQ ID NO 517
<211> LENGTH: 23
<212> TYPE: PRT
<213> ORGANISM: Homo sapiens

<400> SEQUENCE: 517

Met Pro Ser Pro Gly Thr Val Cys Ser Leu Leu Leu Gly Met Leu
1               5                   10                  15

Trp Leu Asp Leu Ala Met Ala
            20

<210> SEQ ID NO 518
<211> LENGTH: 23
<212> TYPE: PRT
<213> ORGANISM: Homo sapiens

<400> SEQUENCE: 518

Met Thr Pro Trp Leu Gly Leu Ile Val Leu Leu Gly Ser Trp Ser Leu
1               5                   10                  15

Gly Asp Trp Gly Ala Glu Ala
            20

<210> SEQ ID NO 519
<211> LENGTH: 23
<212> TYPE: PRT
<213> ORGANISM: Homo sapiens

<400> SEQUENCE: 519

```
Met Gly Asn Ser Cys Tyr Asn Ile Val Ala Thr Leu Leu Leu Val Leu
1               5                   10                  15

Asn Phe Glu Arg Thr Arg Ser
            20
```

<210> SEQ ID NO 520
<211> LENGTH: 23
<212> TYPE: PRT
<213> ORGANISM: Homo sapiens

<400> SEQUENCE: 520

```
Met Glu Ala Val Ala Val Ala Ala Ala Val Gly Val Leu Leu Leu Ala
1               5                   10                  15

Gly Ala Gly Gly Ala Ala Gly
            20
```

<210> SEQ ID NO 521
<211> LENGTH: 23
<212> TYPE: PRT
<213> ORGANISM: Homo sapiens

<400> SEQUENCE: 521

```
Met Thr Pro Ile Leu Thr Val Leu Ile Cys Leu Gly Leu Ser Leu Asp
1               5                   10                  15

Pro Arg Thr His Val Gln Ala
            20
```

<210> SEQ ID NO 522
<211> LENGTH: 23
<212> TYPE: PRT
<213> ORGANISM: Homo sapiens

<400> SEQUENCE: 522

```
Met Ala Gly Cys Val Pro Leu Leu Gln Gly Leu Val Leu Val Leu Ala
1               5                   10                  15

Leu His Arg Val Glu Pro Ser
            20
```

<210> SEQ ID NO 523
<211> LENGTH: 23
<212> TYPE: PRT
<213> ORGANISM: Homo sapiens

<400> SEQUENCE: 523

```
Met Leu Pro Pro Ala Ile His Phe Tyr Leu Leu Pro Leu Ala Cys Ile
1               5                   10                  15

Leu Met Lys Ser Cys Leu Ala
            20
```

<210> SEQ ID NO 524
<211> LENGTH: 23
<212> TYPE: PRT
<213> ORGANISM: Homo sapiens

<400> SEQUENCE: 524

```
Met Glu Ala Pro Ala Ala Gly Leu Phe Leu Leu Leu Leu Gly Thr
1               5                   10                  15

Trp Ala Pro Ala Pro Gly Ser
            20
```

<210> SEQ ID NO 525

```
<211> LENGTH: 23
<212> TYPE: PRT
<213> ORGANISM: Homo sapiens

<400> SEQUENCE: 525

Met Gly Lys Asn Lys Leu Leu His Pro Ser Leu Val Leu Leu Leu Leu
1               5                   10                  15

Val Leu Leu Pro Thr Asp Ala
            20

<210> SEQ ID NO 526
<211> LENGTH: 23
<212> TYPE: PRT
<213> ORGANISM: Homo sapiens

<400> SEQUENCE: 526

Met Ala Leu Ser Val Leu Arg Leu Ala Leu Leu Leu Ala Val Thr
1               5                   10                  15

Phe Ala Ala Ser Leu Ile Pro
            20

<210> SEQ ID NO 527
<211> LENGTH: 23
<212> TYPE: PRT
<213> ORGANISM: Homo sapiens

<400> SEQUENCE: 527

Met Gln Val Ser Thr Ala Ala Leu Ala Val Leu Leu Cys Thr Met Ala
1               5                   10                  15

Leu Cys Asn Gln Val Leu Ser
            20

<210> SEQ ID NO 528
<211> LENGTH: 23
<212> TYPE: PRT
<213> ORGANISM: Homo sapiens

<400> SEQUENCE: 528

Met Arg Gln Ser His Gln Leu Pro Leu Val Gly Leu Leu Leu Phe Ser
1               5                   10                  15

Phe Ile Pro Ser Gln Leu Cys
            20

<210> SEQ ID NO 529
<211> LENGTH: 23
<212> TYPE: PRT
<213> ORGANISM: Homo sapiens

<400> SEQUENCE: 529

Met Lys Val Ser Ala Ala Ala Leu Ala Val Ile Leu Ile Ala Thr Ala
1               5                   10                  15

Leu Cys Ala Pro Ala Ser Ala
            20

<210> SEQ ID NO 530
<211> LENGTH: 41
<212> TYPE: PRT
<213> ORGANISM: Homo sapiens

<400> SEQUENCE: 530

Glu Gly Glu Val Ser Ala Asp Glu Glu Gly Phe Glu Asn Leu Trp Ala
1               5                   10                  15
```

```
Thr Ala Ser Thr Phe Ile Val Leu Phe Leu Leu Ser Leu Phe Tyr Ser
            20                  25                  30

Thr Thr Val Thr Leu Phe Lys Val Lys
        35                  40
```

<210> SEQ ID NO 531
<211> LENGTH: 21
<212> TYPE: PRT
<213> ORGANISM: Homo sapiens

<400> SEQUENCE: 531

```
Leu Leu Leu Leu Phe Trp Leu Gly Trp Leu Gly Met Leu Ala Gly Ala
  1               5                  10                  15

Val Val Ile Ile Val
            20
```

<210> SEQ ID NO 532
<211> LENGTH: 24
<212> TYPE: PRT
<213> ORGANISM: Homo sapiens

<400> SEQUENCE: 532

```
Lys Ser Leu Gly Ile Leu Gly Ile Leu Leu Gly Val Ala Ala Val Cys
  1               5                  10                  15

Thr Ile Ile Ala Leu Ser Val Val
            20
```

<210> SEQ ID NO 533
<211> LENGTH: 20
<212> TYPE: PRT
<213> ORGANISM: Homo sapiens

<400> SEQUENCE: 533

```
Ala Leu Ala Trp Glu Leu Leu Gly Ala Ser Val Leu Leu Ile Ala Val
  1               5                  10                  15

Arg Trp Leu Val
            20
```

<210> SEQ ID NO 534
<211> LENGTH: 21
<212> TYPE: PRT
<213> ORGANISM: Homo sapiens

<400> SEQUENCE: 534

```
Ile Leu Val Leu Leu Ile Leu Ala Val Ile Thr Ile Phe Ala Leu Val
  1               5                  10                  15

Cys Val Leu Leu Val
            20
```

<210> SEQ ID NO 535
<211> LENGTH: 21
<212> TYPE: PRT
<213> ORGANISM: Homo sapiens

<400> SEQUENCE: 535

```
Phe Phe Thr Trp Phe Met Val Ile Ala Leu Leu Gly Val Trp Thr Ser
  1               5                  10                  15

Val Ala Val Val Trp
            20
```

<210> SEQ ID NO 536
<211> LENGTH: 20

-continued

<212> TYPE: PRT
<213> ORGANISM: Homo sapiens

<400> SEQUENCE: 536

Leu Leu Val Ala Val Cys Ala Leu His Leu Gly Val Thr Leu Val Tyr
1               5                   10                  15
Tyr Leu Ala Gly
            20

<210> SEQ ID NO 537
<211> LENGTH: 21
<212> TYPE: PRT
<213> ORGANISM: Homo sapiens

<400> SEQUENCE: 537

Gly Tyr Gly Val Leu Ser Pro Arg Ser Leu Met Pro Gly Ser Leu Glu
1               5                   10                  15
Arg Gly Phe Cys Met
            20

<210> SEQ ID NO 538
<211> LENGTH: 28
<212> TYPE: PRT
<213> ORGANISM: Homo sapiens

<400> SEQUENCE: 538

Lys Leu Leu Leu Gly Ile Gly Ile Leu Val Leu Leu Ile Ile Val Ile
1               5                   10                  15
Leu Gly Val Pro Leu Ile Ile Phe Thr Ile Lys Ala
            20                  25

<210> SEQ ID NO 539
<211> LENGTH: 21
<212> TYPE: PRT
<213> ORGANISM: Homo sapiens

<400> SEQUENCE: 539

Glu Leu Leu Trp Pro Gly Ala Ala Leu Leu Val Leu Leu Gly Val Ala
1               5                   10                  15
Ala Ser Leu Cys Val
            20

<210> SEQ ID NO 540
<211> LENGTH: 24
<212> TYPE: PRT
<213> ORGANISM: Homo sapiens

<400> SEQUENCE: 540

Val Gly Ile Ile Ala Gly Leu Val Leu Leu Gly Ala Val Ile Thr Gly
1               5                   10                  15
Ala Val Val Ala Ala Val Met Trp
            20

<210> SEQ ID NO 541
<211> LENGTH: 17
<212> TYPE: PRT
<213> ORGANISM: Homo sapiens

<400> SEQUENCE: 541

```
Leu Gly Leu Leu Leu Thr Phe Leu Gly Ile Val Ala Ala Val Leu
1               5                   10                  15
Val

<210> SEQ ID NO 542
<211> LENGTH: 21
<212> TYPE: PRT
<213> ORGANISM: Homo sapiens

<400> SEQUENCE: 542

Leu Tyr Ile Ala Gly Phe Ser Leu Leu Ser Phe Leu Leu Arg Arg
1               5                   10                  15
Leu Val Thr Leu Ile
            20

<210> SEQ ID NO 543
<211> LENGTH: 24
<212> TYPE: PRT
<213> ORGANISM: Homo sapiens

<400> SEQUENCE: 543

Trp Leu Val Leu Leu Ile Ser Met Ala Val Cys Ile Ile Ala Met Ile
1               5                   10                  15
Ile Phe Ser Ser Cys Phe Cys Tyr
            20

<210> SEQ ID NO 544
<211> LENGTH: 21
<212> TYPE: PRT
<213> ORGANISM: Homo sapiens

<400> SEQUENCE: 544

Ile Leu Gly Ile Leu Gly Gly Ile Leu Ala Leu Leu Ile Leu Ile Leu
1               5                   10                  15
Leu Leu Leu Leu Phe
            20

<210> SEQ ID NO 545
<211> LENGTH: 21
<212> TYPE: PRT
<213> ORGANISM: Homo sapiens

<400> SEQUENCE: 545

Ala Val Ile Gly Gly Val Val Ala Val Val Phe Ala Met Leu Cys
1               5                   10                  15
Leu Leu Ile Ile Leu
            20

<210> SEQ ID NO 546
<211> LENGTH: 26
<212> TYPE: PRT
<213> ORGANISM: Homo sapiens

<400> SEQUENCE: 546

Ile Tyr Leu Ile Ile Gly Ile Cys Gly Gly Gly Ser Leu Leu Met Val
1               5                   10                  15
Phe Val Ala Leu Leu Val Phe Tyr Ile Thr
            20                  25

<210> SEQ ID NO 547
<211> LENGTH: 21
```

<212> TYPE: PRT
<213> ORGANISM: Homo sapiens

<400> SEQUENCE: 547

Trp Leu Ile Ile Leu Ala Ser Leu Leu Ala Leu Ala Leu Ile Leu Ala
1               5                   10                  15

Val Cys Ile Ala Val
            20

<210> SEQ ID NO 548
<211> LENGTH: 21
<212> TYPE: PRT
<213> ORGANISM: Homo sapiens

<400> SEQUENCE: 548

Trp Ile Thr Ala Val Leu Pro Thr Val Ile Ile Cys Val Met Val Phe
1               5                   10                  15

Cys Leu Ile Leu Trp
            20

<210> SEQ ID NO 549
<211> LENGTH: 22
<212> TYPE: PRT
<213> ORGANISM: Homo sapiens

<400> SEQUENCE: 549

Ile Ile Thr Ala Glu Gly Ile Ile Leu Leu Phe Cys Ala Val Val Pro
1               5                   10                  15

Gly Thr Leu Leu Leu Phe
            20

<210> SEQ ID NO 550
<211> LENGTH: 25
<212> TYPE: PRT
<213> ORGANISM: Homo sapiens

<400> SEQUENCE: 550

Ala Leu Ile Val Gly Thr Leu Ser Gly Thr Ile Phe Phe Ile Leu Leu
1               5                   10                  15

Ile Ile Phe Leu Ser Trp Ile Ile Leu
            20                  25

<210> SEQ ID NO 551
<211> LENGTH: 21
<212> TYPE: PRT
<213> ORGANISM: Homo sapiens

<400> SEQUENCE: 551

Val Val Val Ala Cys Met Ser Ile Met Ala Leu Leu Leu Leu Leu
1               5                   10                  15

Leu Leu Leu Leu Tyr
            20

<210> SEQ ID NO 552
<211> LENGTH: 125
<212> TYPE: DNA
<213> ORGANISM: Homo sapiens -continued

```
<400> SEQUENCE: 552 gaggggagg tgagcgccga cgaggagggc tttgagaacc tgtgggccac cgcctccacc    60
ttcatcgtcc tcttcctcct gagcctcttc tacagtacca ccgtcacctt gttcaaggtg   120
aaatg                                                               125
```

EXPRESSION OF SECRETED AND CELL-SURFACE POLYPEPTIDES

CROSS-REFERENCE TO RELATED APPLICATIONS

This application claims the benefit of U.S. Provisional Application 61/652,006, filed on May 25, 2012, which is incorporated herein by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled CALTE_087A_SEQLIST.TXT, created and last modified on May 23, 2013, which is 127,288 bytes in size. The information in the electronic format of the Sequence Listing is incorporated herein by reference in its entirety.

FIELD

Some embodiments relate generally to methods and compositions for expression of gene products. More particularly, some embodiments relate to co-expression of membrane-bound and secreted polypeptides in desired ratios.

BACKGROUND 2A elements are "self-cleaving" peptides that are derived from viruses 2A elements can be involved in the processing and expression of polyproteins. Without being bound by any particular theory, the presence of the 2A element in the mRNA can cause the translating ribosome to undergo an intra-ribosomal, translational termination-and-restart event during the synthesis of the nascent polypeptide chains. The peptide bond between the first and second polypeptide deriving from the same mRNA is not formed during translation. As a result, when these two polypeptides are liberated from the ribosome, they appear as two separate proteins. Because the apparent effect is as if a single polypeptide had been cleaved by an enzyme post-translationally into two separate polypeptides, for consistency with their historic description, 2A elements may be referred to herein as exemplary "self-cleaving" peptides or as "cleavage sites," though it is understood that 2A peptides can mediate a ribosomal stop-and-restart event, which may be referred to as a "StopGo" action of the 2A element Several 2A elements appear to have near 100% cleavage efficiency in their native contexts, but they can be made to cleave at lower efficiencies when they are mutated at particular amino acid residues or introduced into non-native sequences.

Without being bound by any particular theory, surface and secreted soluble proteins and polypeptides of eukaryotic cells can be processed via the secretory pathway. The secretory pathway is described in detail in Alberts et al., Molecular Biology of the Cell, 4th Edition, New York, Garland Science (2002), which is hereby incorporated by reference in its entirety. Typically, in the cytosol of a cell, ribosomes can assemble on polynucleotides that encode polypeptides, for example mRNAs. Ribosomes can mediate the translation of the polynucleotides to produce the encoded polypeptides. The presence of a signal sequence on the polypeptide can mediate the translocation of the polypeptide to the cell's endoplasmic reticulum. The translocation to the endoplasmic reticulum can be co-translational, for example if the signal sequence is located on an N-terminal portion of the polypeptide. Alternatively, the translocation to the endoplasmic reticulum can be post-translational. Thus, while signal sequences are frequently located on N terminal portions of polypeptides, they can also be located internally, or even on a C terminal portion of the polypeptide, and still mediate translocation to the endoplasmic reticulum. Additionally, signal "patches," can be assembled by particular three-dimensional folding of a polypeptide, and can also mediate translocation to the endoplasmic reticulum. A signal sequence can mediate the polypeptide's entry into the endoplasmic reticulum via one of a plurality of pore in the endoplasmic reticulum membrane. In the absence of an anchor sequence, the entire polypeptide can pass through the pore, and into the lumen of the endoplasmic reticulum. If an anchor sequence is present on the protein or polypeptide, translocation into the endoplasmic reticulum can stop upon the entry of the anchor sequence into the pore, before the entire polypeptide is transported into the endoplasmic reticulum. Accordingly, the protein can remain embedded in the membrane of the endoplasmic reticulum. Luminal and membrane-bound polypeptides in the endoplasmic reticulum can subsequently be transported to the cell's golgi apparatus. Inside the lumen of the endoplasmic reticulum and/or the golgi, the polypeptide, or portions thereof can undergo additional modifications, for example folding, cleavage, and/or glycosylation. From the golgi apparatus, luminal and membrane-bound polypeptides can be transported to the cell membrane, and can be membrane-bound or secreted. Transport between the endoplasmic reticulum, golgi, and cell membrane can be mediated by membrane vesicles. Upon arrival at the cell membrane, membrane vesicles can fuse with the cell membrane. Luminal surfaces of endoplasmic reticulum membrane typically correspond to extracellular surfaces of cell membrane, while cytosolic surfaces of endoplasmic reticulum typically correspond to cytosolic surface of cell membrane. Accordingly, a portion of a transmembrane protein that faces the ER lumen can subsequently face the extracellular environment, and a portion that faces the cytosol can continue to face the cytosol. Cleavage of a luminal portion of a protein or polypeptide from a membrane-bound portion of the polypeptide in the endoplasmic reticulum, golgi, in a membrane vesicle, and/or at the cell surface can allow the cleaved portion to be in the lumen, and/or subsequently secreted from the cell.

B cells are responsible for the production of antibodies in response to foreign antigens. In nature, B cells can produce surface immunoglobulin and secreted antibody from the same immunoglobulin gene via alternative splicing of the pre-messenger RNA.

B cells begin their life in the bone marrow as descendants of the more primitive common hematopoietic stem and progenitor cells. As these cells develop into B cells, they undergo sequential RAG1/2-mediated DNA rearrangement of the heavy and light chain immunoglobulin gene loci in a process called V(D)J rearrangement. Cells that successfully complete this process and assemble a functional B cell receptor (BCR) of the IgM isotype on their surface are able to leave the bone marrow to continue further development in the peripheral lymphoid compartments. The generation of the IgM BCR can be central to B cell development and function, including normal development of B cells, and directing B cell development. In transgenic animals, the provision of a pre-rearranged IgM heavy chain and light chain transgene shuts down the rearrangement of endogenous heavy and light chain genes (allelic exclusion), and guides the ordered development of functional B cells with specificity defined by the transgene.

Mature B cells patrol the body in the general and lymphatic circulations, using their BCRs as antigen sensors. When a cognate antigen engages the BCR, the B cell becomes activated and enters into a germinal center reaction in the lymph node or spleen in a dance of mutual activation with T cells; this process leads to further development into memory B cells or differentiation into antibody-producing plasma cells. The memory B cells will provide a more rapid and higher quality antibody response in the future when the same antigens are encountered again. The plasma cells produce antibodies against the inciting antigens, which leads to their eventual clearance from the body. As B cells differentiate into plasma cells, they switch from producing the membrane-bound IgM BCR to making a soluble, secreted antibody. The genomic machinery for effecting the switch is complex and involves alternative-splicing of the heavy-chain pre-mRNA. The switch replaces the hydrophobic amino acids that form the trans-membrane anchor with a hydrophilic tail that enables the secretion of the BCR as free antibody. The antibody retains the same specificity and isotype as the BCR.

SUMMARY

Some aspects include a polynucleotide construct. The polynucleotide construct can comprise a signal polynucleotide encoding a signal sequence, a first cleavage polynucleotide encoding a first cleavage site in-frame with the signal sequence, and an anchor polynucleotide encoding a membrane anchor polypeptide in-frame with the first cleavage site. In some embodiments, a 3' end of the signal polynucleotide is 5' of a 3' end of the anchor polynucleotide. In some embodiments, the first cleavage polynucleotide encodes a 2A polypeptide. In some embodiments, the first cleavage polynucleotide encodes a 2A polypeptide selected from the group consisting of any one of SEQ ID NO: 1 to SEQ ID NO: 16. In some embodiments, the first cleavage polynucleotide encodes a 2A polypeptide having at least about 85% identity to any one of SEQ ID NO: 1 to SEQ ID NO: 16. In some embodiments, the signal sequence is selected from the group consisting of any one of SEQ ID NO: 33 to SEQ ID NO: 529. In some embodiments, the anchor polynucleotide encodes an membrane anchor polypeptide selected from the group consisting of any one of SEQ ID NO: 530 to SEQ ID NO: 551. In some embodiments, the polynucleotide construct further comprises a first insertion site for a first polypeptide-encoding polynucleotide, wherein the first insertion site is positioned for inserting a first polypeptide-encoding polynucleotide in-frame with the signal polypeptide, the first cleavage polynucleotide, and the anchor polynucleotide. In some embodiments, a ratio of (a) secreted first polypeptide to (b) surface-bound first polypeptide correlates to a known cleavage efficiency of the first cleavage site polypeptide. In some embodiments, the first insertion site is 5' of the first cleavage polynucleotide, and 5' of the anchor polynucleotide. In some embodiments, the signal polynucleotide is 5' of the first insertion site, and the first insertion site is 5' of the cleavage polynucleotide. In some embodiments, the signal polynucleotide is 3' of the first insertion site, and wherein the signal polynucleotide is 5' of the cleavage polynucleotide. In some embodiments, the polynucleotide construct further comprises a second insertion site for a second polypeptide-encoding polynucleotide; and a second cleavage polynucleotide encoding a second cleavage site. In some embodiments, the second insertion site is positioned for inserting the second polypeptide-encoding polynucleotide in-frame with the first polypeptide-encoding polynucleotide, and the second cleavage polynucleotide, polynucleotide. In some embodiments, the second cleavage site is positioned between the first insertion site and the second insertion site. In some embodiments, the polynucleotide construct further comprises a promoter configured to express the signal polynucleotide, the first cleavage polynucleotide, and the anchor polynucleotide in a single transcript. In some embodiments, the polynucleotide construct further comprises a first polypeptide-encoding polynucleotide positioned in-frame with the signal polynucleotide, the first cleavage polynucleotide, and the anchor polynucleotide. In some embodiments, the cleavage polynucleotide is positioned 3' of the anchor polynucleotide. In some embodiments, the cleavage polynucleotide is positioned within the anchor polynucleotide. In some embodiments, the polynucleotide construct comprises, from 5' to 3', a second insertion site for a second polypeptide-encoding polynucleotide, a second cleavage polynucleotide encoding a second cleavage site, a first insertion site for a first polypeptide-encoding polynucleotide, the signal polynucleotide, the first cleavage polynucleotide, and the anchor polynucleotide. In some embodiments, the polynucleotide construct comprises, from 5' to 3', a second polypeptide-encoding polynucleotide, a second cleavage polynucleotide encoding a second cleavage site, a first polypeptide-encoding polynucleotide, the signal polynucleotide, the first cleavage polynucleotide, and the anchor polynucleotide. In some embodiments, the polynucleotide construct comprises, from 5' to 3', a polynucleotide encoding an immunoglobulin light chain, a second cleavage polynucleotide encoding a second cleavage site, a polynucleotide encoding an immunoglobulin heavy chain, the signal polynucleotide, the first cleavage polynucleotide, and the anchor polynucleotide.

Some aspects include a vector comprising any of polynucleotide constructs as described herein. In some embodiments, the vector is a lentiviral vector.

Some aspects include a method of expressing a secreted polypeptide and a surface-bound polypeptide from a single construct in a target cell. The method can comprise providing a construct comprising a first polynucleotide encoding a first polypeptide, a signal polynucleotide encoding a signal sequence with the first polynucleotide, a first cleavage polynucleotide encoding a first cleavage site with the signal sequence, and an anchor polynucleotide encoding a membrane anchor with the first cleavage site. In some embodiments, the signal polynucleotide encoding a signal sequence in-frame with the first polynucleotide, the first cleavage polynucleotide encodes a first cleavage site in-frame with the signal sequence, and the anchor polynucleotide encodes a membrane anchor in-frame with the first cleavage site. In some embodiments, the signal polynucleotide is 5' of the first cleavage polynucleotide, and the first cleavage polynucleotide is 5' of the anchor polynucleotide. The method can include delivering the construct to a target cell, wherein the target cell is capable of transcribing the construct. In some embodiments, each first polypeptide is secreted from the cell if it does not comprise the anchor, and wherein each first polypeptide is bound to a surface of the cell if it comprises the anchor. In some embodiments, delivering comprises integrating the construct into the target cell's genome. In some embodiments, after being delivered to the target cell, the first polynucleotide, signal polynucleotide, first cleavage polynucleotide, and anchor polynucleotide are under the control of a single promoter. In some embodiments, the first cleavage site comprises a 2A polypeptide. In some embodiments, the first cleavage site comprises a 2A polypeptide selected from the group consisting of any one of SEQ ID NO: 1 to SEQ ID NO: 16. In some embodiments, the method further comprises selecting the first cleavage polynucleotide to encode a cleavage site having a desired activity level. In some embodiments, the desired activity level correlates to a ratio of secreted polypeptide to surface-bound polypeptide. In some embodiments, the first polypeptide comprises a fluorescent protein. In some embodiments, each transcript of the plurality further comprises a second polynucleotide encoding a polypeptide, and a second cleavage polynucleotide encoding a second cleavage site. In some embodiments, the second polynucleotide is in-frame with the second cleavage polynucleotide and the first polynucleotide. In some embodiments, the second cleavage site is positioned between the second polynucleotide and the first polynucleotide. In some embodiments, the method further comprises detecting a quantity of the first polypeptide on a surface of the cell. In some embodiments, the method further comprises detecting a quantity of the first polypeptide secreted by the cell.

BRIEF DESCRIPTION OF THE DRAWINGS

FIG. 3B is a bar graph illustrating surface IgG expression as measured by flow cytometry. FIG. 3C is a bar graph illustrating secreted IgG expression, as measured in supernatants by ELISA.

DETAILED DESCRIPTION

Figure 1A:
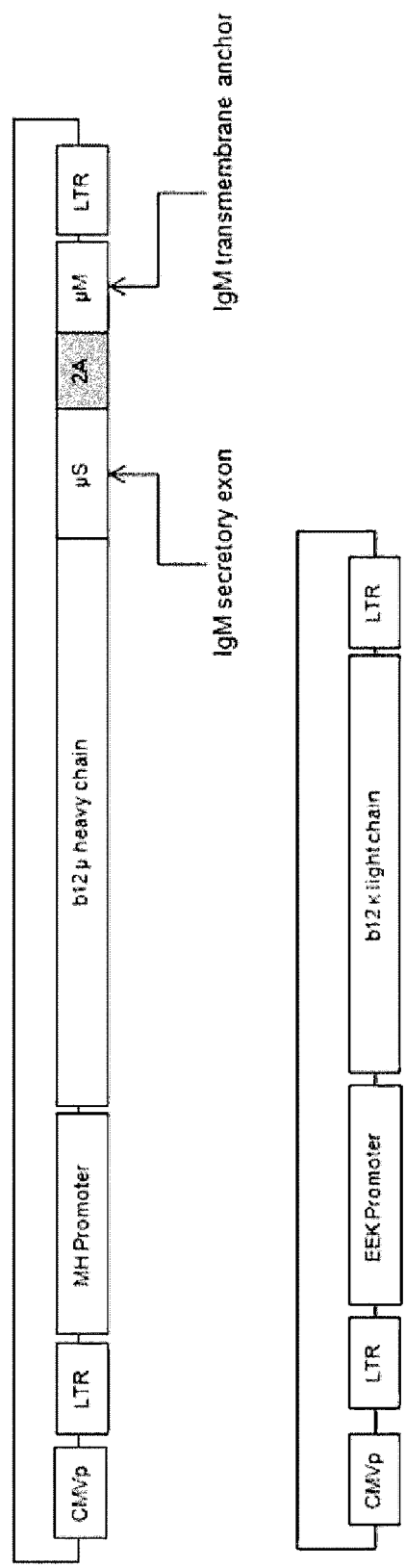
FIG. 1A is a schematic illustration of a first generation "molecular rheostat" vector system. The system included: a first vector encoding a b12μ heavy chain, an IgM secretory exon (μs), a 2A cleavage site, and a membrane anchor; and a second vector encoding a b12κ light chain.

In some embodiments, membrane-bound and secreted polypeptides are coexpressed from a single polynucleotide coding sequence. In some embodiments, the polynucleotide encodes, from 5' to 3', a polypeptide of interest, a signal sequence, a cleavage site, and a membrane anchor. In some embodiments, depending on the efficiency of the cleavage site, the membrane anchor is not attached to the polypeptide once it is expressed, and the polypeptide is secreted as a consequence of the signal sequence. In some embodiments, depending on the efficiency of the cleavage site, the membrane anchor remains attached to the polypeptide, and the polypeptide is membrane-bound. In some embodiments, in order to produce a desired ratio of secreted-to-membrane-bound polypeptide, a cleavage site of known efficiency is selected. A cleavage site of high efficiency can produce a ratio that favors secreted polypeptides. A cleavage site of low efficiency can produce a ratio that favors membrane-bound polypeptides. In some embodiments, the membrane-bound and secreted polypeptide is a B cell receptor heavy chain, and a B cell receptor light chain is co-expressed with the heavy chain, such that a desired ratio of membrane-bound and secreted B cell receptor is produced by the cell.

As used herein "upstream" refers to a position that is in the relative direction of the 5' end of a polynucleotide or the N terminus of a polypeptide. As used herein, "downstream" refers to a position that is in the relative direction of the 3' end of a polynucleotide or the C terminus of a polypeptide.

As used herein, "polypeptide" includes peptides having lengths of at least three amino acid residues. In some embodiments, a polypeptide has a length of at least about 10 amino acid resides, for example at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 amino acid residues, including ranges between any two of the listed values. "Polypeptide" further includes proteins.

As used herein, "surface," "surface-bound," and the like refer to a polypeptide for which at least a portion of the polypeptide is stably inserted on or in the plasma membrane of a cell. In some embodiments, a surface polypeptide or surface protein comprises an anchor as described herein. In some embodiments, a surface polypeptide comprises a single transmembrane domain. In some embodiments, a surface polypeptide comprises two or more transmembrane domains. In some embodiments, a polypeptide can stably associated with the plasma membrane by binding to a surface polypeptide that is inserted in the plasma membrane.

As used herein, "secreted" and the like refer to a polypeptide produced by a cell, and exported by that cell to an extracellular environment, so that the polypeptide is not stably attached to the cell. In some embodiments, a secreted polypeptide comprises a signal sequence. In some embodiments, a secreted polypeptide is soluble in the extracellular environment. In some embodiments, a secreted polypeptide does not include an anchor. While it is understood that the processing pathway that mediates the delivery of both surface-bound and secreted polypeptides to the cell surface is frequently referred to as the "secretory pathway," as used herein, "secreted" does not encompass polypeptides that remain stably attached to the cell membrane after being processed via the secretory pathway.

Cleavage Sites

As used herein "cleavage site" refers to a sequence that mediates the separation of a first polypeptide that would otherwise be in cis to a second polypeptide. Accordingly, for simplicity, "cleavage," "cleavage site," and the like as used herein refer to the separation of any two polypeptides that are encoded by a single polynucleotide in cis. Thus, "cleavage" and "cleavage site," can, but do not necessarily refer to proteolytic sites and events, and can also refer to other mechanisms for mediating the separation of polypeptides, for example ribosomal skipping. In some embodiments, a cleavage site mediates the separation via an intra-ribosomal, translational termination-and-restart event during the synthesis of the nascent polypeptide chains so that a peptide bond is not formed between an upstream amino acid residue and a downstream amino acid residue. For example, such a cleavage site can include a 2A polypeptide as described herein. Exemplary cleavage sites are listed in Table 2. For example, such a cleavage site can comprise a translation termination sequence (e.g. a stop codon) upstream of an internal ribosome entry site. In some embodiments, a cleavage site includes a protease target site. For example, such a protease target site can comprise a furin cleavage site (Arg-X-X-Arg, preferably Arg-X-Lys/Arg-Arg). As used herein, "cleavage nucleotide" refers to a polynucleotide that encodes a cleavage site. Exemplary cleavage polynucleotides are listed in Table 2.

In some embodiments, two or more cleavage sites are provided between two polypeptide-encoding sequences, for example a furin site upstream of a 2A polypeptide.

In some embodiments, a cleavage site comprises a 2A polypeptide. In some embodiments, the 2A polypeptide comprises a wild-type 2A polypeptide from foot-and-mouth disease virus ("F2A"; QLLNFDLLKLAGDVESNPGP; SEQ ID NO: 1). In some embodiments, the 2A polypeptide is selected from Table 1. In some embodiments, the 2A polypeptide is a variant of a 2A polypeptide from Table 1. Variants can include polypeptide sequences having at least about 80%, at least about 85%, at least about 90%, at least about 95%, at least about 97%, at least about 99%, or more, sequence identity to a 2A polypeptide provided in Table 1. Variants can include a deletion of at least one N-terminal amino acid from a 2A polypeptide provided in Table 1, for example a deletion of 1, 2, 3, 4, 5, 6, 7, 8, 9, or 10 amino acids, including ranges between any two of the listed values. Variants can include a deletion of at least one C-terminal amino acid from a 2A polypeptide provided in Table 1, for example a deletion of 1, 2, 3, 4, 5, 6, 7, 8, 9, or 10 amino acids, including ranges between any two of the listed values. As shown in Example 3, deletion of 1 to 7 N-terminal amino acid residues from a wild-type F2A encoding nucleotide yielded a cleavage site that possessed at least some cleavage activity.

In some embodiments, the 2A polypeptide (or polynucleotide encoding the 2A polypeptide) is selected based on its relative activity. By way of example, relative activities of 2A polypeptides can be identified by way of experimental data shown in FIGS. 1B, 1C, 2B, 2C, 3B, 3C, 4A, 4B, 5A, and 5B, and the Examples provided herein. In some embodiments, F2A(wt)(QLLNFDLLKLAGDVESNPGP; SEQ ID NO: 1 F2A(-2)(LNFDLLKLAGDVESNPGP; SEQ ID NO: 3), and F2A(-1) (LLNFDLLKLAGDVESNPGP; SEQ ID NO: 2) are relatively high activity 2A polypeptides. In some embodiments, F2A(-7) (LKLAGDVESNPGP; SEQ ID NO: 8), F2A(19) (QLLNFDLLKLAGDVESNPAP; SEQ ID NO: 12), I2A(0) (TRAEIEDELIRRGIESNPGP; SEQ ID NO: 13), I2A(1) (TRAEIEDELIRRGIESNPGP; SEQ ID NO: 14), I2A(2) (TRAEIEDELIRRGIESNPGP; SEQ ID NO: 15), and I2A(3) (TRAEIEDELIRRGIESNPAP; SEQ ID NO: 16) are relatively low activity 2A polypeptides.

In some embodiments, a polynucleotide encoding a 2A polypeptide (a "2A polynucleotide") listed in Table 1 is provided. In some embodiments, a polynucleotide encoding a 2A is selected from Table 2. In some embodiments, the 2A polynucleotide comprises a polynucleotide sequence having at least about 80%, at least about 85%, at least about 90%, at least about 95%, at least about 97%, at least about 99%, or more, sequence identity to a 2A polynucleotide sequence provided in Table 2. In some embodiments, the 2A polynucleotide comprises a deletion of at least one 5′ polynucleotide triplets (e.g. codons) from a 2A polynucleotide provided in Table 2, for example a deletion of 1, 2, 3, 4, 5, 6, 7, 8, 9, or 10 polynucleotide triplets, including ranges between any two of the listed values, so long as the polypeptide retains some cleavage activity. As shown in Example 3, deletion of 1 to 7 polynucleotide triplets from the 5′ end (corresponding to 1 to 7 N terminal amino acid residues) from a wild-type F2A encoding nucleotide yielded a cleavage site that possessed at least some cleavage activity. As the genetic code is degenerate, it is possible for some single polypeptides to be encoded by two or more different polynucleotides. In some embodiments, the relative activity of a 2A polypeptide depends on the particular nucleic acid sequence that encodes it.

TABLE 1

2A Polypeptide Sequences

| SEQ ID NO: | 2A Polypeptide | Mutation Type | Amino Acid Sequence |
|---|---|---|---|
| 1 | F2A | (wild-type) | QLLNFDLLKLAGDVESNPGP |
| 2 | F2A(-1) | 1aa N-terminal deletion | LLNFDLLKLAGDVESNPGP |
| 3 | F2A(-2) | 2aa N-terminal deletion | LNFDLLKLAGDVESNPGP |
| 4 | F2A(-3) | 3aa N-terminal deletion | NFDLLKLAGDVESNPGP |
| 5 | F2A(-4) | 4aa N-terminal deletion | FDLLKLAGDVESNPGP |
| 6 | F2A(-5) | 5aa N-terminal deletion | DLLKLAGDVESNPGP |
| 7 | F2A(-6) | 6aa N-terminal deletion | LLKLAGDVESNPGP |
| 8 | F2A(-7) | 7aa N-terminal deletion | LKLAGDVESNPGP |
| 9 | F2A(3) | Point mutation | QLLNFDLLKLAGDVQSNPGP |
| 10 | F2A(11) | Point mutation | QLLNFDLLKLAGDVEINPGP |
| 11 | F2A(14) | Point mutation | QLLNFDLLKLAGDVESEPGP |
| 12 | F2A(19) | Point mutation | QLLNFDLLKLAGDVESNPAP |
| 13 | I2A(0) | Wild-type | TRAEIEDELIRRGIESNPGP |
| 14 | I2A(1) | Point mutation | TRAEIEDELIRAGIESNPGP |
| 15 | I2A(2) | Alternative codon | TRAEIEDELIRRGIESNPGP |
| 16 | I2A(3) | Point mutation | TRAEIEDELIRRGIESNPAP |

TABLE 2

Polynucleotides encoding 2A sequences

| SEQ ID NO: | 2A Polypeptide | Polynucleotide sequence | Corresponding Polypeptide SEQ ID NO: |
|---|---|---|---|
| 17 | F2A | CAGCTGTTGAATTTTGACCTTCTTAAGCTTGCGGGAGACGTCGAGTCCAACCCCGGGCCC | 1 |
| 18 | F2A(-1) | CTGTTGAATTTTGACCTTCTTAAGCTTGCGGGAGACGTCGAGTCCAACCCCGGGCCC | 2 |
| 19 | F2A(-2) | TTGAATTTTGACCTTCTTAAGCTTGCGGGAGACGTCGAGTCCAACCCCGGGCCC | 3 |
| 20 | F2A(-3) | AATTTTGACCTTCTTAAGCTTGCGGGAGACGTCGAGTCCAACCCCGGGCCC | 4 |
| 21 | F2A(-4) | TTTGACCTTCTTAAGCTTGCGGGAGACGTCGAGTCCAACCCCGGGCCC | 5 |
| 22 | F2A(-5) | GACCTTCTTAAGCTTGCGGGAGACGTCGAGTCCAACCCCGGGCCC | 6 |
| 23 | F2A(-6) | CTTCTTAAGCTTGCGGGAGACGTCGAGTCCAACCCCGGGCCC | 7 |
| 24 | F2A(-7) | CTTAAGCTTGCGGGAGACGTCGAGTCCAACCCCGGGCCC | 8 |
| 25 | F2A(3) | CAGCTGTTGAATTTTGACCTTCTTAAGCTTGCGGGAGACGTCCAGTCCAACCCCGGGCCC | 9 |
| 26 | F2A(11) | CAGCTGTTGAATTTTGACCTTCTTAAGCTTGCGGGAGACGTCGAGATTAACCCCGGGCCC | 10 |
| 27 | F2A(14) | CAGCTGTTGAATTTTGACCTTCTTAAGCTTGCGGGAGACGTCGAGTCCGAGCCCGGGCCC | 11 |
| 28 | F2A(19) | CAGCTGTTGAATTTTGACCTTCTTAAGCTTGCGGGAGACGTCGAGTCCAACCCCGCGCCC | 12 |
| 29 | I2A(0) | ACGAGGGCGGAGATTGAGGATGAATTGATTCGTCGAGGAATTGAATCAAATCCTGGGCCC | 13 |
| 30 | I2A(1) | ACGAGGGCGGAGATTGAGGATGAATTGATTCGTGCAGGAATTGAATCAAATCCTGGACCC | 14 |
| 31 | I2A(2) | ACGAGGGCGGAGATTGAGGATGAATTGATTCGTCGAGGAATTGAATCAAATCCTGGACCC | 15 |
| 32 | I2A(3) | ACGAGGGCGGAGATTGAGGATGAATTGATTCGTCGAGGAATTGAATCAAATCCTGCGCCC | 16 |

Signal Sequences

As used herein, "signal sequence," including pluralizations, variations, and the like refers to a polypeptide sequence or combination of sequences that are sufficient to mediate the translocation of a polypeptide to the cell surface. Without being bound by any particular theory, translocation of a polypeptide to the cell surface can be mediated by the secretory pathway, including the translocation of a polypeptide from the cytosol to the endoplasmic reticulum, and the subsequent transport of the polypeptide through the golgi, and to the cell membrane, where the protein can remain embedded in the cell membrane, or be secreted from the cell.

As used herein, "signal sequences," include naturally-occurring and synthetic signal sequences, signal "patches" and the like. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. In some embodiments, the signal peptide is a modified HGH signal peptide.

Exemplary *Homo sapiens* signal sequences are provided in Table 3, and include SEQ IS NOs: 33 to 529. In some embodiments, a signal sequence is selected from Table 3. In some embodiments, the signal peptide comprises a sequence having at least about 80%, at least about 85%, at least about 90%, at least about 95%, at least about 97%, at least about 99%, or more, sequence identity to any one of the sequences of Table 3. In some embodiments, a signal polynucleotide encoding any one of the signal sequences is provided.

TABLE 3

Exemplary *H. sapiens* signal Sequences

| Description | Sequence | SEQ ID NO: |
|---|---|---|
| Stromal interaction molecule 2 | MLVLGLLVAGAADG | 33 |
| Glucosidase 2 subunit beta | MLLPLLLLLPMCWA | 34 |
| Pancreatic alpha-amylase | MKFFLLLFTIGFCWA | 35 |
| Complement C1q tumor necrosis factor-related protein 5 | MRPLLVLLLLGLAAG | 36 |
| Pepsin A | MKWLLLLGLVALSEC | 37 |
| Alpha-S1-casein | MRLLILTCLVAVALA | 38 |
| Carboxypeptidase B | MLALLVLVTVALASA | 39 |
| Neuroblastoma suppressor of tumorigenicity 1 | MLRVLVGAVLPAMLL | 40 |
| Complement C1s subcomponent | MWCIVLFSLLAWVYA | 41 |
| Trypsin-1 | MNPLLILTFVAAALA | 42 |
| Mast cell carboxypeptidase A | MRLILPVGLIATTLA | 43 |
| Beta-casein | MKVLILACLVALALA | 44 |
| Trypsin-2 | MNLLLILTFVAAAVA | 45 |
| Phospholipase A2 | MKLLVLAVLLTVAAA | 46 |
| High affinity immunoglobulin gamma Fc receptor I | MWFLTTLLLWVPVDG | 47 |
| Alpha-amylase 2B | MKFFLLLFTIGFCWA | 48 |
| Basic salivary proline-rich protein 1 | MLLILLSVALLALSSA | 49 |
| Amelogenin, X isoform | MGTWILFACLLGAAFA | 50 |
| C-C motif chemokine 13 | MKVSAVLLCLLLMTAA | 51 |
| Folate receptor beta | MVWKWMPLLLLLVCVA | 52 |
| Dipeptidase 1 | MWSGWWLWPLVAVCTA | 53 |
| Platelet glycoprotein Ib alpha chain | MPLLLLLLLLPSPLHP | 54 |
| Elastase-2A | MIRTLLLSTLVAGALS | 55 |
| Vitamin D-binding protein | MKRVLVLLLAVAFGHA | 56 |
| Angiopoietin-related protein 3 | MFTIKLLLFIVPLVIS | 57 |
| Elastase-2B | MIRTLLLSTLVAGALS | 58 |
| Integrin alpha-M | MALRVLLLTALTLCHG | 59 |
| Salivary acidic proline-rich phosphoprotein 1/2 | MLLILLSVALLAFSSA | 60 |
| Bone sialoprotein 2 | MKTALILLSILGMACA | 61 |
| Platelet glycoprotein IX | MPAWGALFLLWATAEA | 62 |
| Bone marrow proteoglycan | MKLPLLLALLFGAVSA | 63 |
| Carboxypeptidase A1 | MRGLLVLSVLLGAVFG | 64 |

TABLE 3-continued

Exemplary *H. sapiens* signal Sequences

| Description | Sequence | SEQ ID NO: |
|---|---|---|
| ADAM 32 | MFRLWLLLAGLCGLLA | 65 |
| T-cell surface glycoprotein CD1a | MLFLLLPLLAVLPGDG | 66 |
| Basic salivary proline-rich protein 4 | MLLILLSVALLALSSA | 67 |
| Proactivator polypeptide | MYALFLLASLLGAALA | 68 |
| Zymogen granule membrane protein 16 | MLTVALLALLCASASG | 69 |
| V-set and transmembrane domain-containing protein 1 | MTAEFLSLLCLGLCLG | 70 |
| Amelotin | MRSTILLFCLLGSTRS | 71 |
| Gastricsin | MKWMVVVLVCLQLLEA | 72 |
| Pancreatic triacylglycerol lipase | MLPLWTLSLLLGAVAG | 73 |
| Aggrecan core protein | MTTLLWVFVTLRVITA | 74 |
| Ephrin type-B receptor 1 | MALDYLLLLLLASAVAA | 75 |
| Alkaline phosphatase, tissue-nonspecific isozyme | MISPFLVLAIGTCLTNS | 76 |
| Stanniocalcin-1 | MLQNSAVLLVLVISASA | 77 |
| Tumor necrosis factor-inducible gene 6 protein | MIILIYLFLLLWEDTQG | 78 |
| Colipase | MEKILILLLVALSVAYA | 79 |
| Alpha-N-acetylgalactosaminidase | MLLKTVLLLGHVAQVLM | 80 |
| Legumain | MVWKVAVFLSVALGIGA | 81 |
| Complement C1r subcomponent | MWLLYLLVPALFCRAGG | 82 |
| Membrane-bound transcription factor site-1 protease | MKLVNIWLLLLVVLLCG | 83 |
| Zinc-alpha-2-glycoprotein | MVPVLLSLLLLLGPAVP | 84 |
| Cerberus | MHLLLFQLLVLLPLGKT | 85 |
| C4b-binding protein beta chain | MFFWCACCLMVAWRVSA | 86 |
| Endothelin-1 | MDYLLMIFSLLFVACQG | 87 |
| Prostate-specific antigen | MWVPVVFLTLSVTWIGA | 88 |
| Matrilysin | MRLTVLCAVCLLPGSLA | 89 |
| Interleukin-17 receptor B | MSLVLLSLAALCRSAVP | 90 |
| Phospholipid transfer protein | MALFGALFLALLAGAHA | 91 |
| Retinol-binding protein 3 | MMREWVLLMSVLLCGLA | 92 |
| Calreticulin | MLLSVPLLLGLLGLAVA | 93 |
| Granulocyte-macrophage colony-stimulating factor | MWLQSLLLLGTVACSIS | 94 |
| Cholesteryl ester transfer protein | MLAATVLTLALLGNAHA | 95 |
| Interleukin-1 receptor type I | MKVLLRLICFIALLISS | 96 |
| Protein disulfide-isomerase | MLRRALLCLAVAALVRA | 97 |
| Protein G6b | MAVFLQLLPLLLSRAQG | 98 |
| Interferon-gamma receptor alpha chain | MALLFLLPLVMQGVSRA | 99 |

TABLE 3-continued

Exemplary *H. sapiens* signal Sequences

| Description | Sequence | SEQ ID NO: |
|---|---|---|
| Carboxypeptidase M | MDFPCLWLGLLLPLVAA | 100 |
| Butyrophilin-like protein 8 | MALMLSLVLSLLKLGSG | 101 |
| Amyloid beta A4 protein | MLPGLALLLLAAWTARA | 102 |
| Prolyl 4-hydroxylase subunit alpha-1 | MIWYILIIGILLPQSLA | 103 |
| SPARC | MRAWIFFLLCLAGRALA | 104 |
| Otoraplin | MARILLLFLPGLVAVCA | 105 |
| Chromogranin-A | MRSAAVLALLLCAGQVTA | 106 |
| Tumor necrosis factor receptor superfamily member 8 | MRVLLAALGLLFLGALRA | 107 |
| Serum amyloid A protein | MKLLTGLVFCSLVLGVSS | 108 |
| CMRF35-like molecule 9 | MRLLVLLWGCLLLPGYEA | 109 |
| Cathepsin G | MQPLLLLLAFLLPTGAEA | 110 |
| Integrin alpha-E | MWLFHTLLCIASLALLAA | 111 |
| Complement factor I | MKLLHVFLLFLCFHLRFC | 112 |
| Lumican | MSLSAFTLFLALIGGTSG | 113 |
| 78 kDa glucose-regulated protein | MKLSLVAAMLLLLSAARA | 114 |
| Mammaglobin-B | MKLLMVLMLAALLLHCYA | 115 |
| Interleukin-9 | MLLAMVLTSALLLCSVAG | 116 |
| Complement factor H-related protein 2 | MWLLVSVILISRISSVGG | 117 |
| Cathepsin D | MQPSSLLPLALCLLAAPA | 118 |
| Alpha-fetoprotein | MKWVESIFLIFLLNFTES | 119 |
| Lipocalin-1 | MKPLLLAVSLGLIAALQA | 120 |
| Arylsulfatase A | MGAPRSLLLALAAGLAVA | 121 |
| Inhibin alpha chain | MVLHLLLFLLLTPQGGHS | 122 |
| Thrombomodulin | MLGVLVLGALALAGLGFP | 123 |
| Glycodelin | MLCLLLTLGVALVCGVPA | 124 |
| CD226 antigen | MDYPTLLLALLHVYRALC | 125 |
| Ephrin-A1 | MEFLWAPLLGLCCSLAAA | 126 |
| Haptoglobin | MSALGAVIALLLWGQLFA | 127 |
| Kininogen-1 | MKLITILFLCSRLLLSLT | 128 |
| Follitropin subunit beta | MKTLQFFFLFCCWKAICC | 129 |
| Apolipoprotein A-I | MKAAVLTLAVLFLTGSQA | 130 |
| Coagulation factor XI | MIFLYQVVHFILFTSVSG | 131 |
| Polymeric immunoglobulin receptor | MLLFVLTCLLAVFPAIST | 132 |
| Translocon-associated protein subunit alpha | MRLLPRLLLLLLVFPAT | 133 |
| Dickkopf-related protein 4 | MVAAVLLGLSWLCSPLGA | 134 |
| Complement factor H | MRLLAKIICLMLWAICVA | 135 |

TABLE 3-continued

Exemplary *H. sapiens* signal Sequences

| Description | Sequence | SEQ ID NO: |
|---|---|---|
| Serum albumin | MKWVTFISLLFLFSSAYS | 136 |
| Tapasin-related protein | MGTQEGWCLLLCLALSGA | 137 |
| Alpha-1-acid glycoprotein 2 | MALSWVLTVLSLLPLLEA | 138 |
| Thrombospondin-1 | MGLAWGLGVLFLMHVCGT | 139 |
| Placenta growth factor | MPVMRLFPCFLQLLAGLA | 140 |
| Serum amyloid A-4 protein | MRLFTGIVFCSLVMGVTS | 141 |
| Granzyme B | MQPILLLLAFLLLPRADA | 142 |
| Interleukin-10 | MHSSALLCCLVLLTGVRA | 143 |
| Interleukin-1 receptor-like 1 | MGFWILAILTILMYSTAA | 144 |
| T-cell-specific surface glycoprotein CD28 | MLRLLLALNLFPSIQVTG | 145 |
| Placental protein 11 | MRACISLVLAVLCGLAWA | 146 |
| Liver carboxylesterase 1 | MWLRAFILATLSASAAWG | 147 |
| Galectin-3-binding protein | MTPPRLFWVWLLVAGTQG | 148 |
| Intelectin-1 | MNQLSFLLFLIATTRGWS | 149 |
| Apolipoprotein A-II | MKLLAATVLLLTICSLEG | 150 |
| Adiponectin | MLLLGAVLLLLALPGHDQ | 151 |
| Histidine-rich glycoprotein | MKALIAALLLITLQYSCA | 152 |
| Alpha-1-acid glycoprotein 1 | MALSWVLTVLSLLPLLEA | 153 |
| Granzyme H | MQPFLLLLAFLLTPGAGT | 154 |
| Retinol-binding protein 4 | MKWVWALLLLAALGSGRA | 155 |
| Alpha-2-HS-glycoprotein | MKSLVLLLCLAQLWGCHS | 156 |
| SID1 transmembrane family member 2 | MFALGLPFLVLLVASVES | 157 |
| Apolipoprotein E | MKVLWAALLVTFLAGCQA | 158 |
| Chymotrypsinogen B | MAFLWLLSCWALLGTTFG | 159 |
| Interleukin-18 receptor 1 | MNCRELPLTLWVLISVST | 160 |
| Lysozyme C | MKALIVLGLVLLSVTVQG | 161 |
| Procollagen-lysine,2-oxoglutarate 5-dioxygenase 1 | MRPLLLLALLGWLLLAEA | 162 |
| C-reactive protein | MEKLLCFLVLTSLSHAFG | 163 |
| Extracellular superoxide dismutase [Cu-Zn] | MLALLCSCLLLAAGASDA | 164 |
| Transcobalamin-2 | MRHLGAFLFLLGVLGALT | 165 |
| Carbonic anhydrase 4 | MRMLLALLALSAARPSAS | 166 |
| CMRF35-like molecule 1 | MPLLTLYLLLFWLSGYSIA | 167 |
| Amiloride-sensitive amine oxidase [copper-containing] | MPALGWAVAAILMLQTAMA | 168 |
| Thyroglobulin | MALVLEIFTLLASICWVSA | 169 |
| Interleukin-3 | MSRLPVLLLLQLLVRPGLQ | 170 |
| Ig heavy chain V-II region SESS | MDILCSTLLLLTVPSGVLS | 171 |

TABLE 3-continued

Exemplary *H. sapiens* signal Sequences

| Description | Sequence | SEQ ID NO: |
|---|---|---|
| Cathepsin E | MKTLLLLLLVLLELGEAQG | 172 |
| Vitronectin | MAPLRPLLILALLAWVALA | 173 |
| Glia-derived nexin | MNWEILPLFLLASVTLPSIC | 174 |
| Histatin-1 | MKFFVFALVLALMISMISA | 175 |
| Glycophorin-B | MYGKIIFVLLLSEIVSISA | 176 |
| Plasma kallikrein | MILFKQATYFISLFATVSC | 177 |
| Ig heavy chain V-I region V35 | MDWTWRILFLVAAATGAHS | 178 |
| Intestinal alkaline phosphatase | MQGPWVLLLLGLRLQLSLG | 179 |
| CD83 antigen | MSRGLQLLLLSCAYSLAPA | 180 |
| Complement C4-B | MRLLWGLIWASSFFTLSLQ | 181 |
| Vasopressin-neurophysin 2-copeptin | MPDTMLPACFLGLLAFSSA | 182 |
| Neutrophil defensin 3 | MRTLAILAAILLVALQAQA | 183 |
| Interleukin-5 | MRMLLEILSLLALGAAYVYA | 184 |
| Ig lambda chain V-VI region EB4 | MAWAPLLLTLLAHCTDCWA | 185 |
| n/a | MKSVLLLTTLLVPAHLVAA | 186 |
| Programmed cell death 1 ligand 2 | MIFLLLMLSLELQLHQIAA | 187 |
| Selenoprotein P | MWRSLGLALALCLLPSGGT | 188 |
| V-set and immunoglobulin domain-containing protein 4 | MGILLGLLLLGHLTVDTYG | 189 |
| Gastric triacylglycerol lipase | MWLLLTMASLISVLGTTHG | 190 |
| Collagen alpha-1(VI) chain | MRAARALLPLLLQACWTAA | 191 |
| Coagulation factor VIII | MQIELSTCFFLCLLRFCFS | 192 |
| Matrix metalloproteinase-9 | MSLWQPLVLVLLVLGCCFA | 193 |
| CD5 antigen-like | MALLFSLILAICTRPGFLA | 194 |
| T-cell surface glycoprotein CD1e | MLLLFLLFEGLCCPGENTA | 195 |
| Interleukin-6 receptor subunit alpha | MLAVGCALLAALLAAPGAA | 196 |
| Ig heavy chain V-I region ND | MDWTWILFLVAAATRVHS | 197 |
| Junctional adhesion molecule-like | MFCPLKLILLPVLLDYSLG | 198 |
| Receptor-type tyrosine-protein phosphatase gamma | MRRLLEPCWWILFLKITSS | 199 |
| Ceruloplasmin | MKILILGIFLFLCSTPAWA | 200 |
| Coagulation factor XII | MRALLLLGFLLVSLESTLS | 201 |
| Matrix Gla protein | MKSLILLAILAALAVVTLC | 202 |
| Glycophorin-A | MYGKIIFVLLLSAIVSISA | 203 |
| Pigment epithelium-derived factor | MQALVLLLCIGALLGHSSC | 204 |
| Interleukin-21 receptor | MPRGWAAPLLLLLQGGWG | 205 |
| Alpha-lactalbumin | MRFFVPLFLVGILFPAILA | 206 |
| Serotransferrin | MRLAVGALLVCAVLGLCLA | 207 |

TABLE 3-continued

Exemplary H. sapiens signal Sequences

| Description | Sequence | SEQ ID NO: |
|---|---|---|
| Fibrinogen alpha chain | MFSMRIVCLVLSVVGTAWT | 208 |
| Integrin beta-7 | MVALPMVLVLLLVLSRGES | 209 |
| Integrin alpha-X | MTRTRAALLLFTALATSLG | 210 |
| Leukosialin | MATLLLLLGVLVVSPDALG | 211 |
| Group XIIB secretory phospholipase A2-like protein | MKLASGFLVLWLSLGGGLA | 212 |
| Beta-2-glycoprotein 1 | MISPVLILFSSFLCHVAIA | 213 |
| Statherin | MKFLVFAFILALMVSMIGA | 214 |
| Complement C4-A | MRLLWGLIWASSFFTLSLQ | 215 |
| C-C motif chemokine 14 | MKISVAAIPFFLLITIALG | 216 |
| Surfactant-associated protein G | MGSGLPLVLLLTLLGSSHG | 217 |
| Dermcidin | MRFMTLLFLTALAGALVCA | 218 |
| Glycophorin-E | MYGKIIFVLLLSGIVSISA | 219 |
| Prokineticin-1 | MRGATRVSIMLLLVTVSDC | 220 |
| Lactotransferrin | MKLVFLVLLFLGALGLCLA | 221 |
| Thy-1 membrane glycoprotein | MNLAISIALLLTVLQVSRG | 222 |
| FK506-binding protein 14 | MRLFLWNAVLTLFVTSLIG | 223 |
| Ig heavy chain V-I region HG3 | MDWTWRVFCLLAVAPGAHS | 224 |
| Myelin-associated glycoprotein | MIFLTALPLFWIMISASRG | 225 |
| Heparin cofactor 2 | MKHSLNALLIFLIITSAWG | 226 |
| Ig heavy chain V-II region ARH-77 | MKHLWFLLLWCQLPDVGVL | 227 |
| Calumenin | MDLRQFLMCLSLCTAFALS | 228 |
| Interstitial collagenase | MHSFPPLLLLLFWGVVSHS | 229 |
| CD27 antigen | MARPHPWWLCVLGTLVGLS | 230 |
| Melanotransferrin | MRGPSGALWLLLALRTVLG | 231 |
| Protein AMBP | MRSLGALLLLLSACLAVSA | 232 |
| Plasma serine protease inhibitor | MQLFLLLCLVLLSPQGASL | 233 |
| Fc receptor-like protein 2 | MLLWSLLVIFDAVTEQADS | 234 |
| Serum amyloid P-component | MNKPLLWISVLTSLLEAFA | 235 |
| Interleukin-10 receptor beta chain | MAWSLGSWLGGCLLVSALG | 236 |
| Chymase | MLLLPLPLLLFLLCSRAEA | 237 |
| Lactase-phlorizin hydrolase | MELSWHVVFIALLSFSCWG | 238 |
| Monocyte differentiation antigen CD14 | MERASCLLLLLLPLVHVSA | 239 |
| Apolipoprotein(a) | MEHKEVVLLLLLFLKSAAP | 240 |
| Histatin-3 | MKFFVFALILALMLSMTGA | 241 |
| Ig lambda chain V-I region BL2 | MTCSPLLLTLLIHCTGSWA | 242 |
| Acrosin | MVEMLPTAILLVLAVSVVA | 243 |
| Oxytocin-neurophysin 1 | MAGPSLACCLLGLLALTSA | 244 |

TABLE 3-continued

Exemplary H. sapiens signal Sequences

| Description | Sequence | SEQ ID NO: |
|---|---|---|
| Ig heavy chain V-III region VH26 | MEFGLSWLFLVAILKGVQC | 245 |
| Interleukin-31 receptor A | MMWTWALWMLPSLCKFSLA | 246 |
| Neural cell adhesion molecule L1 | MVVALRYVWPLLLCSPCLL | 247 |
| Tripeptidyl-peptidase 1 | MGLQACLLGLFALILSGKC | 248 |
| Neutrophil defensin 1 | MRTLAILAAILLVALQAQA | 249 |
| Plasminogen | MEHKEVVLLLLLFLKSGQG | 250 |
| Pulmonary surfactant-associated protein A1 | MWLCPLALNLILMAASGAVC | 251 |
| Beta-neoendorphin-dynorphin | MAWQGLVLAACLLMFPSTTA | 252 |
| Ig kappa chain V-IV region B17 | MVLQTQVFISLLLWISGAYG | 253 |
| Ig kappa chain V-III region VH | MEAPAQLLFLLLLWLPDTTR | 254 |
| Lymphocyte antigen 86 | MKGFTATLFLWTLIFPSCSG | 255 |
| C-C motif chemokine 18 | MKGLAAALLVLVCTMALCSC | 256 |
| Acetylcholine receptor subunit alpha | MEPWPLLLLFSLCSAGLVLG | 257 |
| Ig kappa chain V-III region HAH | METPAQLLFLLLLWLPDTTG | 258 |
| Cystatin-D | MMWPMHTPLLLLTALMVAVA | 259 |
| Thyrotropin subunit beta | MTALFLMSMLFGLACGQAMS | 260 |
| Carboxypeptidase N catalytic chain | MSDLLSVFLHLLLLFKLVAP | 261 |
| Bile salt-activated lipase | MGRLQLVVLGLTCCWAVASA | 262 |
| Prostate stem cell antigen | MKAVLLALLMAGLALQPGTA | 263 |
| Bactericidal/permeability-increasing protein-like 1 | MAWASRLGLLLALLLPVVGA | 264 |
| Neutrophil collagenase | MFSLKTLPFLLLLHVQISKA | 265 |
| Interleukin-17 receptor C | MPVPWFLLSLALGRSPVVLS | 266 |
| Tapasin | MKSLSLLLAVALGLATAVSA | 267 |
| Complement receptor type 2 | MGAAGLLGVFLALVAPGVLG | 268 |
| Glucagon | MKSIYFVAGLFVMLVQGSWQ | 269 |
| Probable G-protein coupled receptor 97 | MATPRGLGALLLLLLLPTSG | 270 |
| Platelet-derived growth factor subunit B | MNRCWALFLSLCCYLRLVSA | 271 |
| Beta-defensin 127 | MGLFMIIAILLFQKPTVTEQ | 272 |
| Pulmonary surfactant-associated protein A2 | MWLCPLALNLILMAASGAAC | 273 |
| Scrapie-responsive protein 1 | MKLMVLVFTIGLTLLLGVQA | 274 |
| Thyrotropin receptor | MRPADLLQLVLLLDLPRDLG | 275 |
| Interleukin-2 | MYRMQLLSCIALSLALVTNS | 276 |
| Secretogranin-1 | MQPTLLLSLLGAVGLAAVNS | 277 |
| Interferon alpha-6 | MALPFALLMALVVLSCKSSC | 278 |
| Interleukin-8 | MTSKLAVALLAAFLISAALC | 279 |

TABLE 3-continued

Exemplary *H. sapiens* signal Sequences

| Description | Sequence | SEQ ID NO: |
|---|---|---|
| Mimecan | MKTLQSTLLLLLLVPLIKPA | 280 |
| Insulin-like 3 | MDPRLPAWALVLLGPALVFA | 281 |
| Beta-2-microglobulin | MSRSVALAVLALLSLSGLEA | 282 |
| Cystatin-SA | MAWPLCTLLLLLATQAVALA | 283 |
| Ig kappa chain V-III region CLL | MEAPAQLLFLLLLWLPDTTG | 284 |
| T-cell receptor gamma chain V region PT-gamma-1/2 | MRWALLVLLAFLSPASQKSS | 285 |
| Interleukin-5 receptor subunit alpha | MIIVAHVLLILLGATEILQA | 286 |
| Kappa-casein | MKSFLLVVNALALTLPFLAV | 287 |
| Urokinase-type plasminogen activator | MRALLARLLLCVLVVSDSKG | 288 |
| Apolipoprotein A-IV | MFLKAVVLTLALVAVAGARA | 289 |
| Ig kappa chain V-III region VG | MEAPAQLLFLLLLWLPDTTG | 290 |
| T-cell receptor alpha chain V region HPB-MLT | IFASLLRAVIASICVVSSMA | 291 |
| Complement component C8 gamma chain | MLPPGTATLLTLLLAAGSLG | 292 |
| Versican core protein | MFINIKSILWMCSTLIVTHA | 293 |
| BMP and activin membrane-bound inhibitor homolog | MDRHSSYIFIWLQLELCAMA | 294 |
| Cholecystokinin | MNSGVCLCVLMAVLAAGALT | 295 |
| Mannose-binding protein C | MSLFPSLPLLLLSMVAASYS | 296 |
| Ig kappa chain V region EV15 | MGSQVHLLSFLLLWISDTRA | 297 |
| Protein PARM-1 | MVYKTLFALCILTAGWRVQS | 298 |
| Ephrin type-A receptor 3 | MDCQLSILLLLSCSVLDSFG | 299 |
| Follistatin-related protein 1 | MWKRWLALALALVAVAWVRA | 300 |
| Anterior gradient protein 2 homolog | MEKIPVSAFLLLVALSYTLA | 301 |
| Apolipoprotein C-III | MQPRVLLVVALLALLASARA | 302 |
| Ig kappa chain V-II region RPMI 6410 | MRLPAQLLGLLMLWVPGSSG | 303 |
| Mucin-like protein 1 | MKFLAVLVLLGVSIFLVSAQ | 304 |
| Interleukin-17F | MVKYLLLSILGLAFLSEAAA | 305 |
| Cystatin-SN | MAQHLSTLLLLLATLAVALA | 306 |
| Secretoglobin family 3A member 1 | MKLAALLGLCVALSCSSAAA | 307 |
| T-cell receptor alpha chain V region PY14 | MLLLLVPVLEVIFTLGGTRA | 308 |
| Ig kappa chain V-III region IARC/BL41 | METPAQLLFLLLLWLPDTTG | 309 |
| Ig lambda chain V region 4A | MAWTPLFLFLLTCCPGGSNS | 310 |
| Neutrophil gelatinase-associated lipocalin | MPLGLLWLGLALLGALHAQA | 311 |
| Thyroxine-binding globulin | MSPFLYLVLLVLGLHATIHC | 312 |

TABLE 3-continued

Exemplary *H. sapiens* signal Sequences

| Description | Sequence | SEQ ID NO: |
|---|---|---|
| Complement C2 | MGPLMVLFCLLFLYPGLADS | 313 |
| Coagulation factor XIII B chain | MRLKNLTFIIILIISGELYA | 314 |
| N-sulphoglucosamine sulphohydrolase | MSCPVPACCALLLVLGLCRA | 315 |
| Tumor necrosis factor receptor superfamily member 5 | MVRLPLQCVLWGCLLTAVHP | 316 |
| Ig kappa chain V-IV region | MVLQTQVFISLLLWISGAYG | 317 |
| Contactin-1 | MKMWLLVSEILVIISITTCLA | 318 |
| Urotensin-2 | MYKLASCCLLFIGFLNPLLS | 319 |
| Midkine | MQHRGFLLLTLLALLALTSA | 320 |
| Beta-microseminoprotein | MNVLLGSVVIFATFVTLCNA | 321 |
| Choriogonadotropin subunit beta | MEMFQGLLLLLLLSMGGTWA | 322 |
| Toll-like receptor 5 | MGDHLDLLLGVVLMAGPVFG | 323 |
| Transthyretin | MASHRLLLLCLAGLVFVSEA | 324 |
| Ig kappa chain V-III region HIC | METPAQLLFLLLLWLPDTTG | 325 |
| Cystatin-S | MARPLCTLLLLMATLAGALA | 326 |
| Uncharacterized protein C17orf99 | MGLPGLFCLAVLAASSFSKA | 327 |
| Integrin beta-1 | MNLQPIFWIGLISSVCCVFA | 328 |
| Interleukin-7 receptor subunit alpha | MTILGTTFGMVFSLLQVVSG | 329 |
| Kin of IRRE-like protein 2 | MLRMRVPALLVLLFCFRGRA | 330 |
| Ig kappa chain V-IV region JI | MVLQTQVFISLLLWISGAYG | 331 |
| Lutropin subunit beta | MEMLQGLLLLLLLSMGGAWA | 332 |
| Phospholipase A2, membrane associated | MKTLLLLAVIMIFGLLQAHG | 333 |
| Platelet-derived growth factor subunit A | MRTLACLLLLGCGYLAHVLA | 334 |
| Apolipoprotein D | MVMLLLLLSALAGLFGAAEG | 335 |
| Acetylcholine receptor subunit epsilon | MARAPLGVLLLLGLLGRGVG | 336 |
| Interleukin-13 | MALLLTTVIALTCLGGFASP | 337 |
| Lymphocyte antigen 6D | MRTALLLLAALAVATGPALT | 338 |
| Basigin | MAAALFVLLGFALLGTHGASG | 339 |
| Cytokine SCM-1 beta | MRLLILALLGICSLTAYIVEG | 340 |
| ADM | MKLVSVALMYLGSLAFLGADT | 341 |
| Dermokine | MKFQGPLACLLLALCLGSGEA | 342 |
| Thrombopoietin | MELTELLLVVMLLLTARLTLS | 343 |
| Protein ARMET | MWATQGLAVALALSVLPGSRA | 344 |
| Endoplasmin | MRALWVLGLCCVLLTFGSVRA | 345 |
| HLA class I histocompatibility antigen, alpha chain F | MAPRSLLLLLSGALALTDTWA | 346 |
| Trefoil factor 3 | MAARALCMLGLVLALLSSSSA | 347 |
| Perforin-1 | MAARLLLLGILLLLLPLPVPA | 348 |

TABLE 3-continued

Exemplary *H. sapiens* signal Sequences

| Description | Sequence | SEQ ID NO: |
|---|---|---|
| Interferon omega-1 | MALLFPLLAALVMTSYSPVGS | 349 |
| Insulin-like growth factor-binding protein 4 | MLPLCLVAALLLAAGPGPSLG | 350 |
| C-X-C motif chemokine 10 | MNQTAILICCLIFLTLSGIQG | 351 |
| Protein Z-dependent protease inhibitor | MKVVPSLLLSVLLAQVWLVPG | 352 |
| Protein kinase C-binding protein NELL2 | MESRVLLRTFCLIFGLGAVWG | 353 |
| Tubulointerstitial nephritis antigen-like | MWRCPLGLLLLLPLAGHLALG | 354 |
| Anterior gradient protein 3 homolog | MMLHSALGLCLLLVTVSSNLA | 355 |
| Biotinidase | MSGARSKLALFLCGCYVVALG | 356 |
| Cysteine-rich secretory protein 1 | MEIKHLLFLVAAACLLPMLSM | 357 |
| Collagen alpha-1(XVI) chain | MWVSWAPGLWLLGLWATFGHG | 358 |
| Interleukin-10 receptor alpha chain | MLPCLVVLLAALLSLRLGSDA | 359 |
| Complement component C1q receptor | MATSMGLLLLLLLLLTQPGAG | 360 |
| E-selectin | MIASQFLSALTLVLLIKESGA | 361 |
| Guanylin | MNAFLLFALCLLGAWAALAGG | 362 |
| T-cell surface glycoprotein CD8 alpha chain | MALPVTALLLPLALLLHAARP | 363 |
| Tumor necrosis factor receptor superfamily member 1A | MGLSTVPDLLLPLVLLELLVG | 364 |
| Microfibril-associated glycoprotein 4 | MKALLALPLLLLLSTPPCAPQ | 365 |
| C-C motif chemokine 19 | MALLLALSLLVLWTSPAPTLS | 366 |
| T-cell receptor beta chain V region CTL-L17 | MGTSLLCWMALCLLGADHADT | 367 |
| Chitinase-3-like protein 1 | MGVKASQTGFVVLVLLQCCSA | 368 |
| T-cell surface glycoprotein CD3 delta chain | MEHSTFLSGLVLATLLSQVSP | 369 |
| Colipase-like protein C6orf126 | MAAALALVAGVLSGAVLPLWS | 370 |
| T-cell surface glycoprotein CD8 beta chain | MRPRLWLLLAAQLTVLHGNSV | 371 |
| Cell surface A33 antigen | MVGKMWPVLWTLCAVRVTVDA | 372 |
| Interferon beta | MTNKCLLQIALLLCFSTTALS | 373 |
| Neuropilin-1 | MERGLPLLCAVLALVLAPAGA | 374 |
| C-X-C motif chemokine 11 | MSVKGMAIALAVILCATVVQG | 375 |
| Leptin receptor | MICQKFCVVLLHWEFIYVITA | 376 |
| VEGF co-regulated chemokine 1 | MKVLISSLLLLLPLMLMSMVS | 377 |
| Dickkopf-related protein 3 | MQRLGATLLCLLLAAAVPTAP | 378 |
| Interferon alpha-5 | MALPFVLLMALVVLNCKSICS | 379 |
| Interleukin-2 receptor alpha chain | MDSYLLMWGLLTFIMVPGCQA | 380 |
| N-acetylmuramoyl-L-alanine amidase | MAQGVLWILLGLLLWSDPGTA | 381 |
| Lactase-like protein | MKPVWVATLLWMLLLVPRLGA | 382 |

TABLE 3-continued

Exemplary *H. sapiens* signal Sequences

| Description | Sequence | SEQ ID NO: |
|---|---|---|
| SLAM family member 5 | MAQHHLWILLLCLQTWPEAAG | 383 |
| Alpha-1B-glycoprotein | MSMLVVFLLLWGVTWGPVTEA | 384 |
| Secretoglobin family 1D member 1 | MRLSVCLLLLTLALCCYRANA | 385 |
| HLA class I histocompatibility antigen, alpha chain E | MVDGTLLLLLSEALALTQTWA | 386 |
| Secreted Ly-6/uPAR-related protein 1 | MASRWAVQLLLVAAWSMGCGE | 387 |
| Uteroglobin | MKLAVTLTLVTLALCCSSASA | 388 |
| Phosphoinositide-3-kinase-interacting protein 1 | MLLAWVQAFLVSNMLLAEAYG | 389 |
| C-type lectin domain family 14 member A | MRPAFALCLLWQALWPGPGGG | 390 |
| Fibroblast growth factor receptor 4 | MRLLLALLGVLLSVPGPPVLS | 391 |
| Complement component C6 | MARRSVLYFILLNALINKGQA | 392 |
| Secretoglobin family 1D member 4 | MRLSVCLLMVSLALCCYQAHA | 393 |
| CD177 antigen | MSAVLLLALLGFILPLPGVQA | 394 |
| Ectonucleotide pyrophosphatase/phosphodiesterase family member 7 | MRGLAVLLTVALATLLAPGAG | 395 |
| Killer cell immunoglobulin-like receptor 2DL1 | MSLLVVSMACVGFFLLQGAWP | 396 |
| T-cell surface glycoprotein CD3 zeta chain | MKWKALFTAAILQAQLPITEA | 397 |
| CD109 antigen | MQGPPLLTAAHLLCVCTAALA | 398 |
| GPI transamidase component PIG-T | MAAAMPLALLVLLLLGPGGWC | 399 |
| Steryl-sulfatase | MPLRKMKIPFLLLFFLWEAES | 400 |
| SLAM family member 6 | MLWLFQSLLFVFCFGPGNVVS | 401 |
| Tetranectin | MELWGAYLLLCLFSLLTQVTT | 402 |
| C-C motif chemokine 15 | MKVSVAALSCLMLVAVLGSQA | 403 |
| FK506-binding protein 2 | MRLSWFRVLTVLSICLSAVAT | 404 |
| Interleukin-22 receptor subunit alpha-2 | MMPKHCFLGFLISFFLTGVAG | 405 |
| Tyrosine-protein kinase receptor Tie-1 | MVWRVPPFLLPILFLASHVGA | 406 |
| Cathepsin W | MALTAHPSCLLALLVAGLAQG | 407 |
| Platelet-activating factor acetylhydrolase | MVPPKLHVLFCLCGCLAVVYP | 408 |
| Tartrate-resistant acid phosphatase type 5 | MDMWTALLILQALLLPSLADG | 409 |
| Laminin subunit beta-1 | MGLLQLLAFSFLALCRARVRA | 410 |
| Tumor necrosis factor receptor superfamily member 11B | MNKLLCCALVFLDISIKWTTQ | 411 |
| C-C motif chemokine 23 | MKVSVAALSCLMLVTALGSQA | 412 |
| C-type lectin domain family 11 member A | MQAAWLLGALVVPQLLGFGHG | 413 |
| Gastrin | MQRLCVYVLIFALALAAFSEA | 414 |

TABLE 3-continued

Exemplary *H. sapiens* signal Sequences

| Description | Sequence | SEQ ID NO: |
|---|---|---|
| Low-density lipoprotein receptor | MGPWGWKLRWTVALLLAAAGT | 415 |
| L-amino-acid oxidase | MAPLALHLLVLVPILLSLVAS | 416 |
| Complement component C9 | MSACRSFAVAICILEISILTA | 417 |
| Natural killer cell receptor 2B4 | MLGQVVTLILLLLLKVYQGKG | 418 |
| Chitotriosidase-1 | MVRSVAWAGFMVLLMIPWGSA | 419 |
| Urokinase plasminogen activator surface receptor | MGHPPLLPLLLLLHTCVPASWG | 420 |
| Fibrinogen-like protein 1 | MAKVFSFILVTTALTMGREISA | 421 |
| T-cell surface glycoprotein CD3 epsilon chain | MQSGTHWRVLGLCLLSVGVWGQ | 422 |
| Cytokine-like protein 1 | MRTPGPLPVLLLLLAGAPAARP | 423 |
| T-cell surface glycoprotein CD3 gamma chain | MEQGKGLAVLILAIILLQGTLA | 424 |
| Complement component C7 | MKVISLFILVGFIGEFQSFSSA | 425 |
| Corticosteroid-binding globulin | MPLLLYTCLLWLPTSGLWTVQA | 426 |
| Beta-defensin 103 | MRIHYLLFALLFLFLVPVPGHG | 427 |
| Plasma protease C1 inhibitor | MASRLTLLTLLLLLLAGDRASS | 428 |
| Interleukin-12 subunit alpha | MCPARSLLLVATLVLLDHLSLA | 429 |
| Neurexophilin-3 | MQLTRCCFVFLVQGSLYLVICG | 430 |
| Protocadherin alpha-2 | MASSIRRGRGAWTRLLSLLLLA | 431 |
| Ig kappa chain V-I region HK102 | MDMRVPAQLLGLLLLWLPGAKC | 432 |
| Tissue factor pathway inhibitor 2 | MDPARPLGLSILLLFLTEAALG | 433 |
| Dolichyl-diphosphooligosaccharide-- protein glycosyltransferase subunit 2 | MAPPGSSTVFLLALTIIASTWA | 434 |
| Ig kappa chain V-I region Walker | MDMRVPAQLLGLLLLWLRGARC | 435 |
| Prostaglandin-H2 D-isomerase | MATHHTLWMGLALLGVLGDLQA | 436 |
| Frizzled-3 | MAMTWIVFSLWPLTVFMGHIGG | 437 |
| Hereditary hemochromatosis protein | MGPRARPALLLLMLLQTAVLQG | 438 |
| Tumor necrosis factor receptor superfamily member 1B | MAPVAVWAALAVGLELWAAAHA | 439 |
| Prenylcysteine oxidase-like | MARAPPLLAALTALLAAAAGG | 440 |
| Transmembrane and immunoglobulin domain-containing protein 2 | MGSPGMVLGLLVQIWALQEASS | 441 |
| Epigen | MALGVPISVYLLFNAMTALTEE | 442 |
| GLIPR1-like protein 1 | MALKNKFSCLWILGLCLVATTS | 443 |
| Apolipoprotein M | MFHQIWAALLYFYGIILNSIYQ | 444 |
| Cytokine receptor common gamma chain | MLKPSLPFTSLLFLQLPLLGVG | 445 |
| Tissue-type plasminogen activator | MDAMKRGLCCVLLLCGAVFVSP | 446 |
| Complement C1q subcomponent subunit A | MEGPRGWLVLCVLAISLASMVT | 447 |
| Tenascin | MGAMTQLLAGVFLAFLALATEG | 448 |

TABLE 3-continued

Exemplary *H. sapiens* signal Sequences

| Description | Sequence | SEQ ID NO: |
|---|---|---|
| Interleukin-6 receptor subunit beta | MLTLQTWLVQALFIFLTTESTG | 449 |
| Leukemia inhibitory factor | MKVLAAGVVPLLLVLHWKHGAG | 450 |
| Alkaline phosphatase, placental type | MLGPCMLLLLLLLGLRLQLSLG | 451 |
| Submaxillary gland androgen-regulated protein 3B | MKSLTWILGLWALAACFTPGES | 452 |
| TGF-beta receptor type-2 | MGRGLLRGLWPLHIVLWTRIAS | 453 |
| Lithostathine-1-alpha | MAQTSSYFMLISCLMFLSQSQG | 454 |
| Major prion protein | MANLGCWMLVLFVATWSDLGLC | 455 |
| Interleukin-12 subunit beta | MCHQQLVISWFSLVFLASPLVA | 456 |
| Cathepsin H | MWATLPLLCAGAWLLGVPVCGA | 457 |
| von Willebrand factor | MIPARFAGVLLALALILPGTLC | 458 |
| Major histocompatibility complex class I-related gene protein | MGELMAFLLPLIIVLMVKHSDS | 459 |
| Apolipoprotein C-II | MGTRLLPALFLVLLVLGFEVQG | 460 |
| Beta-hexosaminidase subunit alpha | MTSSRLWFSLLLAAAFAGRATA | 461 |
| Ig kappa chain V-I region HK101 | MDMRVLAQLLGLLLLCFPGARC | 462 |
| Kallikrein-7 | MARSLLLPLQILLLSLALETAG | 463 |
| Calcitonin gene-related peptide type 1 receptor | MEKKCTLYFLVLLPFFMILVTA | 464 |
| Cartilage matrix protein | MRVLSGTSLMLCSLLLLLQALC | 465 |
| SLAM family member 7 | MAGSPTCLTLIYILWQLTGSAA | 466 |
| Granulocyte-macrophage colony-stimulating factor receptor subunit alpha | MLLLVTSLLLCELPHPAFLLIP | 467 |
| Hepatic triacylglycerol lipase | MDTSPLCFSILLVLCIFIQSSA | 468 |
| Complement C3 | MGPTSGPSLLLLLLTHLPLALG | 469 |
| Integrin beta-2 | MLGLRPPLLALVGLLSLGCVLS | 470 |
| Deoxyribonuclease-1 | MRGMKLLGALLALAALLQGAVS | 471 |
| n/a | MAAGTAVGAWVLVLSLWGAVVG | 472 |
| SLAM family member 8 | MVMRPLWSLLLWEALLPITVTG | 473 |
| C-X-C motif chemokine 9 | MKKSGVLFLLGIILLVLIGVQG | 474 |
| Fibroblast growth factor receptor 3 | MGAPACALALCVAVAIVAGASS | 475 |
| Collagen alpha-1(I) chain | MFSFVDLRLLLLLAATALLTHG | 476 |
| Beta-glucuronidase | MARGSAVAWAALGPLLWGCALG | 477 |
| Angiopoietin-1 receptor | MDSLASLVLCGVSLLLSGTVEG | 478 |
| Elafin | MRASSFLIVVVFLIAGTLVLEA | 479 |
| Ly6/PLAUR domain-containing protein 6 | MEPGPALAWLLLLSLLADCLKA | 480 |
| Phosphatidylethanolamine-binding protein 4 | MGWTMRLVTAALLLGLMMVVTG | 481 |
| Testican-2 | MRAPGCGRLVLPLLLLAAAALA | 482 |

TABLE 3-continued

Exemplary *H. sapiens* signal Sequences

| Description | Sequence | SEQ ID NO: |
|---|---|---|
| Clusterin | MMKTLLLFVGLLLTWESGQVLG | 483 |
| CD99 antigen | MARGAALALLLFGLLGVLVAAP | 484 |
| Ig kappa chain V-I region Daudi | MDMRVPAQLLGLLLLWLRRVRC | 485 |
| Insulin-like peptide INSL5 | MKGSIFTLFLFSVLFAISEVRS | 486 |
| Neuropilin and tolloid-like protein 2 | MALERLCSVLKVLLITVLVVEG | 487 |
| Regenerating islet-derived protein 4 | MASRSMRLLLLLSCLAKTGVLG | 488 |
| Interferon alpha-1/13 | MASPFALLMVLVVLSCKSSCSLG | 489 |
| HLA class II histocompatibility antigen, DQ(3) alpha chain | MILNKALMLGALALTTVMSPCGG | 490 |
| C-C motif chemokine 1 | MQIITTALVCLLLAGMWPEDVDS | 491 |
| MHC class I polypeptide-related sequence A | MGLGPVFLLLAGIFPFAPPGAAA | 492 |
| C-C motif chemokine 4 | MKLCVTVLSLLMLVAAFCSPALS | 493 |
| Cell surface glycoprotein MUC18 | MGLPRLVCAFLLAACCCCPRVAG | 494 |
| Toll-like receptor 3 | MRQTLPCIYFWGGLLPFGMLCAS | 495 |
| HLA class II histocompatibility antigen, DQ(1) alpha chain | MILNKALMLGALALTTVMSPCGG | 496 |
| Hemopexin | MARVLGAPVALGLWSLCWSLAIA | 497 |
| Interferon alpha-10 | MALSFSLLMAVLVLSYKSICSLG | 498 |
| C-C motif chemokine 17 | MAPLKMLALVTLLLGASLQHIHA | 499 |
| Corticotropin-releasing factor receptor 1 | MGGHPQLRLVKALLLLGLNPVSA | 500 |
| Ficolin-3 | MDLLWILPSLWLLLLGGPACLKT | 501 |
| C-C motif chemokine 16 | MKVSEAALSLLVLILIITSASRS | 502 |
| Alpha-type platelet-derived growth factor receptor | MGTSHPAFLVLGCLLTGLSLILC | 503 |
| HLA class II histocompatibility antigen, DQ(W3) alpha chain | MILNKALMLGSLALTTVMSPCGG | 504 |
| Semenogelin-1 | MKPNIIFVLSLLLILEKQAAVMG | 505 |
| HLA class II histocompatibility antigen, DQ(5) alpha chain | MILNKALLLGALALTTVMSPCGG | 506 |
| Uncharacterized protein C11orfB3 | MDSLRKMLISVAMLGAGAGVGYA | 507 |
| Interferon alpha-21 | MALSFSLLMAVLVLSYKSICSLG | 508 |
| Phosphatidylinositol-glycan-specific phospholipase D | MSAFRLWPGLLIMLGSLCHRGSP | 509 |
| Interferon alpha-4 | MALSFSLLMAVLVLSYKSICSLG | 510 |
| Hyaluronan-binding protein 2 | MFARMSDLHVLLLMALVGKTACG | 511 |
| C-C motif chemokine 21 | MAQSLALSLLILVLAFGIPRTQG | 512 |
| Interleukin-17A | MTPGKTSLVSLLLLLSLEAIVKA | 513 |
| Interferon alpha-2 | MALTFALLVALLVLSCKSSCSVG | 514 |

TABLE 3-continued

Exemplary *H. sapiens* signal Sequences

| Description | Sequence | SEQ ID NO: |
|---|---|---|
| Eotaxin | MKVSAALLWLLLIAAAFSPQGLA | 515 |
| C-C motif chemokine 3 | MQVSTAALAVLLCTMALCNQFSA | 516 |
| Appetite-regulating hormone | MPSPGTVCSLLLLGMLWLDLAMA | 517 |
| Metalloproteinase inhibitor 3 | MTPWLGLIVLLGSWSLGDWGAEA | 518 |
| Tumor necrosis factor receptor superfamily member 9 | MGNSCYNIVATLLLVLNFERTRS | 519 |
| Alpha-N-acetylglucosaminidase | MEAVAVAAAVGVLLLAGAGGAAG | 520 |
| Leukocyte immunoglobulin-like receptor subfamily A member 3 | MTPILTVLICLGLSLDPRTHVQA | 521 |
| Vitamin K-dependent protein Z | MAGCVPLLQGLVLVLALHRVEPS | 522 |
| Sclerostin domain-containing protein 1 | MLPPAIHFYLLPLACILMKSCLA | 523 |
| Dolichyl-diphosphooligosaccharide--protein glycosyltransferase subunit 1 | MEAPAAGLFLLLLLGTWAPAPGS | 524 |
| Alpha-2-macroglobulin | MGKNKLLHPSLVLLLLVLLPTDA | 525 |
| Serine protease inhibitor Kazal-type 2 | MALSVLRLALLLLAVTFAASLIP | 526 |
| C-C motif chemokine 3-like 1 | MQVSTAALAVLLCTMALCNQVLS | 527 |
| Transcobalamin-1 | MRQSHQLPLVGLLLFSFIPSQLC | 528 |
| C-C motif chemokine 5 | MKVSAAALAVILIATALCAPASA | 529 |

Membrane Anchors

As used herein, "membrane anchor" and "anchor," including pluralizations and variations and the like refers to a polypeptide sequence or combination of sequences that mediate attachment of a polypeptide to a cell membrane. Typically, membrane anchors are positioned on the C terminus. Without being bound by any particular theory, a polypeptide comprising an N terminal signal sequence can enter the endoplasmic reticulum, and a membrane anchor or portion thereof can provide a "stop" signal so that the membrane anchor can remain embedded in the endoplasmic reticulum membrane (and thus can remain embedded in the cell membrane upon fusion of a vesicle containing the polypeptide with the cell membrane). Accordingly, in some embodiments, the membrane anchor is positioned on the C terminus of a polypeptide. Accordingly, in some embodiments, a polynucleotide encoding a membrane anchor (an "anchor polynucleotide") is positioned downstream of a polypeptide of interest or an insertion site for the same. Without being bound by any particular theory, insertion of a polypeptide's membrane anchor into the cell membrane can be accomplished by insertion of the membrane anchor into the endoplasmic reticulum membrane, and subsequent transportation of the anchored polypeptide to the golgi and cell membrane. Accordingly, in some embodiments, the membrane anchor is positioned downstream of a signal sequence.

In some embodiments, the membrane anchor is substantially hydrophobic. Accordingly, in some embodiments, a majority of the amino acid residues of the membrane anchor are hydrophobic. Exemplary hydrophobic amino acid residues include Valine (V), Leucine (L), Isoleucine (I), Phenylalanine (F), and Methoionine (M). In some embodiments, at least about 50% of the amino acid residues of the membrane anchor, for example about 50%, 60%, 70%, 80%, 90%, or 95% of the amino acid residues of the membrane anchor are hydrophobic. In some embodiments, a membrane anchor facilitates the attachment of a fatty acid sequence, for example a glycosylphosphatidyl-inositol (GPI) anchor, to a polypeptide.

In some embodiments, the membrane anchor comprises the IgM trans-membrane anchor, corresponding to the last 41 aa from the C terminus of the membrane-bound form of human IgM (EGEVSADEEGFENLWATASTFIVL-FLLSLFYSTTVTLFKVK, SEQ ID NO: 530). In some embodiments, the IgM transmembrane anchor is encoded by the polynucleotide having the sequence (GAGGGGGAG-GTGAGCGCCGACGAGGAGGGCTTTGAGAACCT-GTGGGCCACCGC CTCCACCTTCATCGTCCTCTTC-CTCCTGAGCCTCTTCTACAGTACCACCGTCACCT TGTTCAAGGTGAAATG SEQ ID NO: 552). Additional membrane anchor polypeptides and polynucleotides encoding the same are well-known to a person skilled in the art. Exemplary transmembrane domains of *Homo sapiens* polypeptides are provided in Table 4, below, and include SEQ ID NOs: 530 to 551. In some embodiments, a membrane anchor is selected from Table 4. In some embodiments, the membrane anchor has at least about 80%, at least about 85%, at least about 90%, at least about 95%, at least about 97%, at least about 99%, or more, sequence identity to any one of the sequences of Table 4. In some embodiments, an anchor polynucleotide encoding any one of the membrane anchors referenced herein is provided.

TABLE 4

Exemplary *H. sapiens* membrane anchors

| Description | Sequence | SEQ ID NO: |
|---|---|---|
| last 41 aa from the C terminus of the membrane-bound form of human IgM | EGEVSADEEGFENLWATASTFIVLF LLSLFYSTTVTLFKVK | 530 |
| 4F2 cell-surface antigen heavy chain | LLLLFWLGWLGMLAGAVVIIV | 531 |
| Aminopeptidase N | KSLGILGILLGVAAVCTHALSVV | 532 |
| Ankyrin repeat and LEM domain-containing protein | ALAWELLGASVLLIAVRWLV | 533 |
| Membrane primary amine oxidase | ILVLLILAVITIFALVCVLLV | 534 |
| Aspartyl/asparaginyl beta-hydroxylase | FFTWFMVIALLGVWTSVAVVW | 535 |
| Beta-1,4-galactosyltransferase 1 | LLVAVCALHLGVTLVYYLAG | 536 |
| Histo-blood group ABO system transferase | GYGVLSPRSLMPGSLERGFCM | 537 |
| Bone marrow stromal antigen 2 | KLLLGIGILVLLIIVILGVPLIIFTIKA | 538 |
| Linker for activation of T-cells family members | ELLWPGAALLVLLGVAASLCV | 539 |
| HLA class I histocompatibility antigen, A-1 antigen, A-1 alpha chain | VGIIAGLVLLGAVITGAVVAAVMW | 540 |
| Fatty aldehyde dehydrogenase | LGLLLLTFLGIVAAVLV | 541 |
| B-cell receptor-associated protein 31 | LYIAGFSLLLSFLLRRLVTLI | 542 |
| Bone morphogenetic protein receptor type-1A | WLVLLISMAVCIIAMIIFSSCFCY | 543 |
| Cadherin-1 | ILGILGGILALLILILLLLF | 544 |
| Cell adhesion molecule 1 | AVIGGVVAVVVFAMLCLLIIL | 545 |
| T-cell surface antigen CD2 | IYLIIGICGGGSLLMVFVALLVFYIT | 546 |
| CD44 antigen | WLIILASLLALALILAVCIAV | 547 |
| T-lymphocyte activation antigen CD86 | WITAVLPTVIICVMVFCLILW | 548 |
| B-cell antigen receptor complex-associated protein alpha chain | IITAEGIILLFCAVVPGTLLLF | 549 |
| Complement receptor type 1 | ALIVGTLSGTIFFILLIIFLSWIIL | 550 |
| Macrophage colony-stimulating factor 1 receptor | VVVACMSIMALLLLLLLLLY | 551 |

"Molecular Rheostat" Constructs

Cleavage sites can be useful for separating two or more polypeptides encoded by a single nucleic acid sequence, for example a transcript. As such, some embodiments include polynucleotide "molecular rheostat" constructs that comprise at least one cleavage polynucleotide positioned between two polypeptide-encoding polynucleotides.

In some embodiments, the molecular rheostat construct can be configured to provide a signal sequence along with a C-terminal detachable anchor sequence on a desired polypeptide. In some embodiments, the molecular rheostat construct comprises a first polynucleotide encoding a desired polypeptide upstream of, and in-frame with a signal polynucleotide, which in turn is upstream of, and in-frame with an anchor polynucleotide. In some embodiments, the molecular rheostat construct comprises a first insertion site for a desired polynucleotide, upstream of a signal polynucleotide, which in turn is upstream of, and in-frame with an anchor polynucleotide. A cleavage polynucleotide can be positioned between the signal polynucleotide and the anchor polynucleotide of any of the above molecular rheostat constructs. In some embodiments, there are no stop codons between the first polynucleotide or first insertion site and the signal polynucleotide. The cleavage polynucleotide can be selected based on desired activity of the corresponding cleavage site. For example, if a high frequency of separation of the signal polynucleotide and anchor polynucleotide is desired (for example, to produce a high ratio of secreted to surface polypeptide), a high-activity cleavage polynucleotide can be selected. For example, if a low frequency of separation of the signal polynucleotide and anchor polynucleotide is desired (for example, to produce a low ratio of secreted to surface polypeptide), a low-activity cleavage polynucleotide can be selected.

In some embodiments, a high-activity cleavage polynucleotide comprises a polynucleotide that, when provided to a cell as the sole cleavage polynucleotide between the polypeptide-encoding polynucleotide and anchor polynucleotide in the molecular rheostat vector described in Example 3 under the conditions of Example 3, the amount of secreted polypeptide in supernatant is at least 75% of the amount of polypeptide in control supernatant that is produced by the same molar amount of a control vector (as described in Example 3) that lacks the anchor sequence. In some embodiments, a low-activity cleavage polynucleotide comprises a polynucleotide that, when provided to a cell as the sole cleavage polynucleotide between the polypeptide-encoding polynucleotide and anchor polynucleotide in the molecular rheostat vector described in Example 3 under the conditions of Example 3, the amount of secreted polypeptide in supernatant is less than 25% of the amount of polypeptide in supernatant as is produced by the same molar amount of a control vector (as described in Example 3) that lacks the anchor sequence.

In some embodiments, the molecular rheostat construct can be configured to provide a signal sequence on the N terminus, and detachable anchor sequence on the C terminus of a desired polypeptide. In some embodiments, the molecular rheostat construct comprises a signal polynucleotide upstream of, and in-frame with a first polynucleotide encoding a desired polypeptide, which in turn is upstream of, and in-frame with an anchor polynucleotide. In some embodiments, the molecular rheostat construct comprises a signal polynucleotide upstream of, and in-frame with a first insertion site for a polynucleotide encoding a desired polypeptide, and the first insertion site is upstream of, and in-frame with an anchor polynucleotide. In some embodiments, a cleavage polynucleotide is positioned between the first polynucleotide (or first insertion site) and the anchor polynucleotide. In some embodiments, the cleavage polynucleotide is in-frame with the coding sequence of the first polynucleotide, if present, or such that it is in-frame with the insertion site, if the first polynucleotide is not present.

In some embodiments, any of the above molecular rheostat constructs further comprises a second polynucleotide encoding a second desired polypeptide (other than the signal sequence, anchor, or cleave site), or a second insertion site. The second polynucleotide or insertion site can be upstream of the first polynucleotide or first insertion site. A second cleavage polynucleotide can be positioned between the second polynucleotide or insertion site and first polynucleotide or insertion site. The second cleavage polynucleotide can be in-frame with the coding sequence of the second polynucleotide, if present. The second cleavage polynucleotide can be in-frame with the first polynucleotide, if present. In some embodiments, the second cleavage polynucleotide has a high level of activity, for example, to produce a high frequency of separation between the first and second polypeptides. In some embodiments the second polynucleotide is upstream of the first insertion site. In some embodiments, the second polynucleotide is upstream of the first polynucleotide. In some embodiments, the second insertion site is upstream of the first insertion site. In some embodiments, the second insertion site is upstream of the first polynucleotide.

In some embodiments, the construct comprises, from 5' to 3', a second signal polynucleotide, a second polynucleotide encoding a desired polypeptide, a second cleavage polynucleotide, a first polynucleotide encoding a desired polypeptide, a first signal polynucleotide, a first cleavage polynucleotide, and an anchor polynucleotide. In some embodiments, the construct comprises, from 5' to 3', a second signal polynucleotide, a second polynucleotide encoding a desired polypeptide, a second cleavage polynucleotide, a first signal polynucleotide, a first polynucleotide encoding a desired polypeptide, a first cleavage polynucleotide, and an anchor polynucleotide. In some embodiments, the construct comprises, from 5' to 3', a first polynucleotide encoding a desired polypeptide, a first signal polynucleotide, a first cleavage polynucleotide, and an anchor polynucleotide. In some embodiments, the construct comprises, from 5' to 3', a first signal polynucleotide, a first polynucleotide encoding a desired polypeptide, a first cleavage polynucleotide, and an anchor polynucleotide.

In some embodiments, the construct comprises, from 5' to 3', a second signal polynucleotide, a second insertion site, a second cleavage polynucleotide, a first polynucleotide encoding a desired polypeptide, a first insertion site, a first cleavage polynucleotide, and an anchor polynucleotide. In some embodiments, the construct comprises, from 5' to 3', a second signal polynucleotide, a second insertion site, a second cleavage polynucleotide, a first signal polynucleotide, a first insertion site, a first cleavage polynucleotide, and an anchor polynucleotide. In some embodiments, the construct comprises, from 5' to 3', a first insertion site, a first signal polynucleotide, a first cleavage polynucleotide, and an anchor polynucleotide. In some embodiments, the construct comprises, from 5' to 3', a first signal polynucleotide, a first insertion site, a first cleavage polynucleotide, and an anchor polynucleotide.

In some embodiments, the construct comprises, from 5' to 3', a second signal polynucleotide, a second polynucleotide encoding a desired polypeptide, a second cleavage polynucleotide, a first insertion site, a first signal polynucleotide, a first cleavage polynucleotide, and an anchor polynucleotide. In some embodiments, the construct comprises, from 5' to 3', a second signal polynucleotide, a second polynucleotide encoding a desired polypeptide, a second cleavage polynucleotide, a first signal polynucleotide, a first insertion site, a first cleavage polynucleotide, and an anchor polynucleotide. In some embodiments, the construct comprises, from 5' to 3', a second signal polynucleotide, a second insertion site, a second cleavage polynucleotide, a first polynucleotide encoding a desired polypeptide, a first signal polynucleotide, a first cleavage polynucleotide, and an anchor polynucleotide. In some embodiments, the construct comprises, from 5' to 3', a second signal polynucleotide, a second insertion site, a second cleavage polynucleotide, a first signal polynucleotide, a first polynucleotide encoding a desired polypeptide, a first cleavage polynucleotide, and an anchor polynucleotide.

In some embodiments, the construct comprises, from 5' to 3', a second signal polynucleotide, a second polynucleotide encoding a desired polypeptide, a second insertion cleavage polynucleotide, a first polynucleotide encoding a desired polypeptide, a first signal polynucleotide, a first insertion site for a cleavage polynucleotide, and an anchor polynucleotide. In some embodiments, the construct comprises, from 5' to 3', a second signal polynucleotide, a second polynucleotide encoding a desired polypeptide, a second cleavage polynucleotide, a first signal polynucleotide, a first polynucleotide encoding a desired polypeptide, a first insertion site for a cleavage polynucleotide, and an anchor polynucleotide. In some embodiments, the construct comprises, from 5' to 3', a first polynucleotide encoding a desired polypeptide, a first signal polynucleotide, a first insertion site for a cleavage polynucleotide, and an anchor polynucleotide. In some embodiments, the construct comprises, from 5' to 3', a first signal polynucleotide, a first polynucleotide encoding a desired polypeptide, a first insertion site for a cleavage polynucleotide, and an anchor polynucleotide.

In some embodiments, the construct comprises, from 5' to 3', a second signal polynucleotide, a second polynucleotide encoding a desired polypeptide, a second insertion cleavage polynucleotide, a first insertion site for a polynucleotide encoding a desired polypeptide, a first signal polynucleotide, a first insertion site for a cleavage polynucleotide, and an anchor polynucleotide. In some embodiments, the construct comprises, from 5' to 3', a second signal polynucleotide, a second polynucleotide encoding a desired polypeptide, a second cleavage polynucleotide, a first signal polynucleotide, a first insertion site for a polynucleotide encoding a desired polypeptide, a first insertion site for a cleavage polynucleotide, and an anchor polynucleotide. In some embodiments, the construct comprises, from 5' to 3', a first insertion site for a polynucleotide encoding a desired polypeptide, a first signal polynucleotide, a first insertion site for a cleavage polynucleotide, and an anchor polynucleotide. In some embodiments, the construct comprises, from 5' to 3', a first signal polynucleotide, a first insertion site for a polynucleotide encoding a desired polypeptide, a first insertion site for a cleavage polynucleotide, and an anchor polynucleotide. In some embodiments, the polynucleotides encoding peptides of interest, signal polynucleotides, the cleavage polynucleotides, and the anchor polynucleotides of any of the molecular constructs described herein are in-frame with each other.

In some embodiments, the first and second polypeptides form a complex in which the first polypeptide can be membrane-bound or secreted. In some embodiments, each polypeptide of the complex comprises a signal sequence. As such, the complex can be membrane-bound and/or secreted. In some embodiments, the complex comprises an immunoglobulin, for example an IgA, IgD, IgE, IG, or IgM. In some embodiments, the complex comprises a B cell receptor.

In some embodiments, the first desired polypeptide, the second desired polypeptide, or each of the first and second desired polypeptides comprises a marker as described herein.

In some embodiments, a promoter is positioned upstream of the most upstream polynucleotide or insertion site, and configured to drive transcription of portions of the molecular rheostat construct, including, but not limited to, second polynucleotide (if present), second cleavage polynucleotide (if present), first polynucleotide (if present), signal polynucleotide, first cleavage polynucleotide, and/or anchor polynucleotide. In some embodiments, activity of the promoter is modulated by additional cis-regulatory sequences, for example enhancers and/or repressors.

As it can be useful to select a cleavage site having a desired level of activity, in some embodiments, a cleavage polynucleotide having a desired level of activity can be inserted into any of the molecular rheostat constructs described herein. In some embodiments, rather than a particular cleavage polynucleotide, the molecular rheostat construct comprises an insertion site into which a cleavage polynucleotide, or cassette comprising a cleavage polynucleotide can be inserted. In some embodiments, the molecular rheostat construct comprises restriction endonuclease sites flanking the cleavage polynucleotide, or flanking an insertion site for the cleavage polynucleotide so that a desired cleavage polynucleotide can be inserted into the molecular rheostat construct. In some embodiments, the cleavage polynucleotide can be inserted into the construct in a desired orientation, for example through use of different 5' and 3' restriction endonuclease sites flanking the cleavage polynucleotide. In some embodiments, the molecular rheostat construct comprises a GATEWAY (Life Technologies Corporation) destination site into which the cleavage polynucleotide can be inserted, and a plurality of cleavage polynucleotides is provided in GATEWAY (Life Technologies Corporation) entry vectors (for an overview of GATEWAY technology, see, Walhout A J, et al., (2000) Gateway recombinational cloning: application to the cloning of large numbers of open reading frames or ORFeomes. Methods Enzymol 328: 575-592, hereby incorporated by reference in its entirety).

In some embodiments, any of the above molecular rheostat constructs comprises an insertion site instead of an indicated cleavage sequence.

Vectors and Polynucleotide Delivery

A polynucleotide delivery system is any system capable of introducing a polynucleotide, particularly an antigen-specific polynucleotide into a target cell. Polynucleotide delivery systems include both viral and non-viral delivery systems. One of skill in the art will be able to determine the type of polynucleotide delivery system that can be used to effectively deliver a desired polynucleotide into a target cell.

In some embodiments, the polynucleotide is introduced into the target cell in a single polynucleotide delivery system. In some embodiments, a single polynucleotide delivery system is utilized, comprising polynucleotides encoding each subunit of the receptor.

Some embodiments include vectors, for example vectors that comprise one or more cleavage sites. In some embodiments, polynucleotides are delivered to cells via one or more vectors. In some embodiments, the vector is a lentiviral vector. In some embodiments, the lentiviral vector is a pHAGE2 or pHAGE6 vector, or modification thereof.

In some embodiments, a vector comprises a molecular rheostat construct as described herein.

Promoters

In some embodiments, vectors provided herein include a promoter. Various promoters can be operably linked with the coding sequences of a molecular rheostat construct as described herein. In some embodiments, a promoter is operably linked with a first polynucleotide encoding a first desired polypeptide, a first cleavage polynucleotide, and a first anchor polynucleotide. In some embodiments, a promoter is operably linked with a first polynucleotide encoding a first desired polypeptide, a first cleavage polynucleotide, a first anchor polynucleotide, a second polynucleotide encoding a desired polypeptide, a second signal polynucleotide, and a second cleavage polypeptide, if present. In some embodiments, the promoter can drive the expression of the desired polypeptide or polypeptides in a cell comprising a vector that comprises a molecular rheostat construct as described herein. In some embodiments, the cell is infected with a virus derived from a viral vector. The promoter can be naturally-occurring or non-naturally occurring. In some embodiments, the promoter drives expression in a particular cell type or combination of cell types. In some embodiments, the promoter drives expression in a particular cell lineage, for example a B cell lineage. In some embodiments, the promoter drives expression in a particular tissue type or combination of tissue types. In some embodiments, the promoter is inducible. In some embodiments, the promoter is inducible via a hormone, drug, small molecule, or stimulus, such as heat or electromagnetic radiation. Examples of promoters, include, but are not limited to, viral promoters, plant promoters and mammalian promoters. Examples of viral promoters include, but are not limited to cytomegalovirus (CMV) immediate early promoter, CAG promoter (which is a combination of the CMV early enhancer element and chicken beta-actin promoter, described in Alexopoulou et al. BMC Cell Biology 9:2, (2008)), simian virus 40 (SV40) promoter, the 35S RNA and 19S RNA promoters of cauliflower mosaic virus (CaMV) described in Brisson et al., Nature 1984, 310:511-514, the coat protein promoter to tobacco mosaic virus (TMV), and any variants thereof. Examples of plant promoters include, but are not limited to, heat shock promoters, such as soybean hsp17.5-E or hsp17.3-B described in Gurley et al., Mol. Cell. Biol. 1986, 6:559-565, and any variants thereof. Examples of mammalian promoters include, but are not limited to, human elongation factor 1α-subunit (EF1-1α) promoter, human ubiquitin C (UCB) promoter, murine phosphoglycerate kinase-1 (PGK) promoter, and any variants thereof.

Regulatory Elements

In some embodiments, the vector includes one or more regulatory elements. Various posttranscriptional regulatory elements can be used in vectors, for example to increase expression level of the desired protein in a host cell. In some embodiments, the posttranscriptional regulatory element is a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element (RTE), and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

In some embodiments, a vector as described herein includes a prokaryotic replicon (that is, a DNA sequence having the ability to direct autonomous replication and maintenance of the recombinant DNA molecule extrachromosomally in a prokaryotic host cell), such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline. In some embodiments, the vector is a viral vector.

In some embodiments, a vector provided herein includes a gene for a selectable marker that is effective in a eukaryotic cell, such as a drug resistance selection marker. This selectable marker gene can encode a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, vectors disclosed herein include various regulatory elements, such as a transcription initiation region and/or a transcriptional termination region. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In some embodiments, the transcriptional termination region is SV40 late poly(A) sequence.

Markers

One or more of the first polynucleotide encoding a polypeptide of interest, or the second polynucleotide encoding a polypeptide of interest of a molecular rheostat construct as described herein can encode a marker that can be used to identify cells that have been successfully transfected. Accordingly, in some embodiments, the molecular rheostat construct comprises a marker. For example, the construct may comprise a polynucleotide that encodes a marker, such as green fluorescent protein (GFP), red fluorescent protein (RFP), yellow fluorescent protein (YFP), cyan fluorescent protein (CFP), and the like or an enzyme like beta lactamase, horseradish peroxidase, luciferase or herpes simplex virus type 1 thymidine kinase (hsvTK). Substrates for the enzymes can be subsequently provided and cells expressing the antigen specific polypeptide can be identified. For example, the radiotracers 131iodine-FIAU and 124Iiodine-FIAU, which are substrates for hsvTK, can be used to non-invasively identify cells co-expressing hsvTK and the antigen specific polypeptide. (Ponomarev et al. *Neoplasia* 3:480-488 (2001), incorporated herein by reference). In some embodiments, at least the first or second polynucleotide polypeptide of interest encodes a marker in-frame with additional coding sequence of interest, so as to encode a marker fused to additional polypeptide of interest, for example GFP fused to a B cell receptor heavy chain. In addition, since the marker is typically under the control of the same promoter as the polypeptide of interest can be monitored indirectly by observing the marker. For example, in a therapeutic context, T cells or B cells created by the disclosed methods can be identified and their longevity monitored by examining a patient's cells, such as cells in the blood or lymphatic system, for the presence of the marker protein. The marker may also be used to isolate immune cells created by the disclosed methods, for example for subsequent in vitro expansion.

Insertion Sites

In some embodiments, the vector includes one or more insertion sites. An insertion site can be positioned for the insertion of a polynucleotide in a desired location. In some embodiments, the insertion site is for inserting a polynucleotide encoding a desired polypeptide in a desired location. In some embodiments, the insertion site is for inserting a desired cleavage polynucleotide in a desired location. In some embodiments, the insertion site is for inserting a desired signal polynucleotide in a desired location. In some embodiments, the insertion site is for inserting an anchor polynucleotide in a desired location. For example, an insertion site can be positioned upstream of a polynucleotide encoding a signal sequence, cleavage site, and a membrane anchor, so as to facilitate the insertion of a polynucleotide encoding a desired polypeptide upstream of, and in-frame with the signal sequence, cleavage site, and membrane anchor. For example, an insertion site can be positioned between a polynucleotide encoding a polypeptide of interest and an anchor polynucleotide so as to facilitate the insertion of a cleavage polynucleotide of interest, for example a cleavage polynucleotide encoding a cleavage site with a desired activity level.

In some embodiments, the insertion site comprises one or more restriction endonuclease sites. In some embodiments, the insertion site comprises a multiple cloning site (MCS). In some embodiments, the insertion site comprises a GATEWAY destination site.

Desired Polypeptides

As used herein, a "desired polypeptide," which alternatively may be referred to as a "polypeptide of interest" can be any polypeptide or protein, including naturally-occurring and non-naturally occurring proteins. In some embodiments, a polynucleotide encoding one or more desired polypeptides can be inserted into the viral vectors disclosed herein, wherein the polynucleotide is operably linked with the promoter. In some instances, the promoter can drive the expression of the protein(s) of interest in a host cell (e.g., a human muscle cell).

Examples of desired proteins include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof, and the like.

In some embodiments, the desired polypeptides comprise a heavy chain and a kappa light chain of the B cell receptor. In some embodiments, a molecular rheostat construct as described herein comprises a first polynucleotide encoding the heavy chain or a portion thereof, a signal sequence, and an anchor polynucleotide as described herein, so that in the absence of cleavage site activity, the heavy chain will comprise a signal sequence and a C-terminal membrane anchor, and remain membrane-bound, but in the presence of cleavage activity, the heavy chain will comprise a signal sequence, but will not comprise the membrane anchor, and will be secreted. For example, the polynucleotide encoding the heavy chain can be upstream of the cleavage polynucleotide, which can be upstream of the anchor polynucleotide. The coding portion of the polynucleotide encoding the heavy chain can be in-frame with the signal polynucleotide and the anchor polynucleotide. In some embodiments, a polynucleotide encoding the kappa light chain is positioned upstream of the polynucleotide encoding the heavy chain, and a second cleavage polynucleotide can be positioned between the light chain and heavy chain-encoding polynucleotides. In some embodiments, the second cleavage polynucleotide encodes a relatively high-activity cleavage site, resulting in approximately a 1:1 ratio of light chain and heavy chain produced and separated by the molecular rheostat construct. In some embodiments, the second cleavage polynucleotide is inserted in-frame with the coding portion of the light chain and/or heavy chain polynucleotide.

Kits

Depending upon a particular application, it can be useful to select a cleavage site that provides a desired level of activity, and as such, can provide a corresponding desired ratio of secreted-to-surface polypeptides. It can also be useful to insert a desired polynucleotide or polynucleotides encoding a desired polypeptide or polypeptides into a molecular rheostat construct that can be used to express a desired ratio of secreted-to-surface polypeptide. As such, some embodiments include kits.

In some embodiments, the kit includes a molecular rheostat construct as described herein and an assortment of cleavage polynucleotides encoding cleavage sites with various levels of activity, for example some high-activity cleavage sites, and some low-activity cleavage sites. In some embodiments, the molecular rheostat construct comprises an insertion site for one or more polynucleotides encoding a desired polypeptide, and an insertion site for inserting a desired cleavage polynucleotide between an insertion site for a polynucleotide encoding a desired polypeptide and an anchor polypeptide. In some embodiments, the molecular rheostat construct comprises a polynucleotide encoding a desired polypeptide, and an insertion site for inserting a desired cleavage polynucleotide between the a polynucleotide encoding a desired polypeptide and an anchor polypeptide. Such a kit can be useful for selecting a cleavage site with a desired activity level, so as to produce a desired ratio of secreted to surface bound polypeptide.

In some embodiments, the kit includes a library of molecular rheostat constructs as described herein. In some embodiments, the library includes two or more types of construct, each of which comprises a different cleavage polynucleotide. In some embodiments, each construct of the library comprises a polynucleotide encoding a desired polypeptide as described herein. In some embodiments, each construct comprises a polynucleotide encoding a marker as described herein. In some embodiments, the kit includes packaging, and instruction that the contents thereof can be used for the expression of secreted and membrane-bound polypeptide from a single coding sequence, and moreover can be used for the expression of secreted and membrane-bound polypeptide in a desired ratio.

In some embodiments, the kit includes at least one molecular rheostat construct as described herein, and a library of cleavage polynucleotides as described herein. In some embodiments, the library includes two or more cleavage sequences as described herein. In some embodiments, the cleavage polynucleotides of the library are flanked by sequences that facilitate insertion into the construct. In some embodiments, the cleavage polynucleotides of the library are flanked by restriction endonuclease sites that correspond to restriction endonuclease sites of the construct to facilitate insertion of a desired cleavage polynucleotide or polynucleotides into the construct. In some embodiments, the cleavage polynucleotides of the library are in GATEWAY entry vectors, and the construct comprises a GATEWAY destination vector.

Target Cells

In some embodiments, the molecular rheostat construct is expressed in a target cell. Target cells can be selected based on particular applications, for example gene therapy in cells of the hematopoietic lineage. Target cells can include any cell that has the requisite machinery for a polynucleotide to be translated, for a cleavage site to be active and for a signal sequence and anchor sequence to function. In some embodiments, target cells can include germline cells and cell lines, somatic cells and cell lines, embryonic stem cells, and pluripotent stem cells. In some embodiments, target cells are stem cells derived from any of these origins. In some embodiments, target cells comprise induced pluripotent stem cells. When the target cells are germline cells, the target cells can be selected from the group consisting of single-cell embryos and embryonic stem cells (ES). In some embodiments, target cells comprise somatic cells. When the target cells are somatic cells, the cells can include, for example, mature lymphocytes as well as hematopoietic stem cells.

In some embodiments, a target cell is a stem cell or stem cell line, including without limitation heterogeneous populations of cells that contain stem cells. In some embodiments, the target cells are hematopoietic stem cells. In some embodiments, the target cells are primary bone marrow cells. Target cells can be derived from any mammalian organism including without limitation, humans, pigs, cows, horses, sheep, goats, rats, mice, rabbits, dogs, cats and guinea pigs. Target cells may be obtained by any method known in the art.

Target cells may be contacted with a polynucleotide delivery system either in vivo or in vitro. In some embodiments, target cells are maintained in culture and are contacted with the polynucleotide delivery system in vitro. Methods for culturing cells are well known in the art.

In some embodiments, the target cells comprise non-dividing cells. In some embodiments, a lentiviral vector is provided for the transformation of target cells. The lentiviral vector can comprise a molecular rheostat construct as described herein.

Depending on the polynucleotide delivery system that is to be used, target cell division may be required for transformation. Target cells can be stimulated to divide in vitro by any method known in the art. For example, hematopoietic stem cells can be cultured in the presence of one or more growth factors, such as IL-3, IL-6 and/or stem cell factor (SCF).

Transgenic Animals

Some embodiments include transgenic animals comprising cells that express a particular surface polypeptide, secreted polypeptide, and/or combination of the two. A molecular rheostat construct, which can include a polynucleotide encoding a polypeptide of interest, may be integrated either at a locus of a genome where that particular nucleic acid sequence is not otherwise normally found or at the normal locus for the transgene. In some embodiments, a cell comprising the polypeptide-encoding polynucleotide can be identified by a quantity of polypeptide that is bound to the cell's surface. In some embodiments, the transgene comprises nucleic acid sequences derived from the genome of the same species as the transgenic animal. In some embodiments, the transgene comprises nucleic acid sequences derived from a different species than the species of the transgenic animal. In some embodiments, the polypeptide is foreign to the species of animal to which the recipient belongs, foreign only to the particular individual recipient, and/or comprises genetic information already possessed by the recipient. In the last case, the altered or introduced genetic may be expressed differently (e.g. at different times, tissues, and/or subcellular locations) than the native genetic information.

While mice and rats can be used for transgenic experimentation, in some instances alternative animal species can be used. Transgenic procedures have been successfully utilized in a variety of non-murine mammals, including sheep, goats, pigs, dogs, cats, monkeys, chimpanzees, hamsters, rabbits, cows and guinea pigs (see, e.g., Kim et al. *Mol. Reprod. Dev.* 46(4): 515-526 (1997); Houdebine *Reprod. Nutr. Dev.* 35(6):609-617 (1995); Petters *Reprod. Fertil. Dev.* 6(5):643-645 (1994); Schnieke et al. *Science* 278 (5346):2130-2133 (1997); and Amoah J. *Animal Science* 75(2):578-585 (1997)). Accordingly, in some embodiments, a transgenic animal is a mammal. In some embodiments, the transgenic animal is a murine mammal, for example a mouse or rat. In some embodiments, the transgenic animal is a non-murine mammal, for example a sheep, goat, pig, dog, cat, monkey, chimpanzee, hamster, rabbit, cow, or guinea pig.

Transgenic animals can be produced by a variety of different methods including transfection, electroporation, microinjection, gene targeting in embryonic stem cells and recombinant viral and retroviral infection (see, e.g., U.S. Pat. Nos. 4,736,866, 5,602,307; Mullins et al. *Hypertension* 22(4):630-633 (1993); Brenin et al. *Surg. Oncol.* 6(2)99-110 (1997); Tuan (ed.), *Recombinant Gene Expression Protocols, Methods in Molecular Biology* No. 62, Humana Press (1997)). Detailed procedures for producing transgenic animals are readily available to one skilled in the art, including the disclosures in U.S. Pat. Nos. 5,489,743, 5,602,307 and Lois et al. Science 295(5556):868-872 (2002)).

In some embodiments, a transgenic mammal is produced comprising cells that express a desired polypeptide. The transgenic mammal can comprise lymphocytes that express a desired ratio of secreted to membrane-bound polypeptide, or complexes thereof, for example a T cell receptor, B cell receptor, or antibody. The mammal may be produced in such a way that substantially all of the lymphocytes express the desired polypeptide. Thus, in some embodiments the transgenic mammal is produced by a method comprising contacting an embryonic stem cell with a polynucleotide delivery system that comprises an polynucleotide encoding the desired polypeptide. In some embodiments, the polynucleotide delivery system comprises a retroviral vector, for example a lentiviral vector.

Alternatively, the transgenic mammal may be produced in such a way that only a sub-population of cells expresses the desired polypeptide or polypeptides, for example a B cell receptor, T cell receptor, or immunoglobulin. In some embodiments, this sub-population of cells has a unique antigen specificity, and does not express any other antigen-specific polypeptides that are capable of inducing an immune response. In some embodiments, the lymphocytes do not express any other B cell receptors. In some embodiments, such mammals are produced by contacting hematopoietic stem cells with a polynucleotide delivery system comprising an polynucleotide encoding the desired specific polypeptide. The hematopoietic stem cells are then transferred into a mammal where they mature into lymphocytes with a unique antigen specificity. In some embodiments, such mammals are produced by placing the desired polypeptide or polypeptides under the control of a promoter (and/or combination of transcriptional regulatory elements) that only expresses in a certain type of cell, for example a certain lineage, population, or subpopulation of cells. In some embodiments, the promoter is B cell-specific promoter, for example a human B cell receptor κ light chain or human B cell receptor heavy chain promoter. In some embodiments, the B cell receptor κ light chain promoter comprises an EEK promoter. In some embodiments, the B cell receptor heavy chain promoter comprises an MH promoter.

Therapy

Some embodiments include compositions and/or methods for preventing or treating a disease or disorder. Diseases or disorders that are amenable to treatment or prevention by the methods of the present invention include, without limitation, metabolic diseases, genetic diseases (including, but not limiting to disease in which a polypeptide is deleted, or the function of the polypeptide is reduced or eliminated), cancers, autoimmune diseases, and infections, including viral, bacterial, fungal and parasitic infections.

In some embodiments, a mammal is already suffering from a disease or disorder that is to be treated. A polypeptide that is associated with the disease or disorder is identified. The polypeptide may be previously known to be associated with the disease or disorder, or may be identified by any method known in the art. In some embodiments, the disorder relates to the deficiency of a peptide or function thereof (for example, insulin deficiency in a diabetic).

Target cells can be contacted with a polynucleotide delivery system comprising a molecular rheostat construct as described herein that encodes the desired polypeptide. In some embodiments, the construct comprises a polynucleotide that encodes the desired polypeptide. In some embodiments, the polynucleotide comprises a cDNA. The polynucleotide delivery system can comprise a modified lentivirus that is able to infect non-dividing cells, thus avoiding the need for in vitro propagation of the target cells.

In some embodiments, the target cells comprise hematopoietic stem cells, for example bone marrow stem cells. The target cells are preferably obtained from the mammal to be treated, although they may also be heterologous, for example obtained from a donor. Methods for obtaining bone marrow stem cells are well known in the art.

Following transfection of the target cells with the molecular rheostat construct, the target cells can be reconstituted in the mammal according to any method known in the art. In the mammal, the target cells produce offspring that mature into functional antigen-specific immune cells. In some embodiments, the target cells are transformed with the molecular rheostat construct (e.g. the construct is integrated into the genome of the target cells) and the patient will continue to produce the target cells.

Secreted and/or surface polypeptides that target one or more cancer cells, molecules secreted by cancer cells, or molecules that signal to cancer cells can be useful in treating cancer. As such, in some embodiments, methods are provided for treating a patient suffering from cancer. An antigen associated with the cancer is identified and an antigen-specific protein that recognizes the antigen is obtained. In some embodiments, the antigen-specific protein is a B cell receptor or an antibody. An antigen-specific polynucleotide that encodes the antigen-specific polypeptide is cloned into a molecular rheostat construct as described herein. Target cells, preferably hematopoietic stem cells, more preferably primary bone marrow cells, are obtained and contacted with a polynucleotide delivery system that comprises the antigen-specific polynucleotide. The target cells are preferably obtained from the patient, but may be obtained from another source, such as an immunologically compatible donor. The polynucleotide delivery system is preferably a modified retrovirus, more preferably a modified lentivirus as described herein. When the antigen specific protein is a multimer, for example an antibody or B cell receptor, the molecular rheostat construct can comprise nucleotide sequences encoding both (or all chains) of the multimer, for example the heavy and light chains of the B cell receptor or antibody. In some embodiments, a high-activity cleavage site is positioned between the two (or more) sequences to provide approximately equivalent expression levels of the two (or more) chains. The target cells can be transferred back to the patient, where they develop into cells that are capable of generating an immune response when contacted with the identified antigen. In a preferred embodiment the polynucleotide delivery system also comprises a gene that enhances immune cell function. As a result, the gene is expressed in the mature antigen-specific cells where it enhances their therapeutic efficacy. In some embodiments, expansion of the mono-specific population of immune cells is achieved in vivo by contacting the cells with antigen, such as by injecting the patient with purified antigen. There may be situations where the use of several different antigen-specific populations of T cells or B cells is more therapeutically effective than a population of immune cells with a single antigen specificity. Thus, in some embodiments the method of therapy involves the use of a number of different constructs encoding different antigen-specific proteins to produce a number of populations of T cells and/or B cells with a variety of specificities. For example, two populations of T cells could be produced, each of which is specific for a different antigen associated with the same tumor.

In some embodiments, insulin-producing cells or precursors thereof are transformed with at least one molecular rheostat construct comprising a polynucleotide encoding insulin, and configured to produce a desired ratio of secreted and surface-bound insulin. In a molecular rheostat construct, a polynucleotide encoding insulin can be inserted upstream of a cleavage polynucleotide having a moderate-to-high activity level and an anchor polynucleotide. The molecular rheostat construct can then be inserted into a target insulin-producing cell or precursor thereof. In some embodiments, the molecular rheostat construct is inserted via a viral vector, for example a lentiviral vector. Stably transformed target cells can be identified and/or selected-for. In some embodiments, the stably transformed cells are selected for. In some embodiments, the stably transformed cells are expanded. In some embodiments, the stably transformed cells are translated into a host organism, for example a patient in need, such as a diabetic patient. In some embodiments, insulin-producing cells in the host organism are identified, for example by identification of surface-bound insulin. The skilled will appreciate that while insulin production is provided by way of example, the methods of therapy can be applied to a wide variety of gene-replacement and cell-replacement therapies, for example B cell-replacement therapy, T cell-replacement therapy, hormone-producing cell-replacement therapy, and the like.

In the some embodiments, individual populations of target cells are separately transfected, each with a vector encoding an antigen-specific polypeptide with a different specificity. The separate populations of target cells can then be combined and introduced into the patient together. Alternatively, each population can be introduced into the patient separately, in which case the introduction of each population can be separated temporally if so desired.

In some embodiments, a mixture of vectors encoding different antigen-specific polypeptides with distinct specificities is used to infect a single population of target cells, such as hematopoietic stem cells from a patient. The infected population of cells is subsequently administered to the patient, as described above, where they mature into functional immune cells. Although a single target cell may be infected with multiple vectors encoding different antigen-specific polypeptides, mono-specific populations of immune cells will nevertheless be produced.

Methods of Expressing Secreted and Surface Polypeptides

In some embodiments, method of expressing secreted and surface polypeptides are provided. The method can include providing a molecular rheostat construct as described herein. Transcripts of the molecular rheostat construct can be provided. In some embodiments, the molecular rheostat construct is delivered to a target cell as described herein, for example via a polynucleotide delivery system. In some embodiments, the molecular rheostat construct is transcribed by the target cell. In some embodiments, the method includes contacting the cell with an activator for an inducible promoter, or removing a repressor of an inducible promoter. In some embodiments, a plurality of transcripts (of the molecular rheostat construct) is delivered to the target cell. As such, in some embodiments, the target cell can contain a plurality of transcripts of the molecular rheostat construct. In some embodiments, translation of the transcripts is initiated in the target cell. Translation of the transcripts can be performed by one or more ribosomes in the target cell. In some embodiments, the presence of a cleavage polynucleotide of the transcript results in the formation of two separate polypeptides from a single transcript. In some embodiments, the separation results from ribosomal stopping, skipping, and re-initiating of translation. In some embodiments, the separation results from a proteolytic event after the cleavage polynucleotide has been translated. In some embodiments, the secreted and surface polypeptides are expressed by a single target cell. In some embodiments, the secreted and surface polypeptides are expressed by a plurality or population of target cells. In some embodiments, the method is performed in vivo. In some embodiments, the method is performed ex vivo. In some embodiments, the method is performed in vitro.

In some embodiments, a ratio (or range of ratios) of surface-bound polypeptide to secreted polypeptide is desired. As such, in some embodiments, a cleavage polynucleotide is selected based on the activity level of its corresponding cleavage site. Because the corresponding cleavage site is located between the polypeptide and an anchor sequence, a particular ratio of secreted and membrane-bound polypeptide can be achieved, depending of the activity level of the cleavage site. In some embodiments, the cleavage polynucleotide is selected from the polynucleotides of Table 2, or is a variant thereof. In some embodiments, the cleavage polypeptide is selected from the polypeptides of Table 1, or is a variant thereof. In some embodiments, a relatively high ratio of secreted to surface-bound polypeptide is desired, and accordingly a polynucleotide encoding a relatively high activity cleavage site is selected. In some embodiments, a relatively low ratio of secreted to surface-bound polypeptide is desired, and accordingly a polynucleotide encoding a relatively low activity cleavage site is selected. In some embodiments, a ratio of at least about 1:2 of secreted polypeptide to surface-bound polypeptide is desired, for example, at least about 1:2, 3:4, 4:5, 1:1, 5:4, 4:3, 3:2, 4:3, 2:1, 3:1, 4:1, 5:1, 10:1, 15:1, 20:1, 30:1, 40:1, or 50:1, including ranges between any two of the listed values. In some embodiments, a ratio of no more than about 5:1 of secreted polypeptide to surface-bound polypeptide is desired, for example, no more than 5:1, 4:1, 3:1, 2:1, 3:2, 4:3, 5:4, 1:1, 4:5, 3:4, 1:2, 1:3, 1:4, 1:5, 1:10, 1:15, 1:20, 1:30, 1:40, or 1:50, including ranges between any two of the listed values.

In some embodiments, each transcript comprises a first polynucleotide encoding a desired polypeptide. Each transcript can also comprise a signal polynucleotide encoding a signal sequence in-frame with the first polynucleotide. Each transcript can also comprise a cleavage polynucleotide as described herein. Each transcript can also include an anchor polynucleotide as described herein. In some embodiments, the cleavage polynucleotide is downstream of the first polynucleotide. In some embodiments, the cleavage polynucleotide is downstream of the signal polynucleotide. In some embodiments, the anchor polynucleotide is downstream of the cleavage polynucleotide. In some embodiments, the transcript comprises, from 5' to 3', the signal polynucleotide, the first polynucleotide, the cleavage polynucleotide, and the anchor polynucleotide. In some embodiments, the transcript comprises, from 5' to 3', the first polynucleotide, the signal polynucleotide, the cleavage polynucleotide, and the anchor polynucleotide. In some embodiments, the transcript further comprises a second polynucleotide encoding a second desired polypeptide and a second cleavage site as described herein. In some embodiments, the construct comprises, from 5' to 3', a second signal polynucleotide, a polynucleotide encoding an immunoglobulin light chain, a second cleavage polynucleotide encoding a high-activity level cleavage site, a polynucleotide encoding an immunoglobulin heavy chain, a first signal polynucleotide, a first cleavage polynucleotide, and an anchor polynucleotide. In some embodiments, the first cleavage polynucleotide is selected so that the encoded cleavage site has a desired activity level, and as such, a desired ratio of secreted to surface-bound immunoglobulin is produced.

In some embodiments, the transcript encodes a marker as described herein. In some embodiments, the marker is a fluorescent protein as described herein. In some embodiments, the method includes detection of the marker. In some embodiments, for example, if the marker is an enzyme, a method may include contacting the product of the transcript with substrate for the enzyme. In some embodiments, for example if the marker is a fluorescent protein, a method may include detection via flow cytometry or fluorescent microscopy. In some embodiments, the detection of the marker may include contacting the cell with an antibody that specifically binds to the marker. In some embodiments, the antibody further comprises a detectable marker. In some embodiments, the method includes contacting a primary antibody with a secondary antibody that comprises a detectable marker.

In some embodiments, a method of identifying cells expressing a desired polypeptide via detection of the polypeptide bound to the cell surface. A polynucleotide expressing a polypeptide of interest can be positioned upstream of a cleavage polynucleotide and an anchor polynucleotide in a molecular rheostat construct as described herein. The molecular rheostat construct can be delivered to target cells as described herein. In some embodiments, the molecular rheostat construct is transiently expressed by the target cells. In some embodiments, the molecular rheostat construct is stably integrated into the genome of the target cells. In some embodiments, stably transformed target cells are selected. The target cells can express a desired ratio of secreted and surface-bound polypeptide of interest, which can correlate to the activity level of the cleavage site encoded by the cleavage polynucleotide. In some embodiments, the polypeptide of interest comprises a detectable marker, and surface-bound polypeptide of interest is detected through direct detection of the detectable marker. In some embodiments, the target cells are contacted with a detection agent that binds specifically to the polypeptide of interest, for example an antibody or fragment thereof, ligand, or the like. In some embodiments, the detection agent comprises a label. In some embodiments, the detection agent is bound by a second detection agent that comprises a label, for example a secondary antibody. In some embodiments, the method includes identifying the cells in vitro. In some embodiments, the method included identifying the cells ex vivo. In some embodiments, the method included identifying the cells in vivo. In some embodiments, the method further includes detecting an amount of secreted polypeptide. The method can include detecting an amount of secreted polypeptide in supernatants of the cells. In some embodiments, the amount of secreted polypeptide is detected via direct detection of a marker on the secreted polypeptide. In some embodiments, the amount of secreted polypeptide is detected via a binding assay, for example an ELISA, immunoblot, no-wash assay, or the like. As such, in some embodiments, the method can include detecting a ratio of secreted polypeptide (e.g. in supernatant) to surface-bound polypeptide, (e.g. bound to the cell surface). In some embodiments, the method can be used to determine the activity level of a candidate cleavage site. In some embodiments, the method includes comparing the ratio of secreted to surface polypeptide yielded by a cleavage site to that of a similar control construct under similar conditions, in which the control construct is configured to express the polypeptide either without a cleavage site, or without an anchor site.

Methods of Producing a Detectable Genetically Modified Cell

It can be useful to label the surface of a genetically modified cell, for example if a cell is genetically modified to secrete a desired polypeptide. As such, some embodiments include a method of producing a detectable genetically modified cell. In some embodiments, the method comprises providing a cell. The cell can be a target cell as described herein. In some embodiments, the method comprises providing a molecular rheostat construct as described herein. In some embodiments, the method comprises inserting the molecular rheostat construct into a target cell. The molecular rheostat construct can be inserted via a method of polynucleotide delivery as described herein, for example via a vector such as a viral vector. In some embodiments, the molecular rheostat construct is transiently expressed by the cell. In some embodiments, the molecular rheostat construct is stably integrated into the target cell's genome. In some embodiments, stably transformed cells are selected. The method can include detecting an amount of surface-bound polypeptide as described herein. The method can include detecting an amount of secreted polypeptide as described herein. In some embodiments, the coding sequences of the molecular rheostat construct are under the control of a single promoter as described herein. The method can include determining a ratio of secreted to surface-bound polypeptide as described herein. In some embodiments, the method includes identifying the cells in vitro. In some embodiments, the method included identifying the cells ex vivo. In some embodiments, the method included identifying the cells in vivo.

In some embodiments, the molecular rheostat construct is integrated into a chromosomal DNA of the target cell. In some embodiments, the molecular rheostat construct is not integrated into the genome, but is stably incorporated into the target cell, for example via a plasmid containing a selectable marker, in which the cell is cultured under conditions to select for the selectable marker.

In some embodiments, the molecular rheostat construct comprises a promoter as described herein, and the promoter controls the expression of the first polynucleotide encoding a polypeptide of interest, signal polynucleotide, cleavage polynucleotide, anchor polynucleotide, and any additional desired polynucleotides (e.g. a second polynucleotide as described herein, if present). In some embodiments, the molecular rheostat construct is inserted into a genomic location such that it is under the control of a single promoter. In some embodiments, the molecular rheostat construct is targeted to a particular promoter or promoter region via homologous recombination. In some embodiments, selection is performed to identify insertion of the molecular rheostat construct under the control of a promoter with a desired activity.

In some embodiments, the method further comprises providing the transgenic cell to a multicellular organism. In some embodiments, the transgenic cell is a germline cell, and the method comprises generating a multicellular organism from the germline cell. In some embodiments, the method comprises inserting, injecting, or adding transgenic cells to an already-living multicellular organism.

In some embodiments, the method further comprises detecting one or more transgenic cells in the multicellular organism. In some embodiments, surface-bound polypeptide of interest is detected on the cells. In some embodiments, the method includes labeling the cells with a molecule that specifically binds to the surface-bound polypeptide, and further includes a label. The molecule that specifically binds can include an antibody or fragment thereof, aptamer, ligand or receptor of the surface-bound molecule or fragment thereof, small molecule, and the like. Various labels are known to one skilled in the art. Exemplary labels include fluorophores (e.g. xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like), radioisotopes (e.g. $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Se, $^{77}$As, $^{86}$Y, $^{90}$Y, $^{89}$Sr, $^{89}$Zr, $^{94}$Tc, $^{99}$Mo, $^{105}$Pd, $^{105}$Rh, $^{111}$Ag, $^{111}$In, $^{124}$I, $^{125}$I, $^{131}$I, $^{142}$Pr, $^{143}$Pr, $^{149}$Pm, $^{153}$Sm, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, nanoparticles (e.g. comprising gold, platinum, transition metal oxide, and/or any of the radioisotopes described herein), and the like.

In some embodiments, the surface-bound polypeptide is detected by at least one of flow cytometry, ELISA, immunoblotting, immunohistochemistry, immunocytochemistry, fluorescent microscopy, electron microscopy, Raman spectroscopy, in vivo imaging, positron emission tomography, magnetic resonance imaging, and the like. In some embodiments, secreted polypeptide is also detected. In some embodiments, secreted polypeptide is detected, for example in cell supernatants, by at least one of ELISA, immunoblotting, immunohistochemistry, immunocytochemistry, fluorescent microscopy, Raman spectroscopy, an enzymatic assay such as a luciferase detection assay or horesrasdish peroxidase or alkaline phosphatase detection assay (e.g. if the secreted polypeptide comprises an appropriate enzymatic marker or label), and the like. In some embodiments, a ratio of secreted polypeptide to surface-bound polypeptide is determined. In some embodiments, the ratio is a molar ratio.

Additional Alternative Embodiments

Figure 7:
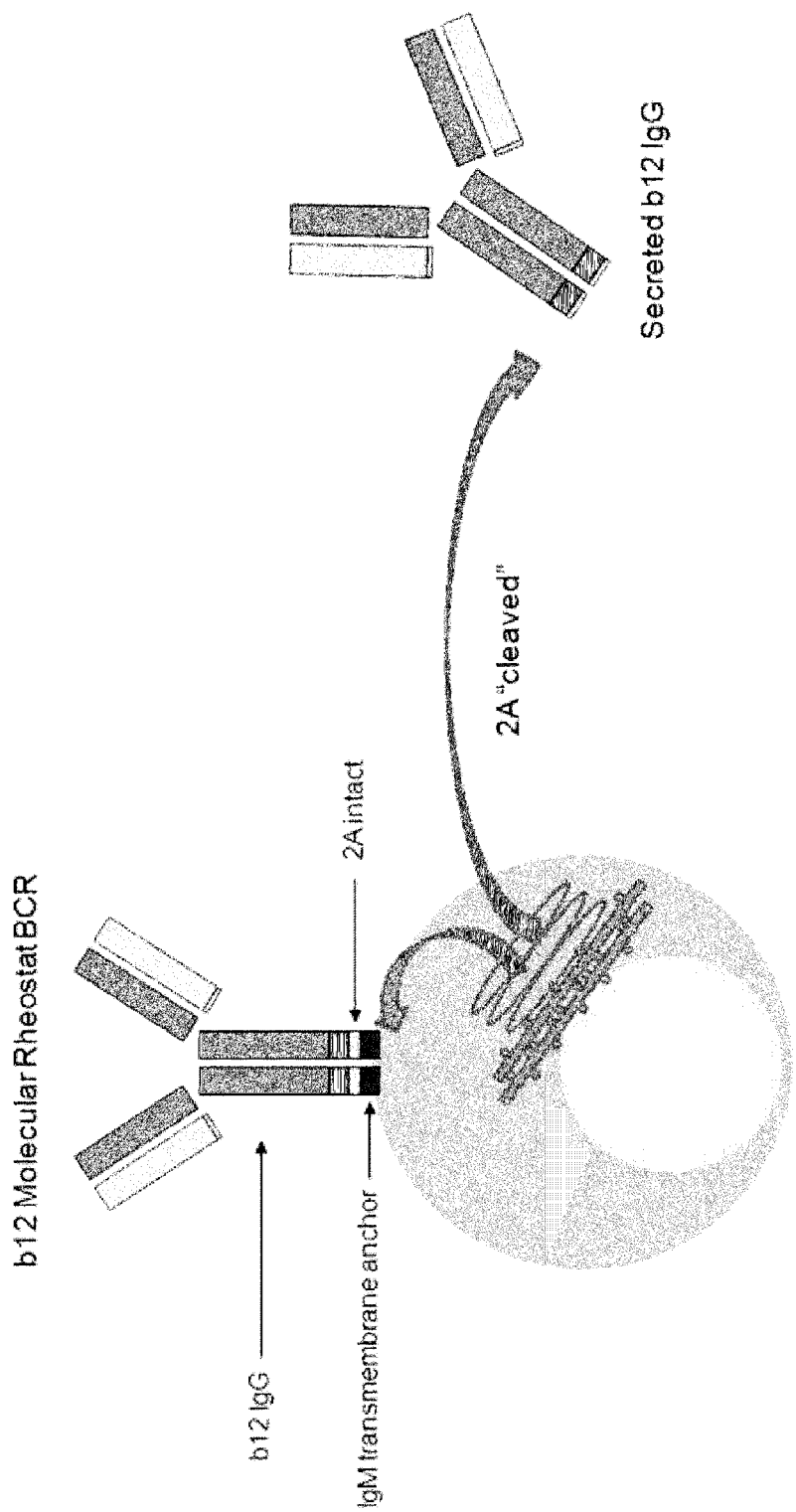
FIG. 7 is a schematic diagram illustrating a model of how a b12 "IgG Molecular Rheostat Immunoglobulin" system can direct tunable simultaneous formation of surface BCR and secreted IgG according to some embodiments herein.

In some embodiments, systems and methods for B cell gene therapy are provided. Various ratios of simultaneous formation of membrane-bound and secreted immunoglobulins can be directed by using appropriate cleavage sequences. Expression systems, polynucleotide delivery systems, and constructs in accordance with some embodiments can be referred to as "molecular rheostat" because the ratio of secreted to surface-bound polypeptide can be tuned by the choice of cleavage sequence (FIG. 7). Some embodiments provide a synthetic approximation to the process of switching through the evolved RNA alternative splicing mechanism, the route the can be used naturally to make membrane and secreted immunoglobulins in B cells.

In some embodiments, libraries of molecular rheostat constructs having different activity levels can be constructed. In some embodiments, a variety of different cleavage polynucleotides are provided, at least some of which are inserted between a polynucleotide encoding a desired polypeptide and an anchor polynucleotide, so as to produce a variety of molecular rheostat constructs that differ by the cleavage polynucleotide contained therein. For example, an IgG can be fused to a membrane anchor of IgM through different cleavage sites (see, e.g. Table 1) so as to construct a library of chimeric IgG/M Molecular Rheostat constructs (see Example 1).

In some embodiments, a single polynucleotide encoding a desired polypeptide is inserted in-frame with a signal polynucleotide, cleavage polynucleotide, and anchor polynucleotide so as to produce both secreted polypeptide and membrane-bound polypeptide from the same coding sequence. In some embodiments, a polynucleotide encoding a desired polypeptide is inserted in-frame with a signal polynucleotide, and upstream of an anchor polynucleotide to produce a molecular rheostat construct. In some embodiments, the molecular rheostat construct is delivered to a target cell via a nucleotide delivery system as described herein. In some embodiments, the cleavage site of the molecular rheostat construct is selected to have a desired activity level. As the cleavage site is inserted between the desired polypeptide and the anchor polynucleotide, the activity level can correlate to a ratio of secreted to surface-bound desired polypeptide. In some embodiments, constructs from the library are selected to produce both membrane-bound BCR and secreted antibody at controllable ratios (see Example 2).

In some embodiments, a method can be used to screen for functional cleavage sites, and/or functional polypeptides of interest. In some embodiments, the method can be automated or partially automated. In some embodiments, a library of constructs can be screened in a multi-well plate format. The method can include providing or producing a target cell that expresses a ratio of secreted to surface-bound polypeptide interest. Such a target cell can be produced as described herein. In some embodiments, a ratio of secreted to surface bound polypeptide is determined as described herein. In some embodiments, an activity level of secreted polypeptide is determined. In some embodiments, an activity level of surface-bound polypeptide is determined. Determination of a polypeptide's activity levels can depend on the polypeptides' specific function, and appropriate assays for making such determinations can be identified by the skilled artisan. For example, if the polypeptide is a receptor or portion thereof, activity can be determining by binding to ligand, or downstream signal transduction activity. If the polypeptide is an antibody or portion thereof, activity can be determined by antigen binding, and/or target neutralization. In some embodiments, ratios of secreted to surface-bound IgG/M encoded by a single polynucleotide can be determined, and various cleavage sites can be screened for activity levels (see Examples 3 and 4)

In some embodiments, activity levels of immunoglobulins, for example B cell receptors are determined. In some embodiments, surface chimeric IgG/M Molecular Rheostat BCRs are produced and signal to B cells. Binding of these BCRs to antigens, for example HIV gp120 antigens can be determined (see Example 5). In some embodiments, the secreted version of b12 IgG produced by these "Molecular Rheostat" constructs binds gp120 and neutralized HIV-1 pseudovirus equally as well as unmodified b12 IgG (see Example 6). In some embodiments, chimeric BCR produced by the Molecular Rheostat system can direct maturation of the B cell lineage (see Example 7). In some embodiments, cells transduced with vectors carrying the Molecular Rheostat Immunoglobulins, exhibit downregulation of CD10. Downregulation of CD 10 can be a sign of the maturation of the progenitor cells upon the expression of the chimeric IgG/M Molecular Rheostat BCRs. This effect can be dose dependent, with greater size of the CD10−/CD34− population being observed in the cells that received the more surface-biased Molecular Rheostat constructs.

For some transgenic cells, it can be useful for a majority of the polypeptide to be secreted, while a small amount of polypeptide remains surface-bound, for example so that a population of genetically modified cells can be easily tagged. Accordingly, is some embodiments, a cleavage polynucleotide encoding a cleavage site with a relatively high activity is selected, so that the ratio of secreted polypeptide to surface-bound polypeptide is relatively high. In some embodiments, a molecular rheostat construct is provided. In some embodiments a construct is selected in which the construct comprises a polynucleotide encoding a desired polypeptide and a cleavage polynucleotide encoding a cleavage site with a desired level of activity, and positioned between the polynucleotide encoding the desired polypeptide and an anchor polynucleotide. In some embodiments a construct is selected in which the construct comprises an insertion site for a polynucleotide encoding a desired polypeptide and a cleavage polynucleotide encoding a cleavage site with a desired level of activity, and positioned between the insertion site and an anchor polynucleotide, and the method comprises inserting a polynucleotide encoding a desired polypeptide in-frame into the insertion site. In some embodiments the construct comprises a polynucleotide encoding a desired polypeptide (or an insertion site therefor) and an insertion site for cleavage polynucleotide positioned between the polynucleotide encoding the desired polypeptide and an anchor polynucleotide, and the method includes selecting a cleavage polynucleotide encoding a cleavage site with a desired activity level (for example a high activity level so as to produce a high ratio of secreted to surface-bound polypeptide), and inserting the cleavage polynucleotide into the insertion site. In some embodiments, the method includes delivering the molecular rheostat construct to a target cell via a polynucleotide delivery system as described herein. In some embodiments, the method includes selecting for target cells comprising the molecular rheostat construct, for example cells that have been stably transformed. In some embodiments, the method includes inducing expression of the molecular rheostat construct. In some embodiments, a resulting desired ratio of surface-bound to secreted polynucleotide is produced.

EXAMPLES

Unless explicitly stated otherwise, the following examples were performed using the following materials and methods:

Transfections 293T cells were grown to 50-75% confluence on 30 cm dishes and were transfected in 15 ml D10 media (DMEM plus 10% heat-inactivated fetal bovine serum, supplemented with 20 mM L-glutamine, 1000 IU/ml penicillin, and 1000 µg/ml streptomycin, filtered through a 0.22 µm PES membrane bottle-top filter) for 24 h. The transfections used the TransIT-293 reagent (Mirus Bio, Madison Wis.) or BioT (Bioland Scientific, Paramount Calif.) according to manufacturer's instructions, using a total of 40 µg DNA.

Lentiviral Vector Production 293T cells were transfected with lentiviral vectors. After 24 h of incubation, the supernatant was pipetted off the cells and filtered through a 0.22 µm PES membrane bottle-top filter into a collection bottle. 15 ml of fresh D10 media was then filtered through the bottle-top filter into the collection bottle to reduce virus waste from supernatant that the filter absorbed. The collected supernatant was stored at 4° C., and 30 ml of fresh D10 media was added to the dish. This collection process into the same collection bottle was repeated 4 to 5 additional times at 12 h intervals. All of the collected supernatant was centrifuged at 10000 rpm for 12-24 h at 4° C. to pellet the virus, and the supernatant was poured off the pellet. The pellet was re-suspended in 500-1000 µL DMEM media (for 293T transductions) or RPMI media 1640 (for OCI-Ly7 or EU12 transductions) and incubated on ice at 4° C. for 12 h.

Lentiviral Transductions 0.5–1×106 293T, OCI-Ly7, or EU12 cells were suspended in 1 mL of D10 media for 293T transductions or C10 media (RPMI 1640 plus 10% heat-inactivated fetal bovine serum, supplemented with 25 µM β-mercapto-ethanol, 1000 IU/ml penicillin, and 1000 µg/ml streptomycin, filtered through a 0.22 µm PES membrane bottle-top filter) for OCI-Ly7 or EU12 transductions in 12 well plates, and 400-600 µL of virus re-suspensions or dilutions thereof was added to each well. 10 mg/mL polybrene (Millipore, Billerica, Mass.) was added so that the final polybrene concentration was 10 µg/mL in each well. The transductions were incubated for 24 h before the cells were passaged.

The EU12 cell line was a kind gift from Dr. Zhixin Zhang (University of Nebraska Medical Center, Omaha, Nebr.) and Dr. Max Cooper (Emory University, Atlanta, Ga.), and was described in detail by Zhang et al. [Zhang Z, Wang Y H, Zemlin M, Findley H W, Bridges S L, et al. (2003) Molecular mechanism of serial VH gene replacement. Ann N Y Acad Sci 987: 270-273.]. The OCI-Ly7 B-cell line was kindly provided by Dr. Louis M. Staudt (National Cancer Institute, NIH, Bethesda, Md.), and was originally described by Tweeddale et al. [Tweeddale M E, Lim B, Jamal N, Robinson J, Zalcberg J, et al. (1987) The presence of clonogenic cells in high-grade malignant lymphoma: a prognostic factor. Blood 69: 1307-1314.].

Cell Line

The 293T-Igαβ cell line was created by infecting 293T cells (purchased from ATCC) with a lentivector carrying the Igα and Igβ genes using the lentiviral transduction procedure described above.

Tissue Culture 293T and 293T Ig-αβ cells were grown in D10 media. The cells were passaged 1:5 every other days. OCI-Ly7 and EU12 cells were grown in C10 media. The cells were passaged 1:5-1:10 every other day to maintain a density between 105-106 cells/ml.

Flow Cytometry

For flow cytometric analysis, cells were first washed in PBS with 2% FBS, and then stained with combinations of the following antibodies: anti-human-IgG-APC (BD Pharmingen, San Diego, Calif.), anti-human-IgG-PE (BD Pharmingen), anti-human-IgM-PE/Cy5 (BD Pharmingen), anti-CD10-PE (Biolegend, San Diego, Calif.). The cells were then analyzed on a BD FACSCalibur flow cytometer.

Cell Sorting

Cells were prepared as in flow cytometric analysis and were sorted using a MoFlo FACS cell sorter.

Calcium Flux Assay

Calcium flux measurements were made using the protocol given by Bondada et. al. (see Zhang Z (2007) VH replacement in mice and humans. Trends Immunol 28: 132-137), with the following modifications: cells were washed, pelleted, and resuspended in Dye Loading Buffer (HBSS with Ca2+ and Mg2+ plus 4% 100 mM probenecid, 2% 1 M HEPES buffer, and 1% heat-inactivated fetal bovine serum) and were incubated with 4 µg/mL Fluo-3 AM and 1 µg/mL FuraRed AM dyes in the presence of 0.02% (w/v) pluronic F-127 for 30 m. The cells were again washed, pelleted, and resuspended in Dye Loading Buffer and were kept at room temperature until they were analyzed on a BD FACSCalibur flow cytometer equipped with a circulating 37° C. water bath on the sample port. During analysis, cells were stimulated with goat F(ab')2 anti-human IgG γ Fc-specific antibodies (Invitrogen, Carlsbad, Calif.) or with goat F(ab')2 anti-human IgM Fc-specific antibodies (Southern Biotech, Birmingham, Ala.) and a ratiometric measurement between the Fluo-3 AM and FuraRed AM dye channels was made for 512 s. On some samples, ionomycin controls were performed to calibrate the dynamic signaling range.

ELISA

Supernatants from cultured cells were analyzed using Human IgG ELISA Quantitation Set (Bethyl Laboratories, Montgomery, Tex.) according to manufacturer's instructions.

Surface Plasmon Resonance Gp120 Binding Assay

The Surface Plasmon Resonance (SPR) gp120-binding assays were performed as previously described by Klein et al. [Klein J S, Gnanapragasam P N, Galimidi R P, Foglesong C P, West A P, Jr., et al. (2009) Examination of the contributions of size and avidity to the neutralization mechanisms of the anti-HIV antibodies b12 and 4E10. Proc Natl Acad Sci USA 106: 7385-7390], with the following modifications: All experiments were done in-house. b12 antibody supernatants were produced from transfection of 293T cells.

In Vitro Neutralization Assay

In vitro neutralization assays were performed as previously described by West et. al. [Galli G, Guise J, Tucker P W, Nevins J R (1988) Poly(A) site choice rather than splice site choice governs the regulated production of IgM heavy-chain RNAs. Proc Natl Acad Sci USA 85: 2439-2443.], with the following modifications: All experiments were done in-house. Pseudoviruses were produced by co-transfecting HEK293T cells with an Env SF162 expression plasmid and a replication-defective backbone plasmid, PSG3minusEnv. Each mutant Fc and unmodified fragment version of b12 samples was tested in duplicates.

Example 1

Production of "Molecular Rheostat" Constructs

The first-generation IgM Molecular Rheostat constructs required two vectors. The light chain vector was made by cloning a b12 κ light chain into the FEEKW vector. The heavy-chain variable region of the b12 IgG antibody (from Dr. Gary Nabel, NIH) was grafted onto a secretory version of the human IgM gene cloned from a BAC containing a partial human heavy chain locus. The resulting secretory form of the IgM heavy chain was then joined via 2A elements to the IgM trans-membrane anchor (corresponding to the last 41 aa from the C-terminus of the membrane-bound form of the human IgM) (SEQ ID NO: 530). These heavy chain genes were then cloned into the FMHW vector. The FEEKW and FMHW vector each contains a human κ light chain and heavy chain promoter, respectively, and were described by Luo et al. previously (Luo X M, et al. (2009) Engineering human hematopoietic stem/progenitor cells to produce a broadly neutralizing anti-HIV antibody after in vitro maturation to human B lymphocytes. Blood 113: 1422-1431, hereby incorporated by reference in its entirety).

FIG. 1A provides a schematic of these constructs. Shown at the top is the design of the heavy chain constructs, containing a secreted IgM heavy chain linked via a 2A element to the transmembrane region (41 aa inclusive of the C-terminus) of the membrane form of the IgM heavy chain. 2A: location of a cleavage site, for example self-cleaving 2A elements. See Table 1 for specific cleavage sites and their sequences. Shown at the bottom of FIG. 1A is the light chain construct, furnishing the b12 κ light chain. CMVp: CMV promoter. LTR: long terminal repeat. MH and EEK promoters: internal B cell specific promoters from human IgM heavy and κ light chain loci, respectively. b12μ heavy chain: IgM heavy chain with variable region corresponding to that of the b12 broadly neutralizing antibody.

Chimeric IgG/M Molecular Rheostat constructs were created by cloning the EEK or MH promoters, the b12 light and heavy chains, the 2A sequences, and an the 3' region of the human IgM BCR gene corresponding to the last 41 amino acids into either a pHAGE2 or pHAGE6 lentiviral vector. Both are third-generation, self-inactivating lentiviral vector backbones based on the pHRST vector (Mostoslavsky G, et al. (2005) Efficiency of transduction of highly purified murine hematopoietic stem cells by lentiviral and oncoretroviral vectors under conditions of minimal in vitro manipulation. Mol Ther 11: 932-940; O'Connell R M, et al. (2010) Lentiviral vector delivery of human interleukin-7 (hIL-7) to human immune system (HIS) mice expands T lymphocyte populations. PLoS ONE 5: e12009, each of which is hereby incorporated by reference in its entirety). See FIG. 2A for a schematic. The light chain and each of the chimeric heavy chains were combined into single constructs co-expressing the light chain and the chimeric heavy chain. The light and heavy chains are joined by another 2A peptide linker (denoted F2Aopt). 2A: location of mutant self-cleaving 2A elements. See FIG. 1B, FIG. 1C, and Table 1 for the specific cleave sites screened and their sequences. 2Aopt: optimized 2A element with a furin cleavage site at 5' end. CMVp: CMV promoter. LTR: long terminal repeat. EEK: internal B cell specific promoter. b12 γ heavy chain: IgG heavy chain with the variable region corresponding to that of the b12 broadly neutralizing antibody

Example 2

IgM Molecular Rheostat Immunoglobulin Genes Mediate Co-Expression of IgM-Like BCR and Secreted IgM Antibody As a pilot experiment to test whether the mutated 2A peptides can mediate co-expression of surface and secreted immunoglobulins, first-generation "Molecular Rheostat" Immunoglobulin genes were constructed by joining the secreted version of the b12 IgM heavy chain to the trans-membrane domain of the IgM BCR via a mutated 2A peptide. The transmembrane domain is defined as the M1 and M2 exons from the human IgM locus and comprises the last 41 amino acids of the membrane bound IgM BCR (FIG. 1A). These were referred to as "IgM Molecular Rheostat" constructs. Different cleavage sites were used, including wild type F2A and two mutant peptides as well as another F2A-like element derived from a silk-worm virus, based on previous work by Donnelly et al. (Donnelly M L, et al. (2001) The 'cleavage' activities of foot-and-mouth disease virus 2A site-directed mutants and naturally occurring '2A-like' sequences. J Gen Virol 82: 1027-1041, hereby incorporated by reference in its entirety), in which they observed reduced cleavage efficiencies when certain mutations are introduced. The four variants (each with a different cleavage site) were designated F2A, F2A(3), F2A(14), and I2A(2). See Table 1 for the nomenclature and the amino acid sequence for each of these cleavage sites.

The IgM Molecular Rheostat genes were clonsed into a lentiviral vector plasmid (FMHW), which also can double as a mammalian expression vector under the control of a CMV promoter (FIG. 1A). These heavy chain vectors were co-transfected with a separate vector carrying the b12 light chain (FEEKW-b12L) and a mammalian expression vector carrying the human Igα and Igβ genes (phIgαβ) into 293T cells. The FMHW vector backbone and the related FEEKW were previously described by Luo et al. (2009) Engineering human hematopoietic stem/progenitor cells to produce a broadly neutralizing anti-HIV antibody after in vitro maturation to human B lymphocytes. Blood 113: 1422-1431, hereby incorporated by reference in its entirety. Briefly, both are lentiviral vectors that contain promoters derived from B-cell-specific genes. The FMHW vector carries the MH promoter, which is composed of a human immunoglobulin heavy chain variable region promoter coupled to the μ-intronic enhancer. The FEEKW vector carries the EEK promoter, which is composed of the human κ light chain promoter coupled to κ light chain enhancer elements. The transfected cells and their supernatants were analyzed by flow cytometry and human IgM ELISA 48 hours later. All transfected cells showed surface expression of the IgM Molecular Rheostat BCR and secreted IgM into their supernatants (FIGS. 1B and 1C).

Figure 1B:
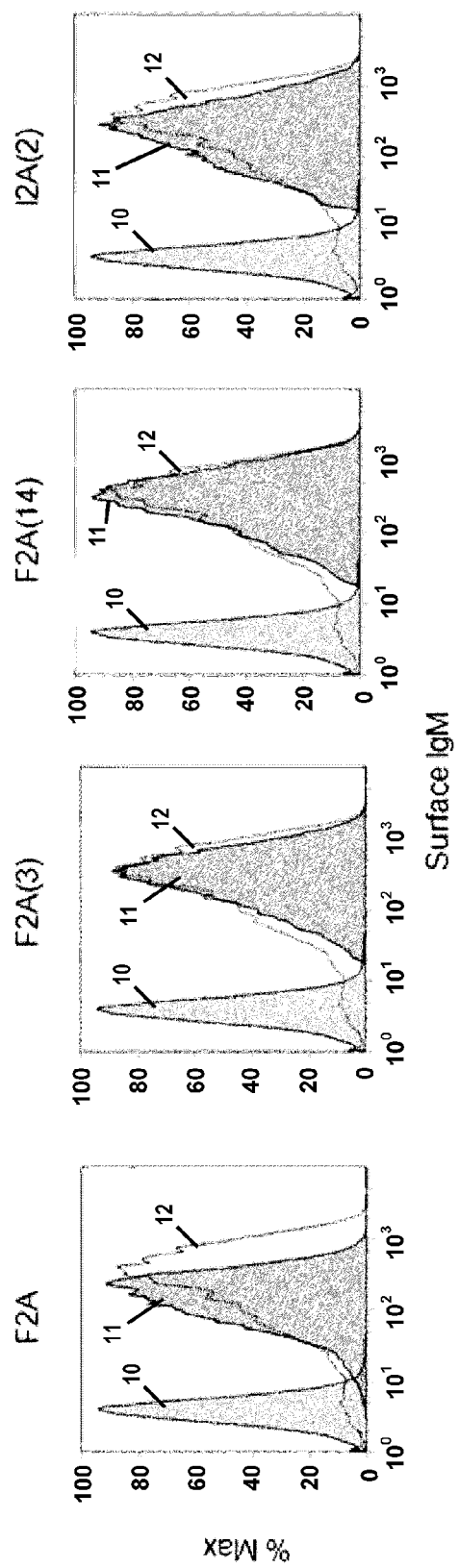
FIG. 1B is a series of graphs illustrating IgM surface staining of 293T cells co-transfected with the same amount of vectors corresponding to those of FIG. 1A (heavy chain to light chain in 1:1 ratio by mass), and comprising the indicate cleavage sequence, and a third construct expressing human Igα and Igβ, and analyzed with flow cytometry. Area 10 represents GPF control. Area 11 represents data for the vector comprising the indicated cleavage sequence; Area 12 represents membrane-bound IgM control.
Figure 1C:
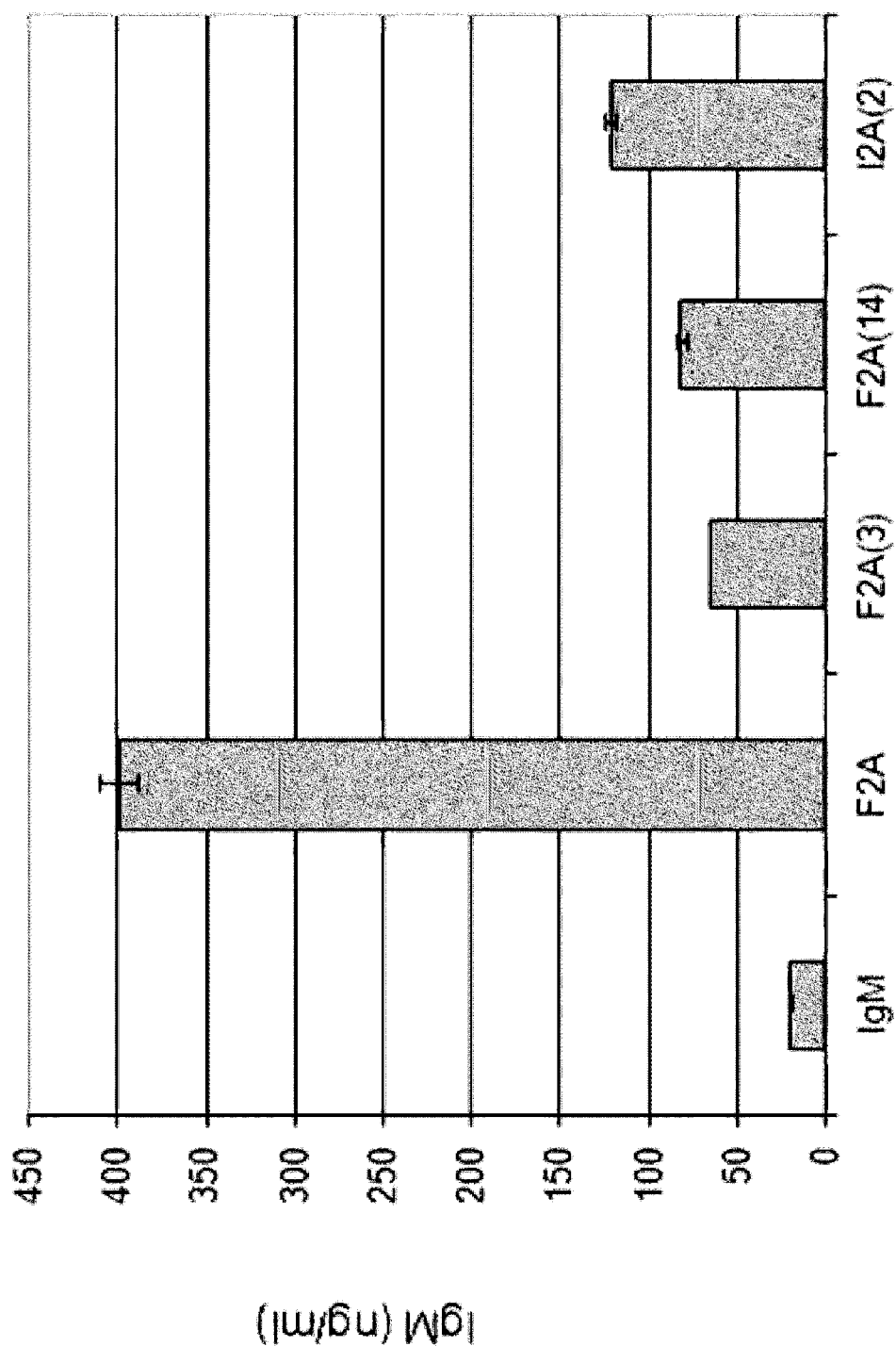
FIG. 1C is a graph depicting data for an IgM ELISA of supernatants of transfected cells.

FIG. 1B shows IgM surface staining of 293T cells co-transfected with the same amount of the IgM Molecular Rheostat constructs (heavy chain to light chain in 1:1 ratio by mass) together with a third construct expressing human Igα and Igβ. The cells were harvested 48 hours post-transfection. All IgM Molecular Rheostat constructs produced surface IgM. Area 12: Membrane-bound IgM control. Area 11: Molecular Rheostat Constructs. Area 10: GFP control. FIG. 1C shows IgM ELISA of supernatants of transfected cells. The constructs expressing different 2A mutants produced different amounts of secreted IgM. IgM: membrane-bound IgM control.

Example 3

Figure 2A:
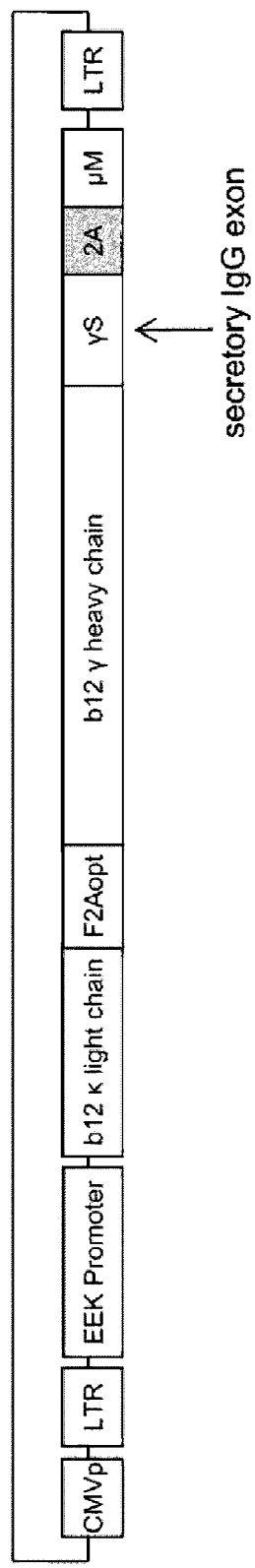
FIG. 2A is schematic illustration of a "molecular rheostat" vector according to some embodiments herein. The light and heavy chains are joined by a 2A cleavage site (denoted F2Aopt). 2A: location of cleavage site, for example a 2A site as provided in Table 1; 2Aopt: optimized 2A element with a furin cleavage site at 59 end; CMVp: CMV promoter; LTR: long terminal repeat; EEK: internal B cell specific promoter. b12 c heavy chain; IgG heavy chain with the variable region corresponding to that of the b12 broadly neutralizing antibody.

Chimeric IgG/M Molecular Rheostat Constructs Mediate Simultaneous Expression of Chimeric IgG/M BCRs and Secreted IgG Antibody The Molecular Rheostat format was adapted to the production of an IgG antibody in an effort to mimic an isotype-switched secretory IgG while preserving the signaling properties of an IgM, which is required for normal B cell development. Furthermore, the ratio of surface-bound to secreted immunoglobulins by making appropriate mutations in the 2A elements was manipulated. In particular, a library of chimeric IgG/M Molecular Rheostat Immunoglobulin genes was constructed, in which a complete secretory b12 IgG is joined to the transmembrane anchor and the intracellular domain of the IgM BCR via different 2A peptides (FIG. 2A). The library included 2A peptides listed in Table 1.

To reduce the number of vectors that need to be transfected and anticipating the need to use the vectors in the context of lentiviral transduction, where it would be advantageous to work with a single vector, we fused the b12 κ light chain with the Molecular Rheostat heavy chain transgene by joining the b12 κ light chain to the b12 IgG heavy chain via a different F2A element, F2Aopt. F2Aopt was codon-optimized for human expression and contained a furin cleavage site before the 2A element.

Additionally, to ensure consistency of Igα and Igβ expression across the cells used to test the Molecular Rheostat constructs and reduce the number of vectors that need to be transfected, 293T cells were engineered to express human Igα and Igβ by repeatedly co-infecting 293T cells with two lentiviral vectors, FUW-Igα and FUW-Igβ, which carry the Igα and Igβ transgenes, respectively, under the control of a ubiquitin C promoter. The resulting cells were denoted 293T-Igαβ cells.

Figure 2B:
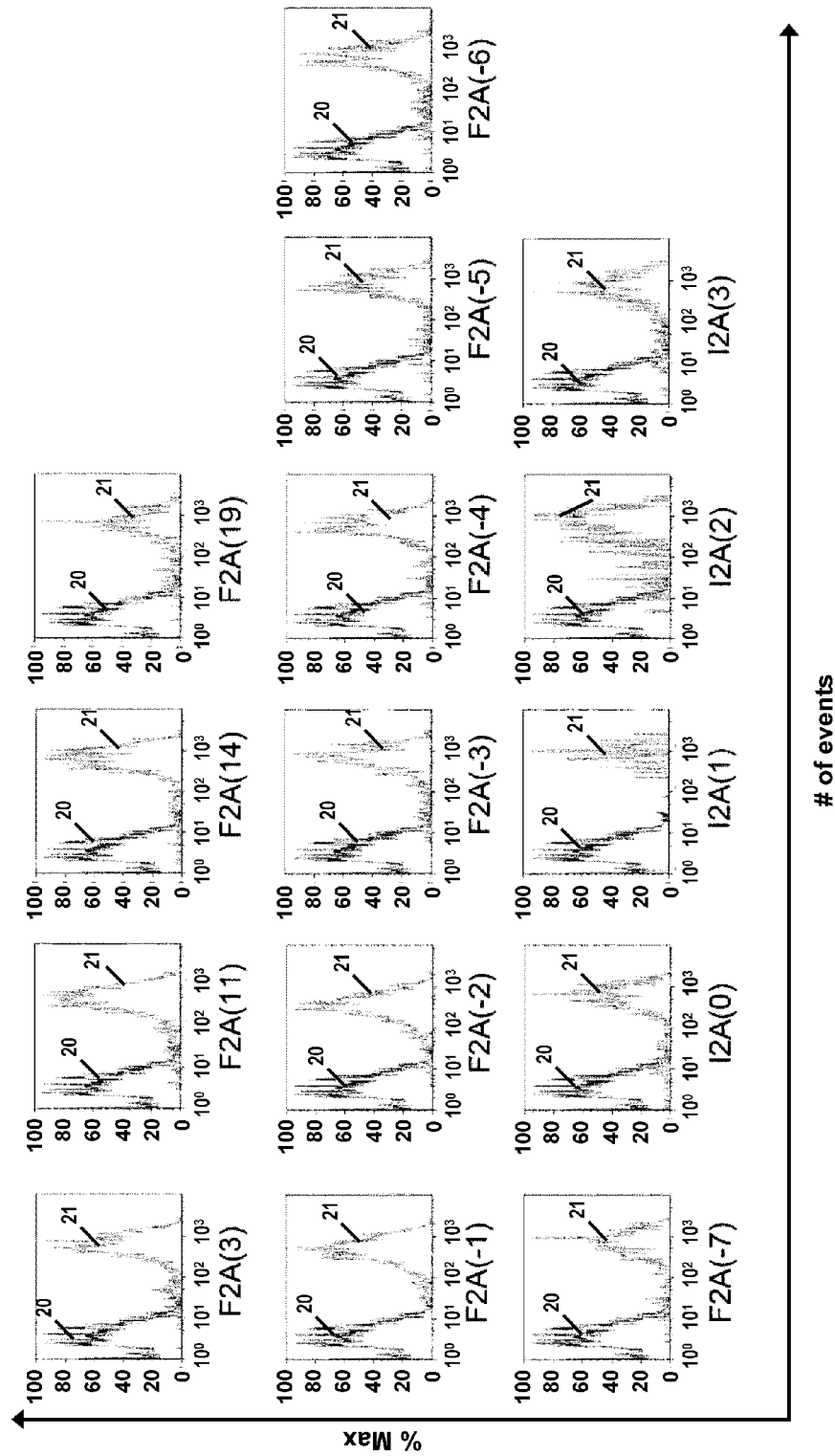
FIG. 2B is a series of graphs illustrating human IgG surface staining of 293T cells co-transfected with the same molar amount of vector corresponding to that of FIG. 2A and comprising the indicated cleavage sequence, and analyzed with flow cytometry. Area 20 represents secretory IgG (L+H) controls, for which secretory the b12 IgG heavy chain is in the first position and light chain in the second position. Area 21 represents data for "molecular rheostat vectors" according to some embodiments herein and comprising the indicated cleavage sequence. All constructs produced surface-bound chimeric IgG/M BCR detected as human IgG.
Figure 2C:
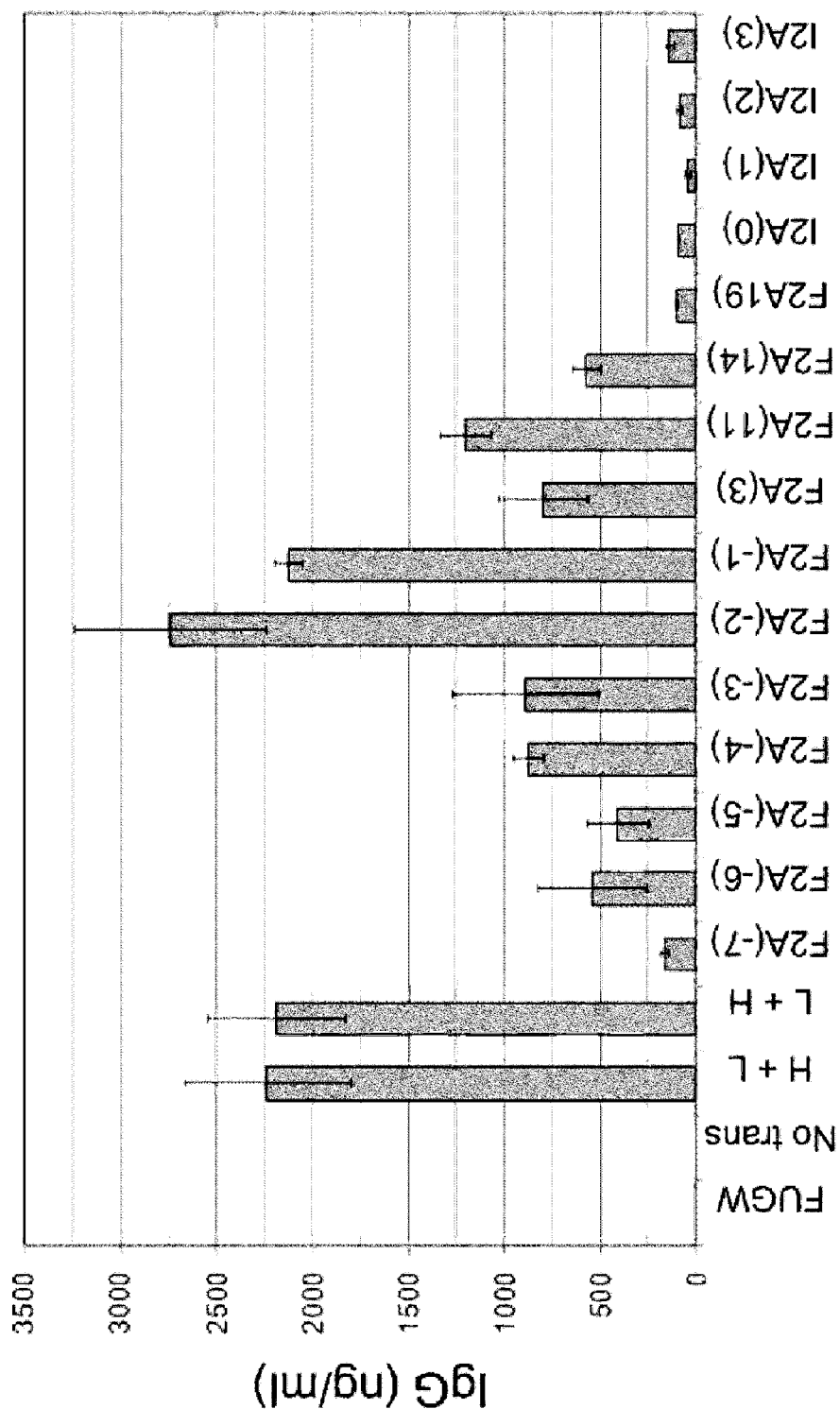
FIG. 2C is a graph depicting data for an IgG ELISA of supernatants of transfected cells. FUGW: GFP containing vector control. L+H and H+L: secretory b12 IgG controls; H+L has the light chain in the first position and heavy chain in the second position; L+H is in the opposite order.

The library of chimeric IgG/M Molecular Rheostat constructs was transfected into the 293T-Igαβ cells, and 48 hours later analyzed the cells and their supernatants for surface IgG by flow cytometry and secreted IgG by ELISA, respectively. All transfected cells showed surface expression of the IgG/M Molecular Rheostat BCR (detected as surface IgG because the extracellular portion of the chimeric BCR is made up of the heavy chain of IgG) and secreted IgG into the culture supernatant (FIGS. 2B and 2C). For the results shown in FIG. 2B, 293T-Igαβ cells were transfected with the same molar amount of chimeric IgG/M Molecular Rheostat constructs, and analyzed for the expression of surface IgG by flow cytometry. All constructs produced surface-bound chimeric IgG/M BCR detected as human IgG. Area 21: Molecular Rheostat Constructs. Area 20: Secretory IgG (L+H) control. The results shown in FIG. 2C refer to IgG ELISA of supernatants of transfected cells.

While the surface expression of the IgG/M Molecular Rheostat BCR appears comparable across all constructs, there was a range of levels of secreted IgG. Without being bound by any particular theory, this suggests that the different Molecular Rheostat constructs could be used to produce a range of ratios of surface to secreted immunoglobulins by judicious choices of the cleavage sites.

Example 4

Chimeric IgG/M Molecular Rheostat Constructs Mediate Expression of a Range of Ratios of Surface BCR to Secretory IgG in the Human B-Cell Line OCI-Ly7

Figure 3A:
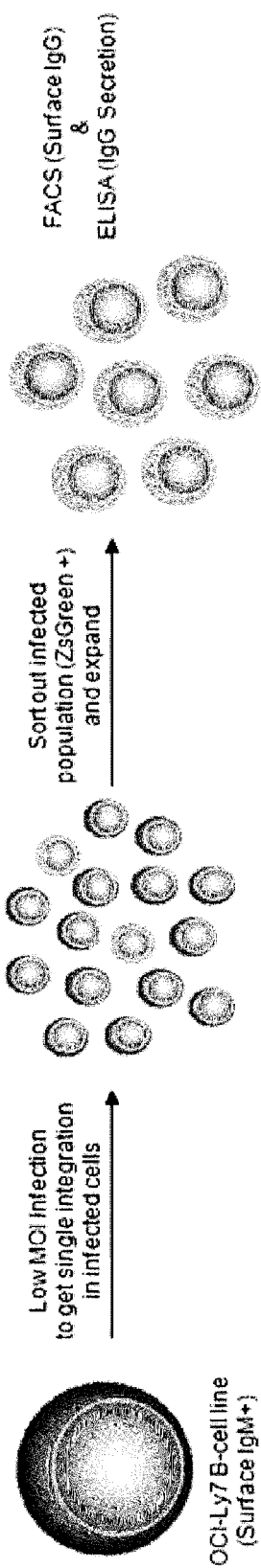
FIG. 3A is schematic diagram indicating an experimental design for measuring the expression of surface to secreted immunoglobulins by IgG "molecular rheostat" constructs according to some embodiments herein.
Figure 3B:
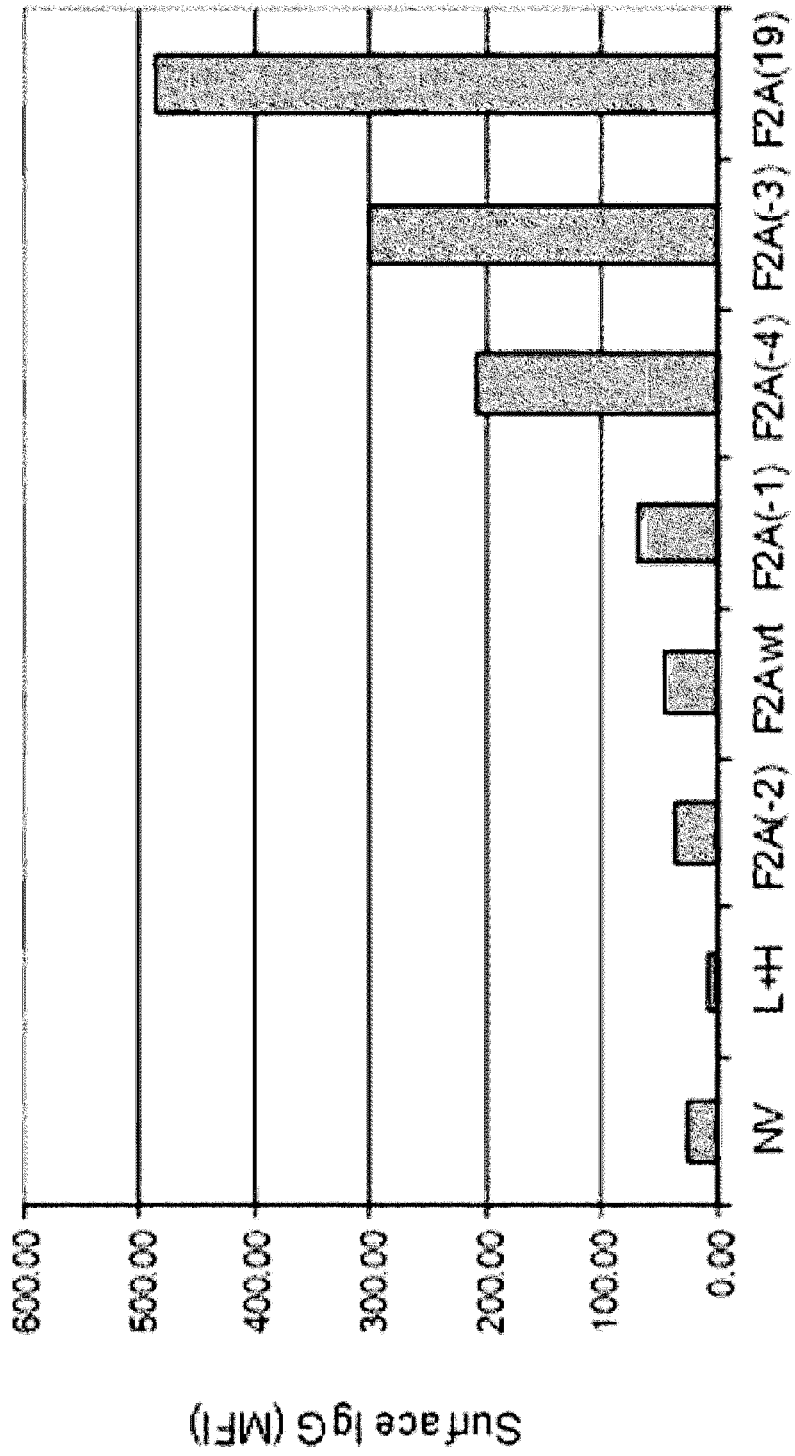
FIGS. 3B and 3C are graphs depicting inversely-related expression of b12 chimeric IgG/M BCR and secreted IgG mediated by mutant 2A polypeptides. Select b12 IgG/M chimeric constructs (based on the experiment with the 293T cells in FIG. 2) were modified to include an additional ZsGreen fluorescent protein gene driven by an IRES 39 of the heavy chain. OCI-Ly7 B cells were infected with at low MOI (, 0.1) with this library of constructs and the cells that express the ZsGreen gene were sorted out by FACS.
Figure 3C:
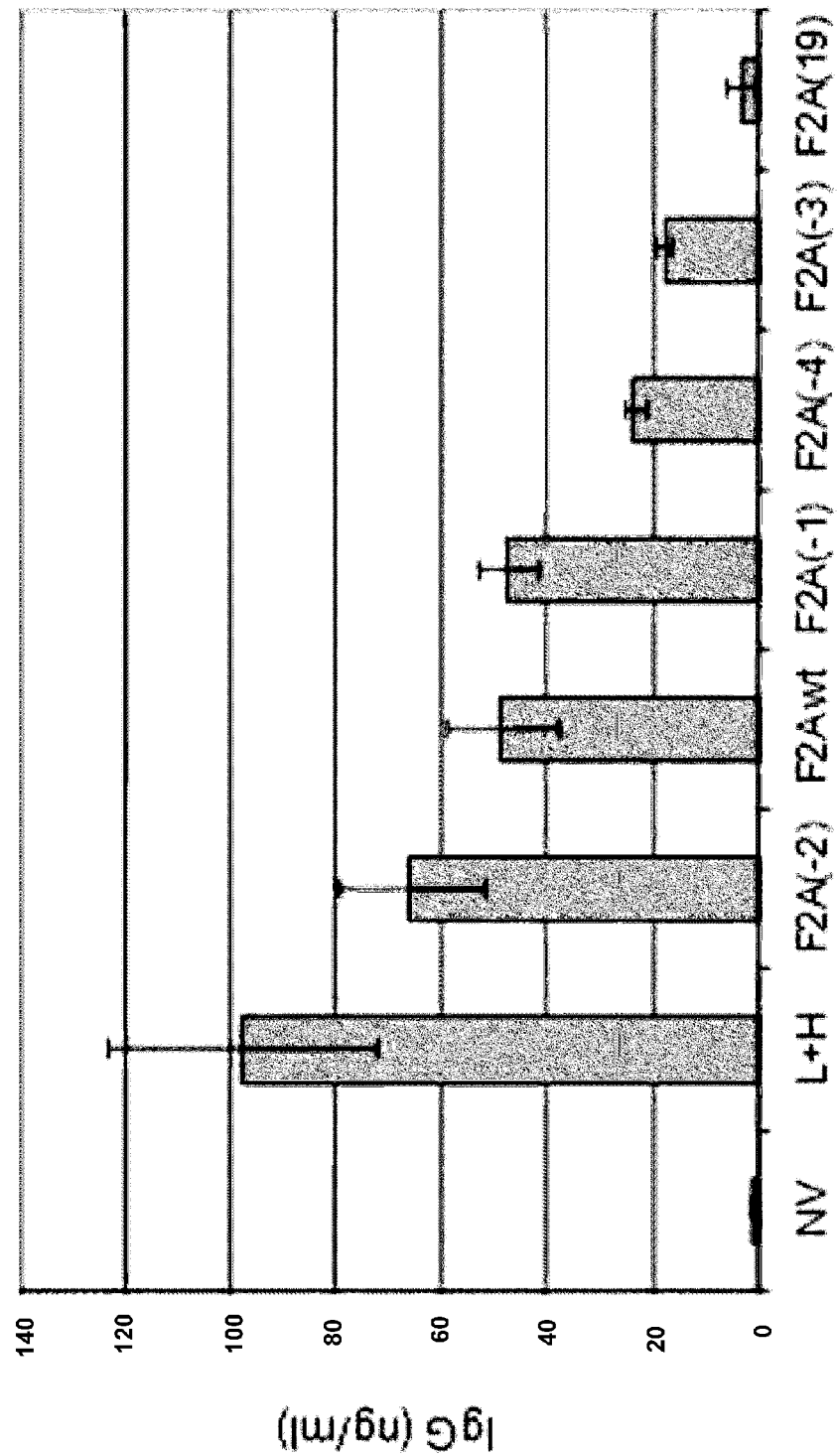
Figure 4A:
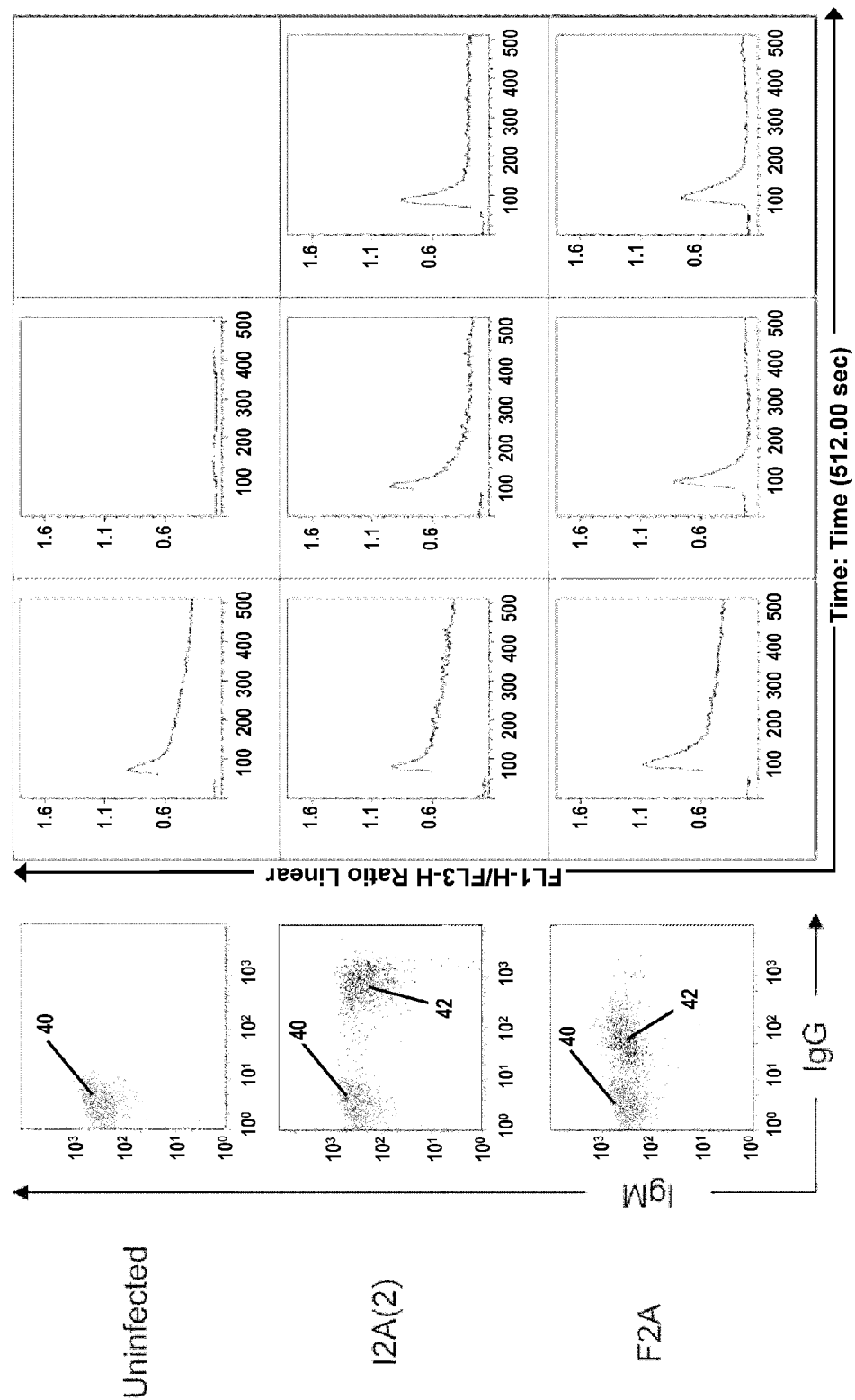
FIG. 4A is a graph illustrating that "molecular rheostat" constructs can generate functional chimeric IgG/M BCRs that signal and bind to HIV gp120. The cells were stimulated in a ratiometric calcium flux assay under different stimulation conditions. OCI-Ly7 B cells were infected with a library of chimeric b12 IgG/M "Molecular Rheostat" constructs that did not contain the IRES-ZsGreen marker gene. 48 hours after infection, cells expressing high amounts of surface IgG by flow cytometry (top 5%) were sorted out. The sorted cells were allowed to rest for 24 hours before anti-BCR stimulation. First column: response of endogenous IgM BCR to anti-IgM stimulation. Second column: high dose (100 ug/ml) anti-IgG stimulation. Third column: low dose (20 ug/ml) anti-IgG stimulation. Area 40: uninfected control cells. Area 42: sorted cells expressing the "Molecular Rheostat" Immunoglobulins.
Figure 4B:
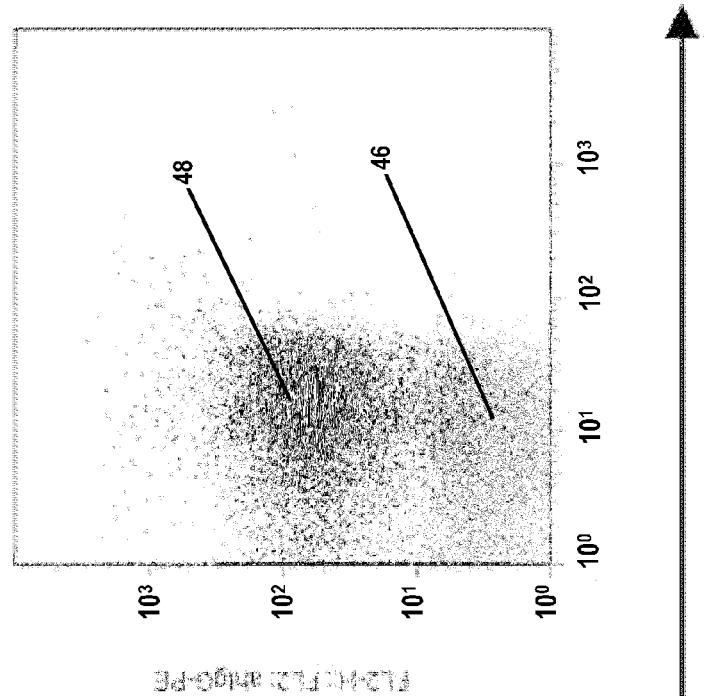
FIG. 4B is a scatter plot indicating Anti-IgG and $gp120_{MN}$ labeling of sorted cells according to FIG. 4A. Area 44 and area 48: I2A(2) and F2A "Molecular Rheostat" Immunoglobulin vector transduced cells, respectively. Area 46: untransduced control cells.
Figure 4B:
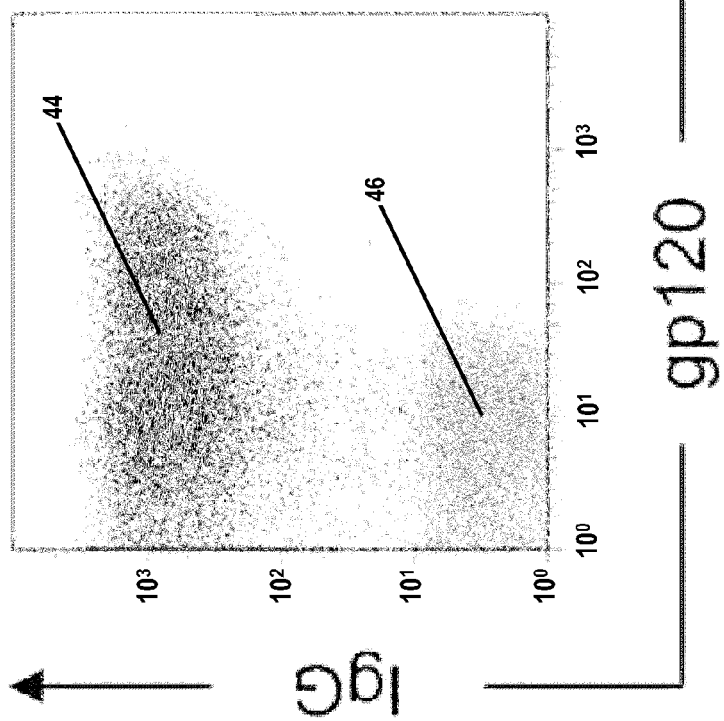
Figure 8:
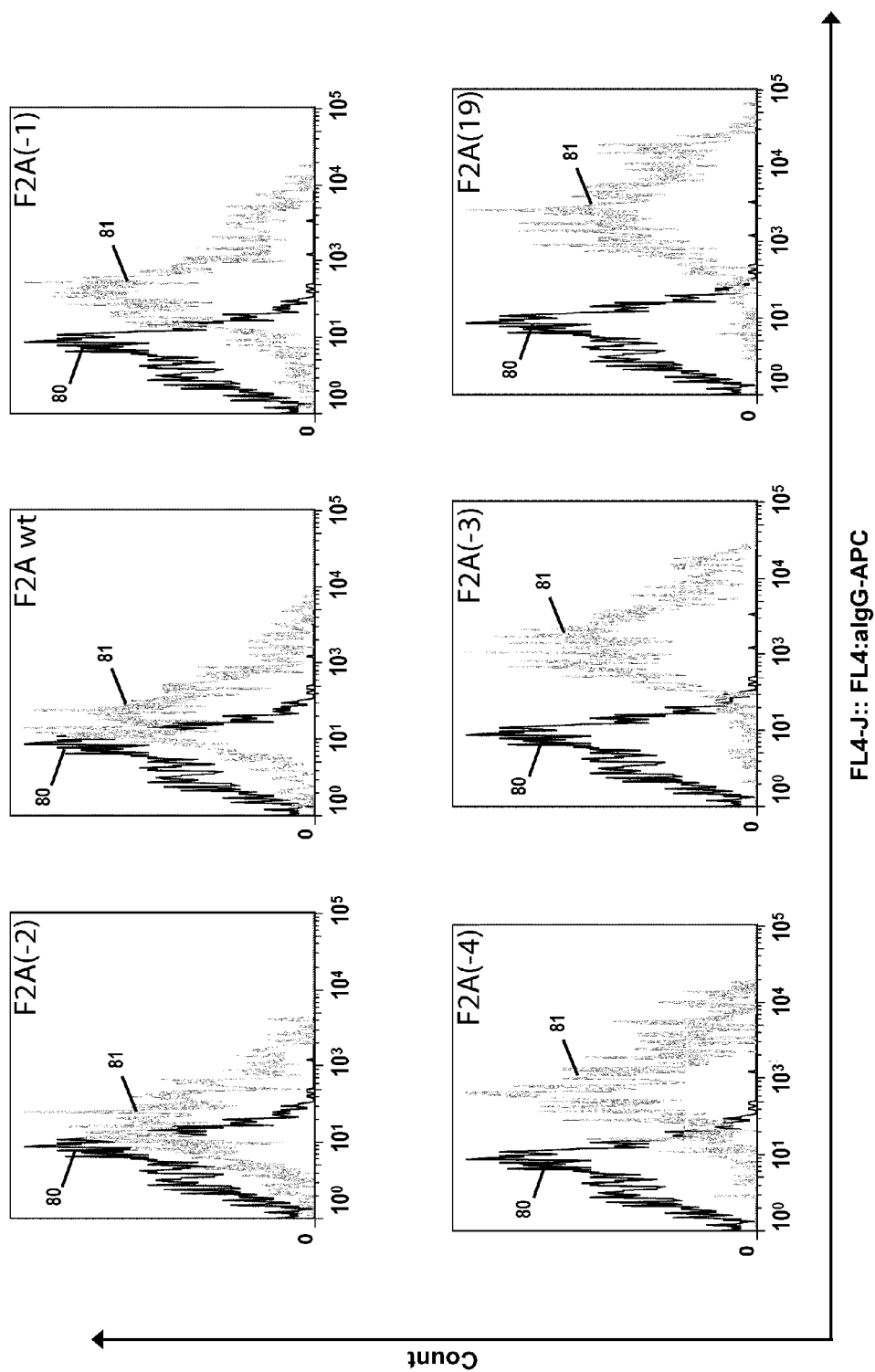
FIG. 8 is a series of FACS histograms of surface IgG expression of OCI-Ly7 cells transduced with different "Molecular Rheostat" constructs according to some embodiments herein. Area 81: surface IgG expression from different mutant 2A peptides in the Molecular Rheostat Immunoglobulin genes. Area 80: control L+H construct (secreted antibody only).

Lentiviral vectors were used to deliver the constructs into the OCI-Ly7 B-cell line, which expresses an endogenous IgM BCR on its surface and therefore should possess the necessary machinery (such as Igα and Igβ co-receptors) for BCR surface expression. These experiments further validated the results that the chimeric IgG/M Molecular Rheostat constructs can mediate a range of expression ratios of surface BCR to secreted antibodies in human B cells. To provide an independent marker of lentiviral transduction other than the expression of the Molecular Rheostat Immunoglobulins, a lentiviral vector, pHAGE2-EEK-IRES-Zs-Green, was constructed, which contains an Internal Ribosomal Entry Site (IRES) driving a ZsGreen fluorescent protein gene. Based on the results in FIG. 2B, six IgG/M Molecular Rheostat genes were selected and cloned them into the first position (before the IRES-ZsGreen) of the pHAGE2-EEK-IRES-ZsGreen vector. OCI-Ly7 cells were then infected with the chimeric IgG/M Molecular Rheostat vectors at low MOI (~0.1) to ensure that nearly every cell that was infected had at most one copy of the transgene (FIG. 3A). 48 hours after infection, we sorted out the ZsGreen positive cells and allowed these cells to expand for another 48 hours. The cells and supernatants were analyzed by flow cytometry and ELISA, respectively (FIG. 3B, left and right panels, respectively). The different mutants produced a range of ratios of surface to secreted immunoglobulins. Significantly, there was an inverse relationship between the amounts of chimeric IgG/M Molecular Rheostat BCR expressed on the surface of the cells vs. the amounts of IgG antibody that was detected in the supernatants, indicating that the mutant 2A elements could be used like a "rheostat", tuning the ratios of surface to secreted immunoglobulins. This inverse relationship was visualized by plotting the MFI (mean fluorescence intensity) of surface IgG staining in the left panel and contrasting this trend with the levels of secreted antibody production in the right panel of FIG. 3B. (See FIG. 8 for original FACS histograms of surface IgG staining.) Biasing the Molecular Rheostat towards producing more surface receptors results in a decrease in antibody secretion. Also notably, the rank order of the relative amounts of surface BCR to secreted immunoglobulin expression recapitulates what was observed from the transfection experiment with 293T-Igαβ cells (see FIGS. 2B and C). For example, from FIGS. 2B and C, F2A(-2) would be expected to make more secreted IgG than F2A(-4), and this was indeed the case when the constructs were expressed in the OCI-Ly7 B cell line as shown in FIGS. 3B and C. Furthermore, F2A(-2) made less surface Molecular Rheostat BCR than F2A(-4), as would be expected if the F2A(-2) peptide mediated more efficient cleavage than the F2A(-4) peptide. The library of mutant constructs together constitutes a Molecular Rheostat that can be used to direct tunable ratios of expression of surface BCR vs. secreted immunoglobulin.

Example 5

IgG/M Molecular Rheostat Constructs Produce Functional b12 IgG/M Chimeric BCRs are Signaling Competent and Bind to HIV gp120

A ratiometric Fluo-3/FuraRed calcium flux assay was developed in which anti-BCR crosslinking antibodies are used to examine whether the BCRs are able to signal in the OCI-Ly7 B cells. This assay was used to test whether the chimeric IgG/M BCRs were functional. Two cleavage sites were selected from the library: F2A, which cleaves with high efficiency, and I2A(2), which does not cleave well. As the ZsGreen protein interferes with the Fluo-3 calcium-sensitive dye used in the assay, those two chimeric IgG/M Molecular Rheostat genes were cloned into lentiviral vectors that do not have the IRES-ZsGreen marker gene. Lentiviral infections of OCI-Ly7 B cells with these vectors resulted in a variegated pattern of expression of the BCRs. The vector containing the I2A(2) element showed generally higher levels of surface BCR expression than F2A, as expected. While both populations responded to BCR stimulation using a control anti-IgM antibody (Southern Biotech, Birmingham, AB) and an anti-IgG antibody (Sigma, St Louis, Mo.), the responses were detectable but modest (data not shown). Without being bound to any particular theory, the modest response may be due to the effect of averaging the calcium signals over the large range of surface expressions. To ensure more homogeneous populations for use in BCR stimulations, the top 10% of IgG positive cells from each of the populations were isolated by FACS (FIG. 4B), and calcium flux assays were performed on the sorted cells. The cells responded robustly to anti-BCR stimulation (FIG. 4A), with a dose-response correlating with the levels of surface IgG/M Molecular Rheostat BCR expression and the concentrations of anti-Ig used. The higher anti-IgG dose (100 ug/ml) gave a stronger calcium signal than the lower dose (20 ug/ml); the cells with more surface Molecular Rheostat BCR expression also generated a stronger and more lasting response.

Additionally, the sorted OCI-Ly7 cells were stained with fluorescently labeled HIV gp120MN and anti-IgG, which respectively interact with the gp120-antigen-binding site of b12 and the γ heavy chain constant region of b12 IgG (FIG. 4C). The Molecular Rheostat BCRs on the cells bound to HIV gp120. Thus, the chimeric IgG/M BCR can bind to HIV antigens.

Example 6

Figure 5A:
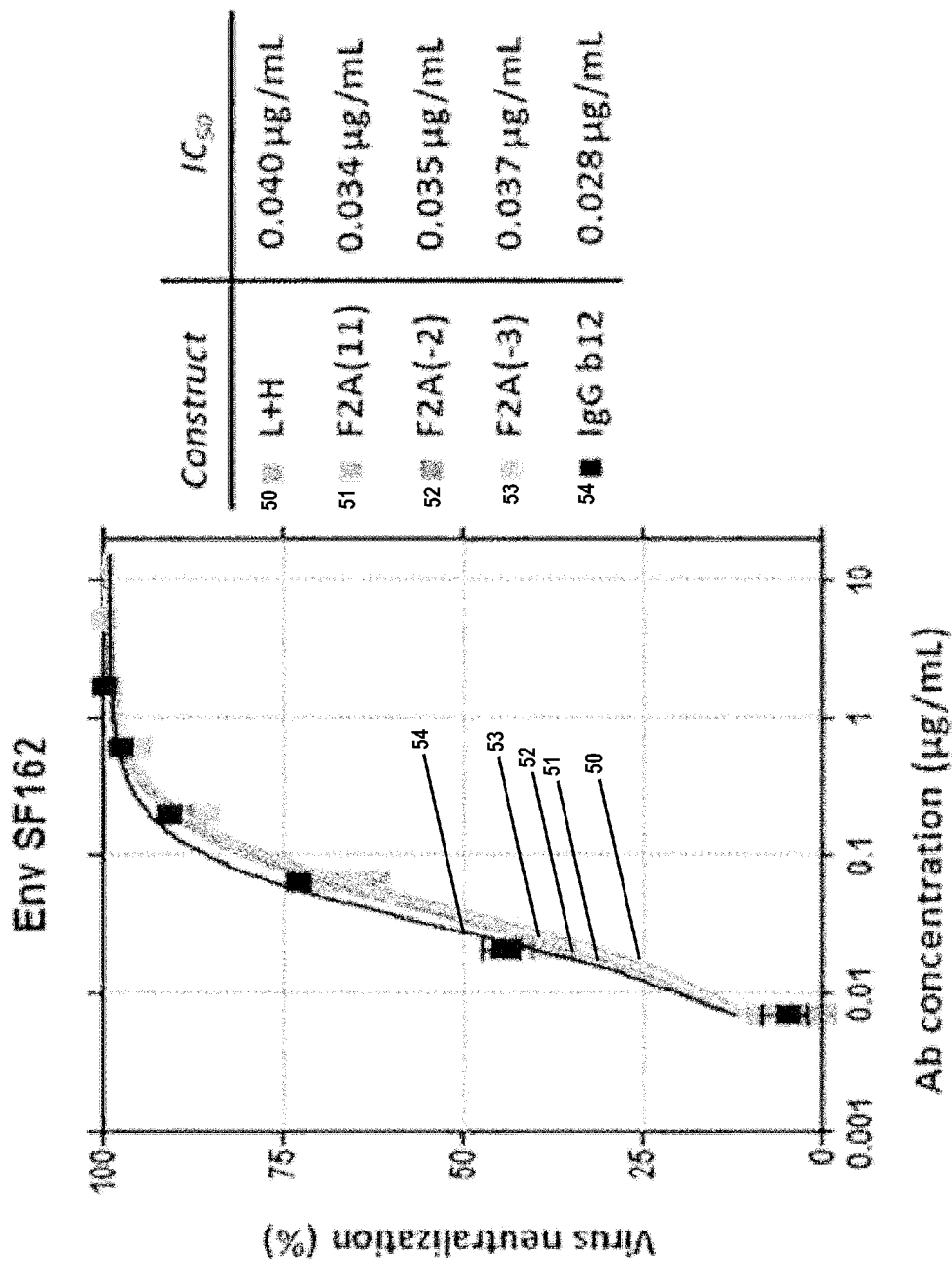
FIG. 5A is a graph illustrating that b12 IgG produced by "Molecular Rheostat" constructs neutralized Env SF162 pseudovirus. An in vitro neutralization assay was performed against Env SF162 pseudovirus. The chimeric IgG/M Molecular Rheostat constructs were transfected into 293T cells and IgG in the supernatants were purified using an affinity column. The purified IgG were used in the neutralization assay. The neutralization curves are nearly identical for all mutant 2A constructs and the control b12 IgG (L+H). The IC50 values are indicated to the right of the graph. IgG b12: a batch of previously purified b12 IgG included as a positive control for the assay.
Figure 5B:
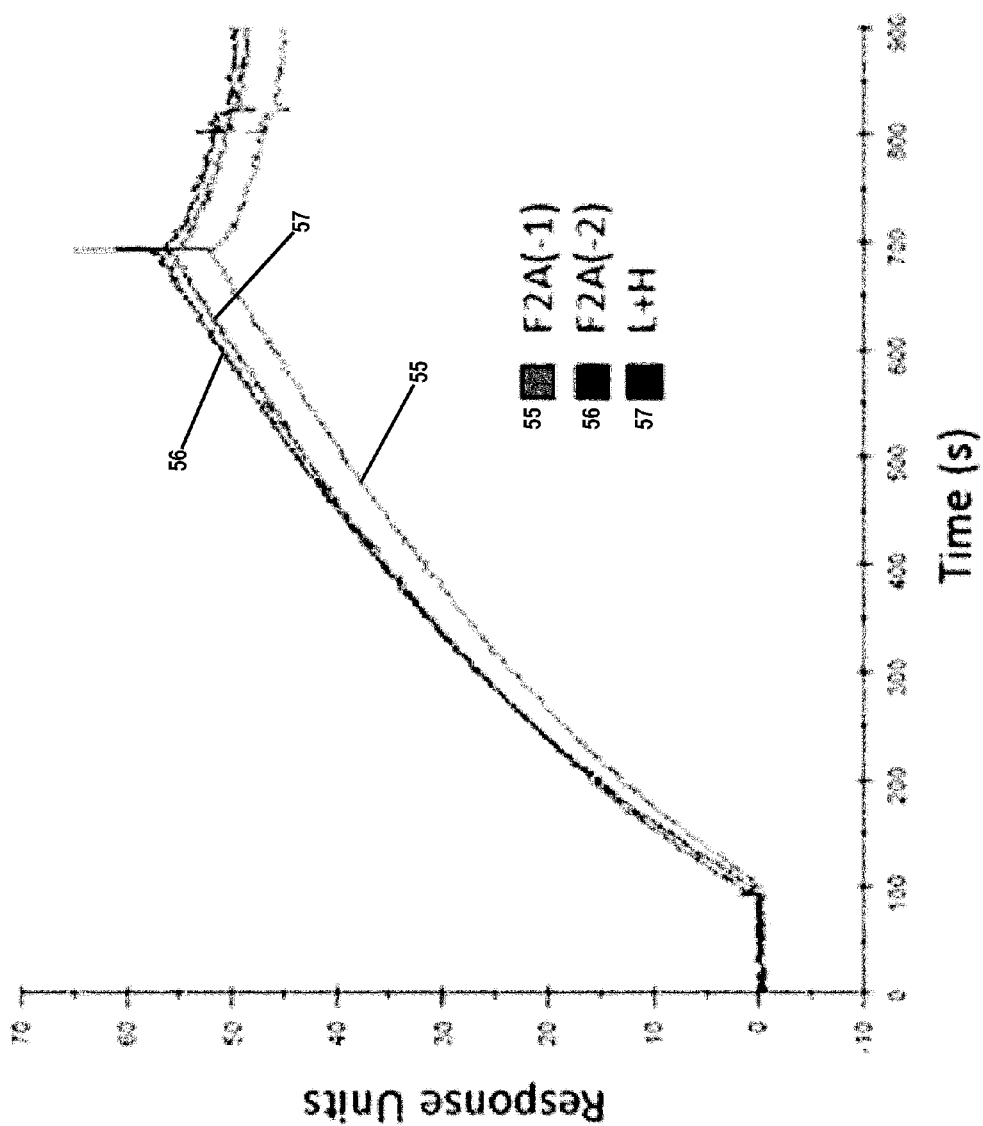
FIG. 5B is a graph illustrating that b12 IgG produced by Molecular Rheostat constructs bound to GP120. A surface plasmon resonance (SPR) GP120 binding assay was performed. Supernatants from transfected 293T cells were diluted with media to the same IgG concentration and used in the SPR binding assay. The plot shows nearly identical SPR traces for each of the two tested 2A mutant constructs (F2A(-1) (55) and F2A(-2)(56) and the control (L+H)(57)).

Chimeric IgG/M Molecular Rheostat Constructs Produce b12 IgG Antibody that Neutralizes HIV Pseudovirus with Same Potency as Unmodified b12 IgG An in vitro pseudovirus neutralization assay was performed using an Env SF162 pseudotyped HIV-1 pseudovirus on the TMZ-b1 reporter cell line with supernatants from 293T cells transfected with several different chimeric IgG/M Molecular Rheostat constructs according to a protocol previously described by Klein et al. (2009) Examination of the contributions of size and avidity to the neutralization mechanisms of the anti-HIV antibodies b12 and 4E10. Proc Natl Acad Sci USA 106: 7385-7390, hereby incorporated by reference in its entirety. The neutralization curves demonstrated that secreted Molecular Rheostat b12 IgG antibodies neutralized the Env SF162 pseudovirus as potently as the control b12 IgG antibody (L+H), with IC50 values nearly identical to that of the control b12 IgG (FIG. 5A). A surface-plasmon resonance gp120-binding assay was also performed. The antibodies tested bound gp120 as well as the control b12 IgG antibody, consistent with the neutralization assay results (FIG. 5B). Thus, the secreted b12 IgG from the Molecular Rheostat system can neutralize infectious virus.

Example 7

Expression of Chimeric IgG/M Molecular Rheostat Immunoglobulins Promote Maturation of EU12 Cells in an In Vitro Model of B Cell Development The promotion of B cell development is one of the major functions performed by the IgM BCR. It thus can offer a stringent test of BCR function. To test whether the chimeric IgG/M Molecular Rheostat Immunoglobulin BCR can direct B cell development, a model of human B cell development using the EU12 cell system (Zhang Z, et al. (2003) Molecular mechanism of serial VH gene replacement. Ann N Y Acad Sci 987: 270-273; Zhang Z (2007) VH replacement in mice and humans. Trends Immunol 28: 132-137, each of which is hereby incorporated by reference in its entirety) was adopted. EU12 cells are derived from a B cell leukemia patient; they are uniformly CD 19+ but exist in a spectrum of primitive (CD34+ and CD10−, or CD34+ and CD10+) to more mature (CD34− and CD10+, or CD34− and CD10−) states. These cells lack a functional BCR, but rarely an IgM BCR is generated spontaneously and the cells proceed to acquire a more mature phenotype.

Figure 6A:
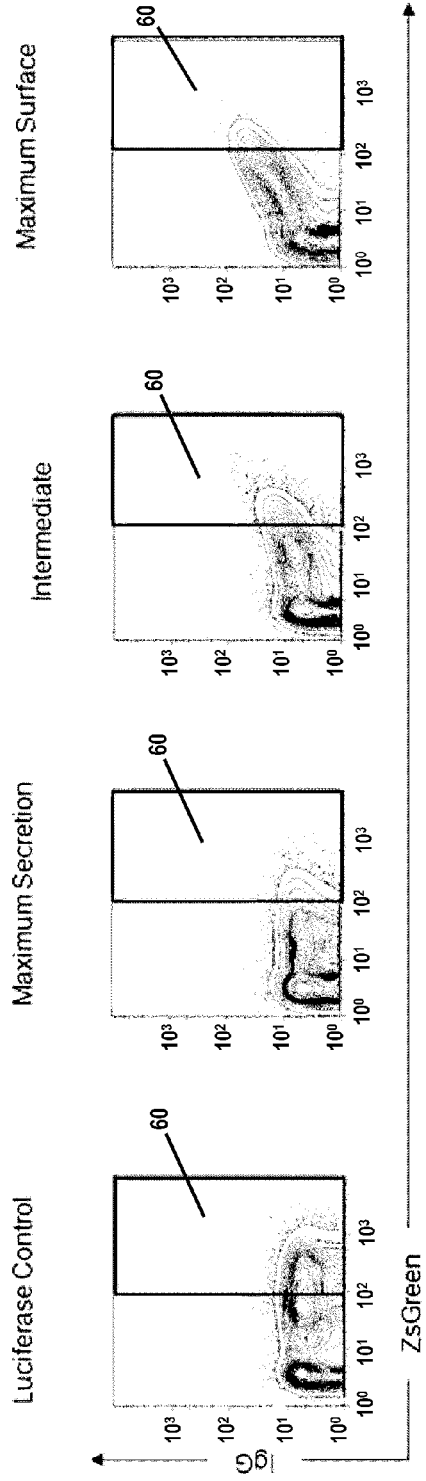
FIG. 6A is a graph illustrating that "Molecular Rheostat" IgG/M BCRs promote downregulation of CD10 in EU12 cells. CD34+ EU12 cells (early B cells) transduced with IRES-driven ZsGreen expressing Molecular Rheostat constructs were analyzed by flow cytometry. Surface BCR levels correlate with ZsGreen intensity. Cells transduced with Molecular Rheostat constructs tuned for higher surface expression showed more surface BCR expression with the same ZsGreen expression. The box (60) shows ZsGreen gating.
Figure 6B:
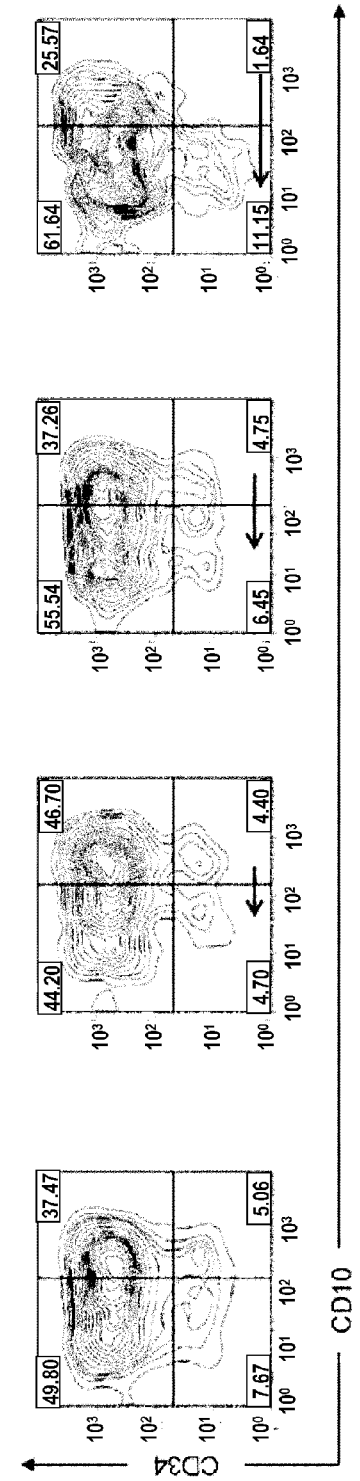
FIG. 6B is a graph illustrating that "Molecular Rheostat" IgG/M BCRs promote downregulation of CD10 in EU12 cells. Gating on high ZsGreen expression, CD10 and CD34 expression was analyzed. Cells transduced with constructs that express higher surface IgG/M BCR levels show a greater extent of CD10 downregulation, suggesting that the Molecular Rheostat BCRs are signaling to the cells and promoting maturation.

Early-stage, CD34+ EU12 cells were isolated by FACS sorting. These cells were then transduced with lentiviral vectors carrying chimeric IgG/M Molecular Rheostat constructs that give rise to respectively low, intermediate, and high surface BCR expression. A luciferase-carrying vector was used as a control. The cells were allowed to expand, and 4 weeks after transduction the surface expression of chimeric IgG/M Molecular Rheostat BCR and maturation markers were analyzed by FACS (FIG. 6). The EU12 cells transduced with Molecular Rheostat constructs tuned at different levels of surface BCR vs. secreted antibody expression showed the expected levels of surface BCR expression (F2A was used for maximum secretion; F2A(11) for intermediate; F2A(19) for maximal surface). Using ZsGreen as a measure of the amount of gene expression from the entire cassette in each cell, the level of chimeric IgG/M BCR expression correlated with the ZsGreen expression level for each of the three Molecular Rheostat constructs (FIG. 6A). CD34 and CD10 expression was analyzed by FACS, gating on the highly expressing cells. It was found that the cells that had been transduced with Molecular Rheostat constructs chosen for higher surface BCR expression and less secreted antibody had larger populations of cells that down-regulated CD10 (FIG. 6B). This provides further evidence that the chimeric IgG/M BCRs were functional BCRs and can promote maturation of B lineage cells.

What is claimed is:

1. A polynucleotide construct comprising:
   a signal polynucleotide encoding a signal sequence sufficient to mediate translocation of a polypeptide comprising said signal sequence to a cell surface;
   a first cleavage polynucleotide encoding a first 2A polypeptide cleavage site in-frame with said signal sequence;
   an anchor polynucleotide encoding a membrane anchor polypeptide in-frame with said first 2A polypeptide cleavage site, wherein said membrane anchor polypeptide is sufficient to attach a polypeptide encoded by said polynucleotide construct to said cell surface, wherein at least one of (a) a majority of amino acids of said membrane anchor polypeptide are hydrophobic, or (b) said membrane anchor polypeptide facilitates the attachment of a fatty acid thereto; and
   a first insertion site for a first polypeptide-encoding polynucleotide encoding a first polypeptide,
   wherein said first insertion site is positioned for inserting a first polypeptide-encoding polynucleotide in-frame with said signal polynucleotide, said first cleavage polynucleotide, and said anchor polynucleotide,
   wherein said first insertion site is configured so that if said first polypeptide is expressed: (i) if said first 2A polypeptide cleavage site is cleaved, said first polypeptide is not attached to said membrane anchor polypeptide, and is thereby a secreted polypeptide; and (ii) if said first 2A polypeptide cleavage site is not cleaved, said first polypeptide comprises said membrane anchor polypeptide, and is thereby a membrane-bound polypeptide,
   wherein said first cleavage polynucleotide is positioned 3' of said first insertion site, and wherein said first cleavage polynucleotide is positioned 5' of a 3' end of said anchor polynucleotide, and
   wherein said signal polynucleotide is 5' of said first cleavage polynucleotide.

2. The polynucleotide construct of claim 1, wherein said first cleavage polynucleotide encodes a first 2A polypeptide cleavage site comprising the amino acid sequence selected from the group consisting of SEQ ID NOs: 2 to 6.

3. The polynucleotide construct of claim 1, wherein said first cleavage polynucleotide encodes a first 2A polypeptide cleavage site comprising an amino acid sequence having at least 85% sequence identity to the amino acid sequence selected from the group consisting of SEQ ID NOs: 2 to 6.

4. The polynucleotide construct of claim 1, wherein said signal polynucleotide encodes a signal sequence comprising the amino acid sequence selected from the group consisting of SEQ ID NOs: 43 to 529.

5. The polynucleotide construct of claim 1, wherein said anchor polynucleotide encodes a membrane anchor polypeptide comprising the amino acid sequence selected from the group consisting of SEQ ID NOs: 540 to 551.

6. The polynucleotide construct of claim 1, wherein a ratio of (a) said secreted polypeptide to (b) said membrane-bound polypeptide correlates to a known cleavage efficiency of said first 2A polypeptide cleavage site.

7. The polynucleotide construct of claim 1, wherein said signal polynucleotide is 5' of said first insertion site, and wherein said first insertion site is 5' of said first cleavage polynucleotide.

8. The polynucleotide construct of claim 1, wherein said signal polynucleotide is 3' of said first insertion site.

9. The polynucleotide construct of claim 1, further comprising:
   a second insertion site for a second polypeptide-encoding polynucleotide; and
   a second cleavage polynucleotide encoding a second 2A polypeptide cleavage site,
      wherein said second insertion site is positioned for inserting said second polypeptide-encoding polynucleotide in-frame with said first polypeptide-encoding polynucleotide, and said second cleavage polynucleotide, and
      wherein said second 2A polypeptide cleavage site is positioned between said first insertion site and said second insertion site.

10. The polynucleotide construct of claim 1, further comprising a promoter configured to express said signal polynucleotide, said first cleavage polynucleotide, and said anchor polynucleotide in a single transcript.

11. The polynucleotide construct of claim 1, further comprising a first polypeptide-encoding polynucleotide positioned in said first insertion site, in-frame with said signal polynucleotide, said first cleavage polynucleotide, and said anchor polynucleotide.

12. The polynucleotide construct of claim 1, comprising, from 5' to 3', a second insertion site for a second polypeptide-encoding polynucleotide, a second cleavage polynucleotide encoding a second 2A polypeptide cleavage site, said first insertion site for a first polypeptide-encoding polynucleotide, said signal polynucleotide, said first cleavage polynucleotide, and said anchor polynucleotide.

13. The polynucleotide construct of claim 1, comprising, from 5' to 3', a second polypeptide-encoding polynucleotide, a second cleavage polynucleotide encoding a second 2A polypeptide cleavage site, a first polypeptide-encoding polynucleotide, said signal polynucleotide, said first cleavage polynucleotide, and said anchor polynucleotide.

14. The polynucleotide construct of claim 1, comprising, from 5' to 3', a polynucleotide encoding an immunoglobulin light chain, a second cleavage polynucleotide encoding a second 2A polypeptide cleavage site, a polynucleotide encoding an immunoglobulin heavy chain, said signal polynucleotide, said first cleavage polynucleotide, and said anchor polynucleotide.

15. A vector comprising the polynucleotide construct of claim 1.

16. The vector of claim 15, wherein said vector is a lentiviral vector.

17. A method of expressing a secreted polypeptide and a surface-bound polypeptide from a single construct in a target cell, the method comprising:
providing a construct comprising:
a first polynucleotide encoding a first polypeptide,
a signal polynucleotide encoding a signal sequence sufficient to mediate translocation of a polypeptide comprising said signal sequence to a surface of said target cell, wherein said signal sequence is in-frame with the first polynucleotide;
a first cleavage polynucleotide encoding a first 2A polypeptide cleavage site in-frame with said signal sequence; and
an anchor polynucleotide encoding a membrane anchor polypeptide in-frame with first 2A polypeptide cleavage site, wherein said membrane anchor polypeptide is sufficient to attach a polypeptide encoded by said construct to said surface of said target cell, wherein at least one of (a) a majority of amino acids of said membrane anchor polypeptide are hydrophobic, or (b) said membrane anchor polypeptide sequence facilitates the attachment of a fatty acid to said membrane anchor polypeptide,
wherein said first polynucleotide is 5' of said first cleavage polynucleotide,
wherein said signal polynucleotide is 5' of said first cleavage polynucleotide, and wherein said first cleavage polynucleotide is 5' of said anchor polynucleotide; and
delivering said construct to a target cell, wherein said target cell transcribes said construct, wherein once transcribed, said first cleavage site is cleaved in a first plurality of first polypeptides, so that said first plurality of first polypeptides do not comprise said membrane anchor polypeptide, and are thereby secreted by said target cell, and wherein said first cleavage site is not cleaved in a second plurality of first polypeptides, so that said second plurality of first polypeptides comprise said membrane anchor polypeptide, and are thereby bound to the surface of said target cell; and
detecting a quantity of said second plurality of first polypeptides on the surface of said target cell.

18. The method of claim 17, wherein said delivering comprises integrating said construct into said target cell's genome.

19. The method of claim 17, wherein after being delivered to said target cell, said first polynucleotide, said signal polynucleotide, said first cleavage polynucleotide, and said anchor polynucleotide are under the control of a single promoter.

20. The method of claim 17, wherein said first 2A polypeptide cleavage site comprises the amino acid sequence selected from the group consisting of SEQ ID NOs: 1 to 6.

21. The method of claim 17, further comprising selecting said first cleavage polynucleotide to encode a 2A polypeptide cleavage site having a desired activity level, wherein said desired activity level correlates to a ratio of secreted polypeptide to surface-bound polypeptide.

22. The method of claim 17, wherein said first polypeptide comprises a fluorescent protein.

23. The method of claim 17, the construct further comprises:
a second polynucleotide encoding a polypeptide; and
a second cleavage polynucleotide encoding a second 2A polypeptide cleavage site, wherein said second polynucleotide is in-frame with said second cleavage polynucleotide and said first polynucleotide, and
wherein said second 2A polypeptide cleavage site is positioned between said second polynucleotide and said first polynucleotide.

24. The method of claim 17, further comprising detecting a quantity of said first plurality of first polypeptide secreted by said target cell.

25. The polynucleotide construct of claim 1, wherein said first insertion site comprises said first polypeptide-encoding polynucleotide.

26. The polynucleotide construct of claim 1, wherein said first cleavage polynucleotide encodes a first 2A polypeptide cleavage site comprising the amino acid sequence selected from the group consisting of SEQ NOs: 7 to 16.

27. The polynucleotide construct of claim 1, wherein said first cleavage polynucleotide encodes a first 2A polypeptide cleavage site comprising an amino acid sequence having at least 85% sequence identity to the amino acid sequence selected from the group consisting of SEQ ID NOs: 7 to 16.

28. The polynucleotide construct of claim 1, wherein said signal polynucleotide encodes a signal sequence comprising the amino acid sequence selected from the group consisting of SEQ ID NOs: 33 to 42.

29. The polynucleotide construct of claim 1, wherein said anchor polynucleotide encodes a membrane anchor polypeptide comprising the amino acid sequence selected from the group consisting of SEQ ID NOs: 530 to 539.

30. The method of claim 17, wherein said first cleavage polynucleotide encodes a first 2A polypeptide cleavage site comprising the amino acid sequence of any one of SEQ ID NOs: 7 to 16.

31. The polynucleotide construct of claim 1, wherein first 2A polypeptide cleavage site does not comprise the amino acid sequence of SEQ ID NO: 1.

32. The method of claim 17, wherein said first 2A polypeptide cleavage site does not comprise the amino acid sequence of SEQ ID NO: 1.

* * * * *